United States Patent
Lanzavecchia et al.

(10) Patent No.: US 12,331,108 B2
(45) Date of Patent: Jun. 17, 2025

(54) ANTIBODIES WITH FUNCTIONAL DOMAINS IN THE ELBOW REGION BETWEEN VARIABLE AND CONSTANT DOMAIN

(71) Applicant: INSTITUTE FOR RESEARCH IN BIOMEDICINE, Bellinzona (CH)

(72) Inventors: Antonio Lanzavecchia, Porza (CH); Luca Piccoli, Bellinzona (CH)

(73) Assignee: Institute for Research in Biomedicine, Bellinzona (CH)

( * ) Notice: Subject to any disclaimer, the term of this patent is extended or adjusted under 35 U.S.C. 154(b) by 343 days.

(21) Appl. No.: 16/635,506

(22) PCT Filed: Jul. 30, 2018

(86) PCT No.: PCT/EP2018/070640
§ 371 (c)(1),
(2) Date: Jan. 30, 2020

(87) PCT Pub. No.: WO2019/025391
PCT Pub. Date: Feb. 7, 2019

(65) Prior Publication Data
US 2020/0325220 A1    Oct. 15, 2020

(30) Foreign Application Priority Data

Jul. 31, 2017  (WO) ................ PCT/EP2017/069357

(51) Int. Cl.
| C07K 16/24 | (2006.01) |
| C07K 16/10 | (2006.01) |
| C07K 16/12 | (2006.01) |
| C07K 16/16 | (2006.01) |

(52) U.S. Cl.
CPC ........ *C07K 16/243* (2013.01); *C07K 16/1018* (2013.01); *C07K 16/1027* (2013.01); *C07K 16/1282* (2013.01); *C07K 16/16* (2013.01); *C07K 2317/31* (2013.01); *C07K 2317/569* (2013.01); *C07K 2317/622* (2013.01); *C07K 2318/10* (2013.01); *C07K 2319/01* (2013.01); *C07K 2319/30* (2013.01)

(58) Field of Classification Search
CPC .............. C07K 16/243; C07K 16/1018; C07K 16/1027; C07K 16/1282; C07K 16/16; C07K 2317/31; C07K 2317/569; C07K 2317/622

See application file for complete search history.

(56) References Cited

U.S. PATENT DOCUMENTS

2014/0235476 A1 *  8/2014  Gu .................. C07K 16/22
                                                          435/254.2

FOREIGN PATENT DOCUMENTS

| WO | 2009/018386 A1 | 2/2009 | |
| WO | 2012088290 A2 | 6/2012 | |
| WO | WO-2016173605 A1 * | 11/2016 | ................ A61P 1/04 |
| WO | 2016/207402 A1 | 12/2016 | |
| WO | 2016208695 A1 | 12/2016 | |
| WO | WO-2016203052 A1 * | 12/2016 | ............. A61K 39/12 |
| WO | WO-2017100372 A1 * | 6/2017 | ............. A61K 38/02 |

OTHER PUBLICATIONS

Hsieh et al., "The structure of a LAIR1-containing human antibody reveals a novel mechanism of antigen recognition," *eLife* 6:e27311, 2017. (11 pages).
International Search Report and Written Opinion, dated Oct. 31, 2018, for International Application No. PCT/EP2018/070640, 10 pages.
Tan et al., "A LAIR1 insertion generates broadly reactive antibodies against malaria variant antigens," *Nature* 529(7584):105-109, 2016. (30 pages).
Yakovlev et al., "Discovery and Characterization of a High Potency Anti-Inflammatory Trispecific TNFα/IL-17A/IL-17F Inhibitor," *PEGS, Boston*, Boston, Massachusetts, Apr. 25-29, 2016. (42 pages).

* cited by examiner

*Primary Examiner* — Anand U Desai
*Assistant Examiner* — Cheom-Gil Cheong
(74) *Attorney, Agent, or Firm* — Fox Rothschild LLP

(57) ABSTRACT

The present invention provides engineered antibodies and antigen binding fragments, in which an additional functional domain is inserted into the elbow region of the antibody or antigen binding fragment. The present invention also provides nucleic acid molecules, such as vectors, encoding such antibodies and antigen binding fragments, host cells and compositions comprising such antibodies, antigen binding fragments or nucleic acid molecules and uses thereof. For example a multispecific antibody format is provided, in which an additional binding site (specificity) is inserted into the elbow region of an antibody or antigen binding fragment.

50 Claims, 10 Drawing Sheets
Specification includes a Sequence Listing.

A) Conventional antibody

B) New formats: IEI-Ig
(In-Elbow-Insert Ig molecules)

C) IEI combined with existing formats

F(ab)2

Fab

CrossMab
Knobs-in-holes
Orthogonal Fab
Fab-arm exchange

Bispecific/
multispecific
formats

DVD-Ig

| | | | | |
|---|---|---|---|---|
| GCE536 | VH1-46 | D | JH6 | |
| C1 | VH3-30 | D | JH6 | |
| C1b | VH3-20 | D | JH3 | |
| C2 | VH3-30 | D | JH6 | LAIR1$^{mut}$ |
| C3 | VH3-30 | D | JH6 | LAIR1$^{gen}$ |
| C4 | VH1-46 | D | JH6 | LAIR1$^{gen}$ |
| C5 | VH1-46 | D | JH6 | PD1 |
| C5b | VH1-46 | D | JH6 | PD1 |
| C6 | VH1-46 | D | JH6 | SLAM |
| C6b | VH1-46 | D | JH6 | SLAM |
| C7 | VH3-20 | D | JH3 | PD1 |
| C8 | VH3-20 | D | JH3 | SLAM |
| C9 | VH3-20 | D | JH3 | 2XST |

Figure 2

| | | | | |
|---|---|---|---|---|
| FI174 | VH1-69 | D | JH4 | |
| C10 | VH1-69 | D | JH4 | T3-VHH |
| C11 | VH1-69 | D | JH4 | TT39.7-ScFv |
| C12 | VH1-69 | D | JH4 | F4-VHH |
| C13 | VH1-69 | D | JH4 | MPE8-ScFv |

Figure 8

ANTIBODIES WITH FUNCTIONAL DOMAINS IN THE ELBOW REGION BETWEEN VARIABLE AND CONSTANT DOMAIN

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480369_408USPC_SEQUENCE_LISTING.txt. The text file is 188 KB, was created on Jan. 30, 2020, and is being submitted electronically via EFS-Web.

The present invention relates to the field of engineered antibodies with an additional functional domain, such as multispecific antibody formats. In particular, the present invention relates to engineered antibodies, in which an additional functional domain is inserted into the elbow region of the antibody. Accordingly, for example a multispecific antibody format is provided, in which an additional binding site (specificity) is inserted into the elbow region of an antibody.

In the recent years a variety of multispecific antibody formats emerged, based on molecular engineering of classical naturally occurring antibodies, such as IgG, which bind specifically to one antigen type. In contrast to classical naturally occurring antibodies, such as IgG, multispecific antibodies are able to bind to two or more distinct targets, thereby offering a large spectrum of applications.

Classical naturally occurring antibodies are Y-shaped molecules comprising four polypeptide chains: two heavy chains and two light chains (FIG. 1A). Each light chain consists of two domains, the N-terminal domain being known as the variable or VL domain and the C-terminal domain being known as the constant domain or CL. Each heavy chain consists of four or five domains, depending on the class of the antibody. The N-terminal domain of the heavy chain is known as the variable or VH domain. The next domain in N—C-terminal direction is known as the first constant or CH1 domain. The next part of the heavy chain is known as the hinge region, which is typically followed by the second, third and, in some cases, fourth constant or CH2, CH3 and CH4 domains respectively. The constant region, which comprises the constant domains, is identical in all antibodies of the same isotype, but differs in antibodies of different isotypes. Heavy chains γ, α and δ have a constant region composed of three tandem (in a line) Ig domains, and a hinge region for added flexibility; heavy chains μ and ε have a constant region composed of four immunoglobulin domains.

In addition to the hinge region, also the elbow region is known to provide flexibility for antigen binding. The elbow region is the junction between the variable domains and the constant domains in the heavy and light chains of the antibody. Typically, the C-terminus of the variable domain (VH or VL) is directly linked to the N-terminus of the most N-terminal constant domain (typically CH1 or CL), and the junction between the C-terminus of the variable domain (VH or VL) and the N-terminus of the most N-terminal constant domain (typically CH1 or CL) is referred to as "elbow" or "elbow region". The elbow region allows for bending and rotation of the variable domains relative to the constant domains. The elbow region is also referred to as "molecular ball-and-socket joint" based on the range of motion provided by the elbow region (Lesk A M, Chothia C. Elbow motion in the immunoglobulins involves a molecular ball-and-socket joint. Nature. 1988 Sep. 8; 335(6186):188-90).

In an assembled antibody, the VL and VH domains associate together to form an antigen binding site. Also, the CL and CH1 domains associate together to keep one heavy chain associated with one light chain. Each heavy chain hinge region includes at least one, and often several, cysteine residues. In the assembled antibody, the cysteine residues in the heavy chains are aligned so that disulfide bonds can be formed between the cysteine residues in the hinge regions covalently bonding the two heavy-light chain heterodimers together. Thus, fully assembled antibodies are monospecific in that they bind one antigen type and bivalent in that they have two independent antigen binding sites.

Based on the structure of such monospecific bivalent classical naturally occurring antibodies, a variety of multispecific antibody formats was designed (for review see Spiess C, Zhai Q, Carter P J. Alternative molecular formats and therapeutic applications for bispecific antibodies. Mol Immunol. 2015 October; 67(2 Pt A):95-106 and Weidle U H, Tiefenthaler G, Weiss E H, Georges G, Brinkmann U. The intriguing options of multispecific antibody formats for treatment of cancer. Cancer Genomics Proteomics. 2013 January-February; 10(1):1-18). In general, prior art multispecific antibody formats can be classified into five distinct structural groups: (i) multispecific IgG, (ii) appended IgG, (iii) multispecific antibody fragments, (iv) multispecific fusion proteins and (v) multispecific antibody conjugates (Spiess C, Zhai Q, Carter P J. Alternative molecular formats and therapeutic applications for bispecific antibodies. Mol Immunol. 2015 October; 67(2 Pt A):95-106).

Multispecific IgG antibody formats are typically monovalent for each specificity (antigen). Initial attempts to couple the binding specificities of two whole antibodies against different target antigens for therapeutic purposes utilized chemically fused heteroconjugate molecules (Staerz et al. (1985), Nature 314: 628-631). Bispecific antibodies were produced from hybrid hybridomas by heterohybridoma techniques (Milstein & Cuello (1983) Nature 305:537-540). Multispecific IgG antibody formats include CrossMab, DAF (two-in-one), DAF (four-in-one), DutaMab, DT-IgG, Knobs-in-holes common LC, Knobs-in-holes assembly, Charge pair, Fab-arm exchange, SEEDbody, Triomab, LUZ-Y, Fcab, κλ-body and orthogonal Fab, for example as described in Spiess C, Zhai Q, Carter P J. Alternative molecular formats and therapeutic applications for bispecific antibodies. Mol Immunol. 2015 October; 67(2 Pt A):95-106.

In appended IgG antibody formats, classical monospecific IgG is engineered by appending additional antigen-binding moieties to the N- and/or C-terminus of the heavy and/or light chain. Examples of such additional antigen-binding moieties include single domain antibodies (unpaired VH or VL), paired antibody variable domains, such as Fv or scFv, or engineered protein scaffolds. Appended IgG antibody formats include DVD-IgG, IgG(H)-scFv, scFv-(H)IgG, IgG(L)-scFv, scFv-(L)IgG, IgG(L,H)-Fv, IgG(H)-V, V(H)—IgG, IgG(L)-V, V(L)-IgG, KIH IgG-scFab, 2scFv-IgG, IgG-2scFv, scFv4-Ig, and Zybody, for example as described in Spiess C, Zhai Q, Carter P J. Alternative molecular formats and therapeutic applications for bispecific antibodies. Mol Immunol. 2015 October; 67(2 Pt A):95-106. DVI-IgG (four in one) is an appended IgG antibody format combined with a multispecific IgG antibody format, as described above. One potential advantage of appended multispecific IgG formats is that they can enable the simultaneous binding of antigen to all variable domains and hence provide a higher specific binding capacity.

Multispecific antibody fragments typically lack one or more constant domains in comparison to naturally occurring antibodies. Multispecific antibody fragments include nanobodies; nanobody-HAS; BiTEs; diabodies; DART; TandAb; scDiabodies; sc-Diabody-CH3; Diabody-CH3; Triple Bodies; Miniantibodies; Minibodies; TriBi minibodies; scFv-CH3 KIH; Fab-scFv; scFv-CH-CL-scFv; F(ab')2; F(ab')2-scFv2; scFv-KIH; Fab-scFv-Fc; Tetravalent HCAb; scDiabody-Fc; Diabody-Fc; Tandem scFv-Fc; and intrabodies, as described, for example, in Spiess C, Zhai Q, Carter P J. Alternative molecular formats and therapeutic applications for bispecific antibodies. Mol Immunol. 2015 October; 67(2 Pt A):95-106. Multispecific fusion proteins include Dock and Lock; ImmTAC; HSAbody; scDiabody-HAS; and Tandem scFv-Toxin, as described for example in Spiess C., Zhai Q. and Carter P. J. (2015) Molecular Immunology 67: 95-106, in particular FIG. 1 and corresponding description, e.g. p. 95-101. Multispecific antibody conjugates include IgG-IgG; Cov-X-Body; and scFv1-PEG-scFv2, as described for example in Spiess C., Zhai Q. and Carter P. J. (2015) Molecular Immunology 67: 95-106, in particular FIG. 1 and corresponding description, e.g. p. 95-101.

Typically, the antibody format is chosen depending on the envisaged application. For example, a long pharmacological half-life is desirable for many applications. It is commonly accomplished by including an Fc region—whereas for other applications a short half-life (and, thus, no Fc region) may be advantageous. Moreover, production yields may play a role, in particular since production of multispecific IgG antibody formats by co-expression of the two distinct light and heavy chains in a single host cell is known to be highly challenging and may result in mispaired antibodies, which may be difficult to remove. In addition, many antibody formats, such as appended IgG antibody formats, typically require linkers in order to provide sufficient flexibility for simultaneous binding of distinct antigens—but the flexible nature of linkers may make them more prone to proteolytic cleavage, potentially leading to poor antibody stability, aggregation and increased immunogenicity. Of note, for certain applications, antibody stability may be more important than binding capacity or vice versa, depending on the application. In addition, the antibody format may be chosen depending on the specificity, i.e. certain antigen binding sites achieve better production yields, stability and/or binding values in a certain antibody format—whereas other specificities achieve better characteristics in other antibody formats (e.g., due to the size/structure/nature of the targeted antigen).

Accordingly, there is a need for further antibody formats providing distinct characteristics. In view thereof, it is the object of the present invention to provide a novel antibody format with additional functionalities, for example multispecific antibodies or antibodies engineered to provide a further functionality, such as a reporter functionality, a translocation functionality, or a carrier functionality. The novel antibody format may optionally be combined with known antibody formats, for example to obtain antibodies with multiple binding sites or bispecific antibodies with additional functionalities. These objects are achieved by means of the subject-matter set out below and in the appended claims.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value×means x±10%.

As used herein, the terms "peptide", "polypeptide", "protein" refer to peptides, oligopeptides, or proteins including fusion proteins, respectively, comprising at least two amino acids joined to each other, preferably by a normal peptide bond, or, alternatively, by a modified peptide bond, such as for example in the cases of isosteric peptides. In particular, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. A peptide, polypeptide or protein may be composed of any of the 20 amino acids defined by the genetic code. Moreover, a peptide, polypeptide or protein may also comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

Preferably, however, a protein, polypeptide or peptide is a "classical" peptide, polypeptide or protein, whereby a "classical" peptide, polypeptide or protein is typically composed of amino acids selected from the 20 amino acids defined by the genetic code, linked to each other by a normal peptide bond.

The term "first polypeptide chain" as used herein refers to a polypeptide which is to be associated with a second polypeptide (the "second polypeptide chain"). In particular, the first and second polypeptide chains are associated through a disulfide bond. The first polypeptide chain may comprise one, two, three antibody heavy constant domains. In a preferred embodiment, it comprises three antibody heavy constant domains: CH1, CH2 and CH3, and a hinge region between CH1 and CH2. Said heavy chain constant domains may be derived from an antibody which is murine, chimeric, synthetic, humanized or human, and monoclonal or polyclonal. The first polypeptide chain may comprise one or more variable domains, preferably variable domains of an antibody heavy chain.

The term "second polypeptide chain" as used herein refers to a polypeptide which is to be associated with the first polypeptide (the "first polypeptide chain"). In particular, the first and second polypeptide chains are associated through a disulfide bond. The second polypeptide chain may comprise an antibody light chain constant region CL. Said light chain constant region may be derived from an antibody which is murine, chimeric, synthetic, humanized or human, and monoclonal or polyclonal. The second polypeptide chain may comprise one or more variable domains, preferably variable domains of an antibody light chain.

In general, an "antibody" is a protein that binds specifically to an antigen. Typically, an antibody comprises a unique structure that enables it to bind specifically to its corresponding antigen, but—in general—antibodies have a similar structure and are, in particular, also known as immunoglobulins (Ig). As used herein, the term "antibody" encompasses various forms of antibodies including, without being limited to, whole antibodies, antibody fragments, in particular antigen binding fragments, human antibodies, chimeric antibodies, humanized antibodies, recombinant antibodies and genetically engineered antibodies (variant or mutant antibodies) as long as the characteristic properties according to the invention are retained. Although the specification, including the claims, may, in some places, refer explicitly to antigen binding fragment(s), antibody fragment(s), variant(s) and/or derivative(s) of antibodies, it is understood that the term "antibody" includes all categories of antibodies, namely, antigen binding fragment(s), antibody fragment(s), variant(s) and derivative(s) of antibodies.

As used herein, the terms "antigen binding fragment," "fragment," and "antibody fragment" are used interchangeably to refer to any fragment of an antibody of the invention that retains (i) the antigen-binding activity of the antibody as well as (ii) the additional functionality provided by the (additional) functional domain, for example a binding activity provided by an (independent) binding site. In antigen binding fragments according to the present invention the characteristic properties according to the invention are retained. In general, examples of antibody fragments include, but are not limited to, a single chain antibody, Fab, Fab' or F(ab')$_2$. Fragments of the antibodies can be obtained from antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Further, the term "antibody" as used herein includes both antibodies and antigen binding fragments thereof.

The term "human antibody", as used herein, is intended to include antibodies having variable and constant regions derived from human immunoglobulin sequences. Human antibodies are well-known in the state of the art (van Dijk, M. A., and van de Winkel, J. G., *Curr. Opin. Chem. Biol.* 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., *Proc. Natl. Acad. Sci. USA* 90 (1993) 2551-2555; Jakobovits, A., et al., *Nature* 362 (1993) 255-258; Bruggemann, M., et al., *Year Immunol.* 7 (1993) 3340). Human antibodies can also be produced in phage display libraries (Hoogenboom, H. R., and Winter, G., *J. Mol. Biol.* 227 (1992) 381-388; Marks, J. D., et al., *J. Mol. Biol.* 222 (1991) 581-597). The techniques of Cole et al. and Boerner et al. are also available for the preparation of human monoclonal antibodies (Cole et al., *Monoclonal Antibodies and Cancer Therapy*, Alan R. Liss, p. 77 (1985); and Boerner, P., et al., *J. Immunol.* 147 (1991) 86-95). Preferably, human monoclonal antibodies are prepared by using improved EBV-B cell immortalization as described in Traggiai E, Becker S, Subbarao K, Kolesnikova L, Uematsu Y, Gismondo M R, Murphy B R, Rappuoli R, Lanzavecchia A. (2004): An efficient method to make human monoclonal antibodies from memory B cells: potent neutralization of SARS coronavirus. Nat Med. 10(8):871-5. The term "human antibody" as used herein also comprises such antibodies which are modified to generate the properties according to the invention as described herein.

Antibodies according to the present invention may be provided in purified form. Accordingly, the antibody according to the present invention, or the antigen binding fragment thereof, may be a purified antibody or antigen-binding fragment. Typically, the antibody will be present in a composition that is substantially free of other polypeptides e.g., where less than 90% (by weight), usually less than 60% and more usually less than 50% of the composition is made up of other polypeptides.

As used herein, the term "variable domain" (also referred to as "variable region"; variable domain of a light chain (V), variable domain of a heavy chain (VH)) refers to the domain of an antibody, or antigen-binding fragment thereof, which is the N-terminal domain in classical naturally occurring antibodies, typically the domain providing the highest variability in classical naturally occurring antibodies, and which is involved directly in the binding of the antibody to the antigen. Typically, the domains of variable human light and heavy chains have the same general structure and each domain comprises framework (FR) regions whose sequences are widely conserved (in particular four framework (FR) regions) and three "hypervariable regions" or complementarity determining regions, CDRs (in particular three "hypervariable regions"/CDRs). The framework regions typically adopt a β-sheet conformation and the CDRs may form loops connecting the β-sheet structure. The CDRs in each chain are usually held in their three-dimensional structure by the framework regions and form together with the CDRs from the other chain the antigen binding site.

As used herein, the term "hypervariable region" refers to the amino acid residues of an antibody which are responsible for antigen-binding. The hypervariable region comprises the "complementarity determining regions" or "CDRs". "Framework" or "FR" regions are those variable domain regions other than the hypervariable region residues as herein defined. CDR and FR regions may be determined according to the standard definition of Kabat et al., Sequences of Proteins of Immunological Interest, 5th ed., Public Health Service, National Institutes of Health, Bethesda, Md. (1991). Typically, in particular in native monospecific IgG antibodies, the three CDRs (CDR1, CDR2, and CDR3) are arranged non-consecutively in the variable domain. In other words, the CDRs on the heavy and/or light chain may be separated for example by framework regions, whereby a framework region (FR) is a region in the variable domain which is less "variable" than the CDR. For example, in an antibody a variable domain (or each variable domain, respectively) may preferably comprise four framework regions, separated by three CDRs. In particular, a variable domain of an antibody (light or heavy chain variable domain VH or VL) comprises from N- to C-terminus the domains FR1, CDR1, FR2, CDR2, FR3, CDR3, and FR4. CDRs on each chain are separated by such framework amino acids. Usually, the three CDRs of a heavy chain and the three CDRs of the connected light chain form together the antigen binding site (paratope). In other words, since in particular in native monospecific IgG antibodies, antigen binding sites are typically composed of two variable domains, there are six CDRs for each antigen binding site (heavy chain: CDRH1, CDRH2, and CDRH3; light chain: CDRL1, CDRL2, and CDRL3). A single antibody, in particular a single native monospecific IgG antibody, usually has two (identical) antigen binding sites and therefore contains twelve CDRs (i.e. 2× six CDRs).

Due to their "multispecificity", i.e. the different antigen binding sites, the heavy chain and/or the light chain of multispecific antibodies, or antigen binding fragments thereof, may (each) comprise more than three CDRs, in particular more than three different CDRs. For example, a multispecific antibody, or antigen binding fragments thereof, may comprise at least two different variable domains, wherein each of said at least two different variable domains is derived from a different monospecific antibody, e.g. of the IgG-type. Since such a monospecific antibody typically comprises three CDRs in the heavy chain and three CDRs in the light chain forming the antigen binding site, a multispecific antibody according to the present invention may in particular comprise three CDRs of a heavy chain of a first antibody and three CDRs of a light chain of a first antibody, three CDRs of a heavy chain of a second antibody and three CDRs of a light chain of a second antibody, optionally three CDRs of a heavy chain of a third antibody and three CDRs of a light chain of a third antibody etc. Thus, the number of CDRs comprised by a heavy chain and/or a light chain of a multispecific antibody is preferably a multiple of three, for example three, six, nine, twelve, etc. It is thereby also preferred that the sum of the CDRs comprised by both, heavy chain and light chain of a multispecific antibody is a multiple of six, for example six, twelve, eighteen etc. Since an "antigen binding site" is typically characterized by the CDRs, i.e. CDRH1, CDRH2, and CDRH3 as well as CDRL1, CDRL2, and CDRL3, it is preferred in the multispecific antibodies according to the present invention that the CDRs are arranged such, that the order (e.g. CDRH1, CDRH2, and CDRH3 and/or CDRL1. CDRL2, and CDRL3 derived from the same monospecific antibody) is maintained to preserve the antigen binding site, i.e. to preserve to ability to specifically bind to a certain site in the antigen. This means that for example the order of CDRH1, CDRH2, and CDRH3 derived from a first monospecific antibody in an amino acid stretch is preferably not interrupted by any CDR derived from a second monospecific antibody. Importantly, if the multipecific antibody comprises antigen binding sites derived from at least two different monospecific antibodies, the CDRs or variable domains of these monospecific antibodies are arranged in the multipecific antibody according to the present invention such that the "antigen receptor" of each monospecific antibody from which the CDRs (or variable regions) are derived, is preserved, i.e. its ability to specifically bind to a certain site in the antigen, is preserved.

In the context of the present invention, a variable domain may be any variable domain (in particular, VH and/or VL) of a naturally occurring antibody or a variable domain may be a modified/engineered variable domain. Modified/engineered variable domains are known in the art. Typically, variable domains are modified/engineered to delete or add one or more functions, e.g., by "germlining" somatic mutations ("removing" somatic mutations) or by humanizing.

As used herein, the term "constant domains" refers to domains of an antibody which are not involved directly in binding an antibody to an antigen, but exhibit various effector functions. Typically, a heavy chain comprises three or four constant domains, depending on the immunoglobulin class: CH1, CH2, CH3, and, optionally, CH4 (in N—C-terminal direction). Accordingly, the constant region of a heavy chain is typically formed (in N- to C-terminal direction) by: CH1—hinge (flexible polypeptide comprising the amino acids between the first and second constant domains of the heavy chain)—CH2-CH3 (-CH4). A light chain typically comprises only one single constant domain, referred to as CL, which typically also forms the constant region of the light chain. In the context of the present invention, a constant domain may be any constant domain (in particular, CL, CH1, CH2, CH3 and/or CH4) of a naturally occurring antibody or a constant domain may be a modified/engineered constant domain. Modified/engineered constant domains are known in the art. Typically, constant domains are modified/engineered to delete or add one or more functions, e.g., in the context of the functionality of the Fc region. Depending on the amino acid sequence of the constant region of their heavy chains, antibodies or immunoglobulins are divided in the classes: IgA, IgD, IgE, IgG and IgM, and several of these may be further divided into subclasses, e.g. IgG1, IgG2, IgG3, and IgG4, IgA1 and IgA2. The heavy chain constant regions that correspond to the different classes of immunoglobulins are called $\alpha$, $\epsilon$, $\gamma$, and $\mu$, respectively. The antibodies according to the invention are preferably of IgG type.

In general, antibodies can be of any isotype (e.g., IgA, IgG, IgM i.e. an $\alpha$, $\gamma$ or $\mu$ heavy chain), but will preferably be IgG. Within the IgG isotype, antibodies may be IgG1, IgG2, IgG3 or IgG4 subclass, whereby IgG1 is preferred. Antibodies may have a $\kappa$ or a $\lambda$ light chain.

As used herein, the term "recombinant antibody" is intended to include all antibodies, which do not occur in nature, for example antibodies expressed using a recombinant expression vector (e.g. providing one or more constant domains) transfected into a host cell.

As used herein, the term "multispecific" in the context of an antibody, or an antigen binding fragment thereof, refers to the ability of the antibody or the antigen binding fragment to bind to at least two different epitopes, e.g. on different antigens or on the same antigen. Thus, terms like "bispecific", trispecific", "tetraspecific" etc. refer to the number of different epitopes to which the antibody can bind to. For example, conventional monospecific IgG-type antibodies have two identical antigen binding sites (paratopes) and can, thus, only bind to identical epitopes (but not to different epitopes). A multispecific antibody, in contrast, has at least two different types of paratopes/binding sites and can, thus, bind to at least two different epitopes. As used herein, "paratope" refers to an antigen binding site of the antibody. Moreover, a single "specificity" may refer to one, two, three or more identical paratopes in a single antibody (the actual number of paratopes/binding sites in one single antibody molecule is referred to as "valency"). For example, a single native IgG antibody is monospecific and bivalent, since it has two identical paratopes. Accordingly, a multispecific antibody comprises at least two (distinct) paratopes/binding sites. Thus, the term "multispecific antibodies" refers to antibodies having more than one paratope and the ability to bind to two or more different epitopes. The term "multispecific antibodies" comprises in particular bispecific antibodies as defined above, but typically also protein, e.g. antibody, scaffolds, which bind in particular to three or more distinct epitopes, i.e. antibodies with three or more paratopes/binding sites.

In particular, the multispecific antibody, or the antigen binding fragment thereof, may comprise two or more paratopes/binding sites, wherein some paratopes/binding sites may be identical so that all paratopes/binding sites of the antibody belong to at least two different types of paratopes/binding sites and, hence, the antibody has at least two specificities. For example, the multispecific antibody or antigen binding fragment thereof may comprise four paratopes/binding sites, wherein each two paratopes/binding sites are identical (i.e. have the same specificity) and, thus, the antibody or fragment thereof is bispecific and tetravalent (two identical paratopes/binding sites for each of the two specificities). Thus, "one specificity" refers in particular to one or more paratopes/binding sites exhibiting the same specificity (which typically means that such one or more paratopes/binding sites are identical) and, thus, "two specificities" may be realized by two, three, four five, six or more paratopes/binding sites as long as they refer to only two specificities. Alternatively, a multispecific antibody may comprise one single paratope/binding site for each (of the at least two) specificity, i.e. the multispecific antibody comprises in total at least two paratopes/binding sites. For example, a bispecific antibody comprises one single paratope/binding site for each of the two specificities, i.e. the antibody comprises in total two paratopes/binding sites. It is also preferred that the antibody comprises two (identical) paratopes/binding sites for each of the two specificities, i.e. the antibody comprises in total four paratopes/binding sites. Preferably the antibody comprises three (identical) paratopes/binding sites for each of the two specificities, i.e. the antibody comprises in total six paratopes/binding sites.

As used herein, the term "antigen" refers to any structural substance which serves as a target for the receptors of an adaptive immune response, in particular as a target for antibodies, T cell receptors, and/or B cell receptors. An "epitope", also known as "antigenic determinant", is the part (or fragment) of an antigen that is recognized by the immune system, in particular by antibodies, T cell receptors, and/or B cell receptors. Thus, one antigen has at least one epitope, i.e. a single antigen has one or more epitopes. An antigen may be (i) a peptide, a polypeptide, or a protein, (ii) a polysaccharide, (iii) a lipid, (iv) a lipoprotein or a lipopeptide, (v) a glycolipid, (vi) a nucleic acid, or (vii) a small molecule drug or a toxin. Thus, an antigen may be a peptide, a protein, a polysaccharide, a lipid, a combination thereof including lipoproteins and glycolipids, a nucleic acid (e.g. DNA, siRNA, shRNA, antisense oligonucleotides, decoy DNA, plasmid), or a small molecule drug (e.g. cyclosporine A, paclitaxel, doxorubicin, methotrexate, 5-aminolevulinic acid), or any combination thereof. Preferably, the antigen is selected from (i) a peptide, a polypeptide, or a protein, (ii) a polysaccharide, (iii) a lipid, (iv) a lipoprotein or a lipopeptide and (v) a glycolipid; more preferably, the antigen is a peptide, a polypeptide, or a protein.

The term "antigen binding site" as used herein refers to the part of the antibody which comprises the area which specifically binds to and is complementary to part or all of an antigen. Where an antigen is large, an antibody may only bind to a particular part of the antigen, which part is termed "epitope". Typically, two variable domains, in particular a heavy chain variable domain VH and a light chain variable domain V, associate to form one an antigen binding site. In particular, the antigen binding site is formed by the three CDRs of the heavy chain variable domain and by the three CDRs of the light chain variable domain together, i.e. by six CDRs, as described above.

The term "specifically binding" and similar reference does not encompass non-specific sticking.

The term "linker" (also referred to as "spacer"), as used herein, refers to a peptide adapted to connect distinct domains of a polypeptide or protein, such as an antibody or an antigen-binding fragment thereof. Linkers are known in the art and described in detail, e.g. in Reddy Chichili V P, Kumar V, Sivaraman J. Linkers in the structural biology of protein-protein interactions. Protein Science: A Publication of the Protein Society. 2013; 22(2):153-167). Typically, linkers are designed such that they do not affect functionality. In particular, a linker does not specifically bind to a target. A linker may contain any amino acids, the amino acids glycine (G) and serine (5) may be preferred. Preferably, the linker is composed of the amino acids glycine (G) and serine (S) ("GS-linker"). If two or more linkers occur in one polypeptide or protein, the linkers may be equal or differ from each other. Furthermore, the linker may have a length of 1, 2, 3, 4, 5, 6, 7, 8, 9, 10, 11, 12, 13, 14, 15, 16, 17, 18, 19 or 20 amino acids.

As used herein, the term "nucleic acid or nucleic acid molecule" is intended to include DNA molecules and RNA molecules. A nucleic acid molecule may be single-stranded or double-stranded.

As used herein, the terms "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

As used herein, "sequence variant" (also referred to as "variant") refers to any alteration in a reference sequence, whereby a reference sequence is any of the sequences listed in the "Tables of Sequences and SEQ ID Numbers" (sequence listing), i.e. SEQ ID NO: 1 to SEQ ID NO: 133. Thus, the term "sequence variant" includes nucleotide sequence variants and amino acid sequence variants. Of note, the sequence variants referred to herein are in particular functional sequence variants, i.e. sequence variants maintaining the biological function of, for example, the antibody. Preferred maintained biological functions in the context of the present invention include (i) the binding of the antibody to its antigens and (ii) the function provided by the (additional) functional domain, for example, the binding of an (independent) binding site to its target. Preferred sequence variants are thus functional sequence variants having at least 70%, at least 75%, at least 80%, at least 85%, at least 88%, at least 90%, at least 92%, at least 95%, at least 96%, at least 97%, at least 98% or at least 99% sequence identity to a reference sequence. The phrase "functional sequence variant thereof having at least 70%, at least 75%, at least 80%, at least 85%, at least 88%, at least 90%, at least 92%, at least 95%, at least 96%, at least 97%, at least 98% or at least 99% sequence identity", as used herein, means (i) that the sequence variant is functional as described herein and (ii) the higher the % sequence identity, the more preferred the sequence variant. In other words, the phrase "functional sequence variant thereof having at least 70%, at least 75%, at least 80%, at least 85%, at least 88%, at least 90%, at least 92%, at least 95%, at least 96% at least 97% at least 98% or at least 99% sequence identity" means in particular that the functional sequence variant has at least 70% sequence identity, preferably at least 75% sequence identity, preferably at least 80% sequence identity, more preferably at least 85% sequence identity, more preferably at least 88% sequence identity, even more preferably at least 90%/sequence identity, even more preferably at least 92% sequence identity, still more preferably at least 95% sequence identity, still more preferably at least 96% sequence identity, particularly preferably at least 97% sequence identity, particularly preferably at least 98% sequence identity and most preferably at least 99% sequence identity to the respective reference sequence.

The term "sequence variant" includes in particular such variants that comprise mutations and/or substitutions in comparison to the reference sequence. Exemplary variants of an Fc moiety sequence include, but are not limited to, those that have an L to A substitution at position CH2 4, CH2 5, or both.

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information) [Blosum 62 matrix; gap open penalty=11 and gap extension penalty=1].

As used herein, a "nucleotide sequence variant" has an altered sequence in which one or more of the nucleotides in the reference sequence is deleted, or substituted, or one or more nucleotides are inserted into the sequence of the reference nucleotide sequence. Nucleotides are referred to herein by the standard one-letter designation (A, C, G, or T). Due to the degeneracy of the genetic code, a "nucleotide sequence variant" can either result in a change in the respective reference amino acid sequence, i.e. in an "amino acid sequence variant" or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 80%, preferably at least 90%, more preferably at least 95% sequence identical to the reference sequence.

An "amino acid sequence variant" has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 80% identical to the reference sequence, preferably, at least 90% identical, more preferably at least 95% identical, most preferably at least 99% identical to the reference sequence. Variant sequences which are at least 90% identical have no more than 10 alterations, i.e. any combination of deletions, insertions or substitutions, per 100 amino acids of the reference sequence.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydoxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the alterations in the sequence variants do not abolish the functionality of the respective reference sequence, in the present case, e.g., the functionality of a sequence of an antibody, or antigen binding fragment thereof, to bind to its antigens and/or the additional functionality provided by the functional domain, for example to bind to a target of an (independent) binding site. Guidance in determining which nucleotides and amino acid residues, respectively, may be substituted, inserted or deleted without abolishing such functionality are found by using computer programs well known in the art.

As used herein, a nucleic acid sequence or an amino acid sequence "derived from" a designated nucleic acid, peptide, polypeptide or protein refers to the origin of the nucleic acid, peptide, polypeptide or protein. Preferably, the nucleic acid sequence or amino acid sequence which is derived from a particular sequence has an amino acid sequence that is essentially identical to that sequence or a portion thereof, from which it is derived, whereby "essentially identical" includes sequence variants as defined above. Preferably, the nucleic acid sequence or amino acid sequence which is derived from a particular peptide or protein, is derived from the corresponding domain in the particular peptide or protein. Thereby, "corresponding" refers in particular to the same functionality. For example, an "extracellular domain" corresponds to another "extracellular domain" (of another protein), or a "transmembrane domain" corresponds to another "transmembrane domain" (of another protein). "Corresponding" parts of peptides, proteins and nucleic acids are thus easily identifiable to one of ordinary skill in the art. Likewise, sequences "derived from" other sequence are usually easily identifiable to one of ordinary skill in the art as having its origin in the sequence.

Preferably, a nucleic acid sequence or an amino acid sequence derived from another nucleic acid, peptide, polypeptide or protein may be identical to the starting nucleic acid, peptide, polypeptide or protein (from which it is derived). However, a nucleic acid sequence or an amino acid sequence derived from another nucleic acid, peptide, polypeptide or protein may also have one or more mutations relative to the starting nucleic acid, peptide, polypeptide or protein (from which it is derived), in particular a nucleic acid sequence or an amino acid sequence derived from another nucleic acid, peptide, polypeptide or protein may be a functional sequence variant as described above of the starting nucleic acid, peptide, polypeptide or protein (from which it is derived). For example, in a peptide/protein one or more amino acid residues may be substituted with other amino acid residues or one or more amino acid residues may be inserted or deleted.

As used herein, the term "mutation" relates to a change in the nucleic acid sequence and/or in the amino acid sequence in comparison to a reference sequence, e.g. a corresponding genomic sequence. A mutation, e.g. in comparison to a genomic sequence, may be, for example, a (naturally occurring) somatic mutation, a spontaneous mutation, an induced mutation, e.g. induced by enzymes, chemicals or radiation, or a mutation obtained by site-directed mutagenesis (molecular biology methods for making specific and intentional changes in the nucleic acid sequence and/or in the amino acid sequence). Thus, the terms "mutation" or "mutating" shall be understood to also include physically making a mutation, e.g. in a nucleic acid sequence or in an amino acid sequence. A mutation includes substitution, deletion and insertion of one or more nucleotides or amino acids as well as inversion of several (two or more) successive nucleotides or amino acids. To achieve a mutation in an amino acid sequence, preferably a mutation may be introduced into the nucleotide sequence encoding said amino acid sequence in order to express a (recombinant) mutated polypeptide. A mutation may be achieved e.g., by altering, e.g., by site-directed mutagenesis, a codon of a nucleic acid molecule encoding one amino acid to result in a codon encoding a different amino acid, or by synthesizing a sequence variant, e.g., by knowing the nucleotide sequence of a nucleic acid molecule encoding a polypeptide and by designing the synthesis of a nucleic acid molecule comprising a nucleotide sequence encoding a variant of the polypeptide without the need for mutating one or more nucleotides of a nucleic acid molecule.

The term "disease" as used in the context of the present invention is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Antibodies and Antigen Binding Fragments with Functional Domains in Elbow

In a first aspect the present invention provides an antibody, or an antigen binding fragment thereof, comprising a first polypeptide chain and a second polypeptide chain, wherein said first polypeptide chain comprises in N- to C-terminal direction
  (i) one or more variable domains;
  (ii) a (additional) functional domain; and
  (iii) one or more constant domains; and wherein said second polypeptide chain comprises in N- to C-terminal direction
  (iv) one or more variable domains forming antigen binding sites with the one or more variable domains (i) of the first polypeptide chain;
  (v) optionally, a (additional) functional domain; and
  (vi) one or more constant domains,
characterized in that said (additional) functional domain (ii) of the first polypeptide chain does not comprise a fragment of the second polypeptide chain and said optional (additional) functional domain (v) of the second polypeptide chain does not comprise a fragment of the first polypeptide chain.

The present invention is based on the surprising finding, that an (additional) functional domain can be inserted into the elbow region of an antibody, i.e. between the variable domain and the most N-terminal constant domain, in particular CH1 or CL. FIG. 1A shows a classical naturally occurring antibody with elbow region indicated by arrows. The present inventors have surprisingly found that antibodies engineered in the elbow region to contain such an additional functional domain can, for example, simultaneously bind (1) to the antigen targeted by their variable domains and (2) to an additional target targeted by a binding site introduced into the antibody's elbow region—as shown by the Examples described herein. In contrast to prior art multispecific antibody formats, in which the additional binding sites are obtained either by replacing a heavy/light chain pair with another heavy/light chain pair with distinct specificity (as in multispecific IgG antibody formats described above, which are often monovalent for each specificity) or by appending additional binding sites to the N- or C-termini of the heavy or light chains (as in appended IgG antibody formats described above), in the antibodies of the present invention the additional functional domain, e.g. the additional binding site (specificity) is inserted into the heavy and/or light chain, namely, into the elbow region. Surprisingly, the variable domain (e.g., VH)N-terminal of the inserted functional domain, such as a binding site, still forms a fully functional antigen binding site with the corresponding variable domain of the other polypeptide chain (e.g., VL)—even if the other polypeptide chain is unmodified in the elbow. The same applies for multispecific antibodies: despite the inserted functional domain, the variable domain(s)N-terminal of the inserted functional domain still associate with the corresponding variable domains in the other polypeptide chain to form functional antigen binding sites (e.g., VH1-VH2 on one polypeptide chain with VL1-VL2 on the other polypeptide chain, etc.).

Accordingly, the antibodies, and antigen binding fragments thereof, according to the present invention are referred to as "in-Elbow-Insert" Ig molecules ("IEI-Ig"). The significance of the present inventors' findings is reflected by the fact, that it gives rise to a variety of new antibody formats, as exemplified in FIG. 1. IEI-Ig antibodies, and antigen binding fragments thereof, according to the present invention can be either based on classical naturally occurring antibodies, as exemplified in FIG. 1B, or they may be combined with other (multispecific) antibody formats to obtain new antibody formats with even more specificities, as exemplified in FIG. 1C.

For example, to obtain an antibody according to the present invention, a classical monospecific antibody, preferably a human monoclonal antibody, may serve as "scaffold" antibody and an additional functional domain, such as a binding site, is inserted into the elbow region (i.e., between the variable and the most N-terminal constant domain, in particular C-terminal of the variable domain and N-terminal of CH1 and/or CL, respectively) of the heavy chain and/or the light chain of the scaffold antibody. In other examples, fragments of a classical monospecific antibody, preferably fragments of a human monoclonal antibody, which comprise (i) at least two polypeptide chains, such as a heavy and a light chain, and (ii) in each polypeptide chain at least a variable domain and a constant domain, may serve as "scaffold antibody", and a functional domain, such as a binding site, is inserted into the elbow region of the first and/or the second polypeptide chain of the scaffold antibody fragment. Preferred examples of such antibody fragments, which may be used as scaffold to obtain an antibody according to the present invention by insertion of a functional domain, such as a binding site, into the elbow region, include Fab, Fab', and F(ab')$_2$. Moreover, any recombinant antibody or fragment thereof, such as a multispecific, in particular a bispecfic, antibody or fragment thereof, which comprises (i) at least two polypeptide chains, such as a heavy and a light chain, and (ii) in each polypeptide chain at least a variable domain and a constant domain, may also serve as "scaffold" antibody, and a functional domain, such as a binding site, is inserted into the elbow region of the first and/or the second polypeptide chain of the recombinant scaffold antibody (fragment).

Preferred examples of antibodies, which may serve as scaffold antibodies include antibodies GCE536 (VH: SEQ ID NO: 1, VL: SEQ ID NO: 2, heavy chain constant region: SEQ ID NO: 3, light chain constant region: SEQ ID NO: 4; Piccoli, L., et al. Neutralization and clearance of GM-CSF by autoantibodies in pulmonary alveolar proteinosis. Nature communications 6, 7375 (2015)); "C1" (see Example 1; VH: SEQ ID NO: 5, VL: SEQ ID NO: 6, heavy chain constant region: SEQ ID NO: 3, light chain constant region: SEQ ID NO: 7); "Cb" (VH: SEQ ID NO: 8, VL: SEQ ID NO: 9, heavy chain constant region: SEQ ID NO: 3, light chain constant region: SEQ ID NO: 4) and F1174 (VH: SEQ ID NO: 10, VL: SEQ ID NO: 11, heavy chain constant region: SEQ ID NO: 3, light chain constant region: SEQ ID NO: 4; Pappas, L., et al. Rapid development of broadly influenza neutralizing antibodies through redundant mutations. Nature 516, 418-422 (2014)).

The antibody according to the present invention or the antigen-binding fragment thereof, may also be obtained by cloning techniques, e.g. by commercially available IgG-vectors or vector sets, which comprise constant domains/regions, e.g. of the heavy and/or light chain. For example, the corresponding variable domains, such as a heavy and a light chain variable domain VH and VL, of a first antibody may be cloned into the respective polypeptide chains as provided by the vector; and, additionally, the additional functional domain may be cloned into the first and/or second polypeptide chain, such that it is located between the (most C-terminal) variable domain and the (most N-terminal) constant domain, i.e. in the elbow region.

The first and/or the second polypeptide chain of the antibody, or the antigen binding fragment thereof, according to the present invention comprises an (additional) functional domain. In particular, the "functional domain" is a peptide or polypeptide, which is linked to the adjacent domains of the polypeptide chain of the antibody or antigen binding fragment by a (usual) peptide bond. In particular, the N-terminus of the (additional) functional domain is linked to the C-terminus of the (most C-terminal) variable domain and the C-terminus of the (additional) functional domain is linked to the N-terminus of the (most N-terminal) constant domain by a peptide bond.

In general, the term "functional domain" refers to a functional unit, e.g. of the antibody or the antigen binding fragment. Typically, a functional domain provides the protein, e.g. the antibody or the antigen binding fragment, with an (additional) functionality. Accordingly, the (additional) functional domain usually contains all amino acids/sequences required to provide the (additional) function. In particular, the (additional) functional domain (ii) of the first polypeptide chain does not comprise a fragment of the second polypeptide chain and the optional (additional) functional domain (v) of the second polypeptide chain does not comprise a fragment of the first polypeptide chain. In other words, the second polypeptide chain (in particular any fragment, such as even a single amino acid, thereof) is neither required for nor involved in the (functionality of the) (additional) functional domain of the first polypeptide chain. Moreover, if the second polypeptide chain also comprises an (additional) functional domain, the first polypeptide chain (in particular any fragment, such as even a single amino acid, thereof) is neither required for nor involved in the (functionality of the) (additional) functional domain of the second polypeptide chain. Rather all amino acids (amino acid sequences) required for or involved in the functionality of the (additional) functional domain of the first and/or second polypeptide chain are contained in the (additional) functional domain of that polypeptide chain itself—no fragments or amino acids of the other polypeptide chain are required/involved. Accordingly, the (additional) functional domain differs, for example, from an antigen binding site formed by the variable domain of the first polypeptide chain together with the variable domain of the second polypeptide chain. In other words, the (additional) functional domain differs, for example, from an antigen binding site formed by variable domains of two different polypeptide chains (however, the (additional) functional domain may still comprise an antigen binding site—if the involved variable domains are located on a single polypeptide chain, as described in more detail below).

Particularly preferably, the (additional) functional domain of the first and/or the second polypeptide chain comprises or consists of an Ig-like domain; for example an Ig-like domain of a protein or (poly)peptide, e.g., as exemplified below. The basic structure of immunoglobulin (Ig) molecules is a tetramer of two light chains and two heavy chains linked by disulphide bonds. There are two types of light chains: kappa and lambda, each composed of a constant domain (CL) and a variable domain (VL). There are five types of heavy chains: alpha, delta, epsilon, gamma and mu, all consisting of a variable domain (VH) and three (in alpha, delta and gamma) or four (in epsilon and mu) constant domains (CH1 to CH4). Ig molecules are highly modular proteins, in which the variable and constant domains have clear, conserved sequence patterns. The domains in Ig and Ig-like molecules are grouped into four types: V-set (variable), C1-set (constant-1), C2-set (constant-2) and I-set (intermediate). Structural studies have shown that these domains share a common core Greek-key beta-sandwich structure, with the types differing in the number of strands in the beta-sheets as well as in their sequence patterns. Immunoglobulin-like domains that are related in both sequence and structure can be found in several diverse protein families. Ig-like domains are involved in a variety of functions, including cell-cell recognition, cell-surface receptors, muscle structure and the immune system.

Preferred examples of Ig-like domains include the Ig-like domains of any one or the following proteins or (poly) peptides: AlBG (alpha-1-B glycoprotein), ACAM, ADAMTSL (ADAMTS like 1), ADAMTSL3 (ADAMTS like 3), AGER (advanced glycosylation end-product specific receptor), ALCAM (activated leukocyte cell adhesion molecule), ALPK3 (alpha kinase 3), AMIGO1 (adhesion molecule with Ig like domain 1), AMIGO2 (adhesion molecule with Ig like domain 2), AMIGO3 (adhesion molecule with Ig like domain 3), AXL (AXL receptor tyrosine kinase), BCAM (basal cell adhesion molecule (Lutheran blood group)), BOC (BOC cell adhesion associated, oncogene regulated), BSG (basigin (Ok blood group)), BTLA (B and T lymphocyte associated), C10orf72, C20orf102, CADM1 (cell adhesion molecule 1), CADM3 (cell adhesion molecule 3), CADM4 (cell adhesion molecule 4), CCDC141 (coiled-coil domain containing 141), CD2, CD3, CD4, CD8, CD19, CD22, CD33, CD47, CD48, CD80, CD84, CD86, CD96, CD101, CD160, CD200, CD244, CD276, CDON (cell adhesion associated, oncogene regulated), CEACAMI (carcinoembryonic antigen related cell adhesion molecule 1), CEACAMS (carcinoembryonic antigen related cell adhesion molecule 5), CEACAM6 (carcinoembryonic antigen related cell adhesion molecule 6), CEACAM7 (carcinoembryonic antigen related cell adhesion molecule 7), CEACAM8 (carcinoembryonic antigen related cell adhesion molecule 8), CEACAMI6 (carcinoembryonic antigen related cell adhesion molecule 16), CEACAM18 (carcinoembryonic antigen related cell adhesion molecule 18), CEACAM20 (carcinoembryonic antigen related cell adhesion molecule 20), CEACAM21 (carcinoembryonic antigen related cell adhesion molecule 21), CHL (cell adhesion molecule L1 like), CILP (cartilage intermediate layer protein), CILP2 (cartilage intermediate layer protein 2), CLMP (CXADR like membrane protein), CNTFR (ciliary neurotrophic factor receptor), CNTN1 (contactin 1), CNTN2 (contactin 2), CNTN3 (contactin 3, CNTN4 (contactin 4), CNTN5 (contactin 5), CNTN6 (contactin 6), CSF1R (colony stimulating factor 1 receptor), CXADR (CXADR, Ig-like cell adhesion molecule), DSCAM (DS cell adhesion molecule), DSCAML1 (DS cell adhesion molecule like 1), EMB (embigin), ESAM (endothelial cell adhesion molecule), F11R (F11 receptor), FAIM3, FCMR (Fc fragment of IgM receptor), HMCN1 (hemicentin 1), HMCN2 (hemicentin 2), FCAR (Fc fragment of IgA receptor), FCER1A (Fc fragment of IgE receptor Ia), FCGR1A (Fc fragment of IgG receptor Ia), FCGR1B (Fc fragment of IgG receptor Ib), FCGR1CP (Fc fragment of IgG receptor Ic, pseudogene), FCGR2A (Fc fragment of IgG receptor IIa), FCGR2B (Fc fragment of IgG receptor IIb), FCGR2C (Fc fragment of IgG receptor IIc), FCGR3A (Fc fragment of IIG receptor IIIa), FCGR3B (Fc fragment of IgG receptor IIIb), FCRH1, FCRH3, FCRH4, FCRL1 (Fc receptor like 1), FCRL2 (Fc receptor like 2), FCRL3 (Fc receptor like 3), FCRL4 (Fc receptor like 4), FCRL5 (Fc receptor like 5), FCRL6 (Fc receptor like 6), FCRLA (Fc receptor like A), FCRLB (Fc receptor like B), FGFR1, FGFR2, FGFR3, FGFR4, FGFRL, FLT1 (fms related tyrosine kinase 1), FLT3 (fms related tyrosine kinase 3), FLT4 (fms related tyrosine kinase 4), FSTL4 (follistatin like 4), FSTL5 (follistatin like 5), GP6 (glycoprotein VI platelet), GPA33 (glycoprotein A33, GPR116, GPR125, ADGRF5 (adhesion G protein-coupled receptor F5), ADGRA2 (adhesion G protein-coupled receptor A2), hEMMPRIN, HEPACAM (hepatic and glial cell adhesion molecule), HEPACAM2 (HEPACAM family member 2), HLA-DMA, HLA-DMB, HLA-DQB, HLA-DQB1, HNT, HSPG2 (heparan sulfate proteoglycan 2), HYST2477, ICAM1 (intercellular adhesion molecule 1), ICAM2 (intercellular adhesion molecule 2), ICAM3 (intercellular adhesion molecule 3), ICAM4 (intercellular adhesion molecule 4 (Landsteiner-Wiener blood group)), ICAM5 (intercellular adhesion molecule 5), DCC (DCC netrin 1 receptor), NEO1 (neogenin 1), IGHA1, IGHD, IGHE, IGDCC4 (immunoglobulin superfamily DCC subclass member 4), IGLON5 (IgLON family member 5), IGSF1 (immunoglobulin superfamily member 1), IGSF2 (immunoglobulin superfamily member 2), IGSF3 (immunoglobulin superfamily member 3), IGSF5 (immunoglobulin superfamily member 5), IGSF9 (immunoglobulin superfamily member 9), IGSF9B (immunoglobulin superfamily member 9B), IGSF10 (immunoglobulin superfamily member 10), IGSF11 (immunoglobulin superfamily member 11), IGSF21 (immunoglobin superfamily member 21), IGSF23 (immunoglobulin superfamily member 23), IL1R1 (interleukin 1 receptor type 1), IL1R2 (interleukin 1 receptor type 2), IL1RAP (interleukin 1 receptor accessory protein), ILIRAPL1 (interleukin 1 receptor accessory protein like 1), ILIRAPL2 (interleukin 1 receptor accessory protein like 2), IL1RL1 (interleukin 1 receptor like 1), IL1RL2 (interleukin 1 receptor like 2), IL6R (interleukin 6 receptor), IL11RA (interleukin 11 receptor subunit alpha), IL12B (interleukin 12B), IL18BP (interleukin 18 binding protein), IL18R1 (interleukin 18 receptor 1), IL18RAP (interleukin 18 receptor accessory protein), ISLR2 (immunoglobulin superfamily containing leucine rich repeat 2), JAM2 (junctional adhesion molecule 2), JAM3 (junctional adhesion molecule 3), KDR (kinase insert domain receptor), KIR-123FM, KIR2DL1 (killer cell immunoglobulin like receptor, two Ig domains and long cytoplasmic tail 1), KIR2DL2 (killer cell immunoglobulin like receptor, two Ig domains and long cytoplasmic tail 2), KIR2DL3 (killer cell immunoglobulin like receptor, two Ig domains and long cytoplasrnic tail 3), KIR2DL4 (killer cell immunoglobulin like receptor, two Ig domains and long cytoplasmic tail 4), KIR2DL5A (killer cell immunoglobulin like receptor, two Ig domains and long cytoplasmic tail 5A), KIR2DL5B (killer cell immunoglobulin like receptor, two Ig domains and long cytoplasmic tail 58), KIR2DLX, KIR2DS1 (killer cell immunoglobulin like receptor, two Ig domains and short cytoplasmic tail 1), KIR2DS2 (killer cell immunoglobulin like receptor, two Ig domains and short cytoplasmic tail 2), KIR2DS3 (killer cell immunoglobulin like receptor, two Ig domains and short cytoplasmic tail 3), KIR2DS4 (killer cell immunoglobulin like receptor, two Ig domains and short cytoplasmic tail 4), KIR2DS5 (killer cell immunoglobulin like receptor, two Ig domains and short cytoplasmic tail 5), kir3d, KIR3DL1 (killer cell immunoglobulin like receptor, three Ig domains and long cytoplasmic tail 1), KIR3DL2 (killer cell immunoglobulin like receptor, three Ig domains and long cytoplasmic tail 2), KIR3DL3 (killer cell immunoglobulin like receptor, three Ig domains and long cytoplasmic tail 3), KIR3DP1 (killer cell immunoglobulin like receptor, three Ig domains pseudogene 1, KIR3DS1 (killer cell immunoglobulin like receptor, three Ig domains and short cytoplasmic tail 1), KIR3DX1 (killer cell immunoglobulin like receptor, three Ig domains X1), KIRREL1 (kirre like nephrin family adhesion molecule 1), KIRREL2 (kirre like nephrin family adhesion molecule 2), KIRREL3 (kirre like nephrin family adhesion molecule 3), KIT (KIT proto-oncogene receptor tyrosine kinase), L1CAM, LAG3 (lymphocyte activating 3), LAIR1 (leukocyte associated immunoglobulin like receptor 1), LAIR2 (leukocyte associated immunoglobulin like receptor 2), LEPR (leptin receptor), LILRA1 (leukocyte immunoglobulin like receptor A1), LILRA2 (leukocyte immunoglobulin like receptor A2), LILRA3 (leukocyte immunoglobulin like receptor A3, LILRA4 (leukocyte immunoglobulin like receptor A4), LILRA5 (leukocyte immunoglobulin like receptor A5), LILRA6 (leukocyte immunoglobulin like receptor A6), LILRB1 (leukocyte immunoglobulin like receptor 81), LILRB2 (leukocyte immunoglobulin like receptor B2), LILRB3 (leukocyte immunoglobulin like receptor B3), LILRB4 (leukocyte immunoglobulin like receptor 84), LILRB5 (leukocyte immunoglobulin like receptor 65), LILRP2, LRIG1, LRIG2, LRIG3, LRITI, LRRC4, LSAMP, LSR (lipolysis stimulated lipoprotein receptor), LY9 (lymphocyte antigen 9), MADCAM1 (mucosal vascular addressin cell adhesion molecule 1), MAG (myelin associated glycoprotein), MALT1 (MALT1 paracaspase), MCAM (melanoma cell adhesion molecule), MDGA1 (MAM domain containing glycosylphosphatidylinositol anchor 1), MDGA2 (MAM domain containing glycosylphosphatidylinositol anchor 2), MERTK (MER proto-oncogene, tyrosine kinase), MFAP3, MIR, MILR1 (mast cell immunoglobulin like receptor 1), MMP23A (matrix metallopeptidase 23A (pseudogene)), MMP23B (matrix metallopeptidase 23B), MUSK (muscle associated receptor tyrosine kinase), MXRA5 (matrix remodeling associated 5), MYBPC3, MYOM1 (myomesin 1), MYOM2 (myomesin 2), MYOM3 (myomesin 3), NCA, NCAM1, NCAM2, NCR1 (natural cytotoxicity triggering receptor 1), NEGR1, NEO1, NFASC, NOPE, NPHS1 (NPHS1, nephrin), NPTN (neuroplastin), NRCAM (neuronal cell adhesion molecule), NTRK1 (neurotrophic receptor tyrosine kinase 1), NRG1, NT, NTRK3, OBSCN, OBSL1 (obscurin like 1), OPCML, OSCAR (osteoclast associated, immunoglobulin-like receptor), PAPLN, PDCD1LG2 (programmed cell death 1 ligand 2), PDGFRA (platelet derived growth factor receptor alpha), PDGFRB (platelet derived growth factor receptor beta), PDGFRL (platelet derived growth factor receptor like), PECAMI (platelet and endothelial cell adhesion molecule 1), PRODH2, PSG1 (pregnancy specific beta-1-glycoprotein 1), PSG2 (pregnancy specific beta-1-glycoprotein 2), PSG3 (pregnancy specific beta-1-glycoprotein 3), PSG4 (pregnancy specific beta-1-glycoprotein 4), PSG5 (pregnancy specific beta-1-glycoprotein 5), PSG6 (pregnancy specific beta-1-glycoprotein 6), PSG7 (pregnancy specific beta-1-glycoprotein 7 (gene/pseudogene)), PSG8 (pregnancy specific beta-1-glycoprotein 8), PSG9 (pregnancy specific beta-1-glycoprotein 9), PSG10 (pregnancy specific beta-1-glycoprotein 10), PSG11 (pregnancy specific beta-1-glycoprotein 11), PSG11s' (pregnancy specific beta-1-glycoprotein 11s'), PTGFRN (prostaglandin F2 receptor inhibitor), PTK7 (protein tyrosine kinase 7 (inactive)), PTPRD (protein tyrosine phosphatase, receptor type D), PTPRK (protein tyrosine phosphatase, receptor type K), PTPRM (protein tyrosine phosphatase, receptor type M), PTPRS protein tyrosine phosphatase, receptor type S), PTPRT (protein tyrosine phosphatase, receptor type T), PTPsigma, PUNC, PVR (poliovirus receptor), PVRL1, PVRL2, PVRL4, NECTIN1 (nectin cell adhesion molecule 1), NECTIN2 (nectin cell adhesion molecule 2), NECTIN3 (nectin cell adhesion molecule 3), RAGE, ROBO3 (roundabout guidance receptor 3), SCN1B (sodium voltage-gated channel beta subunit 1), SDK1 (sidekick cell adhesion molecule 1), SDK2 (sidekick cell adhesion molecule 2), SEMA3A (semaphorin 3A), SEMA3B (semaphorin 3B), SEMA3E (semaphorin 3E), SEMA3F (semaphorin 3F), SEMA3G (semaphorin 3G), SEMA4C (semaphorin 4C), SEMA4D (semaphorin 4D), SEMA4G (semaphorin 4G), SEMA7A 8semaphorin 7A (John Milton Hagen blood group)), SIGIRR (single Ig and TIR domain containing), SIGLECi (sialic acid binding Ig like lectin 1), SIGLEC5 (sialic acid binding Ig like lectin 5), SIGLEC6 (sialic acid binding Ig like lectin 6), SIGLEC7 (sialic acid binding Ig like lectin 7), SIGLEC8 (sialic acid binding Ig like lectin 8), SIGLEC9 (sialic acid binding Ig like lectin 9), SIGLEC10 (sialic acid binding Ig like lectin 10), SIGLEC11 (sialic acid binding Ig like lectin 11), SIGLEC12 (sialic acid binding Ig like lectin 12 (gene/pseudogene)), SIGLEC14 (sialic acid binding Ig like lectin 14), SIGLEC15 (sialic acid binding Ig like lectin 15), SLAMF1 (signaling lymphocytic activation molecule family member 1), SLAMF6 (SLAM family member 6), SLAMF8 (SLAM family member 8), SIRPG; TARM1 (T-cell-interacting, activating receptor on myeloid cells 1), TEK (TEK receptor tyrosine kinase), THY1 Thy-1 cell surface antigen), TIE1 (tyrosine kinase with immunoglobulin like and EGF like domains 1), TMEM81 (transmembrane protein 81), TMIGD1 (transmembrane and immunoglobulin domain containing 1), TMIGD2 (transmembrane and immunoglobulin domain containing 2), TTN (titin), TYRO3 (TYRO3 protein tyrosine kinase), UNC5D, VCAM1 (vascular cell adhesion molecule 1), VSIG1 (V-set and immunoglobulin domain containing 1), VSIG2 (V-set and immunoglobulin domain containing 2), VSIG4 (V-set and immunoglobulin domain containing 4), VSIG10 (V-set and immunoglobulin domain containing 10), VSIG10L (V-set and immunoglobulin domain containing 10 like), VSTM1 (V-set and transmembrane domain containing 1), VTCN1 (V-set domain containing T-cell activation inhibitor 1), ZPBP (zona pellucida binding protein), or ZPBP2 (zona pellucida binding protein 2).

More preferably, the Ig-like domain is an Ig-like domain of any one of the following proteins: CD2, CD3, CD4, CD8, CD19, CD22, CD33, CD80, CD86, in particular of CD4.

Further preferred examples of Ig-like domains are described herein below.

It is also preferred that the (additional) functional domain of the first and/or the second polypeptide chain comprises or consists of an extra- and/or intracellular domain of a (known) protein. Moreover, the (additional) functional domain of the first and/or the second polypeptide chain may preferably comprise or consist of a domain of a (known) soluble globular protein. More preferably, the (additional) functional domain of the first and/or the second polypeptide chain comprises or consists of an extracellular domain of a (known) protein or a domain of a (known) soluble globular protein.

Preferably, the (additional) functional domain of the first and/or the second polypeptide chain has a length of up to 1000 amino acids, more preferably of up to 750 amino acids, even more preferably of up to 500 amino acids, still more preferably of up to 400 amino acids, particularly preferably of up to 300 amino acids and most preferably of up to 275 or 250 amino acids. Moreover, it is preferred that the (additional) functional domain of the first and/or the second polypeptide chain has a length of 5 to 1000 amino acids, more preferably of 10 to 750 amino acids, even more preferably of 20 to 500 amino acids, still more preferably of 50 to 400 amino acids, particularly preferably of 70 to 300 amino acids and most preferably of 75 to 275 or of 100 to 250 amino acids.

It is also preferred that (additional) functional domain of the first and/or the second polypeptide chain has a size of up to 150 kDa, more preferably of up to 100 kDa, even more preferably of up to 80 kDa, still more preferably of up to 70 kDa, particularly preferably of up to 50 kDa and most preferably of up to 30 or 25 kDa. Moreover, it is preferred that the (additional) functional domain of the first and/or the second polypeptide chain has a size of 0.5 kDa to 150 kDa, more preferably of 1 kDa to 100 kDa, even more preferably of 2.5 kDa to 80 kDa, still more preferably of 5 kDa to 70 kDa, particularly preferably of 7.5 kDa to 50 kDa and most preferably of 10 kDa to 30 or 25 kDa.

The (additional) functional domain of the first and/or the second polypeptide chain may comprise a monomeric domain or multimeric domains. A monomeric domain is a domain, which mediates its functionality without the involvement of any further (additional) domain. Multimeric domains, for example two domains forming a dimer or three domains forming a trimer, mediate their functionality together, in particular as multimer, e.g., as dimer or trimer.

In case of multimeric domains, the (additional) functional domain of the first and/or the second polypeptide chain may comprise linkers as described herein to provide sufficient flexibility to form the multimer, in particular a linker may be located (directly) adjacent to one or more multimeric domain(s), e.g. in between two multimeric domains or on each side of all multimeric domains. Preferably, the (additional) functional domain of the first and/or the second polypeptide chain comprises or consists of one or more monomeric domain(s).

In general, the (additional) functional domain of the first and/or the second polypeptide chain may comprise or consist of one single protein domain or of more than one protein domain. "More than one protein domain" may be multimeric domains as described above and/or one or more monomeric domains as described above. For example, the (additional) functional domain of the first and/or the second polypeptide chain may comprise or consist of two or three monomeric domains, which may mediate the same or distinct functionality and/or which may optionally be connected by a linker. For example, the (additional) functional domain of the first and/or the second polypeptide chain may comprise 1, 2, 3, 4, 5, 6, 7, 8, 9, or 10 (distinct) protein domains.

Preferably, the (additional) functional domain is a human protein, peptide or polypeptide or a fragment (in particular a domain) or derivative thereof.

In particular, the (additional) functional domain is not a linker (peptide), such as a GS-linker. Even though the (additional) functional domain may optionally comprise a linker (peptide), such as a GS-linker, it does preferably not consist of a linker (peptide), such as a GS-linker. In other words, even if the (additional) functional domain comprises a linker (peptide), such as a GS-linker, it preferably comprises an additional amino acid sequence mediating a function distinct from (purely) linking two peptides to each other. Accordingly, the (additional) functional domain is preferably distinct from a linker (peptide), such as a GS-linker. In particular, the (additional) functional domain may not comprise a linker (peptide), such as a GS-linker. In general, the functionality provided by the (additional) functional domain is preferably not a mere linkage of two (poly-)peptides. Even though the (additional) functional domain may "link" two (poly-)peptides, such as the adjacent variable and constant domain, and, optionally, provide flexibility, the (additional) functional domain preferably provides for an (additional) function distinct from (poly-)peptide linkage and flexibility.

Preferably, the second polypeptide chain comprises an (additional) functional domain (v). In this case, the first and the second polypeptide chains both comprise an (additional) functional domain, thereby resulting in an antibody, or antigen-binding fragment thereof, with two distinct (separate) (additional) functional domains. The (additional) functional domains of the first polypeptide chain and of the second polypeptide chain may be the same or distinct, i.e. the same or different functional domains. In other words, even if the (additional) functional domains of the first and second polypeptide chains have an identical amino acid sequence, those (additional) functional domains are "independent", i.e. they mediate their functions independently from each other. For example, the (additional) functional domains of the first and second polypeptide chain bind to separate targets (e.g., separate antigens or separate epitopes of the same antigen; separate molecules or separate parts of the same molecule) and neither of the independent binding sites requires or involves the other in order to bind to its target.

However, more preferably the second polypeptide chain comprises no (additional) functional domain (v) and that the C-terminus of the most C-terminal variable domain of the second polypeptide chain is preferably directly coupled to the N-terminus of the most N-terminal constant domain of the second polypeptide chain. For example, if the second polypeptide chain is a light chain, the C-terminus of the most C-terminal VL domain (or of the only VL domain) is preferably directly coupled to the N-terminus of the CL domain. For example, if the second polypeptide chain is a heavy chain, the C-terminus of the most C-terminal VH domain (or of the only VH domain) is preferably directly coupled to the N-terminus of the CH1 domain.

Accordingly, the present invention also provides an antibody, or antigen binding fragment thereof, comprising a first polypeptide chain and a second polypeptide chain, wherein said first polypeptide chain comprises in N- to C-terminal direction
  (i) one or more variable domains;
  (ii) an (additional) functional domain and
  (iii) one or more constant domains; and
wherein said second polypeptide chain comprises in N- to C-terminal direction
  (iv) one or more variable domains forming antigen binding sites with the one or more variable domains of the first polypeptide chain; and
  (v) one or more constant domains,
characterized in that the C-terminus of the most C-terminal variable domain of the second polypeptide chain is directly coupled to the N-terminus of the most N-terminal constant domain of the second polypeptide chain.

Again, the term "functional domain" refers to a functional unit, e.g. of the antibody or the antigen binding fragment, as described above. Briefly, a functional domain typically provides the protein, e.g. the antibody or the antigen binding fragment, with an (additional) functionality as described above. Accordingly, the (additional) functional domain usually contains all amino acids/sequences required to provide the (additional) function. In particular, the (additional) functional domain (ii) of the first polypeptide chain does not comprise a fragment of the second polypeptide chain, as described above in more detail.

Particularly preferably, the (additional) functional domain of the first polypeptide chain comprises or consists of an Ig-like domain as described above. Preferred examples of Ig-like domains include those as described above and those as described herein below.

It is also preferred that the (additional) functional domain of the first polypeptide chain comprises or consists of an extra- and/or intracellular domain of a (known) protein. Moreover, the (additional) functional domain of the first polypeptide chain may preferably comprise or consist of a domain of a (known) soluble globular protein. More preferably, the (additional) functional domain of the first polypeptide chain comprises or consists of an extracellular domain of a (known) protein or a domain of a (known) soluble globular protein.

Preferably, the (additional) functional domain of the first polypeptide chain has a length of up to 1000 amino acids, more preferably of up to 750 amino acids, even more preferably of up to 500 amino acids, still more preferably of up to 400 amino acids, particularly preferably of up to 300 amino acids and most preferably of up to 275 or 250 amino acids. Moreover, it is preferred that the (additional) functional domain of the first polypeptide chain has a length of to 1000 amino acids, more preferably of 10 to 750 amino acids, even more preferably of to 500 amino acids, still more preferably of 50 to 400 amino acids, particularly preferably of 70 to 300 amino acids and most preferably of 75 to 275 or of 100 to 250 amino acids.

It is also preferred that (additional) functional domain of the first polypeptide chain has a size of up to 150 kDa, more preferably of up to 100 kDa, even more preferably of up to 80 kDa, still more preferably of up to 70 kDa, particularly preferably of up to 50 kDa and most preferably of up to 30 or 25 kDa. Moreover, it is preferred that the (additional) functional domain of the first polypeptide chain has a size of 0.5 kDa to 150 kDa, more preferably of 1 kDa to 100 kDa, even more preferably of 2.5 kDa to 80 kDa, still more preferably of 5 kDa to 70 kDa, particularly preferably of 7.5 kDa to 50 kDa and most preferably of 10 kDa to 30 or 25 kDa.

The (additional) functional domain of the first polypeptide chain may comprise a monomeric domain or multimeric domains as described above. Moreover, the (additional) functional domain of the first polypeptide chain may comprise or consist of one single protein domain or of more than one protein domain as described above.

Preferably, the (additional) functional domain is a human protein, peptide or polypeptide or a fragment (in particular a domain) or derivative thereof.

In particular, the (additional) functional domain is not a linker (peptide), such as a GS-linker as described above. Even though the (additional) functional domain may optionally comprise a linker (peptide), such as a GS-linker, it does preferably not consist of a linker (peptide), such as a GS-linker. In other words, even if the (additional) functional domain comprises a linker (peptide), such as a GS-linker, it preferably comprises an additional amino acid sequence mediating a function distinct from (purely) linking two peptides to each other. Accordingly, the (additional) functional domain is preferably distinct from a linker (peptide), such as a GS-linker. In particular, the (additional) functional domain may not comprise a linker (peptide), such as a GS-linker. In general, the functionality provided by the (additional) functional domain is preferably not a mere linkage of two (poly-)peptides. Even though the (additional) functional domain may "link" two (poly-)peptides, such as the adjacent variable and constant domain, and, optionally, provide flexibility, the (additional) functional domain preferably provides for an (additional) function distinct from (poly-)peptide linkage and flexibility.

Moreover, the C-terminus of the most C-terminal variable domain of the second polypeptide chain is preferably directly coupled to the N-terminus of the most N-terminal constant domain of the second polypeptide chain. For example, if the second polypeptide chain is a light chain, the C-terminus of the most C-terminal VL domain (or of the only VL domain) is preferably directly coupled to the N-terminus of the CL domain. For example, if the second polypeptide chain is a heavy chain, the C-terminus of the most C-terminal VH domain (or of the only VH domain) is preferably directly coupled to the N-terminus of the CH1 domain.

In general, it is preferred in the antibody, or the antigen binding fragment thereof, according to the present invention that the one or more constant domains of the first polypeptide chain is/are heavy chain constant domains, preferably comprising at least a CH1 constant domain and the constant domain of the second polypeptide chain is a light chain constant domain CL. More preferably, the one or more constant domains of the first polypeptide chain is/are heavy chain constant domains, preferably comprising at least a CH1 constant domain, the one or more variable domains of the first polypeptide chain is/are heavy chain variable domains VH, the constant domain of the second polypeptide chain is a light chain constant domain CL and the one or more variable domains of the second polypeptide chain is/are light chain variable domains VL. In other words, it is preferred that the first polypeptide chain is or is derived from a heavy chain and the second polypeptide chain is or is derived from a light chain. It is particularly preferred that the constant region of the first polypeptide chain comprises three constant domains, namely CH, CH2 and CH3 (in particular, in N- to C-terminal direction CH1-CH2-CH3), most preferably with a hinge region between CH1 and CH2.

Alternatively, it is also preferred in the antibody, or the antigen binding fragment thereof, according to the present invention that the constant domains of the first polypeptide chain is a light chain constant domain CL and the one or more constant domains of the second polypeptide chain is/are heavy chain constant domains, preferably comprising at least a CH1 constant domain. More preferably, the constant domains of the first polypeptide chain is a light chain constant domain CL, the one or more variable domains of the first polypeptide chain is/are light chain variable domains VL, the one or more constant domains of the second polypeptide chain is/are heavy chain constant domains, preferably comprising at least a CH1 constant domain, and the one or more variable domains of the second polypeptide chain is/are heavy chain variable domains VH. In other words, it is preferred that the second polypeptide chain is or is derived from a heavy chain and the first polypeptide chain is or is derived from a light chain. It is particularly preferred that the constant region of the second polypeptide chain comprises three constant domains, namely CH1, CH2 and CH3 (in particular, in N- to C-terminal direction CH1-CH2-CH3), most preferably with a hinge region between CH1 and CH2.

Moreover, it is preferred that in the first and/or second polypeptide chain, the constant domains directly adjacent to the (additional) functional domain (and/or the variable region, if the second polypeptide does not comprise an (additional) functional domain) do not contribute to the Fc region. In native antibodies, the constant region next to the variable domains, CH1 and CL, do typically not contribute to the Fc region. Accordingly, it is preferred that one polypeptide chain (the first or the second) comprises a CH1 constant domain, whereas the other polypeptide chain (the other of the first or the second) comprises a CL constant domain.

Preferably, the heavy chain constant domain, in particular CH1 or any other heavy chain constant domain, is selected from the following classes: γ, α, µ, ε and δ; preferably γ, such as from IgG1, IgG2, IgG3 or IgG4.

Moreover, it is preferred that the light chain constant domain, in particular CL, is selected from the following classes: κ and λ.

Preferably, antibody, or the antigen binding fragment thereof, according to according to the present invention is a recombinant antibody or antigen binding fragment. As used herein, the term "recombinant" means that the recombinant antibody or antibody fragment does not occur in nature.

Preferably, the functional domain (ii) of the first polypeptide chain and/or the functional domain (v) of the second polypeptide chain of the antibody or the antigen binding fragment according to the present invention comprises or consists of a carrier domain, a reporter domain, a tag, a localization domain, an (independent) binding site, an enzyme or enzymatic domain, a receptor or a functional fragment thereof, or a ligand or a functional fragment thereof.

Preferably, the functional domain (ii) of the first polypeptide chain and/or the functional domain (v) of the second polypeptide chain the antibody, or the antigen binding fragment thereof, according to the present invention comprises or consists of an enzyme or an enzymatic domain thereof. An "enzyme" is a polypeptide or protein catalyst, i.e. an enzyme typically accelerates a chemical reaction. The molecules upon which enzymes may act are called substrates and the enzyme converts the substrates into different molecules known as products. Almost all metabolic processes in the cell need enzymes in order to occur at rates fast enough to sustain life. Preferred enzymes include oxidoreductases, transferases, hydrolases, lysases, isomerases and ligases. For enzymes, which form a dimer, the functional domain of the first and/or second polypeptide chain may comprise two identical domains connected by a linker. For example, enzymes may be useful to activate a pro-drug at a specific site, e.g. a tumor. Examples of preferred enzymes and uses of antibodies comprising such enzymes are described in Andrady C, Sharma S K, Chester K A; Antibody-enzyme fusion proteins for cancer therapy; Immunotherapy. 2011 February; 3(2):193-211 and in Boado R J1, Zhang Y, Zhang Y, Xia C F, Wang Y, Pardridge W M; Genetic engineering of a lysosomal enzyme fusion protein for targeted delivery across the human blood-brain barrier; Biotechnol Bioeng. 2008 Feb. 1; 99(2):475-84.

Preferred enzymes are selected from the group consisting of dehydrogenase, luciferase, DMSO reductase, Alcohol dehydrogenase (NAD), Alcohol dehydrogenase (NADP), Homoserine dehydrogenase, Aminopropanol oxidoreductase, Diacetyl reductase, Glycerol dehydrogenase, Propanediol-phosphate dehydrogenase, glycerol-3-phosphate dehydrogenase (NAD+), D-xylulose reductase, L-xylulose reductase, Lactate dehydrogenase, Malate dehydrogenase, Isocitrate dehydrogenase, HMG-CoA reductase, Glucose oxidase, L-gulonolactone oxidase, Thiamine oxidase, Xanthine oxidase, Acetaldehyde dehydrogenase, Glyceraldehyde 3-phosphate dehydrogenase, Pyruvate dehydrogenase, Oxoglutarate dehydrogenase, Biliverdin reductase, Monoamine oxidase, Dihydrofolate reductase, Methylenetetrahydrofolate reductase, Sarcosine oxidase, Dihydrobenzophenanthridine oxidase, NADH dehydrogenase, Urate oxidase, Nitrite reductase, Nitrate reductase, Glutathione reductase, Thioredoxin reductase, Sulfite oxidase, Cytochrome c oxidase, Coenzyme Q—cytochrome c reductase, Catechol oxidase, Laccase, Cytochrome c peroxidase, Catalase, Myeloperoxidase, Thyroid peroxidase, Glutathione peroxidase, 4-hydroxyphenylpyruvate dioxygenase, *Renilla*-luciferin 2-monooxygenase, Cypridina-luciferin 2-monooxygenase, Firefly luciferase, Watasenia-luciferin 2-monooxygenase, Oplophorus-luciferin 2-monooxygenase, Aromatase, CYP2D6, CYP2E1, CYP3A4, Cytochrome P450 oxidase, Nitric oxide dioxygenase, Nitric oxide synthase, Aromatase, Phenylalanine hydroxylase, Tyrosinase, Superoxide dismutase, Ceruloplasmin, Nitrogenase, Deiodinase, Glutathione S-transferase, Catechol-O-methyl transferase, DNA methyltransferase, Histone methyltransferase, ATCase, Ornithine transcarbamoylase, Aminolevulinic acid synthase, Choline acetyltransferase, Factor XIII, Gamma glutamyl transpeptidase, Transglutaminase, Hypoxanthine-guanine phosphoribosyltransferase, Thiaminase, Alanine transaminase, Aspartate transaminase, Butyrate kinase, Nuclease, Endonuclease, Exonuclease, Acid hydrolase, Phospholipase A, Phospholipase C, Acetylcholinesterase, Cholinesterase, Lipoprotein lipase, Ubiquitin carboxy-terminal hydrolase L1, Phosphatase, Alkaline phosphatase, Fructose bisphosphatase, CGMP specific phosphodiesterase type 5, Phospholipase D, Restriction enzyme Type 1, Restriction enzyme Type 2, Restriction enzyme Type 3, Restriction enzyme Type 4, Deoxyribonuclease 1, RNase H, Ribonuclease, Amylase, Sucrase, Chitinase, Lysozyme, Maltase, Lactase, Beta-galactosidase, Hyaluronidase, Adenosylmethionine hydrolase, S-adenosyl-L-homocysteine hydrolase, Alkenylglycerophosphocholine hydrolase, Alkenylglycerophosphoethanolamine hydrolase, Cholesterol-5,6-oxide hydrolase, Hepoxilin-epoxide hydrolase, Isochorismatase, Leukotriene-A4 hydrolase, Limonene-1,2-epoxide hydrolase, Microsomal epoxide hydrolase, Trans-epoxysuccinate hydrolase, Alanine aminopeptidase, Angiotensin converting enzyme, Serine protease, Chymotrypsin, Trypsin, Thrombin, Factor X, Plasmin, Acrosin, Factor VII, Factor IX, Prolyl oligopeptidase, Factor XI, Elastase, Factor XII, Proteinase K, Tissue plasminogen activator, Protein C, Separase, Pepsin, Rennet, Renin, Trypsinogen, Plasmepsin, Matrix metalloproteinase, Metalloendopeptidase, Urease, Beta-lactamase, Arginase, Adenosine deaminase, GTP cyclohydrolase I, Nitrilase, Helicase, DnaB helicase, RecQ helicase, ATPase, NaKATPase, ATP synthase, Kynureninase, Haloacetate dehalogenase, Lyase, Ornithine decarboxylase, Uridine monophosphate synthetase, Aromatic-L-amino-acid decarboxylase, RubisCO, Carbonic anhydrase, Tryptophan synthase, Phenylalanine ammonia-lyase, Cystathionine gamma-lyase, Cystathionine beta-lyase, Leukotriene C4 synthase, Dichloromethane dehalogenase, Halohydrin dehalogenase, Adenylate cyclase, Guanylate cyclase, Amino-acid racemase: Phenylalanine racemase, Serine racemase, Mandelate racemase, UDP-glucose 4-epimerase, Methylmalonyl CoA epimerase, FKBP: FKBP1A, FKBP1B, FKBP2, FKBP3, FKBP5, FKBP6, FKBP8, FKBP9, FKBP10, FKBP52, FKBPL, Cyclophilin, Parvulin, Prolyl isomerase, 2-chloro-4-carboxymethylenebut-2-en-1,4-olide isomerase, Beta-carotene isomerase, Farnesol 2-isomerase, Furylfuramide isomerase, Linoleate isomerase, Maleate isomerase, Maleylacetoacetate isomerase, Maleylpyruvate isomerase, Parvulin, Photoisomerase, Prolycopene isomerase, Prolyl isomerase, Retinal isomerase, Retinol isomerase, Zeta-carotene isomerase, Enoyl CoA isomerase, Protein disulfide isomerase, Phosphoglucomutase, Muconate cycloisomerase, 3-carboxy-cis,cis-muconate cycloisomerase, Tetrahydroxypteridine cycloisomerase, Inositol-3-phosphate synthase, Carboxy-cis,cis-muconate cyclase, Chalcone isomerase, Chloromuconate cycloisomerase, (+)-bornyl diphosphate synthase, Cycloeucalenol cycloisomerase, Alpha-pinene-oxide decyclase, Dichloromuconate cycloisomerase, Copalyl diphosphate synthase, Ent-copalyl diphosphate synthase, Syn-copalyl-diphosphate synthase, Terpentedienyl-diphosphate synthase, Halimadienyl-diphosphate synthase, (S)-beta-macrocarpene synthase, Lycopene epsilon-cyclase, Lycopene beta-cyclase, Prosolanapyrone-III cycloisomerase, D-ribose pyranase, Steroid Delta Isomerase, Topoisomerase, 6-carboxytetrahydropterin synthase, FARSB, Glutamine synthetase, CTP synthase, Argininosuccinate synthetase, Pyruvate carboxylase, Acetyl-CoA carboxylase, and DNA ligase.

More preferred enzymes may be selected from the group consisting of carboxypeptidase, β-lactamase, cytosine deaminase, β-glucuronidase, purine nucleoside phosphorylase, granzyme B, caspase and RNase, such as HPR (human pancreatic RNase, barnase, bovine seminal RNase, onconase, RapLR1, angiogenin, dicer, DIS3-like exonuclease 2, phosphodiesterase ELAC 2, RNase HIII, RNase T2, and tRNA splicing ribonuclease.

A functional fragment of an enzyme may be any fragment of an enzyme, which has the ability to mediate a functionality. Usually, such fragments are referred to as "domains". Accordingly, the functional fragment of an enzyme may be any domain of the enzyme. Preferred examples include functional fragments (e.g., domains) of the (exemplified) enzymes described above. Preferably, the functional fragment of the enzyme, which is comprised by the (additional) functional domain is a catalytic domain of an enzyme. The catalytic domain of an enzyme is the region of an enzyme that interacts with its substrate to cause the enzymatic reaction. For example, the (additional) functional domain of the first polypeptide chain and/or of the second polypeptide chain may be a catalytic domain of any one of the following enzymes: carboxypeptidase, β-lactamase, cytosine deaminase, β-glucuronidase, purine nucleoside phosphorylase, granzyme B, caspase and RNase, such as HPR (human pancreatic RNase, barnase, bovine seminal RNase, onconase, RapLR1, angiogenin, dicer, DIS3-like exonuclease 2, phosphodiesterase ELAC 2, RNase HIII, RNase T2, and tRNA splicing ribonuclease.

Preferably, the functional domain (ii) of the first polypeptide chain and/or the functional domain (v) of the second polypeptide chain of the antibody or the antigen binding fragment according to the present invention comprises or consists of a carrier domain. As used herein, a "carrier domain" refers to an amino acid sequence, which provides for conjugation of the antibody to another molecule. In a preferred example, the carrier domain provides for conjugation of the antibody, or the antigen binding fragment thereof, for example to a drug, to an imaging agent, or to a nanoparticle. In general, preferred examples of conjugates, which may be useful in the context of the present invention, are described in Wu, A. M., and Senter, P. D. (2005) Arming antibodies: Prospects and challenges for immunoconjugates. Nat. Biotechnol. 23, 1137-1146.

For example, drugs, which may be conjugated to the antibody include anticancer drugs, such as those described in Thomas A, Teicher B A, Hassan R; Antibody-drug conjugates for cancer therapy; Lancet Oncol. 2016 June; 17(6): e254-62. doi: 10.1016/S1470-2045(16)30030-4. For example, imaging agents, which may be conjugated to the antibody, are described in Steve Knutson, Erum Raja, Ryan Bomgarden, Marie Nlend, Aoshuang Chen, Ramaswamy Kalyanasundaram, and Surbhi Desai; Development and Evaluation of a Fluorescent Antibody-Drug Conjugate for Molecular Imaging and Targeted Therapy of Pancreatic Cancer; PLoS One 2016; 11(6): e0157762. Such drugs are preferably cytotoxic agents. Preferred examples of drugs, which may be conjugated to the antibody or antigen binding fragment of the present invention, include doxorubicin, truncated *Pseudomonas* exotoxin A, maytansinoid DM1.

Examples of imaging agents, which may be conjugated to the antibody or antigen binding fragment of the present invention, include radioisotopes, such as those described in Schubert M, Bergmann R, Förster C, Sihver W, Vonhoff S, Klussmann S, Bethge L, Walther M, Schlesinger J, Pietzsch J, Steinbach J, Pietzsch H J; Novel Tumor Pretargeting System Based on Complementary I-Configured Oligonucleotides; Bioconjug Chem. 2017 Apr. 19; 28(4):1176-1188 and in Bhusari P, Vatsa R, Singh G, Parmar M, Bal A, Dhawan D K, Mittal B R, Shukla J; Development of Lu-177-trastuzumab for radioimmunotherapy of HER2 expressing breast cancer and its feasibility assessment in breast cancer patients; Int J Cancer. 2017 Feb. 15; 140(4):938-947. Preferred examples of radioisotopes include $^{90}$Y, $^{131}$I, and $^{177}$Lu.

Further examples of imaging agents, which may be conjugated to the antibody or antigen binding fragment of the present invention, include fluorescent dyes, quantum dots, and iron oxide. Examples of fluorescent dyes include those described below as reporter domains. An example of iron oxide nanoparticles is described in Hengyi Xu, Zoraida P. Aguilar, Lily Yang, Min Kuang, Hongwei Duan, Yonghua Xiong, Hua Wei, and Andrew Wang: Antibody Conjugated Magnetic Iron Oxide Nanoparticles for Cancer Cell Separation in Fresh Whole Blood. Biomaterials. 2011 December; 32(36): 9758-9765.

Antibody conjugates (i.e. antibodies conjugated to other molecules) are known in the art. In particular, the molecule conjugated to the antibody may be linked to the antibody by a cleavable or non-cleavable linker (e.g., as described in: Thomas H. Pillow. Novel linkers and connections for antibody-drug conjugates to treat cancer and infectious disease. Pharmaceutical Patent Analyst Vol. 6, No. 1, Feb. 3, 2017, doi: 10.4155, ppa-2016-0032; or in: Beck A, Goetsch L, Dumontet C, Corvaïa N. Strategies and challenges for the next generation of antibody-drug conjugates. Nat Rev Drug Discov. 2017 May; 16 (5): 315-337). Examples of such linkers, which may be used to link the molecule to the antibody or antigen binding fragment, are described, for example in EP 2927227 and in Thomas H. Pillow. Novel linkers and connections for antibody-drug conjugates to treat cancer and infectious disease. Pharmaceutical Patent Analyst Vol. 6, No. 1, Feb. 3, 2017. However, in the prior art the linkers are attached directly to the Ig-domains of the antibody (namely, to the variable and/or constant domains of the antibody), which may interfere with the functionality of the Ig-domains of the antibody. In view thereof, the (additional) functional domain of the antibody or the antigen binding fragment according to the present invention may be used for attachment of a linker to the antibody. Preferred linkers differ from "classical" linkers in that they are engineered to contain additional cysteines or lysines. Preferably, the carrier domain comprises one or more non-canonical amino acids useful for site-specific conjugation, e.g., as described in Link A J, Mock M L, Tirrell D A. Non-canonical amino acids in protein engineering. Curr Opin Biotechnol. 2003 December; 14 (6): 603-9. Moreover, the carrier domain may be designed such that it is recognized by specific enzymes (such as Formylglycin Generating Enzyme, Sortase and/or Transglutaminases), that modify specific amino acids that then can be used for conjugation as described in section 6 of Dennler P., Fischer E., Schibli R. Antibody conjugates: From heterogeneous populations to defined reagents. Antibodies. 2015; 4:197-224.

Further preferred carrier domains are domains for conjugation, such as genetically modified cross-reacting material (CRM) of diphtheria toxin, tetanus toxoid (T), meningococcal outer membrane protein complex (OMPC), diphtheria toxoid (D), and H. influenzae protein D (HiD), for example as described in Pichichero M E: Protein carriers of conjugate vaccines: characteristics, development, and clinical trials, Hum Vaccin Immunother. 2013 December; 9(12):2505-23.

Preferably, the functional domain (ii) of the first polypeptide chain and/or the functional domain (v) of the second polypeptide chain of the antibody or the antigen binding fragment according to the present invention comprises or consists of a reporter domain. A reporter domain is typically encoded by a reporter gene. Reporter domains are such domains, whose presence (e.g., in a cell, organism) can be easily observed. Reporter domains include, for example, fluorescent proteins, such as GFP/EGFP (green fluorescent protein/enhanced green fluorescent protein), YFP (yellow fluorescent protein), RFP (red fluorescent protein), and CFP (cyan fluorescent protein), luciferases and enzymes such as beta-galactosidase and peroxidase. Reporter domains can be useful for in vivo and ex vivo approaches. For example, fluorescent proteins cause a cell to fluoresce when excited with light of a particular wavelength, luciferases cause a cell to catalyze a reaction that produces light, and enzymes such as beta-galactosidase convert a substrate to a colored product. There are several different ways to measure or quantify a reporter depending on the particular reporter and what kind of characterization data is desired. In general, microscopy is useful for obtaining both spatial and temporal information on reporter activity, particularly at the single cell level. Flow cytometers are best suited for measuring the distribution in reporter activity across a large population of cells. Plate readers are generally best for taking population average measurements of many different samples over time. Enzyme, such as beta-galactosidase and peroxidase, which can react to a given substrate, may be useful, for example, for ex-vivo stainings of human samples, e.g. in tumor diagnosis.

Preferably, the reporter domain comprises or consists of an amino acid sequence coding for GFP/EGFP, YFP, RFP, CFP, luciferase, beta-galactosidase, or peroxidase. In addition, fluorescent tags as described below are also useful as reporter domains.

Preferably, the functional domain (ii) of the first polypeptide chain and/or the functional domain (v) of the second polypeptide chain of the antibody or the antigen binding fragment according to the present invention comprises or consists of a localization domain. In general, a localization domain directs a protein to a certain target, e.g. on the level of an organism or a cell. A localization domain can direct the antibody or the antigen binding fragment according to the present invention to a particular physical location in the cell, such as the nucleus, the membrane, the periplasm, secretion outside of the cell, to a specific part of the body, or elsewhere.

For example, in order to direct the antibody or the antigen binding fragment according to the present invention into a cell, the (additional) functional domain may comprise or consist of a cell penetrating peptide. The term "cell penetrating peptides" ("CPPs", also referred to as "protein transduction domain"/"PTD") is generally used to designate short peptides that are able to transport different types of cargo molecules across plasma membrane, and, thus, facilitate cellular uptake of various molecular cargoes (from nanosize particles to small chemical molecules and large fragments of DNA). Cell penetrating peptides typically have an amino acid composition that either contains a high relative abundance of positively charged amino acids such as lysine or arginine or have a sequence that contains an alternating pattern of polar/charged amino acids and non-polar, hydrophobic amino acids. These two types of structures are referred to as polycationic or amphipathic, respectively. Typically, cell penetrating peptides (CPPs) are peptides of 8 to 50 residues that have the ability to cross the cell membrane and enter into most cell types. Alternatively, they are also called protein transduction domain (PTDs) reflecting their origin as occurring in natural proteins. Frankel and Pabo simultaneously to Green and Lowenstein described the ability of the trans-activating transcriptional activator from the human immunodeficiency virus 1 (HIV-TAT) to penetrate into cells (Frankel, A. D. and C. O. Pabo, Cellular uptake of the tat protein from human immunodeficiency virus. Cell, 1988. 55(6): p. 1189-93). In 1991, transduction into neural cells of the Antennapedia homeodomain (DNA-binding domain) from *Drosophila melanogaster* was described (oliot, A., et al., Antennapedia homeobox peptide regulates neural morphogenesis. Proc Natl Acad Sci USA, 1991. 88(5): p. 1864-8). In 1994, the first 16-mer peptide CPP called Penetratin was characterized from the third helix of the homeodomain of Antennapedia (Derossi, D., et al., The third helix of the Antennapedia homeodomain translocates through biological membranes. J Biol Chem, 1994. 269(14): p. 10444-50), followed in 1998 by the identification of the minimal domain of TAT, required for protein transduction (Vives, E., P. Brodin, and B. Lebleu, A truncated HIV-1 Tat protein basic domain rapidly translocates through the plasma membrane and accumulates in the cell nucleus. J Biol Chem, 1997. 272(25): p. 16010-7). Over the past two decades, dozens of peptides were described from different origins including viral proteins, e.g. VP22 (Elliott, G. and P. O'Hare, Intercellular trafficking and protein delivery by a herpesvirus structural protein. Cell, 1997. 88(2): p. 223-33), or from venoms, e.g. melittin (Dempsey, C. E., The actions of melittin on membranes. Biochim Biophys Acta, 1990. 1031(2): p. 143-61), mastoporan (Konno, K., et al., Structure and biological activities of eumenine mastoparan-AF (EMP-AF), a new mast cell degranulating peptide in the venom of the solitary wasp (Anterhynchium flavomarginatum micado). Toxicon, 2000. 38(11): p. 1505-15), maurocalcin (Esteve, E., et al., Transduction of the scorpion toxin maurocalcine into cells. Evidence that the toxin crosses the plasma membrane. J Biol Chem, 2005. 280(13): p. 12833-9), crotamine (Nascimento, F. D., et al., Crotamine mediates gene delivery into cells through the binding to heparan sulfate proteoglycans. J Biol Chem, 2007. 282(29): p. 21349-60) or buforin (Kobayashi, S., et al., Membrane translocation mechanism of the antimicrobial peptide buforin 2. Biochemistry, 2004. 43(49): p. 15610-6). Synthetic CPPs were also designed including the poly-arginine (R8, R9, R10 and R12) (Futaki, S., et al., Arginine-rich peptides. An abundant source of membrane-permeable peptides having potential as carriers for intracellular protein delivery. J Biol Chem, 2001. 276(8): p. 5836-40) or transportan (Pooga, M., et al., Cell penetration by transportan. FASEB J, 1998. 12(1): p. 67-77). Any of the above described CPPs may be used as cell penetrating peptide in the antibody or antigen binding fragment according to the present invention. Various CPPs, which can be used as cell penetrating peptide in the antibody or antigen binding fragment according to the present invention are also disclosed in the review: Milletti, F., Cell-penetrating peptides: classes, origin, and current landscape. Drug Discov Today 17 (15-16): 850-60, 2012.

Another example of a localization domain, which may be used in the antibody or antigen binding fragment according to the present invention is a domain for crossing the blood brain barrier, for example as described in Farrington G K, Caram-Salas N, Haqqani A S, Brunette E, Eldredge J, Pepinsky B, Antognetti G, Baumann E, Ding W, Garber E, Jiang S, Delaney C, Boileau E, Sisk W P, Stanimirovic D B. A novel platform for engineering blood-brain barrier-crossing bispecific biologics. FASEB J. 2014 November; 28(11): 4764-78.

A further example of a localization domain is a nuclear localization domain. A nuclear localization domain directs a protein, in particular the antibody or antigen-binding fragment according to the present invention, to the cell nucleus. A nuclear localization domain may be useful for an antibody or antigen-binding fragment to block the activity of a transcription factor and to modulate gene expression. Preferred examples of nuclear localization domains are described in Kalderon D, Roberts B L, Richardson W D, Smith A E (1984) "A short amino acid sequence able to specify nuclear location" Cell 39 (3 Pt 2): 499-509 and in Lusk C P, Blobel G, King M C (May 2007) "Highway to the inner nuclear membrane: rules for the road" Nature Reviews Molecular Cell Biology 8 (5): 414-20.

Preferably, the functional domain (ii) of the first polypeptide chain and/or the functional domain (v) of the second polypeptide chain the antibody, or the antigen binding fragment thereof, according to the present invention comprises or consists of a tag. More preferably, the tag is an affinity tag, a solubilization tag, a chromatography tag, an epitope tag or a fluorescence tag.

A tag is a peptide sequence grafted onto a recombinant protein. Examples of tags include affinity tags, solubilization tags, chromatography tags, epitope tags, fluorescence tags and protein tags. Affinity tags may be used to purify proteins from their crude biological source using an affinity technique. Examples of affinity tags include chitin binding protein (CBP), maltose binding protein (MBP), and glutathione-S-transferase (GST). A further example is the poly (His) tag which binds to metal matrices. Solubilization tags may be used, especially for recombinant proteins expressed in chaperone-deficient species such as *E. coli*, to assist in the proper folding in proteins and keep them from precipitating. Examples of solubilization tags include thioredoxin (TRX) and poly(NANP). Chromatography tags may be used to alter chromatographic properties of the protein to afford different resolution across a particular separation technique. Chromatography tags often consist of polyanionic amino acids, such as FLAG-tag. Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag and NE-tag. These tags are particularly useful for western blotting, immunofluorescence and immunoprecipitation experiments, although they also find use in antibody purification. Fluorescence tags may be used to give visual readout on a protein. GFP and its variants are the most commonly used fluorescence tags. GFP may be used as a folding reporter (fluorescent if folded, colorless if not). Protein tags may allow specific enzymatic modification (such as biotinylation by biotin ligase) or chemical modification (such as reaction with FIAsH-EDT2 for fluorescence imaging). Tags may be combined, for example, in order to connect proteins to multiple other components. Tags may be removable by chemical agents or by enzymatic means, such as proteolysis or intein splicing.

Preferred examples of tags include, but are not limited to, the following: twin-Strep-Tag (SAWSHPQFEKGGGSGGGSGGSAWSHPQFEK; SEQ ID NO: 20); AviTag, a peptide allowing biotinylation by the enzyme BirA and so the protein can be isolated by streptavidin (GLNDIFEAQKIEWHE; SEQ ID NO: 21); Calmodulin-tag, a peptide bound by the protein calmodulin (KRRWKKNFIAVSAANRFKKISSSGAL; SEQ ID NO: 22); polyglutamate tag, a peptide binding efficiently to anion-exchange resin such as Mono-Q (EEEEEE; SEQ ID NO: 23); E-tag, a peptide recognized by an antibody (GAPVPYPDPLEPR; SEQ ID NO: 24); FLAG-tag, a peptide recognized by an antibody (DYKDDDDK; SEQ ID NO: 25); HA-tag, a peptide from hemagglutinin recognized by an antibody (YPYDVPDYA; SEQ ID NO: 26); His-tag, 5-histidines bound by a nickel or cobalt chelate (HHHHHH; SEQ ID NO: 27); Myc-tag, a peptide derived from c-myc recognized by an antibody (EQKLISEEDL; SEQ ID NO: 28); NE-tag, an 18-amino-acid synthetic peptide (TKENPRSNQEESYDDNES; SEQ ID NO: 29) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, a peptide derived from Ribonuclease A (KETAAAKFERQHMDS; SEQ ID NO: 30); SBP-tag, a peptide which binds to streptavidin (MDEKTTGWRGGHVVEGLAGELEQLRARLEHHPQGQREP; SEQ ID NO: 31); Softag 1, for mammalian expression (SLAELLNAGLGGS; SEQ ID NO: 32); Softag 3, for prokaryotic expression (TQDPSRVG; SEQ ID NO: 33); Strep-tag, a peptide which binds to streptavidin or the modified streptavidin called streptactin (Strep-tag II: WSHPQFEK; SEQ ID NO: 34); TC tag, a tetracysteine tag that is recognized by FlAsH and ReAsH biarsenical compounds (CCPGCC; SEQ ID NO: 35); V5 tag, a peptide recognized by an antibody (GKPIPNPLLGLDST; SEQ ID NO: 36); VSV-tag, a peptide recognized by an antibody (YTDIEMNRLGK; SEQ ID NO: 37); Xpress tag (DLYDDDDK; SEQ ID NO: 38); Isopeptag, a peptide which binds covalently to pilin-C protein (TDKDMTITFTNKKDAE; SEQ ID NO: 39); SpyTag, a peptide which binds covalently to SpyCatcher protein (AHIVMVDAYKPTK; SEQ ID NO: 40); SnoopTag, a peptide which binds covalently to SnoopCatcher protein (KLGDIEFIKVNK; SEQ ID NO: 41); Ty1 tag (EVHTNQDPLD; SEQ ID NO: 42); BCCP (Biotin Carboxyl Carrier Protein), a protein domain biotinylated by BirA enabling recognition by streptavidin; glutathione-S-transferase (GST)-tag, a protein which binds to immobilized glutathione; green fluorescent protein-tag, a protein which is spontaneously fluorescent and can be bound by nanobodies; HaloTag, a mutated bacterial haloalkane dehalogenase that covalently attaches to a reactive haloalkane substrate, this allows attachment to a wide variety of substrates; maltose binding protein (MBP)-tag, a protein which binds to amylose agarose; Nus (N-utilization substance)-tag; Thioredoxin (Trx)-tag; *Fasciola hepatica* 8-kDa antigen (Fh8)-tag; Small ubiquitin modified (SUMO)-tag; Solubility-enhancer peptide sequences (SET)-tags; IgG domain B1 of Protein G (GB1)-tag; IgG repeat domain ZZ of Protein A (ZZ)-tag; Solubility ehhancing bbiquitous Tag (SNUT)-tag; Seventeen kilodalton protein (Skp)-tag; Phage T7 protein kinase (T7PK)-tag *E. coli* secreted protein A (EspA)-tag Monomeric bacteriophage T7 0.3 protein (Orc protein)/Mocr-tag; *E. coli* trypsin inhibitor (Ecotin)-tag; Calcium-binding protein (CaBP)-tag; Stress-responsive arsenate reductase (ArsC)-tag N-terminal fragment of translation initiation factor IF2 (IF2-domain I)-tag; Expressivity tag (N-terminal fragment of translation initiation factor IF2); Stress-responsive proteins RpoA, SlyD, Tsf, RpoS, PotD, Crr-tags; *E. coli* acidic proteins msyB, yjgD, rpoD tags (see, e.g., Costa S, Almeida A, Castro A, Domingues L. Fusion tags for protein solubility, purification and immunogenicity in *Escherichia coli*: the novel Fh8 system. Frontiers in Microbiology. 2014; 5:63, in particular Table 1 in Costa et al., 2014).

Accordingly, it is preferred that the tag comprises or consists of an amino acid sequence according to any one of SEQ ID NO: 20-42 or a sequence variant thereof. Most preferably, the tag is a Strep-tag, in particular according to SEQ ID NO: 20 or 34.

Preferably, the functional domain (ii) of the first polypeptide chain and/or the functional domain (v) of the second polypeptide chain the antibody, or the antigen binding fragment thereof, according to the present invention comprises or consists of a receptor or a functional fragment thereof. A "receptor" is a polypeptide or protein, which binds a specific (signal) molecule, its ligand, and which may initiate a response, e.g. in a cell. In nature, receptors are in particular located on or in the cell membrane (cell surface receptors) or intracellularly (intracellular receptors). Preferred receptors include ion channel-linked (ionotropic) receptors, G protein-linked (metabotropic) hormone receptors, and enzyme-linked hormone receptors, cytoplasmic receptors and nuclear receptors. For receptors, which form a dimer, the functional domain of the first and/or second polypeptide chain may comprise two identical domains connected by a linker.

Preferred receptors are receptors comprising an Ig-like domain. In particular, the receptor may be an inhibitor receptor comprising an Ig-like domain or an activating receptor comprising an Ig-like domain. Preferred examples of inhibitory receptors comprising an Ig-like domain include programmed cell death protein 1 (PD-1 or PD1), cytotoxic T-lymphocyte-associated protein 4 (CTLA4), B- and T-lymphocyte attenuator (BTLA), T-cell immunoglobulin and mucin-domain containing-3 (TIM-3; also known as Hepatitis A virus cellular receptor 2 (HAVCR2)), T cell immunoreceptor with Ig and ITIM domains (TIGIT), Cell surface glycoprotein CD200 receptor 1 (CD200R1), 284 (CD244; SLAMF4), Trem (Triggering receptor expressed on myeloid cells)-like transcript 2 (TLT2), Leukocyte immunoglobulin-like receptor subfamily B member 4 (LILRB4), and Killer Cell Immunoglobulin Like Receptor, Two Ig Domains And Long Cytoplasmic Tail 2 (KIR2DL2). Preferred examples of activating receptors comprising an Ig-like domain include Inducible T-cell COStimulator (ICOS) and CD28. Particularly preferably, the receptor is programmed cell death protein 1 (PD-1 or PD1) or Signaling lymphocytic activation molecule (SLAM).

Further preferred receptors are soluble receptors, for example as disclosed in Heaney M L, Golde D W. Soluble receptors in human disease. J Leukoc Biol. 1998 August; 64(2):135-46. Examples thereof include TNFR (tumor necrosis factor receptor), p55, p75, Fas (CD95), nerve growth factor receptor, CD27, CD30, growth hormone receptor, GM-CSF receptor, erythropoietin receptor (EpoR), thrombopoietin receptor, G-CSF receptor, IL-1RI (interleukin 1 receptor I), IL-1RII (interleukin 1 receptor II), IL-2Rα (interleukin 2 receptor α, Tac, CD25), IL-4R (interleukin 4 receptor), IL-5Rα (interleukin 5 receptor α), IL-7R (interleukin 7 receptor), IL-6Rα (interleukin 6 receptor α), gp130, CNTFR (ciliary neurotrophic factor receptor), LIFR (leukemia inhibitory factor receptor), leptin receptor, IL-11R (interleukin 11 receptor), IL-12 p40 (interleukin 12 receptor p40), stem cell factor receptor (c-kit), interferon receptor, lipopolysaccharide receptor (CD14), complement receptor type I (CD35), hyaluronate receptor (CD44), CD58, IgE receptor (FcεRII, CD23), IgG receptor (FcγRII), ICAM-1 (CD54), ICAM-3 (CD50), transforming growth factor β receptor III, epidermal growth factor receptor (c-erb B), vascular endothelial growth factor receptor, platelet derived growth factor receptor, fibroblast growth factor, colony stimulating factor-1 receptor (MCFR, c-fms), ARK (adrenergic receptor kinase), Tie (angiopoietin receptor), insulin receptor, insulin-like growth factor-II receptor, and mannose 6-phosphate receptor.

More preferably, the soluble receptor is a soluble cytokine receptor, such as a class I cytokine receptor superfamily receptor, a class II cytokine receptor superfamily receptor, an IL-1/TLR family receptor, a TGF-β receptor family receptor, a TNFR superfamily receptor, or IL-17R. Preferred receptors of class I cytokine receptor superfamily include IL-4Rα, IL-5Rα, IL-6Rα, IL-7Rα, IL-9Rα, EpoR, G-CSFR, GM-CSFRa, gp130, and LIFRα. Preferred receptors of class II cytokine receptor superfamily include type I IFNR, such as IFNAR and IFNAR2α. Preferred receptors of IL-1/TLR family include IL-1RII and IL-1RacP. Preferred receptors of TGF-β receptor family include TβR-I and activin receptor-like kinase 7. Preferred receptors of the TNFR superfamily include TNFRSF6/Fas/CD95 and TNFRSF9/4-1BB/CD137. Accordingly, preferred examples of cytokine receptors include IL-4Rα, IL-5Rα, IL-6Rα, IL-7Rα, IL-9Rα, EpoR, G-CSFR, GM-CSFRα, gp130, LIFRα, IFNAR1, IFNAR2α, IL-1RII, IL-1RacP, TβR-I, activin receptor-like kinase 7, TNFRSF6/Fas/CD95, TNFRSF9/4-1BB/CD137 and IL-17R. An antibody or antigen-binding fragment comprising a functional domain comprising such a receptor or a functional fragment thereof may modulate the inflammatory response while the antibody reaches its target. For example, soluble type II IL-1 receptors (sIL-1RII), which are generated primarily by proteolytic cleavage in response to a variety of stimuli, can attenuate excessive IL-1 bioactivity by preferentially binding IL-10. For example, soluble IL-1RAcP, which is generated by alternative splicing rather than by ectodomain cleavage. For example, soluble IL-6 receptors bind IL-6 with an affinity similar to the membrane IL-6R, thereby prolonging the IL-6 half-life.

A functional fragment of a receptor may be any fragment of a receptor, which has the ability to mediate a functionality. Usually, such fragments are referred to as "domains". Accordingly, the functional fragment of a receptor may be any domain of the receptor. Preferred examples include functional fragments (e.g., domains) of the (exemplified) receptors described above. Preferably, the functional fragment of the receptor, which is comprised by the (additional) functional domain is an extracellular domain of a receptor. For example, the (additional) functional domain of the first polypeptide chain and/or of the second polypeptide chain may be an extracellular domain of any of the following receptors IL-4Rα, IL-5Rα, IL-6Rα, IL-7Rα, IL-9Rα, EpoR, G-CSFR, GM-CSFRα, gp130, LIFRα, IFNAR1, IFNAR2α, IL-1RII, IL-1RacP, TβR-I, activin receptor-like kinase 7, TNFRSF6/Fas/CD95, TNFRSF9/4-1BB/CD137, IL-17R, p55, p75, nerve growth factor receptor, CD27, CD30, growth hormone receptor, thrombopoietin receptor, IL-1RI (interleukin 1 receptor I), IL-2Rα (interleukin 2 receptor α, Tac, CD25), CNTFR (ciliary neurotrophic factor receptor), leptin receptor, IL-11R (interleukin 11 receptor), It-12 p40 (interleukin 12 receptor p40), stem cell factor receptor (c-kit), interferon receptor, lipopolysaccharide receptor (CD14), complement receptor type I (CD35), hyaluronate receptor (CD44), CD58, IgE receptor (FcεRII, CD23), IgG receptor (FcγRII), ICAM-1 (CD54), ICAM-3 (CD50), transforming growth factor β receptor III, epidermal growth factor receptor (c-erb B), vascular endothelial growth factor receptor, platelet derived growth factor receptor, fibroblast growth factor, colony stimulating factor-1 receptor (MCFR, c-fms), ARK (adrenergic receptor kinase), Tie (angiopoietin receptor), insulin receptor, insulin-like growth factor-III receptor, and mannose 6-phosphate receptor.

Preferably, the functional fragment of the receptor, which is comprised by the (additional) functional domain is an Ig-like domain. For example, the (additional) functional domain of the first polypeptide chain and/or the second polypeptide chain may be an Ig-like domain of any of the following receptors PD1, SLAM, LAIR1, CTLA4, BTLA, TIM-3, TIGIT, CD200R1, 2B4 (CD244), TLT2, LILRB4, KIR2DL2, ICOS or CD28. Preferably, the functional domain (ii) of the first polypeptide chain and/or the functional domain (v) of the second polypeptide chain the antibody, or the antigen binding fragment thereof, according to the present invention does not comprise a transmembrane domain. Most preferably, the receptor comprises or consists of an amino acid sequence as set forth in any one of SEQ ID NOs 13-15 or a functional sequence variant thereof.

Moreover, it is particularly preferred that the functional domain of the first polypeptide chain and/or of the second polypeptide chain comprises or consists of a mutated Leukocyte-associated immunoglobulin-like receptor 1 (LAIR1) fragment as described in WO 2016/207402 A1. The mutated LAIR1 fragment as set forth in SEQ ID NO: 13, or a sequence variant thereof having at least 70%, preferably at least 75%, more preferably at least 80%, even more preferably at least 85%, still more preferably 90, particularly preferably 95%, and most preferably at least 98% sequence identity, is most preferred.

Particularly preferably, the functional domain of the first polypeptide chain and/or of the second polypeptide chain comprises or consists of an Ig-like fragment of PD1 or SLAM, such as an amino acid sequence as set forth in SEQ ID NO: 14 or in SEQ ID NO: 15; or a sequence variant thereof having at least 70%, preferably at least 75%, more preferably at least 80%, even more preferably at least 85%, still more preferably 90%, particularly preferably 95%, and most preferably at least 98% sequence identity.

Preferably, the functional domain (ii) of the first polypeptide chain and/or the functional domain (v) of the second polypeptide chain the antibody, or the antigen binding fragment thereof, according to the present invention comprises or consists of a ligand or a functional fragment thereof. A "ligand" is a molecule, which specifically binds to a specific site on a protein or any other molecule. In the context of the present invention, the ligand is a peptide, polypeptide or protein, since it is comprised in a polypeptide chain. Binding of a ligand occurs in particular by intermolecular forces, such as ionic bonds, hydrogen bonds and Van der Waals forces. Preferred examples of ligands are cytokines and ligands of any one of the receptors described above, in particular of the receptors PD1, SLAM, LAIR1, CTLA4, BTLA, TIM-3, TIGIT, CD200R1, 264 (CD244), TLT2, LILRB4, KIR2DL2, ICOS or CD28, such as PD-L1, PD-L2, 87-1, 7-2, B7-H4 (B7 homolog), galectin-9, poliovirus receptor (PVR), OX-2 membrane glycoprotein, CD48, B7-H3 (B7 homolog), MHCI, and ICOS-L.

Preferably, the ligand is a cytokine or a functional fragment thereof. Cytokines are usually small proteins (~5-20 kDa) that are important in cell signaling. They are released by cells and affect the behavior of other cells, and sometimes affect the behavior of the releasing cell itself. A cytokine may be selected from chemokines such as the SIS family of cytokines, the SIG family of cytokines, the SCY family of cytokines, the Platelet factor-4 superfamily and intercrines, CC chemokine ligands (CCL)-1 to -28 (in particular CCL12), CXCL1-CXCL17, XCL1 (lymphotactin-α) and XCL2 (lymphotactin-β), fractalkine (or $CX_3CL1$); interferons, such as Type I IFN, Type II IFN, and Type III IFN, in particular IFN-α, IFN-β, IFN-γ, IFN-ε, IFN-κ, IFN-ω, L10R2 (also called CRF2-4) and IFNLR1 (also called CRF2-12); interleukins, such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36; lymphokines, such as IL-2, IL-3, 1L-4, IL-5, IL-6, GM-CSF, and Interferon-gamma; tumor necrosis factors, such as CD40LG (TNFSF5); CD70 (TNFSF7); EDA; FASLG (TNFSF6); LTA (TNFSF1); LTB (TNFSF3); TNF, TNFa, TNFSF4 (OX40L); TNFSF8 (CD153); TNFSF9; TNFSF10 (TRAIl); TNFSF11 (RANKL); TNFSF12 (TWEAK); TNFSF3; TNFSF13B; TNFSF4; TNFSF15; and TNFSF18; and colony stimulating factors, such as CSF1 (also known as "macrophage colony-stimulating factor"), CSF2 (also known as "granulocyte macrophage colony-stimulating factor"; GM-CSF and sargramostim), CSF3 (also known as "granulocyte colony-stimulating factor"; G-CSF and filgrastim), as well as synthetic CSFs, such as Promegapoietin. Accordingly, preferred examples of cytokines include IL-1, IL-2, IL-3, IL-4, IL-5, IL-6, IL-7, IL-8, IL-9, IL-10, IL-11, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, CCL-1, CCL-2, CCL-3, CCL-4, CCL-5, CCL-6, CCL-7, CCL-8, CCL-9, CCL-10, CCL-11, CCL-12, CCL-13, CCL-14, CCL-15, CCL-16, CCL-17, CCL-18, CCL-19, CCL-20, CCL-21, CCL-22, CCL-23, CCL-24, CCL-25, CCL-26, CCL-27, CCL-28, CXCL1, CXCL2, CXCL3, CXCL4, CXCL5, CXCL6, CXCL7, CXCL8, CXCL9, CXCL10, CXCL11, CXCL12, CXCL13, CXCL14, 15, C5, CXCL16, CXCL17, XCL1, XCL2, fractalkine, IFN-α, IFN-β, IFN-γ, IFN-ε, IFN-κ, IFN-ω, IL10R2, IFNLR1, CD40LG, CD70, EDA, FASLG (TNFSF6), LTA (TNFSF1), LTB (TNFSF3), TNFa, TNFSF4 (OX40L), TNFSF8 (CD153), TNFSF9, TNFSF10 (TRAIL), TNFSF11 (RANKL), TNFSF12 (TWEAK), TNFSF13, TNFSF13B, TNFSF14, TNFSF15, TNFSF18, CSF1, CSF2 (GM-CSF), and CSF3 (G-CSF). More preferred examples of cytokines include IL-2, IL6, IL-10, IL-12, IL-15, IL-17, interferons, GM-CSF, and TNF. Cytokines are produced by a broad range of cells, including immune cells like macrophages, B lymphocytes, T lymphocytes and mast cells, as well as endothelial cells, fibroblasts, and various stromal cells, whereby a given cytokine may be produced by more than one type of cell. An antibody or antigen-binding fragment comprising a functional domain comprising such a cytokine or a functional fragment thereof may elicit a pro-inflammatory immunostimulating response or an anti-inflammatory immunosuppressive or cytotoxic response, depending on the cytokine selected.

Other preferred ligands include, for example, hormones, which are peptides, polypeptides or proteins. Hormones are signaling molecules, which are transported by the circulatory system to target distant organs, in particular to regulate physiology and behaviour. Hormones are typically produced by glands in multicellular organisms. A particularly preferred hormone is (human) growth hormone. Further examples of hormones include TRH, vasopressin, insulin, prolactin, ACTH, oxytocin, atrial-natriuretic peptide (ANP), glucagon, somatostatin, cholecystokinin, gastrin, leptin, angiotensin II, basic fibroblast growth factor-2, and parathyroid hormone-related protein.

A functional fragment of a ligand may be any fragment of a ligand, which has the ability to mediate a functionality. Usually, such fragments are referred to as "domains". Accordingly, the functional fragment of a ligand may be any domain of the ligand. Preferred examples include functional fragments (e.g., domains) of the (exemplified) ligands described above. Preferably, the functional fragment of the ligand, which is comprised by the (additional) functional domain is an Ig-like domain.

Preferably, the functional domain (ii) of the first polypeptide chain and/or the functional domain (v) of the second polypeptide chain of the antibody, or the antigen binding fragment, according to the present invention, comprises or consists of an (independent) binding site. Accordingly, it is preferred that the first and/or the second polypeptide chain of the antibody, or the antigen binding fragment thereof, according to the present invention comprises an (independent) binding site.

In general, the "(independent) binding site" is a region of the polypeptide chain to which a specific target (e.g., a molecule and/or an ion) can bind to, in particular by forming a chemical bond, for example a non-covalent bond. A non-covalent bond is a relatively weak chemical bond that does not involve an intimate sharing of electrons. Multiple noncovalent bonds often stabilize the conformation of macromolecules and mediate highly specific interactions between molecules. Accordingly, the binding site is a functional domain of the first and/or the second polypeptide chain, which provides binding functionality. In particular, the binding site is not a linker, such as a GS-linker. Even though the binding site may optionally comprise a linker (peptide), such as a GS-linker, it does preferably not consist of a linker (peptide), such as a GS-linker. In other words, even if the binding site comprises a linker (peptide), such as a GS-linker, it preferably comprises an additional amino acid sequence mediating a function distinct from (purely) linking two peptides to each other. Accordingly, the binding site is preferably distinct from a linker (peptide), such as a GS-linker. In particular, the binding site may not comprise a linker (peptide), such as a GS-linker. A linker does typically not provide a binding functionality.

Importantly, the (independent) binding site (ii) of the first polypeptide chain does not comprise a fragment of the second polypeptide chain. Accordingly, the optional independent binding site (v) of the second polypeptide chain does not comprise a fragment of the first polypeptide chain. In other words, the second polypeptide chain (in particular any fragment, such as even a single amino acid, thereof) is not required for or involved in the independent binding site of the first polypeptide chain. Moreover, if the second polypeptide chain also comprises an independent binding site, the first polypeptide chain (in particular any fragment, such as even a single amino acid, thereof) is not required for or involved in the independent binding site of the second polypeptide chain. Accordingly, the independent binding site differs from an antigen binding site formed by the variable domain of the first polypeptide chain together with the variable domain of the second polypeptide chain. In other words, the independent binding site differs from an antigen binding site formed by variable domains of two different polypeptide chains (however, the independent binding site may still comprise an antigen binding site—if the involved variable domains are located on a single polypeptide chain, as described in more detail below).

Preferably, the (independent) binding site is selected from the group consisting of receptors and functional fragments thereof, ligands and functional fragments thereof, CD molecules and functional fragments thereof, single chain antibodies and antigen binding fragments thereof, antigens and functional fragments thereof, and tags.

More preferably, the (independent) binding site comprises or consists of a receptor or a functional fragment thereof. Receptors are typically able to bind to a (specific) ligand. Accordingly, receptors may be also referred to as (independent) binding sites. Various receptors are described above and preferred embodiments and examples thereof apply accordingly.

In the context of the binding site, a functional fragment of a receptor is such a fragment of the receptor, which retains the receptor's ability to bind to its ligand. Since the binding site may comprise a receptor or a functional fragment thereof, it is the binding function of the receptor, to which the term "functional" refers to in the context of the binding site. Other fragments/domains of the receptor may be preferably not comprised by the (independent) binding site. For example, a receptor may comprise one or more transmembrane domain(s), which are usually not involved in the receptor's binding function, and which are, thus, preferably not included in the (independent) binding site. Accordingly, it is most preferred that the fragment of the receptor, which is comprised by the (independent) binding site, is merely the receptor's binding site (in particular without any further domains of the receptor).

It is also more preferred that, the (independent) binding site comprises or consists of a ligand or a functional fragment thereof. Ligands are typically able to bind to a (specific) receptor.

Accordingly, ligands may be also referred to as (independent) binding sites. Various ligands are described above and preferred embodiments and examples thereof apply accordingly.

In the context of the binding site, a functional fragment of a ligand is such a fragment of the ligand, which retains the ligand's binding ability. Since the binding site may comprise a ligand or a functional fragment thereof, it is the binding function of the ligand, to which the term "functional" refers to in the context of the binding site. Other fragments/domains of the ligand may be preferably not comprised by the (independent) binding site. Accordingly, it is most preferred that the fragment of the ligand, which is comprised by the (independent) binding site, is merely the ligand's binding site (in particular without any further domains of the ligand).

Preferably, the (independent) binding site of the first polypeptide chain and/or of the second polypeptide chain is a CD (cluster of differentiation) molecule or a functional fragment thereof. A CD (cluster of differentiation) molecule is a cell surface marker. CD molecules often act as receptors or ligands or are involved in cell adhesion. The CD nomenclature was developed and is maintained through the HLDA (Human Leukocyte Differentiation Antigens) workshop started in 1982. Examples of CD molecules, which may serve as binding sites in the context of the present invention, may be retrieved, for example, from a variety of sources known to the person skilled in the art, such as the ebioscience CD chart accessible on the ebioscience web site as "human-cd-chart" her, BD Bioscience's "Human and Mouse CD Marker Handbook" (retrievable at the BD biosciences web site as "cd marker handbook" or from the Human Cell Differentiation Molecules (HCDM) org web site. Accordingly, the (independent) binding site of the first polypeptide chain and/or of the second polypeptide chain may be a CD marker, or a functional fragment thereof, for example a (human) CD marker described in the BD Bioscience's "Human and Mouse CD Marker Handbook" or in other sources of "CD marker charts", which typically also indicate the binding partners, such that an appropriate binding site can be selected.

A functional fragment of a CD molecule is such a fragment of the CD molecule, which retains the CD molecule's binding ability. In the context of the present invention, the binding site may comprise a CD molecule or a functional fragment thereof, and, accordingly, it is the binding function of the CD molecule to which the term "functional" refers to. Other fragments/domains of the CD molecule may be preferably not comprised by the (independent) binding site. Accordingly, it is most preferred that the fragment of the CD molecule, which is comprised by the (independent) binding site, is merely the CD molecule's binding site (in particular without any further domains of the CD molecule). Preferably, the functional fragment of the CD molecule, which is comprised by the (independent) binding site is an Ig-like domain.

Preferably, the (independent) binding site of the first polypeptide chain and/or of the second polypeptide chain is a single chain antibody (such as scFv or VHH) or an antigen binding fragment thereof. It is also preferred that the (independent) binding site of the first polypeptide chain and/or of the second polypeptide chain is an antigen or a functional fragment thereof, such as an epitope.

Preferably, the (independent) binding site of the first polypeptide chain and/or of the second polypeptide chain is a single chain antibody or an antigen binding fragment thereof. A single chain antibody is a recombinant antibody consisting of one single polypeptide chain only. Preferred examples of single chain antibodies include single chain antibodies without constant domains, such as single domain antibodies, single chain antibodies based on single chain variable fragments (scFv's) and single chain diabodies (scDb), and single chain antibodies with constant domains, such as single chain Fab fragments (scFab; Hust M, Jostock T, Menzel C, Voedisch B, Mohr A, Brenneis M, Kirsch M I, Meier D, Dubel S. Single chain Fab (scFab) fragment. BMC Biotechnol. 2007 Mar. 8; 7:14).

Preferred examples of single chain antibodies based on single chain variable fragments (scFv's) include scFv (one single VH and one single VL domain) and tandem scFv's, such as tandem-di-scFv (BiTE), tandem-tri-scFv and tandem-tetra-scFv.

A single domain antibody (also referred to as "nanobody") is an antibody fragment comprising/consisting of one single (monomeric) variable domain only. Like a whole antibody, a single domain antibody is able to bind selectively to a specific antigen. The first single domain antibodies were engineered from heavy-chain antibodies found in camelids; these are called "VHH" or "VHH fragments". Cartilaginous fishes also have heavy-chain antibodies (IgNAR, 'immunoglobulin new antigen receptor'), from which single-domain antibodies, called "$V_{NAR}$" or "$V_{NAR}$ fragments", can be obtained. An alternative approach is to split the dimeric variable domains from common immunoglobulin G (IgG) from humans or mice into monomers. Accordingly, single domain antibodies may be derived from heavy or light chain variable domains (VH or VL). Preferred examples of single domain antibodies include VHH, VNAR, IgG-derived VH and IgG-derived VL.

Most preferably, the functional domain of the first polypeptide chain and/or of the second polypeptide chain is a VHH or an scFv. A most preferred example of a VHH is T3-VHH or F4-VHH. For example, the single domain antibody preferably comprises or consists of an amino acid sequence as set forth in SEQ ID NO: 16 or 18 or a sequence variant thereof having at least 70%, preferably at least 75%, more preferably at least 80%, even more preferably at least 85%, still more preferably 90%, particularly preferably 95%, and most preferably at least 98% sequence identity. A most preferred example of an scFv is TT39.7-scFv or MPE8-scFv. For example, the single domain antibody preferably comprises or consists of an amino acid sequence as set forth in SEQ ID NO: 17 or 19 or a sequence variant thereof having at least 70%, preferably at least 75%, more preferably at least 80%, even more preferably at least 85%, still more preferably 90%, particularly preferably 95%, and most preferably at least 98% sequence identity.

Preferably, the (independent) binding site of the first polypeptide chain and/or of the second polypeptide chain is an antigen or a functional fragment thereof, in particular an epitope. An antigen is a molecule, or a portion of a molecule capable of being bound by an antibody. As the antigen, or the functional fragment thereof, is comprised by the polypeptide chain, it is understood that in the context of the present invention, if the binding site is an antigen or a functional fragment thereof, said antigen or functional fragment thereof is a peptide or polypeptide. An antigen typically comprises one or more epitopes. The epitope is that part of the antigen, which is bound by an antibody ("recognized" by an antibody). Preferred examples of antigens include, but are not limited to, serum proteins, e.g. cytokines such as IL4, IL5, IL9 and IL13, bioactive peptides, cell surface molecules, e.g. receptors, transporters, ion-channels, viral and bacterial proteins, RAGE (Receptor for Advanced Glycosylation End Products), GPVI and collagen.

A functional fragment of an antigen is such a fragment of the antigen, which retains the antigen's binding ability. Accordingly, the fragment of the antigen is preferably an epitope or it comprises one or more epitopes. Other fragments/domains of the antigen may be preferably not comprised by the (independent) binding site. Accordingly, it is most preferred that the fragment of the antigen, which is comprised by the (independent) binding site, is an epitope or includes more than one epitope (in particular without any further domains of the antigen).

It is also preferred that the (independent) binding site of the first polypeptide chain and/or of the second polypeptide chain is a tag comprising a binding site. Most tags are able to bind, e.g. affinity tags. Accordingly, those tags, which have the ability to bind to another molecule, may be also referred to as (independent) binding sites. Various tags, including tags comprising a binding site, are described above and preferred embodiments and examples apply accordingly.

Most preferably, the (additional) functional domain of the first polypeptide chain and/or of the second polypeptide chain is an Ig-like domain, an scFv, a VHH or a Strep-tag. In particular, the (additional) functional domain of the first polypeptide chain and/or of the second polypeptide chain preferably comprises or consists of an amino acid sequence as set forth in any of SEQ ID NOs 13-20, or a functional sequence variant thereof having at least 80%, preferably at least 85%, more preferably at least 90%, even more preferably at least 95% and most preferably at least 98% sequence identity.

Preferably, the first polypeptide chain comprises one single variable domain (i)N-terminal of the (additional) functional domain (ii) and the second polypeptide chain comprises one single variable domain (iv)N-terminal of the optional (additional) functional domain (v) or N-terminal of the one or more constant domains (vi), the one single variable domain (iv) of the second polypeptide chain forming an antigen binding site with the variable domain (i) of the first polypeptide chain. Preferred examples of such antibodies and antigen binding fragments, according to the present invention are shown in FIGS. 1B and 1C (all formats of FIGS. 1B and 1C, except the antibody based on DVD-Ig shown in the lowest panel of FIG. 1C).

Alternatively, the first polypeptide chain may comprise two or more variable domains (i)N-terminal of the (additional) functional domain (ii) and the second polypeptide chain may comprise two or more variable domains (iv)N-terminal of the optional (additional) functional domain (v) or N-terminal of the one or more constant domains (vi), the two or more variable domains (iv) of the second polypeptide chain forming antigen binding sites with the two or more variable domains (i) of the first polypeptide chain. For example, the scaffold antibody, into whose elbow region the (additional) functional domain is inserted, may be a bispecific antibody of the DVD-Ig format, for example as shown in FIG. 1C, lowest panel "DVD-Ig".

It is also preferred that the first polypeptide chain comprises a single chain antibody, such as an scFv or a single domain antibody, for example VHH, N-terminal of the most N-terminal variable domain (i) and/or C-terminal of the most C-terminal constant domain (iii). Alternatively or additionally, the second polypeptide chain may comprise a single chain antibody, such as an scFv or a single domain antibody, for example VHH, N-terminal of the most N-terminal variable domain (i) or C-terminal of the most C-terminal constant domain (vi). Preferred examples thereof are shown in FIG. 1C and include scFv-(H)IgG, IgG(H)-scFv, scFv-(L)gG, IgG(L)-scFv, V-(H)IgG, IgG(H)-V, V-(L)IgG, and IgG(L)-V antibodies with one or more (additional) functional domains inserted into the elbow of the heavy and/or light chain(s).

Preferably, the first polypeptide chain and the second polypeptide chain each comprise one single constant domain, in particular a CL domain and a CH1 domain, respectively. Preferred examples thereof are shown in FIG. 1C and include F(ab)$_2$ and Fab antibody fragments with one or more (additional) functional domains inserted into the elbow of the heavy and/or light chain(s).

Alternatively, it is also preferred that the first polypeptide chain or the second polypeptide chain comprises one single constant domain, in particular a CL domain; and the other of the first polypeptide chain or the second polypeptide chain comprises a CH1 domain and one or more further constant domains, such as a CH2 and/or CH3 domain. Preferred examples of such antibodies and antigen binding fragments, according to the present invention are shown in FIGS. 1B and 1C (all formats of FIGS. 1B and 1C, except the antibody fragments based on F(ab)$_2$ and Fab shown in the upper panels of FIG. 1C).

Preferably, the antibody, or the antigen binding fragment thereof, according to the present invention comprises an Fc moiety, in particular an Fc region. More preferably, the Fc moiety is derived from human origin, e.g. from human IgG1, IgG2, IgG3, and/or IgG4, whereby human IgG1 is particularly preferred.

As used herein, the term "Fc moiety" refers to a sequence derived from the portion of an immunoglobulin heavy chain beginning in the hinge region just upstream of the papain cleavage site (e.g., residue 216 in native IgG, taking the first residue of heavy chain constant region to be 114) and ending at the C-terminus of the immunoglobulin heavy chain. Accordingly, an Fc moiety may be a complete Fc moiety or a portion (e.g., a domain) thereof. A complete Fc moiety comprises at least a hinge domain, a CH2 domain, and a CH3 domain (e.g., EU amino acid positions 216-446). An additional lysine residue (K) is sometimes present at the extreme C-terminus of the Fc moiety, but is often cleaved from a mature antibody. Each of the amino acid positions within an Fc moiety have been numbered according to the art-recognized EU numbering system of Kabat, see e.g., by Kabat et al., in "Sequences of Proteins of Immunological Interest", U.S. Dept. Health and Human Services, 1983 and 1987.

Preferably, in the context of the present invention an Fc moiety comprises at least one of: a hinge (e.g., upper, middle, and/or lower hinge region) domain, a CH2 domain, a CH3 domain, or a variant, portion, or fragment thereof. In preferred embodiments, an Fc moiety comprises at least a hinge domain, a CH2 domain or a CH3 domain. More preferably, the Fc moiety is a complete Fc moiety. The Fc moiety may also comprises one or more amino acid insertions, deletions, or substitutions relative to a naturally-occurring Fc moiety. For example, at least one of a hinge domain, CH2 domain or CH3 domain (or portion thereof) may be deleted. For example, an Fc moiety may comprise or consist of: (i) hinge domain (or portion thereof) fused to a CH2 domain (or portion thereof), (ii) a hinge domain (or portion thereof) fused to a CH3 domain (or portion thereof), (iii) a CH2 domain (or portion thereof) fused to a CH3 domain (or portion thereof), (iv) a hinge domain (or portion thereof), (v) a CH2 domain (or portion thereof), or (vi) a CH3 domain or portion thereof.

It will be understood by one of ordinary skill in the art that the Fc moiety may be modified such that it varies in amino acid sequence from the complete Fc moiety of a naturally occurring immunoglobulin molecule, while retaining at least one desirable function conferred by the naturally-occurring Fc moiety. Such functions include Fc receptor (FcR) binding, antibody half-life modulation, ADCC function, protein A binding, protein G binding, and complement binding. The portions of naturally occurring Fc moieties, which are responsible and/or essential for such functions are well known by those skilled in the art.

For example, to activate the complement cascade C1q binds to at least two molecules of IgG1 or one molecule of IgM, attached to the antigenic target (Ward, E. S., and Ghetie, V., Ther. Immunol. 2 (1995) 77-94). Burton, D. R., described (Mol. Immunol. 22 (1985) 161-206) that the heavy chain region comprising amino acid residues 318 to 337 is involved in complement fixation. Duncan, A. R., and Winter, G. (Nature 332 (1988) 738-740), using site directed mutagenesis, reported that Glu318, Lys320 and Lys322 form the binding site to C1q. The role of Glu318, Lys320 and Lys 322 residues in the binding of C19 was confirmed by the ability of a short synthetic peptide containing these residues to inhibit complement mediated lysis.

For example, FcR binding can be mediated by the interaction of the Fc moiety (of an antibody) with Fc receptors (FcRs), which are specialized cell surface receptors on hematopoietic cells. Fc receptors belong to the immunoglobulin superfamily, and were shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC; Van de Winkel, J. G., and Anderson, C. L., J. Leukoc. Biol. 49 (1991) 511-524). FcRs are defined by their specificity for immunoglobulin classes; Fc receptors for IgG antibodies are referred to as FcγR, for IgE as FcεR, for IgA as FcαR and so on and neonatal Fc receptors are referred to as FcRn. Fc receptor binding is described for example in Ravetch, J. V., and Kinet, J. P., Annu. Rev. Immunol. 9 (1991) 457-492; Capel, P. J., et al., Immunomethods 4 (1994) 25-34; de Haas, M., et al., J Lab. Clin. Med. 126 (1995) 330-341; and Gessner, J. E., et al., Ann. Hematol. 76 (1998) 231-248.

Cross-linking of receptors by the Fc domain of native IgG antibodies (FcγR) triggers a wide variety of effector functions including phagocytosis, antibody-dependent cellular cytotoxicity, and release of inflammatory mediators, as well as immune complex clearance and regulation of antibody production. Therefore, Fc moieties providing cross-linking of receptors (FcγR) are preferred. In humans, three classes of FcγR have been characterized, which are: (i) FcγRI (CD64), which binds monomeric IgG with high affinity and is expressed on macrophages, monocytes, neutrophils and eosinophils; (ii) FcγRII (CD32), which binds complexed IgG with medium to low affinity, is widely expressed, in particular on leukocytes, is known to be a central player in antibody-mediated immunity, and which can be divided into FcγRIIA, FcγRIIB and FcγRIIC, which perform different functions in the immune system, but bind with similar low affinity to the IgG-Fc, and the ectodomains of these receptors are highly homologous; and (iii) FcγRIII (CD16), which binds IgG with medium to low affinity and exists as two types: FcγRIIIA found on NK cells, macrophages, eosinophils and some monocytes and T cells and mediating ADCC and FcγRIIIB, which is highly expressed on neutrophils. FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils.

Regarding FcγRI binding, modification in native IgG of at least one of E233-G236, P238, D265, N297, A327 and P329 reduces binding to FcγRI. IgG2 residues at positions 233-236, substituted into IgG1 and IgG4, reduces binding to FcγRI by $10^3$-fold and eliminated the human monocyte response to antibody-sensitized red blood cells (Armour, K. L., et al. Eur. J. Immunol. 29 (1999) 2613-2624). Regarding FcγRII binding, reduced binding for FcγRIIA is found e.g. for IgG mutation of at least one of E233-G236, P238, D265, N297, A327, P329, D270, Q295, A327, R292 and K414. Regarding FcγRII binding, reduced binding to FcγRIIIA is found e.g. for mutation of at least one of E233-G236, P238, D265, N297, A327, P329, D270, Q295, A327, S239, E269, E293, Y296, V303, A327, K338 and D376. Mapping of the binding sites on human IgG1 for Fc receptors, the above mentioned mutation sites and methods for measuring binding to FcγRI and FcγRIIA are described in Shields, R. L., et al., J. Biol. Chem. 276 (2001) 6591-6604.

Regarding binding to the crucial FcγRII, two regions of native IgG Fc appear to be critical for interactions of FcγRIIs and IgGs, namely (i) the lower hinge site of IgG Fc, in particular amino acid residues L, L, G, G (234-237, EU numbering), and (ii) the adjacent region of the CH2 domain of IgG Fc, in particular a loop and strands in the upper CH2 domain adjacent to the lower hinge region, e.g. in a region of P331 (Wines, B. D., et al., J. Immunol. 2000; 164: 5313-5318). Moreover, FcγRI appears to bind to the same site on IgG Fc, whereas FcRn and Protein A bind to a different site on IgG Fc, which appears to be at the CH2-CH3 interface (Wines, B. D., et al., J. Immunol. 2000; 164: 5313-5318).

For example, the Fc moiety may comprise or consist of at least the portion of an Fc moiety that is known in the art to be required for FcRn binding or extended half-life. Alternatively or additionally, the Fc moiety of the antibody of the invention comprises at least the portion of known in the art to be required for Protein A binding and/or the Fc moiety of the antibody of the invention comprises at least the portion of an Fc molecule known in the art to be required for protein G binding. Accordingly, a preferred Fc moiety comprises at least the portion known in the art to be required for FcγR binding. As outlined above, a preferred Fc moiety may thus at least comprise (i) the lower hinge site of native IgG Fc, in particular amino acid residues L, L, G, G (234-237, EU numbering), and (ii) the adjacent region of the CH2 domain of native IgG Fc, in particular a loop and strands in the upper CH2 domain adjacent to the lower hinge region, e.g. in a region of P331, for example a region of at least 3, 4, 5, 6, 7, 8, 9, or 10 consecutive amino acids in the upper CH2 domain of native IgG Fc around P331, e.g. between amino acids 320 and 340 (EU numbering) of native IgG Fc.

Preferably, the antibody, or antigen binding fragment thereof, according to the present invention comprises an Fc region. As used herein, the term "Fc region" refers to the portion of an immunoglobulin formed by two or more Fc moieties of antibody heavy chains. For example, the Fc region may be monomeric or "single-chain" Fc region (i.e., a scFc region). Single chain Fc regions are comprised of Fc moieties linked within a single polypeptide chain (e.g., encoded in a single contiguous nucleic acid sequence). Exemplary scFc regions are disclosed in WO 2008/143954 A2. Preferably, the Fc region is a dimeric Fc region. A "dimeric Fc region" or "dcFc" refers to the dimer formed by the Fc moieties of two separate immunoglobulin heavy chains. The dimeric Fc region may be a homodimer of two identical Fc moieties (e.g., an Fc region of a naturally occurring immunoglobulin) or a heterodimer of two non-identical Fc moieties.

The Fc moieties of the Fc region may be of the same or different class and/or subclass. For example, the Fc moieties may be derived from an immunoglobulin (e.g., a human immunoglobulin) of an IgG1, IgG2, IgG3 or IgG4 subclass. Preferably, the Fc moieties of Fc region are of the same class and subclass. However, the Fc region (or one or more Fc moieties of an Fc region) may also be chimeric, whereby a chimeric Fc region may comprise Fc moieties derived from different immunoglobulin classes and/or subclasses. For example, at least two of the Fc moieties of a dimeric or single-chain Fc region may be from different immunoglobulin classes and/or subclasses. Additionally or alternatively, the chimeric Fc regions may comprise one or more chimeric Fc moieties. For example, the chimeric Fc region or moiety may comprise one or more portions derived from an immunoglobulin of a first subclass (e.g., an IgG1, IgG2, or IgG3 subclass) while the remainder of the Fc region or moiety is of a different subclass. For example, an Fc region or moiety of an Fc polypeptide may comprise a CH2 and/or CH3 domain derived from an immunoglobulin of a first subclass (e.g., an IgG1, IgG2 or IgG4 subclass) and a hinge region from an immunoglobulin of a second subclass (e.g., an IgG3 subclass). For example, the Fc region or moiety may comprise a hinge and/or CH2 domain derived from an immunoglobulin of a first subclass (e.g., an IgG4 subclass) and a CH3 domain from an immunoglobulin of a second subclass (e.g., an IgG1, IgG2, or IgG3 subclass). For example, the chimeric Fc region may comprise an Fc moiety (e.g., a complete Fc moiety) from an immunoglobulin for a first subclass (e.g., an IgG4 subclass) and an Fc moiety from an immunoglobulin of a second subclass (e.g., an IgG1, IgG2 or IgG3 subclass). For example, the Fc region or moiety may comprise a CH2 domain from an IgG4 immunoglobulin and a CH3 domain from an IgG1 immunoglobulin. For example, the Fc region or moiety may comprise a CH1 domain and a CH2 domain from an IgG4 molecule and a CH3 domain from an IgG1 molecule. For example, the Fc region or moiety may comprise a portion of a CH2 domain from a particular subclass of antibody, e.g., EU positions 292-340 of a CH2 domain. For example, an Fc region or moiety may comprise amino acids a positions 292-340 of CH2 derived from an IgG4 moiety and the remainder of CH2 derived from an IgG1 moiety (alternatively, 292-340 of CH2 may be derived from an IgG1 moiety and the remainder of CH2 derived from an IgG4 moiety).

Moreover, an Fc region or moiety may (additionally or alternatively) for example comprise a chimeric hinge region. For example, the chimeric hinge may be derived, e.g. in part, from an IgG1, IgG2, or IgG4 molecule (e.g., an upper and lower middle hinge sequence) and, in part, from an IgG3 molecule (e.g., an middle hinge sequence). In another example, an Fc region or moiety may comprise a chimeric hinge derived, in part, from an IgG1 molecule and, in part, from an IgG4 molecule. In another example, the chimeric hinge may comprise upper and lower hinge domains from an IgG4 molecule and a middle hinge domain from an IgG1 molecule. Such a chimeric hinge may be made, for example, by introducing a proline substitution (Ser228Pro) at EU position 228 in the middle hinge domain of an IgG4 hinge region. In another embodiment, the chimeric hinge can comprise amino acids at EU positions 233-236 are from an IgG2 antibody and/or the Ser228Pro mutation, wherein the remaining amino acids of the hinge are from an IgG4 antibody. Chimeric hinges, which may be used in the Fc moiety of the antibody according to the present invention, are described in US 2005/0163783 A1.

In the present invention it is preferred that the Fc moiety, or the Fc region, comprises or consists of an amino acid sequence derived from a human immunoglobulin sequence (e.g., from an Fc region or Fc moiety from a human IgG molecule). However, polypeptides may comprise one or more amino acids from another mammalian species. For example, a primate Fc moiety or a primate binding site may be included in the subject polypeptides. Alternatively, one or more murine amino acids may be present in the Fc moiety or in the Fc region.

Preferably, the antibody according to the present invention comprises, in particular in addition to an Fc moiety as described above, other parts derived from a constant region, in particular from a constant region of IgG, preferably from a constant region of IgG1, more preferably from a constant region of human IgG1. More preferably, the antibody according to the present invention comprises, in particular in addition to an Fc moiety as described above, all other parts of the constant regions, in particular all other parts of the constant regions of IgG, preferably all other parts of the constant regions of IgG1, more preferably all other parts of the constant regions of human IgG1.

Particularly preferred sequences of constant regions are the amino acid sequences according to SEQ ID NOs: 3, 4 or 7. Preferably, the heavy chain constant region comprises or consists of IgG1 CH1-CH2-CH3, in particular comprising or consisting of the amino acid sequence according to SEQ ID NO: 3 or a functional sequence variant thereof, as described herein. Preferably, the light chain constant region comprises or consists of IgG1 CL, in particular comprising or consisting of the amino acid sequence according to SEQ ID NO: 4 or a functional sequence variant thereof, as described herein.

It is also preferred that the antibody, or the antigen binding fragment thereof, according to the present invention does not comprise an Fc region or an Fc moiety. In particular, the constant domains required for the elbow (CH1 and CL) are typically not involved in the Fc moiety or Fc region. Therefore, the antibody, or the antigen binding fragment thereof, according to the present invention does preferably not comprise an Fc region or an Fc moiety. Examples of such antibodies (or antibody fragments) include those based on Fab or F(ab)$_2$ (IEI-Fab or IEI-F(ab)$_2$).

Preferably, the first polypeptide chain and/or the second polypeptide chain of the antibody or the antigen binding fragment according to the present invention comprises one or more linkers. For example, the first polypeptide chain and/or the second polypeptide chain of the antibody or the antigen binding fragment according to the present invention may comprise 1, 2, 3, 4, 5, 6, 7, 8, 9 or 10 linkers. More preferably, the first polypeptide chain and/or the second polypeptide chain of the antibody or the antigen binding fragment according to the present invention comprises one linker or two linkers. It is also preferred that the first polypeptide chain and/or the second polypeptide chain of the antibody or the antigen binding fragment according to the present invention comprises three or four linkers. In general, a linker may provide more flexibility to the polypeptide chain. Preferably, the first polypeptide chain and/or the second polypeptide chain comprises a linker between the constant region and the (additional) functional domain. Alternatively, the first polypeptide chain and/or the second polypeptide chain may not comprise a linker between the constant region and the (additional) functional domain. If the second polypeptide does not comprise a (additional) functional domain, the second polypeptide chain may comprise a linker between the constant region and the variable region. Alternatively, the second polypeptide chain may not comprise a linker between the constant region and the variable region. Preferably, the first polypeptide chain and/or the second polypeptide chain comprises a linker between the (additional) functional domain and the variable domain, in particular the most C-terminal variable domain. Alternatively, the first polypeptide chain and/or the second polypeptide chain may not comprise a linker between the (additional) functional domain and the variable domain, in particular the most C-terminal variable domain. If the first polypeptide chain and/or the second polypeptide chain comprises more than one variable domain, it is also preferred that the first polypeptide chain and/or the second polypeptide chain comprises one or more linkers between the variable domains. Alternatively, the first polypeptide chain and/or the second polypeptide chain may not comprise one or more linkers between the variable domains. More preferably, the first polypeptide chain and/or the second polypeptide chain comprises alinker between the constant region and the (additional) functional domain and a linker between the (additional) functional domain and the variable domain, in particular the most C-terminal variable domain. Alternatively, the first polypeptide chain and/or the second polypeptide chain may comprise neither a linker between the constant region and the (additional) functional domain nor a linker between the (additional) functional domain and the variable domain, in particular the most C-terminal variable domain. Moreover, the first polypeptide chain may comprise a linker between the constant region and the (additional) functional domain and a linker between the (additional) functional domain and the variable domain, in particular the most C-terminal variable domain, while the second polypeptide chain may comprise neither a (additional) functional domain nor a linker between the between the constant region and the variable region. It is also preferred—if the first polypeptide chain and/or the second polypeptide chain comprises more than one variable domain—that the first polypeptide chain and/or the second polypeptide chain comprises a linker between the constant region and the (additional) functional domain; a linker between the (additional) functional domain and the variable domain, in particular the most C-terminal variable domain; and one or more linkers between the variable domains.

If the first polypeptide chain and/or the second polypeptide chain comprises more than one linker, the linkers may be the same or different.

Preferably, a linker consists of up to 20 amino acids, such as 1, 2, 3, 4, 5, 6, 7, 8, 9, 10, 11, 12, 13, 14, 15, 16, 17, 18, 19 or 20 amino acids, more preferably of up to 15 amino acids, such as 1, 2, 3, 4, 5, 6, 7, 8, 9, 10, 11, 12, 13, 14 or 15 amino acids, even more preferably of up to 10 amino acids, such as 1, 2, 3, 4, 5, 6, 7, 8, 9, or 10 amino acids, and still more preferably of up to 5 amino acids, such as 1, 2, 3, 4, or 5 amino acids. The linker may be derived from naturally occurring amino acid sequences, such as flanking regions, or from non-natural amino acid sequences. Preferably, the (additional) functional domain corresponds to a single exon or to more than one exons and the amino acid sequence of the linker is retrieved from the intronic sequences flanking that single exon or the more than one exons. For example, (i) the linker between a variable region and a (additional) functional domain (which is encoded by an exon or a sequence variant thereof) may be encoded by the flanking intronic sequence immediately before (in 5'-3' direction) the exon or sequence variant thereof to be used as "(additional) functional domain" and/or (ii) the linker between a (additional) functional domain (which is encoded by an exon or a sequence variant thereof) and a constant region may be encoded by the flanking intronic sequence immediately after (in 5'-3' direction) the exon or sequence variant thereof to be used as "(additional) functional domain". Preferably, the linker does not contain any Cys (C) residues. Preferably, the linker comprises or consists of one or more Glycin (Gly) residues and/or one or more Serin (Ser) residues ("GS linker"). Preferred examples of GS-linkers include the amino acid sequences according to SEQ ID NOs 43-48, most preferably the linker is according to SEQ ID NO: 45. Preferred examples of intronic sequence linkers include the amino acid sequences according to SEQ ID NOs 49-52. Most preferably, the linker comprises or consists of an amino acid sequence as set forth in any one of SEQ ID NOs 43-52.

For example, the first polypeptide chain and/or the second polypeptide chain may comprise (in N-to-C-terminal direction) a linker as set forth in SEQ ID NO: 49, or a functional sequence variant thereof, directly followed by a (additional) functional domain as set forth in SEQ ID NO: 14, or a functional sequence variant thereof. Moreover, the first polypeptide chain and/or the second polypeptide chain may comprise (in N-to-C-terminal direction) a (additional) functional domain as set forth in SEQ ID NO: 14, or a functional sequence variant thereof, directly followed by a linker as set forth in SEQ ID NO: 50, or a functional sequence variant thereof. Most preferably, the first polypeptide chain and/or the second polypeptide chain may comprise (in N-to-C-terminal direction) (a variable domain, directly followed by) a linker as set forth in SEQ ID NO: 49, or a functional sequence variant thereof, directly followed by a (additional) functional domain as set forth in SEQ ID NO: 14, or a functional sequence variant thereof, directly followed by a linker as set forth in SEQ ID NO: 50, or a functional sequence variant thereof (directly followed by a constant domain.

For example, the first polypeptide chain and/or the second polypeptide chain may comprise (in N-to-C-terminal direction) a linker as set forth in SEQ ID NO: 51, or a functional sequence variant thereof, directly followed by a (additional) functional domain as set forth in SEQ ID NO: 15, or a functional sequence variant thereof. Moreover, the first polypeptide chain and/or the second polypeptide chain may comprise (in N-to-C-terminal direction) a (additional) functional domain as set forth in SEQ ID NO: 15, or a functional sequence variant thereof, directly followed by a linker as set forth in SEQ ID NO: 52, or a functional sequence variant thereof. Most preferably, the first polypeptide chain and/or the second polypeptide chain may comprise (in N-to-C-terminal direction) (a variable domain, directly followed by) a linker as set forth in SEQ ID NO: 51, or a functional sequence variant thereof, directly followed by a (additional) functional domain as set forth in SEQ ID NO: 15, or a functional sequence variant thereof, directly followed by a linker as set forth in SEQ ID NO: 52, or a functional sequence variant thereof (directly followed by a constant domain.

Alternatively, it is also preferred that the first polypeptide chain and/or the second polypeptide does not comprise any linkers.

Preferably, the first polypeptide chain of the antibody or the antigen binding fragment thereof according to the present invention comprises or consists of (in N-to-C-terminal direction): V-D-CH1, wherein
V is a variable domain (i);
D is an (additional) functional domain (ii); and
CH1 is a CH1 constant domain (iii).
V and D and/or D and CH1 may be linked via a linker as described above or may be directly linked to each other.

More preferably, the first polypeptide chain of the antibody or the antigen binding fragment thereof according to the present invention comprises or consists of (in N-to-C-terminal direction): V-D-CH1-CH2-CH3, wherein
V-D-CH1 is as described above; and
CH2 and CH3 are a CH2 constant domain and a CH3 constant domain, respectively.

It is also preferred that the first polypeptide chain of the antibody or the antigen binding fragment thereof according to the present invention comprises or consists of (in N-to-C-terminal direction): $(V)_A$-D-CH1, wherein
V-D-CH1 is as described above;
A is an integer from 1 to 5, preferably from 1 to 4, more preferably from 1 to 3 and even more preferably 1 or 2; and
the variable domains V may be coupled to each other directly or via a linker.

Preferably, the second polypeptide chain of the antibody or the antigen binding fragment thereof according to the present invention comprises or consists of (in N-to-C-terminal direction): V-CL, wherein
V is a variable domain (iv); and
CL is a constant domain (vi).
V and CL may be linked via a linker as described above or may be directly linked to each other.

It is also preferred that the second polypeptide chain of the antibody or the antigen binding fragment thereof according to the present invention comprises or consists of (in N-to-C-terminal direction): (V)A-CL, wherein
V-CL is as described above;
A being an integer from 1 to 5, preferably from 1 to 4, more preferably from 1 to 3 and even more preferably 1 or 2; and
the variable domains V may be coupled to each other directly or via a linker.

For example, the variable domain (i) of the first polypeptide chain of the antibody or the antigen binding fragment thereof according to the present invention may comprise or consist of an amino acid sequence as set forth in any one of SEQ ID NOs 1, 5, 8, or 10, or a functional sequence variant thereof having at least 80%, preferably at least 85%, more preferably at least 90%, even more preferably at least 95% and most preferably at least 98% sequence identity.

For example, the variable domain (iv) of the second polypeptide chain chain of the antibody or the antigen binding fragment thereof according to the present invention may comprise or consist of an amino acid sequence as set forth in any one of SEQ ID NOs 2, 6, 9 or 11, or a functional sequence variant thereof having at least 80%, preferably at least 85%, more preferably at least 90%, even more preferably at least 95% and most preferably at least 98% sequence identity.

Preferably, the antibody, or the antigen binding fragment thereof, according to the present invention comprises one single or two first polypeptide chains and one single or two second polypeptide chains. Examples of such antibodies, or antigen binding fragments thereof are shown in FIGS. 1B and 1C. It is also preferred that the first polypeptide chain and the second polypeptide chain are linked by a disulfide bond, thereby forming a pair. In particular, the heavy chain and the light chain of the antibody, or the antigen binding fragment thereof, according to the present invention may be linked by a disulfide bond, thereby forming a pair. Moreover, it is also preferred that the antibody, or the antigen binding fragment thereof, comprises two first polypeptide chains and two second polypeptide chains and that the two first polypeptide chains and/or the two second polypeptide chains are linked by one or more, such as two, disulfide bonds. In particular, the two heavy chains of the antibody, or the antigen binding fragment thereof, may be linked by one or more, such as two, disulfide bonds.

Preferably, the antibody, or the antigen binding fragment thereof, according to the present invention is bivalent for each specificity/antigen. In particular, it is preferred that the (additional) functional domain(s) comprise(s) or consist(s) of (an) (independent) binding site(s) and (1) the (independent) binding site(s) and (2) the antigen binding site(s) formed by the one or more variable domains of the first pair of first and second polypeptide chains correspond to (1) the (independent) binding site(s) and (2) the antigen binding site(s) formed by the one or more variable domains of the second pair of first and second polypeptide chains. Alternatively, the antibody, or the antigen binding fragment thereof, may be monovalent for each specificity (antigen).

Accordingly, it is preferred that the antigen binding site(s) formed by the one or more variable domains of the first pair of first and second polypeptide chains and the antigen binding site(s) formed by the one or more variable domains of the second pair of first and second polypeptide chains are the same or distinct.

Moreover, it is preferred that the antibody, or the antigen binding fragment thereof, according to the present invention comprises at least two (additional) functional domains, which may be the same or distinct. For example, the antibody, or the antigen binding fragment thereof, according to the present invention may comprise 2 or 4 (additional) functional domains, which may be the same or distinct.

If the antibody or the antigen binding fragment according to the present invention comprises more than one (additional) functional domain, for example in the same or in distinct polypeptide chains, the (additional) functional domains may be the same or distinct. Preferably, they may belong to the same or distinct group of functional domains. For example, at least two or all (additional) functional domains may comprise or consist of (independent) binding sites. For example, at least two or all (additional) functional domains may comprise or consist of carrier domains. For example, at least two or all (additional) functional domains may comprise or consist of reporter domains. For example, at least two or all (additional) functional domains may comprise or consist of tags. For example, at least two or all (additional) functional domains may comprise or consist of localization domains. Even if the (additional) functional domains belong to the same group of functional domains, the subgroup and, in particular, their amino acid sequence, may still be the same or distinct. For example, at least two or all (additional) functional domains may comprise or consist of the same amino acid sequences. Alternatively, it is also preferred that the (additional) functional domains belong to distinct group of functional domains. For example, one (additional) functional domain may comprise or consist of an (independent) binding site, while another (additional) functional domain of the antibody or antigen binding fragment may comprise or consist of a carrier domain. For example, one (additional) functional domain may comprise or consist of an (independent) binding site, while another (additional) functional domain of the antibody or antigen binding fragment may comprise or consist of a reporter domain. For example, one (additional) functional domain may comprise or consist of an (independent) binding site, while another (additional) functional domain of the antibody or antigen binding fragment may comprise or consist of a tag. For example, one (additional) functional domain may comprise or consist of an (independent) binding site, while another (additional) functional domain of the antibody or antigen binding fragment may comprise or consist of a localization domain. For example, one (additional) functional domain may comprise or consist of a carrier domain, while another (additional) functional domain of the antibody or antigen binding fragment may comprise or consist of a reporter domain. For example, one (additional) functional domain may comprise or consist of a carrier domain, while another (additional) functional domain of the antibody or antigen binding fragment may comprise or consist of a tag. For example, one (additional) functional domain may comprise or consist of a carrier domain, while another (additional) functional domain of the antibody or antigen binding fragment may comprise or consist of a localization domain. For example, one (additional) functional domain may comprise or consist of a reporter domain, while another (additional) functional domain of the antibody or antigen binding fragment may comprise or consist of a tag. For example, one (additional) functional domain may comprise or consist of a reporter domain, while another (additional) functional domain of the antibody or antigen binding fragment may comprise or consist of a localization domain. For example, one (additional) functional domain may comprise or consist of a localization domain, while another (additional) functional domain of the antibody or antigen binding fragment may comprise or consist of a tag.

Furthermore, it is preferred that the antibody, or the antigen binding fragment thereof, according to the present invention comprises two first polypeptide chains and two second polypeptide chains forming a first and a second pair of first and second polypeptide chains, and wherein the first pair of first and second polypeptide chains comprises at least one (additional) functional domain(s) and/or the second pair of first and second polypeptide chains comprises at least one (additional) functional domain(s). For example, the first pair of first and second polypeptide chains may comprise at least one (additional) functional domain(s), while the second pair of first and second polypeptide chains may not comprise an (additional) functional domain. For example, the first pair of first and second polypeptide chains may not comprise an (additional) functional domain, while the second pair of first and second polypeptide chains may comprise at least one (additional) functional domain(s). Most preferably, both, the first pair of first and second polypeptide chains comprises at least one (additional) functional domain(s) and the second pair of first and second polypeptide chains comprises at least one (additional) functional domain(s).

Preferably, the antibody, or the antigen binding fragment thereof, according to the present invention is derived from an IgG-like antibody, a Fab or a F(ab)$_2$. In other words, the antibody, or the antigen binding fragment thereof, comprises all of the variable and constant regions of an IgG-like antibody, a Fab or a F(ab)$_2$. In particular, an IgG-like antibody, a Fab or a F(ab)$_2$ may be used as "scaffold" antibodies, into whose elbow region a (additional) functional domain is inserted.

Preferably, the two or more variable domains (i) and (iv) of the antibody, or the antigen binding fragment thereof, according to the present invention are derived from a monoclonal antibody. In particular, the two or more variable domains (i) and (iv) of the antibody, or the antigen binding fragment thereof, according to the present invention are (correspond to) the two or more variable domains a monoclonal antibody.

It is also preferred that the variable domains and/or the constant domains of the antibody, or the antigen binding fragment thereof, according to the present invention are human or humanized. In particular, the variable domains and/or the constant domains of the antibody, or the antigen binding fragment thereof, according to the present invention correspond to the variable domains and/or the constant domains of human or humanized antibody, or antigen binding fragment thereof.

Preferably, the (additional) functional domain(s) of the antibody, or the antigen binding fragment thereof, according to the present invention comprise(s) or consist(s) of an amino acid sequence, which is human or humanized.

Preferably, the first polypeptide chain of the antibody, or the antigen binding fragment thereof, according to the present invention comprises or consists of an amino acid sequence as set forth in any one of SEQ ID NOs 53, 55, 56, 58, 59, 60, 61, 62, 64, 65, 66, 68, 69 or 70, or a functional sequence variant thereof having at least 80%, preferably at least 85%, more preferably at least 90%, even more preferably at least 95% and most preferably at least 98% sequence identity, and/or the second polypeptide chain of the antibody, or the antigen binding fragment thereof, according to the present invention comprises or consists of an amino acid sequence as set forth in any one of SEQ ID NOs 54, 57, 63, or 67, or a functional sequence variant thereof having at least 80%, preferably at least 85%, more preferably at least 90%, even more preferably at least 95% and most preferably at least 98% sequence identity.

Preferably, the first and/or the second polypeptide chain of the antibody, or the antigen binding fragment thereof, according to the present invention may not comprise or consist of an amino acid sequence as set forth in any one of SEQ ID NOs 75-92. It is also preferred that the first and/or the second polypeptide chain of the antibody, or the antigen binding fragment thereof, according to the present invention may not comprise or consist of an amino acid sequence as set forth in any one of SEQ ID NOs 96-112. More preferably, the first and/or the second polypeptide chain of the antibody, or the antigen binding fragment thereof, according to the present invention may not comprise or consist of an amino acid sequence as set forth in any one of SEQ ID NOs 75-95. Even more preferably, the (additional) functional domain comprised by the first and/or the second polypeptide chain of the antibody, or the antigen binding fragment thereof, according to the present invention may not comprise or consist of an amino acid sequence as set forth in any one of SEQ ID NOs 113-130. Still more preferably, the (additional) functional domain comprised by the first and/or the second polypeptide chain of the antibody, or the antigen binding fragment thereof, according to the present invention may not comprise or consist of an amino acid sequence as set forth in any one of SEQ ID NOs 113-133. Most preferably, the first and/or the second polypeptide chain of the antibody, or the antigen binding fragment thereof, according to the present invention may not comprise or consist of an amino acid sequence as set forth in any one of SEQ ID NOs 75-133. Optionally, the (additional) functional domain comprised by the first and/or the second polypeptide chain of the antibody, or the antigen binding fragment thereof, according to the present invention may not comprise or consist of a (mutated) LAIR1 fragment.

Nucleic Acid Molecule

In another aspect, the present invention also provides a nucleic acid molecule comprising a first polynucleotide encoding the first polypeptide chain of the antibody, or antigen-binding fragment thereof, according to the present invention and/or a second polypeptide encoding the second polypeptide chain of the antibody, or antigen-binding fragment thereof, according to the present invention.

A nucleic acid molecule is a molecule comprising, preferably consisting of nucleic acid components. The term nucleic acid molecule preferably refers to DNA or RNA molecules. In particular, it is used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Preferably, the nucleic acid molecule is a DNA molecule or an RNA molecule. Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA. Nucleic acid sequences encoding part or all of the first and/or second polypeptide chains are preferred. Preferably provided herein are thus nucleic acid sequences encoding part or all of the light and heavy chains, in particular VH and VL sequences and/or (additional) functional domains of the exemplary antibodies or antigen binding fragments of the invention.

It is also preferred that nucleic acid molecule according to the invention includes a nucleic acid sequence having at least 70%, at least 75%, at least 80%, at least 85%, at least 88%, at least 90%, at least 92%, at least 95%, at least 96%, at least 97%, at least 98% or at least 99% identity to the nucleic acid encoding a (additional) functional domain, a VH sequence and/or a VL sequence used in an (exemplary) antibody or antigen binding fragment thereof according to the present invention.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the (additional) functional domains, a VH sequence and/or a VL sequence of an (exemplary) antibody of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

Vector

Further included within the scope of the invention are vectors, for example, expression vectors, comprising a nucleic acid molecule according to the present invention. Preferably, a vector comprises a nucleic acid molecule as described above.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Cells

In a further aspect, the present invention also provides cell expressing the antibody, or the antigen binding fragment thereof, according to the present invention and/or comprising the nucleic acid molecule or the vector according the present invention.

Examples of such cells include but are not limited to, eukaryotic cells, e.g., yeast cells, animal cells or plant cells. Preferably, the cells are mammalian cells, more preferably a mammalian cell line. Preferred examples include human cells, CHO cells, HEK293T cells, PER.C6 cells, NS0 cells, human liver cells, myeloma cells or hybridoma cells.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Moreover, the cells of the present invention may be transfected stably or transiently with the vector according to the present invention, e.g. for expressing the antibody, or the antigen binding fragment thereof, according to the present invention. Preferably, the cells are stably transfected with the vector according to the present invention encoding the antibody, or the antigen binding fragment thereof, according to the present invention. Alternatively, it is also preferred that the cells are transiently transfected with the vector according to the present invention encoding the antibody, or the antigen binding fragment thereof, according to the present invention.

Composition

The present invention also provides a composition comprising one or more of:
 (i) the antibody, or the antibody fragment thereof, according to the present invention;
 (ii) the nucleic acid molecule according to the present invention;
 (iii) the vector comprising the nucleic acid according to the present invention; and/or
 (iv) the cell expressing the antibody according to the present invention and/or comprising the vector or the nucleic acid molecule according to the present invention.

In other words, the present invention also provides a composition comprising the antibody, or the antigen binding fragment thereof, according to the present invention, the nucleic acid according to the present invention, the vector according to the present invention and/or the cell according to the present invention.

Preferably, the composition is a pharmaceutical composition. The pharmaceutical composition may preferably also contain a pharmaceutically acceptable carrier, diluent and/or excipient. Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. In general, pharmaceutically acceptable carriers in a pharmaceutical composition according to the present invention may be active components or inactive components.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in a pharmaceutical composition may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, similar to Synagis™ and Herceptin™, for reconstitution with sterile water containing a preservative). The composition may be prepared e.g., as an ointment, cream or powder. The composition may be prepared for e.g., as a tablet or capsule, as a spray, or as a syrup (optionally flavored). The composition may be prepared e.g., as an inhaler, using a fine powder or a spray. The composition may be prepared e.g., as drops. The composition may be in kit form, designed such that a combined composition can be reconstituted, e.g. just prior to administration. For example, a lyophilized antibody may be provided in kit form with sterile water or a sterile buffer.

It is preferred that the active ingredient in the composition is an antibody molecule, an antibody fragment or variants and derivatives thereof, in particular the active ingredient in the composition is an antibody, an antibody fragment or variants and derivatives thereof, according to the present invention. The composition may contain agents which protect the antibody from degradation in the gastrointestinal tract, but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

The composition may take the form of a suspension, solution or emulsion in an oily or aqueous vehicle and, in particular, it may contain formulatory agents, such as suspending, preservative, stabilizing and/or dispersing agents. Alternatively, the antibody molecule may be in dry form, for reconstitution before use with an appropriate sterile liquid.

The composition may comprise a vehicle, such as water or saline. A vehicle is typically understood to be a material that is suitable for storing, transporting, and/or administering a compound, such as a pharmaceutically active compound, in particular the antibodies according to the present invention. For example, the vehicle may be a physiologically acceptable liquid, which is suitable for storing, transporting, and/or administering a pharmaceutically active compound, in particular the antibodies according to the present invention.

The composition may be an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. The composition according to the present invention may be provided for example in a pre-filled syringe.

The composition as defined above may also be in a dosage form including, but not limited to, capsules, tablets, aqueous suspensions or solutions. In the case of tablets, carriers commonly used include lactose and corn starch. Lubricating agents, such as magnesium stearate, are also typically added. For capsule form, useful diluents include lactose and dried cornstarch. When aqueous suspensions are required, the active ingredient may be combined with emulsifying and suspending agents. If desired, certain sweetening, flavoring or coloring agents may also be added.

Further examples of carriers comprised by the composition include, but are not limited to, mineral oil, liquid petrolatum, white petrolatum, propylene glycol, polyoxyethylene, polyoxypropylene compound, emulsifying wax and water. Alternatively, the composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

In one embodiment, a composition of the invention may include antibodies of the invention, wherein the antibodies may make up at least 50% by weight (e.g., 60%, 70%, 75%, 80%, 85%, 90%, 95%, 96%, 97%, 98%, 99% or more) of the total protein in the composition. In such a composition, the antibodies are preferably in purified form.

Pharmaceutical compositions may include an antimicrobial particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. For example, a concentration of 10±2 mg/ml NaCl is typical.

Further, pharmaceutical compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilization may be adjusted to between 5 and 8, or between 5.5 and 7, or around 6.1 prior to lyophilization.

The compositions of the invention may also comprise one or more immunoregulatory agents. In one embodiment, one or more of the immunoregulatory agents include(s) an adjuvant.

Production of Antibodies

Antibodies according to the invention can be made by any method known in the art. For example, a scaffold antibody may be provided and genetically engineered at the elbow region(s). To obtain a scaffold antibody, for example, the general methodology for making monoclonal antibodies using hybridoma technology is well known (Kohler, G. and Milstein, C., 1975; Kozbar et al. 1983). In particular, the alternative EBV immortalization method described in WO2004/076677 may be used.

A preferred method is described in WO 2004/076677. In this method B cells producing the antibody of the invention are transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Another preferred method is described in WO 2010/046775. In this method plasma cells are cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab' and F(ab')2 fragments.

For example, the present invention also provides a process for producing an antibody, or an antigen-binding fragment thereof, according to the present invention comprising:

Transforming an eukaryotic host cell by (e.g., as described above) incorporating one or more nucleic acid molecule(s) as described above encoding a first polypeptide chain and a second polypeptide chain, e.g. a vector according to the present invention as described above;

cultivating the host cell under suitable conditions so that said nucleic acid molecules are expressed;

causing or allowing said first and second polypeptide chains to combine to form the antibody, or antigen-binding fragment thereof; and optionally, purifying the antibody, or antigen-binding fragment thereof, from the culture medium.

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example E. coli, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

For example, the cell line may be transfected with two vectors, a first vector encoding the first polypeptide chain, e.g. a heavy chain polypeptide, and a second vector encoding the second polypeptide chain, e.g. a light chain polypeptide. Alternatively, a single vector may be used, the vector including sequences encoding the first and the second polypeptide chain, e.g. light chain and heavy chain polypeptides.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Methods and Uses

In a further aspect, the present invention provides the use of the antibody, or the antigen binding fragment thereof, according to the present invention, the nucleic acid according to the present invention, the vector according to the present invention, the cell according to the present invention or the (pharmaceutical) composition according to the present invention for use in medicine.

Accordingly, the present invention also provides a method of preventing or treating a disease or disorder in a subject comprising the step of administering the antibody, or the antigen binding fragment thereof, according to the present invention, the nucleic acid according to the present invention, the vector according to the present invention, the cell according to the present invention or the (pharmaceutical) composition according to the present invention to the subject.

It is understood that the one or more specificity/specificities of the antibody, or the antigen binding fragment thereof, according to the present invention may be chosen according to the disease or disorder to be prevented and/or treated. For example, for prevention and/or treatment of malaria, the antibody, or the antigen binding fragment thereof, may comprise a specificity against a malaria antigen, for example an antigen binding site (formed by variable domains) and/or a (additional) functional domain in the elbow region, which specifically binds to a malaria antigen. An example thereof is a mutated LAIR1 fragment as described herein, in particular a mutated LAIR1 fragment as described in WO 2016/207402 A1, e.g. comprising an amino acid sequence according to SEQ ID NO: 13 or a sequence variant thereof having at least 70%, preferably at least 75%, more preferably at least 80%, even more preferably at least 85%, still more preferably 90%, particularly preferably 95%, and most preferably at least 98% sequence identity. An antibody comprising such a specificity (such a (antigen) binding site) may be in particular useful for providing immunity to blood stage malaria parasites (in particular *Plasmodium falciparum*).

Diseases to be treated and/or prevented by use of the antibody/the antigen binding fragment according to the present invention; the nucleic acid molecule according to the present invention; the vector according to the present invention; the cell according to the present invention; or the composition according to the present invention include cancer, infectious diseases, and autoimmunity disorders. Thereby, treatment and/or prevention of cancer and/or infectious diseases is preferred.

Preferably, the antibody/the antigen binding fragment according to the present invention; the nucleic acid molecule according to the present invention; the vector according to the present invention; the cell according to the present invention; or the composition according to the present invention may be used for (the preparation of a medicament for) the prophylaxis, treatment and/or amelioration of cancer or tumor diseases. In general, the term "cancer" includes solid tumors, in particular malignant solid tumors, such as sarcomas, carcinomas and lymphomas, and blood cancer, such as leukemias. Cancers include carcinomas, sarcomas, lymphomas, keukemias, germ cell tumors and blastomas.

Preferably, the antibody/the antigen binding fragment according to the present invention; the nucleic acid molecule according to the present invention; the vector according to the present invention; the cell according to the present invention; or the composition according to the present invention may be used for (the preparation of a medicament for) the prophylaxis, treatment and/or amelioration of an infectious disease. Infectious diseases include viral, retroviral, bacterial and protozoological infectious diseases.

Moreover, the antibody/the antigen binding fragment according to the present invention; the nucleic acid molecule according to the present invention; the vector according to the present invention; the cell according to the present invention; or the composition according to the present invention may be used for (the preparation of a medicament for) the prophylaxis, treatment and/or amelioration of autoimmune disorders. Typically, autoimmune diseases arise from an abnormal immune response of the body against substances and tissues normally present in the body (autoimmunity). This may be restricted to certain organs or may involve a particular tissue in different places. Autoimmune diseases may be classified by corresponding type of hypersensitivity: type I (i.e. urticaria induced by autologous serum), type II, type III, or type IV.

In addition, the antibody, or the antigen binding fragment thereof, according to the present invention, the nucleic acid according to the present invention, the vector according to the present invention, the cell according to the present invention or the (pharmaceutical) composition according to the present invention may also be useful for (in vitro) diagnosis. Methods of diagnosis may include contacting an antibody or an antibody fragment with a sample. Such samples may be isolated from a subject, for example an isolated tissue sample taken from, for example, nasal passages, sinus cavities, salivary glands, lung, liver, pancreas, kidney, ear, eye, placenta, alimentary tract, heart, ovaries, pituitary, adrenals, thyroid, brain, skin or blood, preferably plasma or serum. The methods of diagnosis may also include the detection of an antigen/antibody complex, in particular following the contacting of an antibody or an antibody fragment with a sample. Such a detection step is typically performed at the bench, i.e. without any contact to the human or animal body. Examples of detection methods are well-known to the person skilled in the art and include, e.g., ELISA (enzyme-linked immunosorbent assay).

Also for diagnosis, it is understood that the one or more specificity/specificities of the antibody, or the antigen binding fragment thereof, according to the present invention may be chosen according to the disease or disorder to be prevented and/or treated, essentially as described above for prevention and/or treatment of diseases.

Moreover, the present invention also provides an assay for detecting an antigen or for quantification of antigen binding comprising:

incubating an antigen with the antibody, or the antigen binding fragment thereof, according to the present invention under conditions which permit binding of the antigen to the polyvalent antibody; and detecting antigen-antibody binding.

For example, such an assay may be useful in the context of diagnosis as described above.

BRIEF DESCRIPTION OF THE FIGURES

In the following a brief description of the appended figures will be given. The figures are intended to illustrate the present invention in more detail. However, they are not intended to limit the subject matter of the invention in any way.

(B) Preferred examples of antibodies according to the present invention (n-elbow-insert Ig molecules; IEI Ig) derived from the classical monospecific antibody shown in (A): antibody comprising one single (additional) functional domain in the elbow region of each heavy chain but no elbow insert in the light chain; antibody comprising one single (additional) functional domain in the elbow region of each light chain but no elbow insert in the heavy chain; antibody comprising one single (additional) functional domain in the elbow region of each heavy chain and of each light chain; antibody comprising two (additional) functional domains in the elbow region of each heavy chain but no elbow insert in the light chain; and antibody comprising two (additional) functional domains in the elbow region of each light chain but no elbow insert in the heavy chain.

(C) Preferred examples of antigen binding fragments and antibodies according to the present invention (In-elbow-insert Ig molecules; IEI Ig) derived from antibody fragments or from bispecific antibodies: F(ab) fragment comprising one single (additional) functional domain in the elbow region of each heavy chain but no elbow insert in the light chain; F(ab)$_2$ fragment comprising one single (additional) functional domain in the elbow region of each light chain but no elbow insert in the heavy chain; Fab fragment comprising one single (additional) functional domain in the elbow region of each heavy chain but no elbow insert in the light chain; Fab fragment comprising one single (additional) functional domain in the elbow region of each light chain but no elbow insert in the heavy chain; CrossMab/Knobs-in-holes/orthogonal Fab/Fab-arm exchange antibodies comprising one single (additional) functional domain in the elbow region of one single heavy chain but no elbow insert in the light chains and in the other heavy chain; scFv-(H)gG comprising one single (additional) functional domain in the elbow region of each heavy chain but no elbow insert in the light chain; IgG(H)-scFv comprising one single (additional) functional domain in the elbow region of each heavy chain but no elbow insert in the light chain; scFv-(L)IgG comprising one single (additional) functional domain in the elbow region of each heavy chain but no elbow insert in the light chain; IgG(L)-scFv comprising one single (additional) functional domain in the elbow region of each heavy chain but no elbow insert in the light chain; and DVD-Ig comprising one single (additional) functional domain in the elbow region of each heavy chain but no elbow insert in the light chain.

FIG. 2 shows for Example 1 a scheme of the seven antibody constructs according to the present invention (C2 to C8) compared to scaffold antibodies (GCE536, C1).

Figure 1:
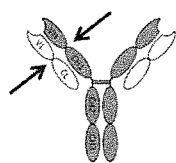
FIG. 1 (A) classical monospecific antibody comprising two heavy chains (grey), each with a single variable domain VH and three constant domains CH1, CH2 and CH3, and two light chains (white), each with a single variable domain VL and a single constant domain CL. The elbow region is indicated by arrows.
Figure 1:
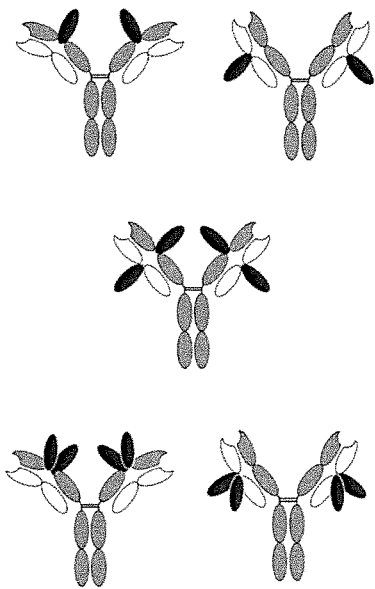
Figure 1:
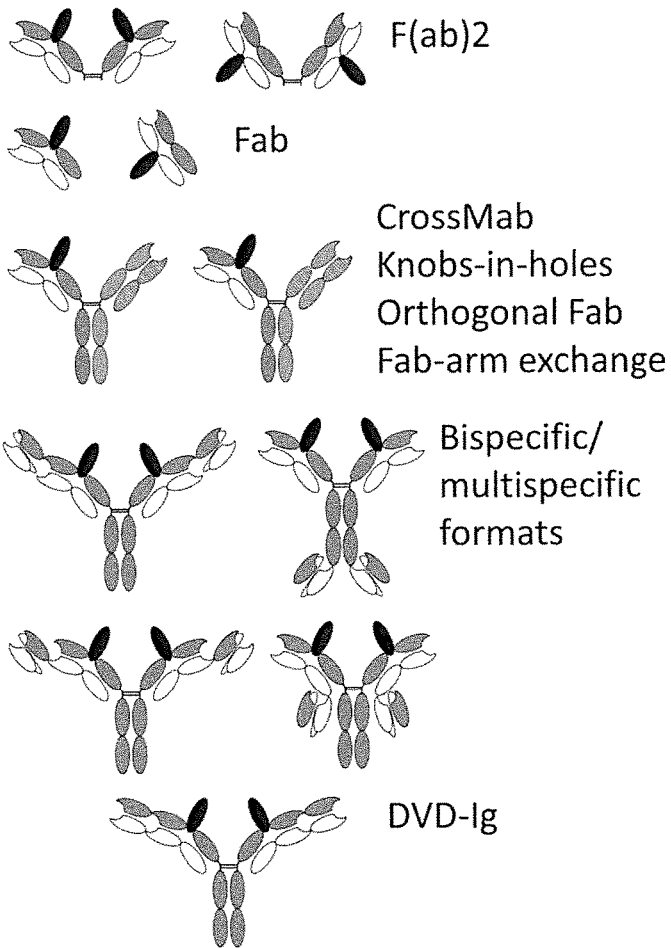
Figure 3:
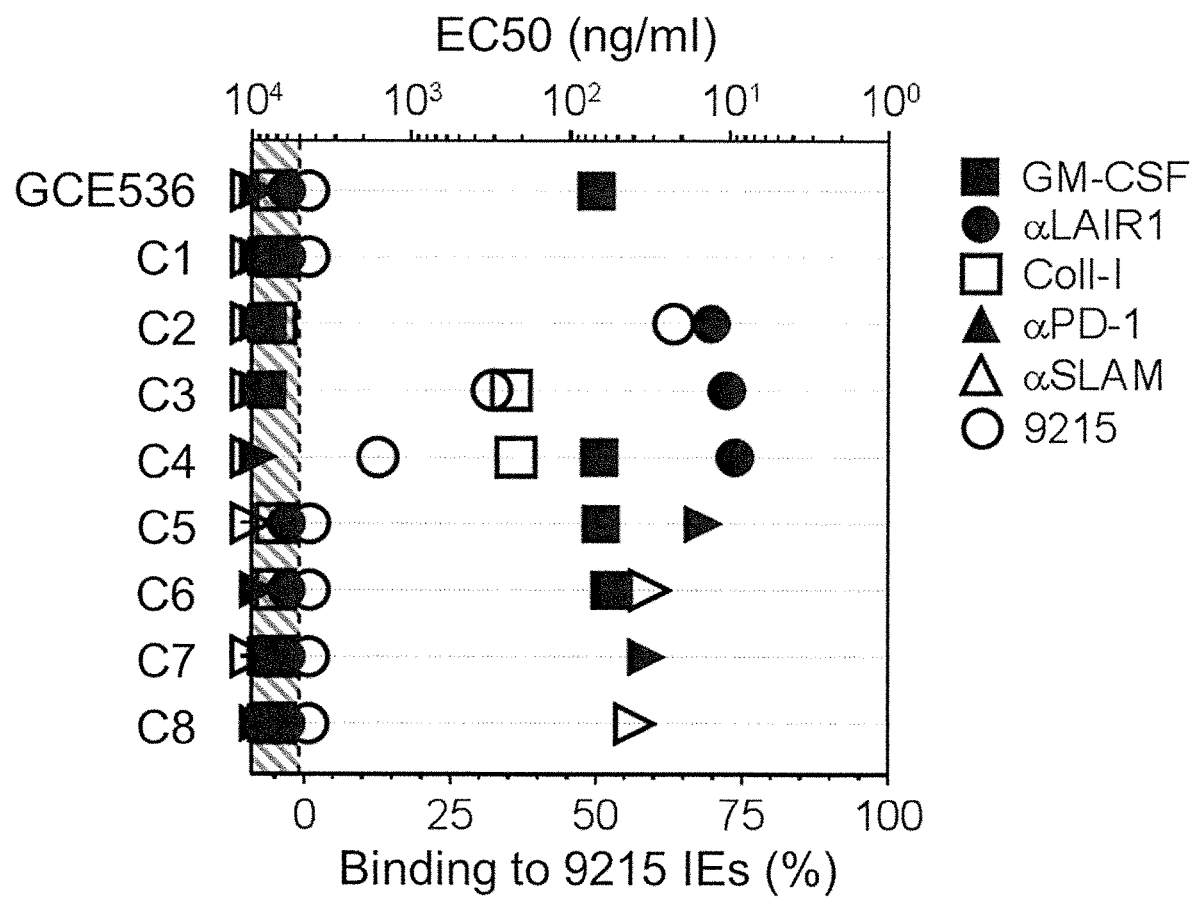

FIG. 3 shows for Example 2 the EC50 values determined by non-linear regression analysis of binding values (OD) and relative antibody concentrations in the ELISA tests made using a set of antigens or anti-domain antibodies. The constructs were also tested for binding to IEs (isolate 9215) and binding values (%) at a concentration of 1 µg/ml are shown.

Figure 4:
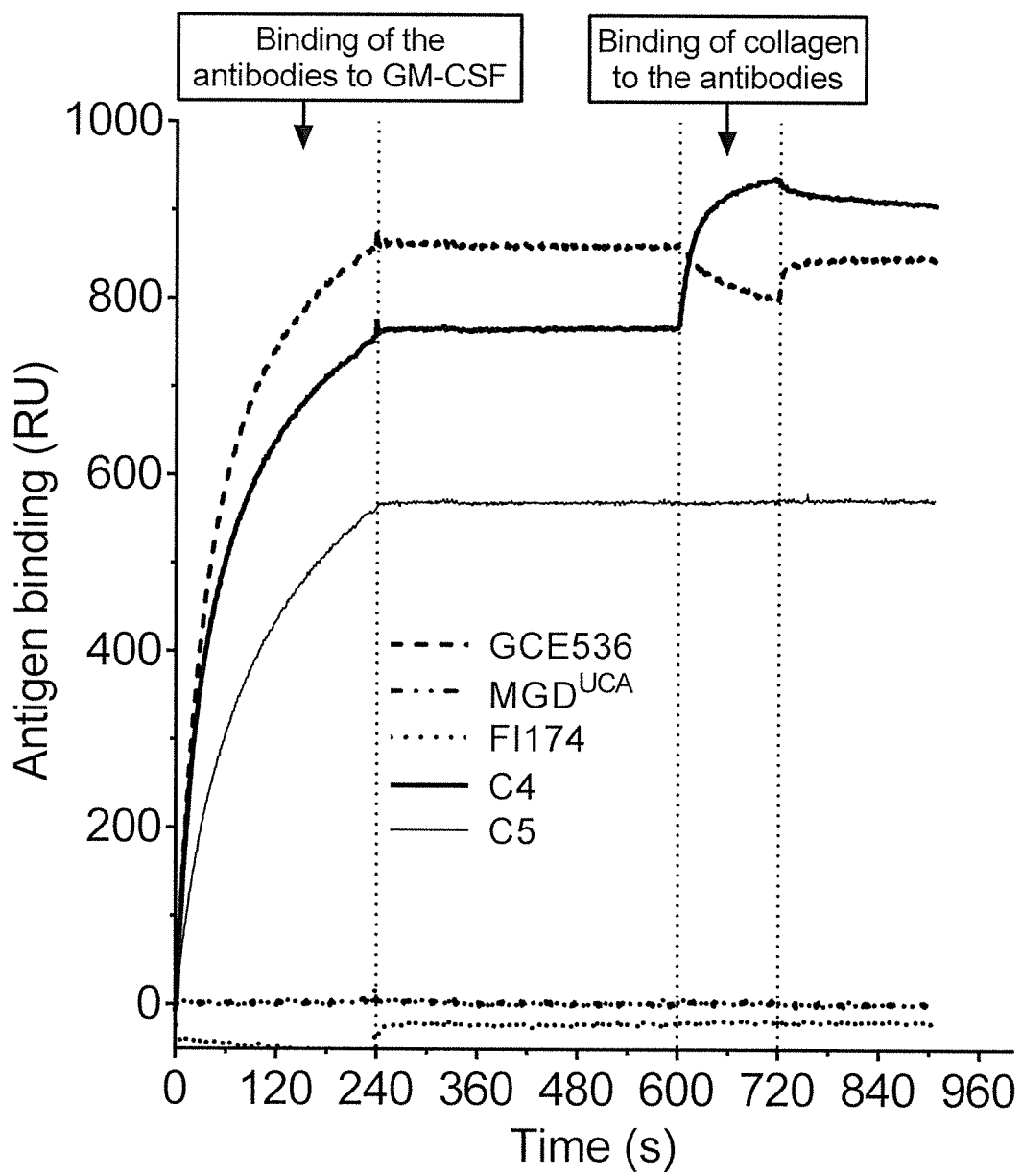

FIG. 4 shows for Example 3 the SPR binding curves of C4 and different controls to GM-CSF and collagen. C4 and C5 that use GCE536 as scaffold bind to GM-CSF, but only C4 is then bound by collagen. Non-specific FI174 and collagen-specific MGD$^{UCA}$ antibodies don't show any specific binding signal.

Figure 5:
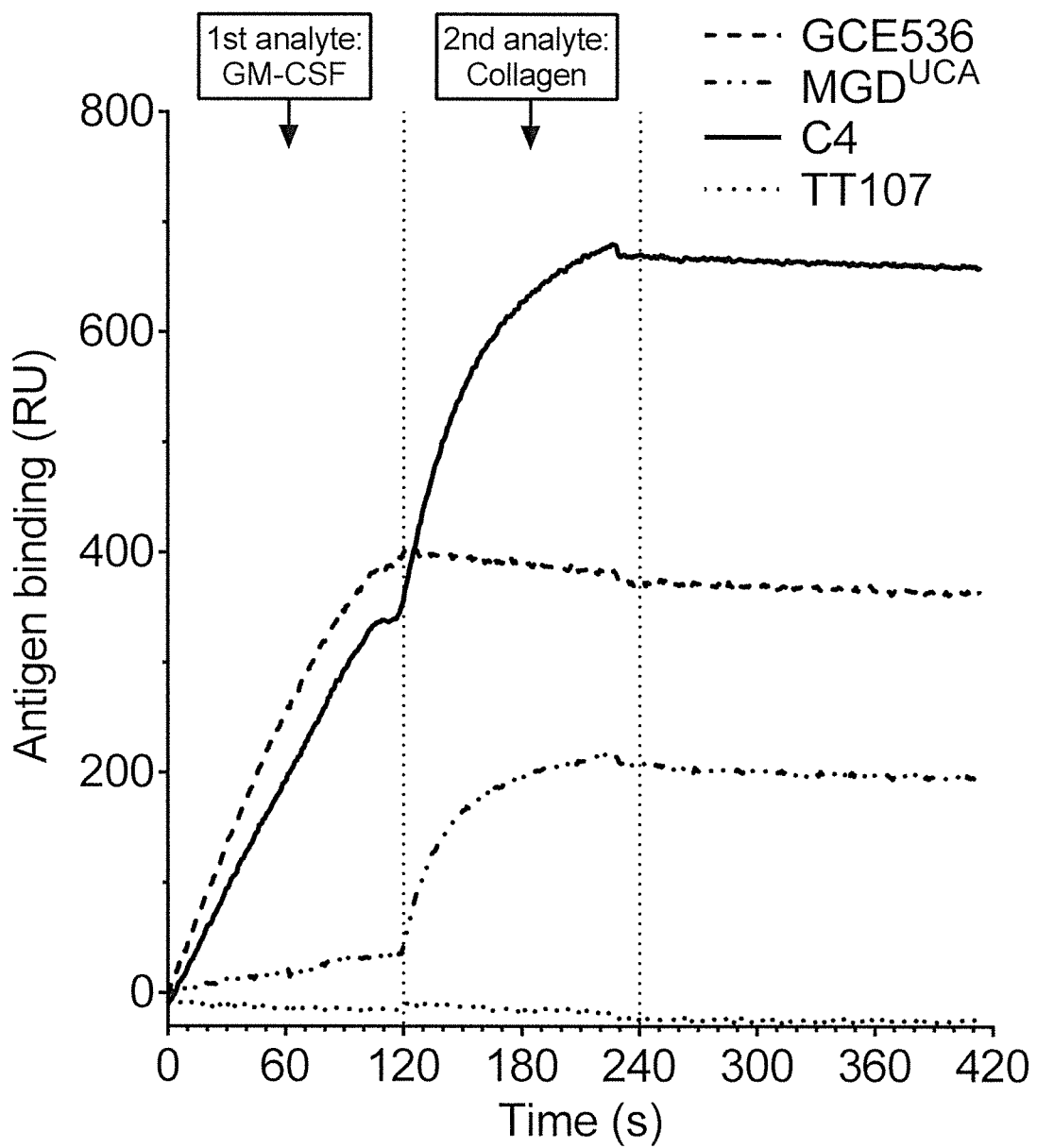

FIG. 5 shows for Example 3 the SPR binding curves of C4 and different controls to GM-CSF and collagen. C4 and GCE536 bind to GM-CSF, but only C4 is then recognized by collagen. Collagen-specific MGD$^{UCA}$ antibody binds to collagen only. Control antibody TT107 is a T-specific monoclonal antibody, which does not show any specific binding signal in SPR experiment.

Figure 6:
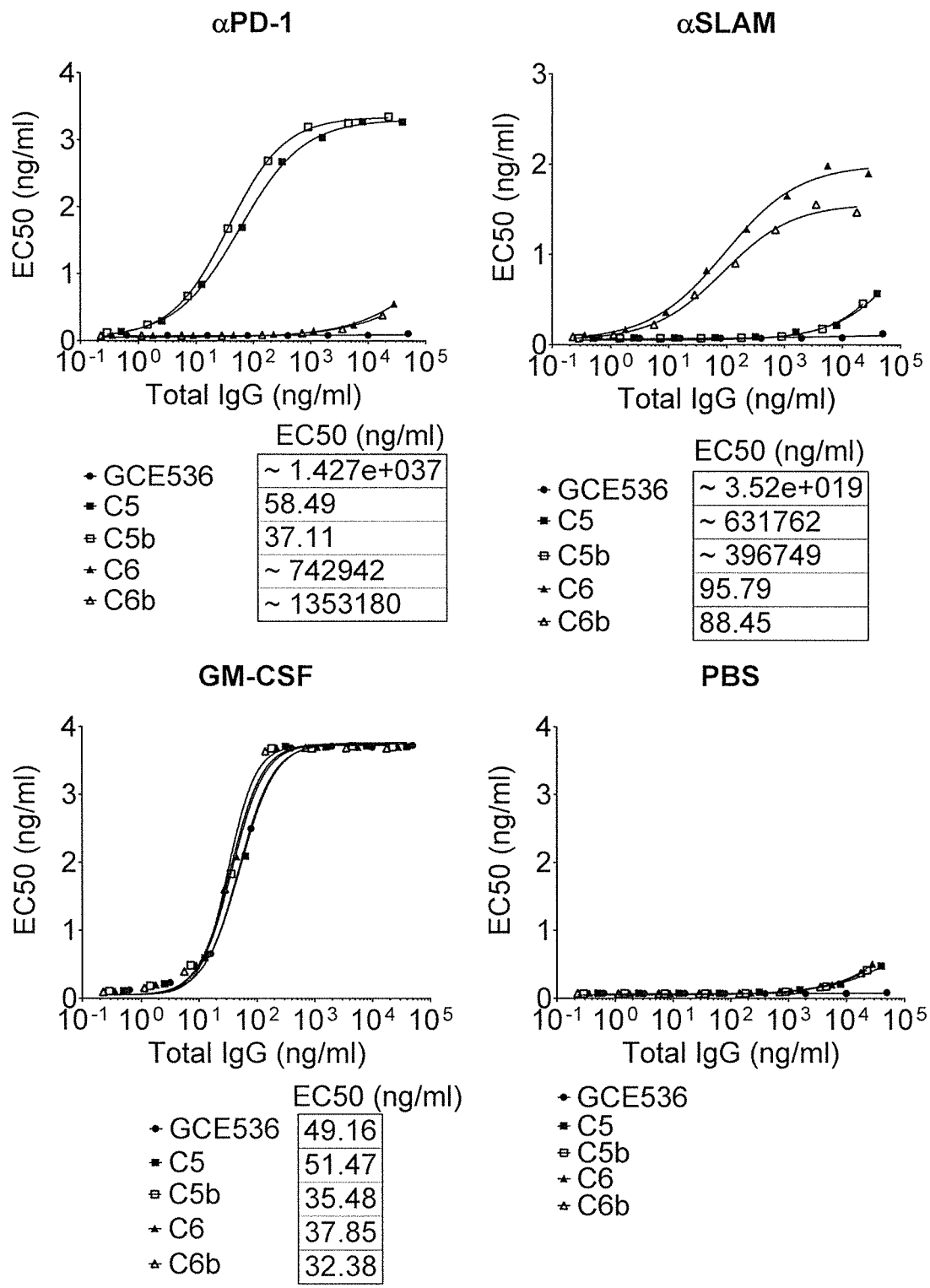

FIG. 6 shows for Example 4 the ELISA binding curves of C5, C5b, C6 and C6b constructs to GM-CSF or by anti-PD1 or anti-SLAM antibodies, compared to the scaffold antibody (GCE536). PD1-containing C5 and C5b and SLAM-containing C6 and C6b constructs are recognized by anti-PD1 or anti-SLAM antibodies, respectively. All the constructs bind to GM-CSF as GCE536. The presence of linkers in C5b and C6 does not affect binding.

Figure 7:
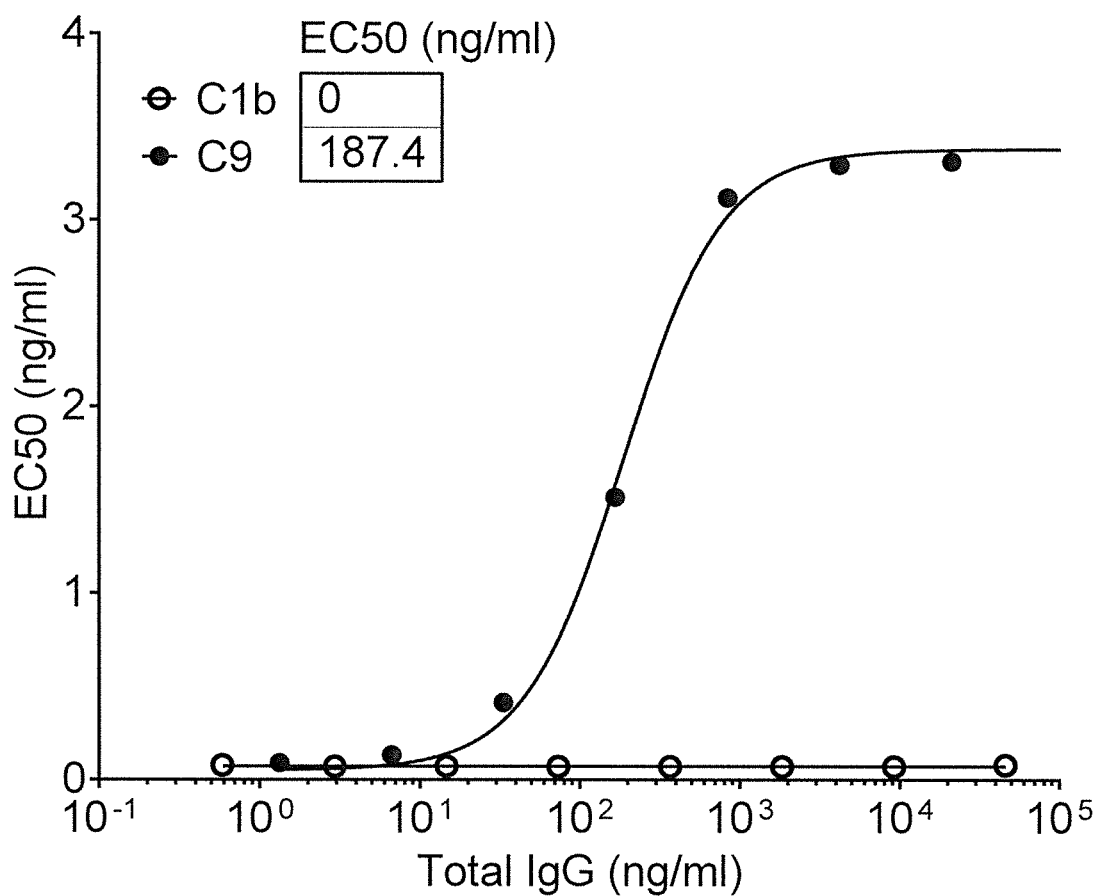

FIG. 7 shows for Example 6 the ELISA binding curve of a Strep-tactin antibody to C9 construct compared to the scaffold C1b. The Twin Strep-tag inserted in the elbow of C9 construct is specifically recognized by the Strep-tactin antibody.

FIG. 8 shows for Example 7 a scheme of the four additional antibody constructs (C9 to C12) compared to the scaffold antibody (F174).

Figure 9:
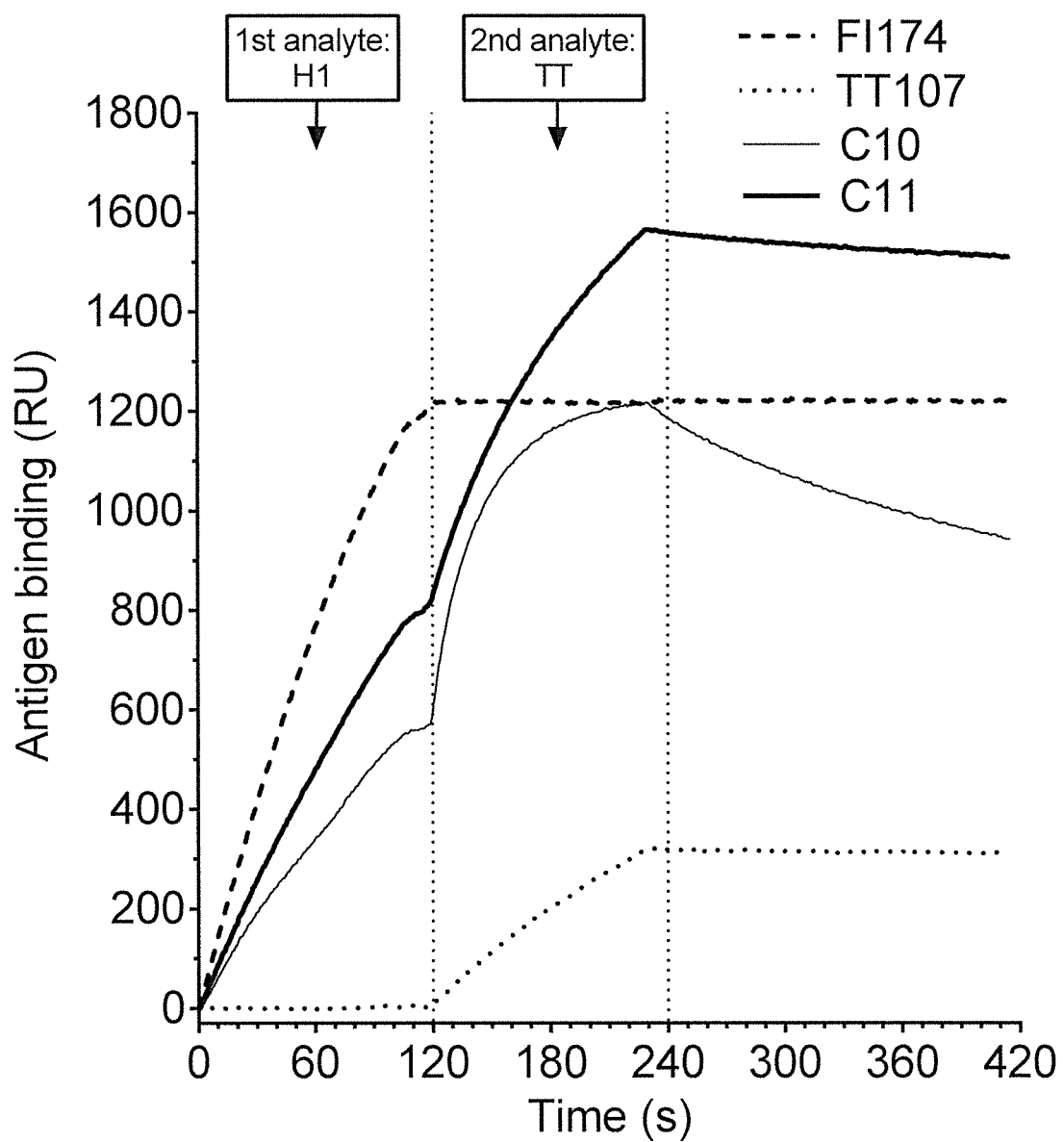

FIG. 9 shows for Example 8 the SPR binding curves of C9 and C10 and different controls to H1 and TT. C9 and C10 show dual binding to both H1 and TT. TT107 is a TT-specific monoclonal antibody.

Figure 10:
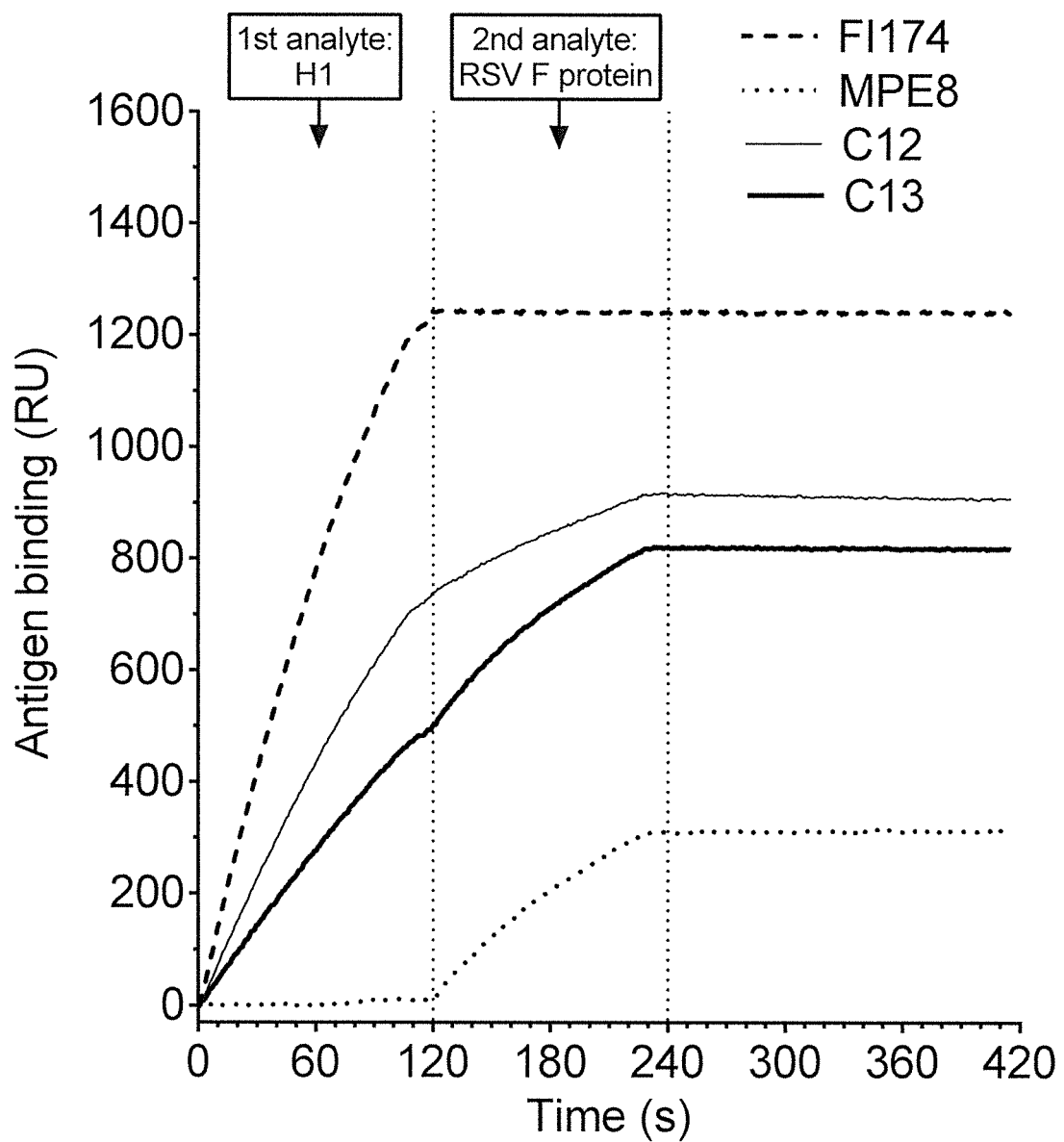

FIG. 10 shows for Example 8 the SPR binding curves of C11 and C12 and different controls to H1 and RSV F protein. C11 and C12 show dual binding to both H1 and RSV F protein. MPE8 is a RSV F protein-specific monoclonal antibody.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Design and Construction of Antibody Variants Inserting Different Ig-Like Functional Domains into the Elbow Region of Scaffold Antibodies To investigate the effect of distinct (additional) functional domains inserted into the elbow region of an antibody on antibody specificity, seven different constructs (named "C2-C8") were designed, in which unmutated LAIR1 (SEQ ID NO: 12), mutated LAIR1 (SEQ ID NO: 13) or other Ig-like domains were inserted into the elbow region of an antibody that was used as a scaffold. Constructs C2-C3 have the same complete constant region of the heavy chain as construct C1 (VH: SEQ ID NO: 5, VL: SEQ ID NO: 6, heavy chain constant region: SEQ ID NO: 3, light chain constant region: SEQ ID NO: 7). Constructs C4-C6 have the same complete constant region of the heavy chain as the antibody GCE536 (VH: SEQ ID NO: 1, VL: SEQ ID NO: 2, heavy chain constant region: SEQ ID NO: 3, light kappa chain constant region: SEQ ID NO: 4; Piccoli, L., et al. Neutralization and clearance of GM-CSF by autoantibodies in pulmonary alveolar proteinosis. Nature communications 6, 7375 (2015)). Constructs C7-C8 have the same complete constant region of the heavy chain as construct C1b (VH: SEQ ID NO: 8, VL: SEQ ID NO: 9, heavy chain constant region: SEQ ID NO: 3, light chain constant region: SEQ ID NO: 4). The light chain of the constructs was not modified in comparison to the scaffold antibodies. All construct were finally expressed as monoclonal antibodies (heavy and light chains).

The following constructs were produced and are shown schematically in FIG. 2:

1. "C1" (VH: SEQ ID NO: 5, VL: SEQ ID NO: 6, heavy chain constant region: SEQ ID NO: 3, light chain lambda constant region: SEQ ID NO: 7) is a recombinant monospecific antibody for control purposes. C1 is formed by (in this order from N- to C-terminus): the expression product of a V (variable) gene segment of a heavy chain variable domain ("VH3-30"); the expression product of a D (diversity) gene segment of a heavy chain variable domain ("D"); the expression product of a J (Joining) gene segment element of a heavy chain variable domain ("JH6"); the expression product of a C (constant) gene segment of a heavy chain constant region (IgG1 isotype); and on a separate chain: the expression product of a V (variable) gene segment of a light chain variable domain and the expression product of a J (Joining) gene segment element of a light chain variable domain; the expression product of a C (constant) gene segment of a light chain lambda constant region.

2. "C1b" (VH: SEQ ID NO: 8, VL: SEQ ID NO: 9, heavy chain constant region: SEQ ID NO: 3, light chain kappa constant region: SEQ ID NO: 4) is a recombinant monospecific antibody for control purposes. C1 is formed by (in this order from N- to C-terminus): the expression product of a V (variable) gene segment of a heavy chain variable domain ("VH3-20"); the expression product of a D (diversity) gene segment of a heavy chain variable domain ("D"); the expression product of a J (Joining) gene segment element of a heavy chain variable domain (H3; the expression product of a C (constant) gene segment of a heavy chain constant region (IgG1 isotype); and on a separate chain: the expression product of a V (variable) gene segment of a light chain variable domain and the expression product of a J (Joining) gene segment element of a light chain variable domain; the expression product of a C (constant) gene segment of a light chain kappa constant region.

3. In construct "C2" a mutated LAIR-1 fragment ("LAIR1$^{mut}$"; SEQ ID NO: 13) was inserted into the elbow region of recombinant monospecific antibody "C1" (see above). In the mutated LAIR1 fragment, the binding of LAIR1 to collagen is abolished, but the mutated LAIR1 fragment binds strongly to *P. falciparum* infected erythrocytes (Tan, J., Pieper, K., Piccoli, L., et al. A LAIR insertion generates broadly reactive antibodies against malaria variant antigens. Nature 529, 105-109 (2016); WO 2016/207402 A1). Construct "C2" (complete heavy chain: SEQ ID NO: 53, complete light chain: SEQ ID NO: 54) is formed by (in this order from N- to C-terminus): the expression product of a V (variable) gene segment of a heavy chain variable domain of C1 ("VH3-30"); the expression product of a D (diversity) gene segment of a heavy chain variable domain of C1 ("D"); the expression product of a J (Joining) gene segment element of a heavy chain variable domain of C ("JH6"); the expression product of the mutated LAIR-1 fragment of MGD21 ("LAIR$^{D21}$"); the expression product of a C (constant) gene segment of a heavy chain constant region (IgG1 isotype); and on a separate chain: the expression product of a V (variable) gene segment of a light chain variable domain of C1 and the expression product of a j (Joining) gene segment element of a light chain variable domain of C1; the expression product of a C (constant) gene segment of a light chain constant region.

4. In construct "C3" an unmutated LAIR-1 fragment ("LAIR1$^{gen}$"; SEQ ID NO: 12) was inserted into the elbow region of recombinant monospecific antibody "C1" (see above). Construct "C3" (complete heavy chain: SEQ ID NO: 55, complete light chain: SEQ ID NO: 54) is formed by (in this order from N- to C-terminus): the expression product of a V (variable) gene segment of a heavy chain variable domain of C ("VH3-30"); the expression product of a D (diversity) gene segment of a heavy chain variable domain of C1 ("D"); the expression product of a J (Joining) gene segment element of a heavy chain variable domain of C1 ("JH6"); the expression product of the unmutated LAIR-1 fragment ("LAIR1$^{gen}$"); the expression product of a C (constant) gene segment of a heavy chain constant region (IgG1 isotype); and on a separate chain: the expression product of a V (variable) gene segment of a light chain variable domain of C1 and the expression product of a J (Joining) gene segment element of a light chain variable domain of C1; the expression product of a C (constant) gene segment of a light chain constant region.

5. In construct "C4" an unmutated LAIR-1 fragment ("LAIR1$^{gen}$"; SEQ ID NO: 13) was inserted into the elbow region of antibody GCE536. Construct "C4" (complete heavy chain: SEQ ID NO: 56, complete light chain: SEQ ID NO: 57) is formed by (in this order from N- to C-terminus): the expression product of a V (variable) gene segment of a heavy chain variable domain of GCE536 ("VH1-46"); the expression product of a D (diversity) gene segment of a heavy chain variable domain of GCE536 ("D"); the expression product of a J (Joining) gene segment element of a heavy chain variable domain of GCE536 ("JH6"); the expression product of the unmutated LAIR-1 fragment ("LAIR1$^{gem}$"); the expression product of a C (constant) gene segment of a heavy chain constant region (IgG1 isotype); and on a separate chain: the expression product of a V (variable) gene segment of a light chain variable domain of GCE536 and the expression product of a J (Joining) gene segment element of a light chain variable domain of GCE536; the expression product of a C (constant) gene segment of a light chain constant region.

6. In construct "C" an extracellular Ig-like domain of PD1 molecule ("PD1"; SEQ ID NO: 14) was inserted into the elbow region of antibody GCE536. Construct "C5" (complete heavy chain: SEQ ID NO: 58, complete light chain: SEQ ID NO: 57) is formed by (in this order from N- to C-terminus): the expression product of a V (variable) gene segment of a heavy chain variable domain of GCE536 ("VH1-46"); the expression product of a D (diversity) gene segment of a heavy chain variable domain of GCE536 ("D"); the expression product of a J Coining) gene segment element of a heavy chain variable domain of GCE536 ("JH6"); the expression product of an extracellular Ig-like domain of PD1 molecule ("PD1"); the expression product of a C (constant) gene segment of a heavy chain constant region (IgG1 isotype); and on a separate chain: the expression product of a V (variable) gene segment of a light chain variable domain of GCE536 and the expression product of a J (Joining) gene segment element of a light chain variable domain of GCE536; the expression product of a C (constant) gene segment of a light chain constant region.

7. In construct "C5b" an extracellular Ig-like domain of PD1 molecule ("PD1"; SEQ ID NO: 14) with flanking intronic sequences ("15-mer JH-PD1"; SEQ ID NO: 49 and "15-mer PD1-CH1" linkers"; SEQ ID NO: 50) was inserted into the elbow region of antibody GCE536. Construct "C5" (complete heavy chain: SEQ ID NO: 59, complete light chain: SEQ ID NO: 57) is formed by (in this order from N- to C-terminus): the expression product of a V (variable) gene segment of a heavy chain variable domain of GCE536 ("VH1-46"); the expression product of a D (diversity) gene segment of a heavy chain variable domain of GCE536 ("D"); the expression product of a J (Joining) gene segment element of a heavy chain variable domain of GCE536 ("JH6"); the expression product of a linker ("15-mer JH-PD1"); the expression product of an extracellular Ig-like domain of PD1 molecule ("PD1"); the expression product of a linker ("15-mer PD1-CH"); the expression product of a C (constant) gene segment of a heavy chain constant region (IgG1 isotype); and on a separate chain: the expression product of a V (variable) gene segment of a light chain variable domain of GCE536 and the expression product of a J (Joining) gene segment element of a light chain variable domain of GCE536; the expression product of a C (constant) gene segment of a light chain kappa constant region.

8. In construct "C6" an extracellular Ig-like domain of SLAM molecule ("SLAM"; SEQ ID NO: 15) was inserted into the elbow region of antibody GCE536. Construct "C6" (complete heavy chain: SEQ ID NO: 60, complete light chain: SEQ ID NO: 57) is formed by (in this order from N- to C-terminus): the expression product of a V (variable) gene segment of a heavy chain variable domain of GCE536 ("VH1-46"); the expression product of a D (diversity) gene segment of a heavy chain variable domain of GCE536 ("D"); the expression product of a J (Joining) gene segment element of a heavy chain variable domain of GCE536 ("JH6"); the expression product of an extracellular Ig-like domain of SLAM molecule ("SLAM"); the expression product of a C (constant) gene segment of a heavy chain constant region (IgG1 isotype); and on a separate chain: the expression product of a V (variable) gene segment of a light chain variable domain of GCE536 and the expression product of a J (Joining) gene segment element of a light chain variable domain of GCE536; the expression product of a C (constant) gene segment of a light chain constant region.

9. In construct "C6b" an extracellular Ig-like domain of SLAM molecule ("SLAM"; SEQ ID NO: 15) with flanking intronic sequences ("15-mer JH-SLAM"; SEQ ID NO: 51 and "15-mer SLAM-CH1" linkers"; SEQ ID NO: 52) was inserted into the elbow region of antibody GCE536. Construct "C6" (complete heavy chain: SEQ ID NO: 61, complete light chain: SEQ ID NO: 57) is formed by (in this order from N- to C-terminus): the expression product of a V (variable) gene segment of a heavy chain variable domain of GCE536 ("VH1-46"); the expression product of a D (diversity) gene segment of a heavy chain variable domain of GCE536 ("D"); the expression product of a J (Joining) gene segment element of a heavy chain variable domain of GCE536 ("JH6"); the expression product of a linker ("15-mer JH-SLAM"); the expression product of an extracellular Ig-like domain of SLAM molecule ("SLAM"); the expression product of a linker ("15-mer SLAM-CH"); the expression product of a C (constant) gene segment of a heavy chain constant region (IgG1 isotype); and on a separate chain: the expression product of a V (variable) gene segment of a light chain variable domain of GCE536 and the expression product of a J (Joining) gene segment element of a light chain variable domain of GCE536; the expression product of a C (constant) gene segment of a light chain kappa constant region.

10. In construct "C7" an extracellular Ig-like domain of PD1 molecule ("PD1"; SEQ ID NO: 14) was inserted into the elbow region of recombinant monospecific antibody "C1b" (see above). Construct "C7" (complete heavy chain: SEQ ID NO: 62, complete light chain: SEQ ID NO: 63) is formed by (in this order from N- to C-terminus): the expression product of a V (variable) gene segment of a heavy chain variable domain ("VH3-20"); the expression product of a D (diversity) gene segment of a heavy chain variable domain ("D"); the expression product of a J (Joining) gene segment element of a heavy chain variable domain ("H3"); the expression product of an extracellular Ig-like domain of PD1 molecule ("PD1"); the expression product of a C (constant) gene segment of a heavy chain constant region (IgG1 isotype); and on a separate chain: the expression product of a V (variable) gene segment of a light chain variable domain and the expression product of a J (Joining) gene segment element of a light chain variable domain; the expression product of a C (constant) gene segment of a light chain constant region.

11. In construct "C8" an extracellular Ig-like domain of SLAM molecule ("SLAM"; SEQ ID NO: 15) was inserted into the elbow region of recombinant monospecific antibody "C1b" (see above). Construct "C8" (complete heavy chain: SEQ ID NO: 64, complete light chain: SEQ ID NO: 63) is formed by (in this order from N- to C-terminus): the expression product of a V (variable) gene segment of a heavy chain variable domain ("VH3-20"); the expression product of a D (diversity) gene segment of a heavy chain variable domain ("D"); the expression product of a J (Joining) gene segment element of a heavy chain variable domain ("JH3"); the expression product of an extracellular Ig-like domain of SLAM molecule ("SLAM"); the expression product of a C (constant) gene segment of a heavy chain constant region (IgG1 isotype); and on a separate chain: the expression product of a V (variable) gene segment of a light chain variable domain and the expression product of a J (Joining) gene segment element of a light chain variable domain; the expression product of a C (constant) gene segment of a light chain constant region.

Example 2: Ig-Like Domains can be Inserted in the Elbow Region of Antibodies Resulting in Functional Antibodies The eight antibody constructs described in Example 1 were produced recombinantly by transient transfection. To this end, antibody heavy and light chains were cloned into human IgG1, Igκ and Igλ expression vectors and expressed by transient transfection of Expi293F Cells (ThermoFisher Scientific) using polyethylenimine (PEI). Cell lines were routinely tested for *mycoplasma* contamination.

Next, the antibody constructs C1-C8 and control antibody GCE536 (see Example 1) were tested for staining of 9215 IEs (infected erythrocytes) and binding values (%) at 1 µg/ml antibody concentration were calculated by interpolation of binding curves fitted to a sigmoidal curve model (Graphpad Prism 6). In addition, binding to recombinant human collagen, anti-human LAIR1 antibody, recombinant human GM-CSF, an anti-PD1 and an anti-SLAM antibody was tested by ELISA. Briefly, total IgGs were quantified using 96-well MaxiSorp plates (Nunc) coated with goat anti-human IgG (SouthernBiotech, 2040-01) using Certified Reference Material 470 (ERMs-DA470, Sigma-Aldrich) as a standard. To test specific binding of antibody constructs, ELISA plates were coated with 2 µg ml$^{-1}$ of type I recombinant human collagen (Millipore, CC050), 2 µg ml$^{-1}$ of an anti-human LAIR1 antibody (clone DX26, BD Biosciences 550810), 1 µg ml$^{-1}$ of recombinant human GM-CSF (Gentaur), 2 µg ml$^{-1}$ of an anti-PD1 or an anti-SLAM antibody (R&D Systems, AF1086 and AF164). Plates were blocked with 1% bovine serum albumin (BSA) and incubated with titrated antibodies, followed by AP-conjugated goat anti-human IgG, Fcγ fragment specific (Jackson Immuno Research, 109-056-098). Plates were then washed, substrate (p-NPP, Sigma) was added and plates were read at 405 nm.

Results of the different binding studies are shown in FIG. 3. Antibody constructs carrying LAIR1 stained IEs and were recognized by an anti-LAIR1 antibody. Insertion of LAIR1, PD1 or SLAM Ig-like domains into the elbow region of an anti-GM-CSF antibody did not affect binding to GM-CSF (constructs C4-C6), indicating that this site is permissive for insertions of different domains without affecting the original antibody specificity. In contrast, insertion of LAIR1 into the CDR3 abolished binding to GM-CSF (data not shown). Accordingly, the elbow region is permissive for insertions of different domains, without affecting the original antibody specificity.

Example 3: Constructs Containing an Ig-Like Domain in the Elbow can Simultaneously Bind to Two Different Antigens To test whether the bispecific constructs carrying a binding site in the elbow region, are able to simultaneously bind with both specificities, simultaneous binding was investigated by surface plasmon resonance (SPR). To this end, bispecific construct C4, which has a V(D) region specific for GM-CSF and carries unmutated LAIR1 (binding site for collagen) in the elbow, was tested for simultaneous binding to GM-CSF and collagen by surface plasmon resonance (SPR).

In one experiment, GM-CSF was immobilized on the surface of a sensor chip and the constructs were injected, followed by injection of collagen. Antibodies C5 and GCE536 (cf. above), antibody MGD$^{UCA}$ (contains unmutated LAIR1 and is, thus, able to bind collagen; Tan, J., Pieper, K., Piccoli, L., et al. A LAIR1 insertion generates broadly reactive antibodies against malaria variant antigens. Nature 529, 105-109 (2016); VH: SEQ ID NO: 71, VL: SEQ ID NO: 72, heavy chain constant region: SEQ ID NO: 3, light chain constant region: SEQ ID NO: 4) and antibody F1174 (specific for influenza H1 hemagglutinin; Pappas, L., et al. Rapid development of broadly influenza neutralizing antibodies through redundant mutations. Nature 516, 418-422 (2014); (VH: SEQ ID NO: 10, VL: SEQ ID NO: 11, heavy chain constant region: SEQ ID NO: 3, light chain constant region: SEQ ID NO: 4) were used as controls. Briefly, GM-CSF (200 nM) was stabilized in 10 mM acetate buffer, pH 4.5, and immobilized onto an ethyl(dimethylaminopropyl) carbodiimide/N-Hydroxysuccinimide (EDC/NHS) pre-activatedProteOnsensor chip (Bio-Rad) through amine coupling; unreacted groups were blocked by injection of 1M ethanolamine HCL. HEPES buffered saline (HBS) (10 mMHEPES, pH7.4, 150 mM NaCl, 3 mM EDTA, 0.005% surfactant Tween-20) was used as a running buffer. All injections were made at a flowrate of 100 µl/min. Monoclonal antibodies were diluted in HBS to 10 nM and injected for 240 s onto the GM-CSF-coated chip, followed by injection of collagen (50 nM) for 120 s. One channel of the chip was injected with HBS and used as reference for the analysis. Each binding interaction of the monoclonal antibodies to GM-CSF and collagen was assessed using a ProteONXPR36 instrument (Bio-Rad) and the data were processed with ProteOn Manager software.

Results are shown in FIG. 4. Both constructs C4 and C5, which use GCE536 as scaffold (see Example 1), bind to GM-CSF. Of C4 and C5, only C4 (which carries LAIR1 in the elbow region—whereas C5 carries an Ig-like domain of PD1 in the elbow region) is then bound by collagen. Monospecific anti-GM-CSF antibody GCE536 binds only to GM-CSF, but not to collagen. Anti-H1 antibody FI74 and collagen-specific MGD$^{UCA}$ antibody do not show any specific binding signal. In summary, those data show that bispecific construct C4 bound to GM-CSF and then collagen bound to the LAIR1 domain of C4.

In a second experiment, protein A was used to capture the construct followed by co-injection of the analytes (GM-CSF followed by collagen). In this experiment antibodies GCE536 and MGD$_{UCA}$ (all described in Examples 1 and 2) and antibody TT107 (specific for tetanus toxoid (TT); VH: SEQ ID NO: 73, VL: SEQ ID NO: 74, heavy chain constant region: SEQ ID NO: 3, light chain constant region: SEQ ID NO: 4) were used as controls. Briefly, Protein A (25 µg/ml) was stabilized in 10 mM acetate buffer, pH 4.5, and immobilized onto an ethyl(dimethylaminopropyl) carbodiimide/

N-Hydroxysuccinimide (EDC/NHS) pre-activatedProteOn-sensor chip (Bio-Rad) through amine coupling; unreacted groups were blocked by injection of 1M ethanolamine HCl. HEPES buffered saline (HBS) (10 mMHEPES, pH7.4, 150 mM NaCl, 3 mM EDTA, 0.005% surfactant Tween-20) was used as a running buffer. All injections were made at a flowrate of 100 μl/min. Monoclonal antibodies were diluted in HBS to 10 nM and injected for 240 s onto the Protein A-coated chip for capturing, followed by co-injection of GM-CSF collagen (50 nM) immediately followed by collagen (50 nM) for total 110 s. One channel of the chip was injected with HBS and used as reference for the analysis. Each binding interaction of the monoclonal antibodies to GM-CSF and collagen was assessed using a ProteONXPR36 instrument (Bio-Rad) and the data were processed with ProteOn Manager software.

Results are shown in FIG. 5. Construct C4 and GCE536 bind to GM-CSF. However, only C4 is then recognized by collagen. Collagen-specific MGD$^{UCA}$ antibody binds to collagen only. Control antibody TT107 is a TT (tetanus toxoid)-specific monoclonal antibody, which does not show any specific binding signal in this SPR experiment. In summary those results show that constructs containing a (additional) functional domain, such as an Ig-like domain, in the elbow region can simultaneously bind to (i) the binding partner of the elbow binding site and (ii) the antigen recognized by the variable domains of the scaffold antibody.

Example 4: Ig-Like Domains can be Inserted Together with Flanking Linkers in the Elbow Region of Antibodies Resulting in Functional Antibodies The antibody constructs C5b and C6b contain the same domain (either PD1 or SLAM) inserted in the elbow in C5 and C6 constructs, respectively, with two additional 15-mer amino acid linkers inserted between JH and the domain, and between the domain and CH1. The constructs were tested for binding to recombinant human GM-CSF, an anti-PD1 and an anti-SLAM antibody by ELISA. Briefly, total IgGs were quantified using 96-well MaxiSorp plates (Nunc) coated with goat anti-human IgG (SouthernBiotech, 2040-01) using Certified Reference Material 470 (ERMs-DA470, Sigma-Aldrich) as a standard. To test specific binding of antibody constructs, ELISA plates were coated with 1 μg ml$^{-1}$ of recombinant human GM-CSF (Gentaur), 2 μg ml$^{-1}$ of an anti-PD1 or an anti-SLAM antibody (R&D Systems, AF1086 and AF164). Plates were blocked with 1% bovine serum albumin (BSA) and incubated with titrated antibodies, followed by AP-conjugated goat anti-human IgG, Fcγ fragment specific (Jackson Immuno Research, 109-056-098). Plates were then washed, substrate (p-NPP, Sigma) was added and plates were read at 405 nm.

Results of the different binding studies are shown in FIG. 6. Insertion of PD1 or SLAM Ig-like domains with flanking linkers into the elbow region of an anti-GM-CSF antibody did not affect binding to GM-CSF, indicating that this site is permissive for insertions also of different domains with flanking linkers without affecting the original antibody specificity. In addition, the presence of the linkers did not alter the Ig-like domain since both C5 and C5b were equally recognized by an anti-PD1 antibody. Similar results were obtained for C6 and C6b recognized by an anti-SLAM antibody. Taken together, these findings suggest that domains can be inserted in the elbow with additional linkers that distance such domains from the main antibody scaffold.

Without being bound to any theory, it is assumed that the linkers can provide enhanced flexibility of the insert.

Example 5: Design of an Antibody Containing a Molecular Tag Inserted in the Elbow Region To investigate the possibility to use a tag inserted into the elbow region of an antibody for antibody detection, one construct (named "C9") was designed, in which a twin Strep-tag was inserted into the elbow region of the heavy chain of scaffold antibody C1b (cf. Example 1). The light chain of the construct was not modified in comparison to the scaffold antibody. The construct was finally expressed as monoclonal antibody (heavy and light chains).

Construct "C9" is shown schematically in FIG. 2. In construct "C9" a twin Strep-tag ("2XST"; SEQ ID NO: 20) was inserted into the elbow region of a recombinant monospecific antibody "C1b" (see above). Construct "C9" (complete heavy chain: SEQ ID NO: 65, complete light chain: SEQ ID NO: 63) is formed by (in this order from N- to C-terminus): the expression product of a V (variable) gene segment of a heavy chain variable domain ("VH3-20"); the expression product of a D (diversity) gene segment of a heavy chain variable domain ("D"); the expression product of a J (Joining) gene segment element of a heavy chain variable domain ("JH3"); the expression product of a twin Strep-tag ("2XST"); the expression product of a C (constant) gene segment of a heavy chain constant region (IgG1 isotype); and on a separate chain: the expression product of a V (variable) gene segment of a light chain variable domain and the expression product of a J (Joining) gene segment element of a light chain variable domain; the expression product of a C (constant) gene segment of a light chain kappa constant region.

Example 6: Molecular Tags can be Inserted in the Elbow Region of Antibodies Resulting in Functional Antibodies The antibody construct "C9" described in Example 5 was produced recombinantly by transient transfection. To this end, antibody heavy and light chains were cloned into human IgG1 and Igx expression vectors and expressed by transient transfection of Expi293F Cells (ThermoFisher Scientific) using polyethylenimine (PEI). Cell lines were routinely tested for *mycoplasma* contamination.

Next, the antibody construct C9 and control antibody C1b (see Example 1) were tested for recognition by Strep-tag-specific Strep-tactin molecule by ELISA. Briefly, total IgGs were quantified using 96-well MaxiSorp plates (Nunc) coated with goat anti-human IgG (SouthernBiotech, 2040-01) using Certified Reference Material 470 (ERMs-DA470, Sigma-Aldrich) as a standard. To test specific recognition of the antibody construct, ELISA plates were coated with 10 μg $ml^{-1}$ of an anti-human IgG antibody (SouthernBiotech), plates were blocked with 1% bovine serum albumin (BSA) and incubated with titrated antibodies, followed by AP-conjugated Strep-Tactin (Iba Lifesciences). Plates were then washed, substrate (p-NPP, Sigma) was added and plates were read at 405 nm.

Results are shown in FIG. 7. Antibody construct "C9" carrying a Strep-tag was efficiently and specifically recognized by Strep-tag-specific Strep-tactin, whereas the control "C1b" antibody that does not carry Strep-tag was not recognized. These results suggest that the elbow is permissive for insertion of molecular tags that allow recognition and tracing of an antibody.

Example 7: Design of Antibodies Containing a Single-Chain-Antibody Variable Domain (VHH) or a Single-Chain Variable Fragment (ScFv) Inserted in the Elbow Region To investigate whether insertion of (additional) functional domains other than Ig-like domains into the elbow region results in functional multispecific antibodies, four new constructs were designed (C9-C12). In the four new constructs C9-C12, a single-chain-antibody variable domain (VHH) or a single-chain variable fragment (ScFv), specific for tetanus toxoid (TT) or for the fusion (F) protein of the respiratory syncytial virus (RSV), respectively, were inserted into the elbow region of an antibody specific for influenza H1 hemagglutinin (FI174; Pappas, L., et al. Rapid development of broadly influenza neutralizing antibodies through redundant mutations. *Nature* 516, 418-422 (2014); VH: SEQ ID NO: 10, VI: SEQ ID NO: 11, heavy chain constant region: SEQ ID NO: 3, light kappa chain constant region: SEQ ID NO: 12/SEQ ID NO: 4). The light chain of the constructs was not modified in comparison to the scaffold antibody FI1174. All construct were finally expressed as monoclonal antibodies (heavy and light chains).

The following variants were produced and are shown schematically in FIG. 8:
1. In construct "C10" an anti-T VHH ("T3-VHH"; Rossotti, M. A., et al. Increasing the potency of neutralizing single-domain antibodies by functionalization with a CD11b/CD18 binding domain. mAbs 7, 820-828 (2015); SEQ ID NO: 16) was inserted into the elbow region of F1174. Construct "C10" (complete heavy chain: SEQ ID NO: 66, complete light chain: SEQ ID NO: 67) is formed by (in this order from N- to C-terminus): the expression product of a V (variable) gene segment of a heavy chain variable domain of FI174 ("VH"); the expression product of a D (diversity) gene segment of a heavy chain variable domain of F1174 ("D"); the expression product of a J (Joining) gene segment element of a heavy chain variable domain of FI174 ("JH"); the expression product of an anti-TT VHH ("T3-VHH"; Rossotti, M. A., et al. Increasing the potency of neutralizing single-domain antibodies by functionalization with a CD11b/CD18 binding domain. mAbs 7, 820-828 (2015)); the expression product of a C (constant) gene segment of a heavy chain constant region (IgG1 isotype); and on a separate chain: the expression product of a V (variable) gene segment of a light chain variable domain of FI74 and the expression product of a J (Joining) gene segment element of a light chain variable domain of FI174; the expression product of a C (constant) gene segment of a light chain constant region.
2. In construct "C11" an anti-TT ScFv ("TT39.7-ScFv"; SEQ ID NO: 17) was inserted into the elbow region of FI74. Construct "C11" (complete heavy chain: SEQ ID NO: 68, complete light chain: SEQ ID NO: 67) is formed by (in this order from N- to C-terminus): the expression product of a V (variable) gene segment of a heavy chain variable domain of F1174 ("VH"); the expression product of a D (diversity) gene segment of a heavy chain variable domain of F1174 ("D"); the expression product of a J (Joining) gene segment element of a heavy chain variable domain of F1174 ("JH"); the expression product of an anti-ScFv ("TT39.7-ScFv"); the expression product of a C (constant) gene segment of a heavy chain constant region (IgG1 isotype); and on a separate chain: the expression product of a V (variable) gene segment of a light chain variable domain of FI174 and the expression product of a J (Joining) gene segment element of a light chain variable domain of FI174; the expression product of a C (constant) gene segment of a light chain constant region.
3. In construct "C12" an anti-RSV F protein VHH ("F4-VHH"; Rossey, I., et al. Potent single-domain antibodies that arrest respiratory syncytial virus fusion protein in its prefusion state. Nature communications 8, 14158 (2017); SEQ ID NO: 18) was inserted into the elbow region of F1174. Construct "C12" (complete heavy chain: SEQ ID NO: 69, complete light chain: SEQ ID NO: 67) is formed by (in this order from N- to C-terminus): the expression product of a V (variable) gene segment of a heavy chain variable domain of FI1174 ("VH"): the expression product of a D (diversity) gene segment of a heavy chain variable domain of FI174 ("D"); the expression product of a J (Joining) gene segment element of a heavy chain variable domain of FI174 ("H"); the expression product of an anti-RSV F protein VHH ("F4-VHH"; Rossey, I., et al. Potent single-domain antibodies that arrest respiratory syncytial virus fusion protein in its prefusion state. Nature communications 8, 14158 (2017)); the expression product of a C (constant) gene segment of a heavy chain constant region (IgG1 isotype); and on a separate chain: the expression product of a V (variable) gene segment of a light chain variable domain of FI174 and the expression product of a J (Joining) gene segment element of a light chain variable domain of F1174; the expression product of a C (constant) gene segment of a light chain constant region.
4. In construct "C13" an anti-RSV F protein ScFv ("MPE8-ScFv"; Corti, D., et al. Cross-neutralization of four paramyxoviruses by a human monoclonal antibody. Nature 501, 439-443 (2013); SEQ ID NO: 19) was inserted into the elbow region of FI174. Construct "C13" (complete heavy chain: SEQ ID NO: 70, complete light chain: SEQ ID NO: 67) is formed by (in this order from N- to C-terminus): the expression product of a V (variable) gene segment of a heavy chain variable domain of FI74 ("VH"); the expression product of a D (diversity) gene segment of a heavy chain variable domain of F1174 ("D"); the expression product of a J (Joining) gene segment element of a heavy chain variable domain of F1174 ("H"); the expression product of an anti-RSV F protein ScFv ("MPE8-ScFv"; Corti, D., et al. Cross-neutralization of four paramyxoviruses by a human monoclonal antibody. Nature 501, 439-443 (2013)); the expression product of a C (constant) gene segment of a heavy chain constant region (IgG1 isotype); and on a separate chain: the expression product of a V (variable) gene segment of a light chain variable domain of FI74 and the expression product of a J (Joining) gene segment element of a light chain variable domain of FI174; the expression product of a C (constant) gene segment of a light chain constant region.

Example 8: VHH and ScFv can be Inserted in the Elbow Region Resulting in Functional Bispecific Antibodies The four new antibody constructs described in Example 4 were produced recombinantly by transient transfection. To this end, antibody heavy and light chains were cloned into human IgG1, Igκ and Igλ expression vectors and expressed by transient transfection of Expi293F Cells (ThermoFisher Scientific) using polyethylenimine (PEI). The constructs were tested for dual binding to (i) H1 and (ii) either TT or RSV F protein by surface plasmon resonance (SPR).

In a first experiment, constructs C10 and C11 (with TT-specific VHH or scFv in elbow region of FI74) were analyzed. To this end, protein A was used to capture the constructs followed by co-injection of the analytes (H1 as first analyte immediately followed by TT). As controls TT-specific antibody TT107 and the H1-specific antibody FI174 were used. Briefly, protein A (25 µg/ml) was stabilized in 10 mM acetate buffer, pH 4.5, and immobilized onto an ethyl(dimethylaminopropyl) carbodiimide/N-Hydroxysuccinimide (EDC/NHS) pre-activatedProteOnsensor chip (Bio-Rad) through amine coupling; unreacted groups were blocked by injection of 1M ethanolamine HCl. HEPES buffered saline (HBS) (10 mMHEPES, pH7.4, 150 mM NaCl, 3 mM EDTA, 0.005% surfactant Tween-20) was used as a running buffer. All injections were made at a flowrate of 100 µl/min. Monoclonal antibodies were diluted in HBS to 10 nM and injected for 240 s onto the Protein A-coated chip for capturing, followed by co-injection of H1 California hemagglutinin (50 nM) immediately followed by tetanus toxoid (50 nM) for total 110 s. One channel of the chip was injected with HBS and used as reference for the analysis. Each binding interaction of the monoclonal antibodies to H1 and TT was assessed using a ProteONXPR36 instrument (Bio-Rad) and the data were processed with ProteOn Manager software. Results are shown in FIG. 9. Constructs C10 and C11 (carrying a TT-specific domain (VHH or ScFv)) bound both H1 and TT, while control antibodies FI174 and TT107 recognize only H1 or only TT, respectively.

In a second experiment, constructs C12 and C13 (with RSV F-protein-specific VHH or scFv in elbow region of FI174) were analyzed. To this end, protein A was used to capture the constructs followed by co-injection of the analytes (H1 as first analyte immediately followed by RSV F protein). As controls RSV F protein-specific antibody MPE8 and the H1-specific antibody F1174 were used. Briefly, protein A (25 µg/ml) was stabilized in 10 mM acetate buffer, pH 4.5, and immobilized onto an ethyl(dimethylaminopropyl) carbodiimide/N-Hydroxysuccinimide (EDC/NHS) pre-activatedProteOnsensor chip (Bio-Rad) through amine coupling; unreacted groups were blocked by injection of 1M ethanolamine HC. HEPES buffered saline (HBS) (10 mMHEPES, pH7.4, 150 mM NaCl, 3 mM EDTA, 0.005% surfactant Tween-20) was used as a running buffer. All injections were made at a flowrate of 100 µl/min. Monoclonal antibodies were diluted in HBS to 10 nM and injected for 240 s onto the Protein A-coated chip for capturing, followed by co-injection of H1 California hemagglutinin (50 nM) immediately followed by RSV F protein (50 nM) for total 110 s. One channel of the chip was injected with HBS and used as reference for the analysis. Each binding interaction of the monoclonal antibodies to H1 and RSV F protein was assessed using a ProteONXPR36 instrument (Bio-Rad) and the data were processed with ProteOn Manager software. Results are shown in FIG. 10. Constructs C12 and C13 (carrying a RSV F protein-specific domain (VHH or ScFv)) bound both H1 and RSV F protein, while control antibodies FI174 and MPE8 recognize only H1 or only RSV F protein, respectively.

In summary, the data show that insertion of VHH or ScFv domains into the elbow region of FI174 did not affect binding to H1 hemagglutin, indicating that this site is permissive for insertions of different domains without affecting the original antibody specificity, as already shown above for the Ig-like domains. Dual simultaneous recognition of the two different specific antigens by the VDJ region of the antibody scaffold and the VHH or ScFv domains inserted in the elbow indicates that it is possible to generate functional and bispecific antibodies carrying different types of inserts in the elbow.

TABLE OF SEQUENCES AND SEQ ID NUMBERS (SEQUENCE LISTING):

| SEQ ID NO | Sequence | Remarks |
|---|---|---|
| SEQ ID NO: 1 | QLQLVQSGTEVKKPGASVKVSCKSSGYVFTSYYLV WVRQAPGQGLEWMATISPGDVNTSYEQRFQGRV TVTTDASTNTVDMELRSLRSEDTAVYYCARGPRSKP PYLYFALDVWGQGTAVTVSS | GCE536 VH aa |
| SEQ ID NO: 2 | EIVLTQSPGTLSLSPGETAILSCRASQSVSSSLLAWYQ QKPGQAPRLLIYGASNRATGIRGRFSGSGSGTDFTL TISRLEPEDFVLYYCQHYGSRVTFGQGTKLEIK | GCE536 VL aa |
| SEQ ID NO: 3 | ASTKGPSVFPLAPSSKSTSGGTAALGCLVKDYFPEPV TVSWNSGALTSGVHTFPAVLQSSGLYSLSSVVTVPS SSLGTQTYICNVNHKPSNTKVDKRVEPKSCDKTHT CPPCPAPELLGGPSVFLFPPKPKDTLMISRTPEVTCVV VDVSHEDPEVKFNWYVDGVEVHNAKTKPREEQYN STYRVVSVLTVLHQDWLNGKEYKCKVSNKALPAPIE KTISKAKGQPREPQVYTLPPSREEMTKNQVSLTCLVK GFYPSDIAVEWESNGQPENNYKTTPPVLDSDGSFFL YSKLTVDKSRWQQGNVFSCSVMHEALHNHYTQKS LSLSPGK | Human HC IgG1 constant region aa |
| SEQ ID NO: 4 | RTVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC | Human LC kappa constant region aa |
| SEQ ID NO: 5 | QVQLAQYGGGAVQPGGSLRLSCVVSGFRFSLYGI HWVRQAPGKGLEWLSLIENHGRKIYYAESVKGRIT VSRDNFKNVAYLEMYRLSTEDTAIYYCARNDGLGR YTDAGGTHRTAYLDYWGRGTLVTVSS | C1 VH aa |

-continued

| TABLE OF SEQUENCES AND SEQ ID NUMBERS (SEQUENCE LISTING): | | |
|---|---|---|
| SEQ ID NO | Sequence | Remarks |
| SEQ ID NO: 6 | SYEVTQPPSVSVSPGQAARITCSGDELPRTDISWYQ QTSGQAPVLVIYEGTKRPSGIPERFSGSVSGAMATL MISEAQLEDEGDYYCFSIDTSGNHGGAFGTGTKLT VL | C1 VL aa |
| SEQ ID NO: 7 | GQPKAAPSVTLFPPSSEELQANKATLVCLISDFYPGA VTVAWKADSSPVKAGVETTTPSKQSNNKYAASSYL SLTPEQWKSHRSYSCQVTHEGSTVEKTVAPTECS | Human LC lambda constant region aa |
| SEQ ID NO: 8 | DVQLVESGGGVVRPGVSLRLSCVASGESEKNYDM AWVRQVPGKGLEWVCGINWNGSLRGYADSVKG RFLISRDHAKDSLYLQMSRLRAEDTALYYCARDPGY NTGRDHPYDLWGQGTMVTSS | C1b VH aa |
| SEQ ID NO: 9 | DIQMTQSPSTLSASVGDRVTITCRASQSISSWLAWY QQKPGKAPKLLIYKASSLGSGVPSRFSGSGSTQFT LTISSLQPDDFATYYCQQYNNYPYTFGQGTKLEIK | C1b VL aa |
| SEQ ID NO: 10 | QVQLVQSGAEVRKPGSSVKVSCKTSGGIIRKYALS WVRQAPGQGLEWMGGIIAIFGTTNYAQKFQGRV TINADESTSTVYLELSSLTSEDTAIYYCAGSATYYESRF DYWGQGTLVTVSS | FI174 VH aa |
| SEQ ID NO: 11 | EIVLTQSPGTLSLSPGARATLSCRASQSVSSSSLAWY QQKPGQAPRLLIYDASSRATGIPDRFSGSGSGTDFT LTISRLEPEDFAVYYCHQYGDSRKTFGQGTKVEIK | FI174 VL aa |
| SEQ ID NO: 12 | EDLPRPSISAEPGTVIPLGSHVTFVCRGPVGVQTFRL ERESRSTYNDTEDVSQASPSESEARFRIDSVSEGNAG PYRCIYYKPPKWSEQSDYLELLVK | unmutated LAIR1 fragment aa |
| SEQ ID NO: 13 | EDLPRPSISAEPGTVIPLGSHVTFVCRGPVGVQTFRL ERERNYLYSDTEDVSQTSPSESEARFRIDSVNAGNA GLFRCIYYKSRKWSEQSDYLELVVK | mutated LAIR1 fragment aa |
| SEQ ID NO: 14 | DSPDRPWNPPTFSPALLVVTEGDNATFTCSFSNTSE SFVLNWYRMSPSNQTDKLAAFPEDRSQPGQDCRF RVTQLPNGRDFHMSVVRARRNDSGTYLCGAISLAP KAQIKESLRAELRVT | PD-1 fragment aa |
| SEQ ID NO: 15 | EQVSTPEIKVLNKTQENGTCTLILGCTVEKGDHVAY SWSEKAGTHPLNPANSSHLLSLTLGPQHADNIYICT VSNPISNNSQTFSPWPGCRTDPS | SLAM fragment aa |
| SEQ ID NO: 16 | MAQVQLVESGGGLVQAGGSLTLSCAASGSTSRSY ALGWFRQAPGKEREFVAHVGQTAEFAQGRFTISR DFAKNTVSLQMNDLKSDDTAIYYCVASNRGWSPS RVSYWGQGTQVTVSS | T3-VHH aa |
| SEQ ID NO: 17 | QITLKESGPTLVKPTQTLTLTCTFSGFSLSTSRVGVG WIRQPPGKALEWLSLIYWDDEKHYSPSLKNRVTISK DSSKNQVVLTLTDMDPVDTGTYYCAHRGVDTSG WGFDYWGQGALVTVSSGGGGSGGGGSGGGGS QSALTQPASVSGSPGQSITISCSGAGSDVGGHNFV SWYQQYPGKAPKLMIYDVKNRPSGVSYRFSGSKSG YTASLTISGLQAEDEATYFCSSYSSSSTLIIFGGGTRLT VL | TT39.7-scFv aa |
| SEQ ID NO: 18 | QVQLQESGGGLVQPGGSLRLSCAASGFTLDYYYIG WFRQAPGKEREAVSCISGSSGSTYYPDSVKGRFTISR DNAKNTVYLQMNSLKPEDTAVYYCATIRSSSWGG CVHYGMDYWGKGTQVTVSS | F4-VHH aa |
| SEQ ID NO: 19 | EVQLVESGGGLVKPGGSLRLSCAASGFTFSSYSMN WVRQAPGKGLEWVSSISASSSYSDYADSAKGRFTIS RDNAKTSLFLQMNSLRAEDTAIYFCARARATGYSSI TPYFDIWGQGTLVTVSSGGGGSGGGGSGGGGSQ SVVTQPPSVSGAPGQRVTISCTGSSSNIGAGYDVH WYQQLPGTAPKLLIYDNNNRPSGVPDRFSASKSGT SASLAITGLQAEDEADYYCQSYDRNLSGVFGTGTK VTVL | MPE8-scFv aa |

-continued

TABLE OF SEQUENCES AND SEQ ID NUMBERS (SEQUENCE LISTING):

| SEQ ID NO | Sequence | Remarks |
| --- | --- | --- |
| SEQ ID NO: 20 | SAWSHPQFEKGGGSGGGSGGSAWSHPQFEK | twin StrepTag aa |
| SEQ ID NO: 21 | GLNDIFEAQKIEWHE | AviTag |
| SEQ ID NO: 22 | KRRWKKNFIAVSAANRFKKISSSGAL | Calmodulin-tag |
| SEQ ID NO: 23 | EEEEE | polyglutamate tag |
| SEQ ID NO: 24 | GAPVPYPDPLEPR | E-tag |
| SEQ ID NO: 25 | DYKDDDDK | FLAG-tag |
| SEQ ID NO: 26 | YPYDVPDYA | HA-tag |
| SEQ ID NO: 27 | HHHHHH | His-tag |
| SEQ ID NO: 28 | EQKLISEEDL | Myc-tag |
| SEQ ID NO: 29 | TKENPRSNQEESYDDNES | NE-tag |
| SEQ ID NO: 30 | KETAAAKFERQHMDS | S-tag |
| SEQ ID NO: 31 | MDEKTTGWRGGHVVEGLAGELEQLRARLEHHPQGQREP | SBP-tag |
| SEQ ID NO: 32 | SLAELLNAGLGGS | Softag 1 |
| SEQ ID NO: 33 | TQDPSRVG | Softag 3 |
| SEQ ID NO: 34 | WSHPQFEK | Strep-tag |
| SEQ ID NO: 35 | CCPGCC | TC tag |
| SEQ ID NO: 36 | GKPIPNPLLGLDST | V5 tag |
| SEQ ID NO: 37 | YTDIEMNRLGK | VSV-tag |
| SEQ ID NO: 38 | DLYDDDDK | Xpress tag |
| SEQ ID NO: 39 | TDKDMTITFTNKKDAE | Isopeptag |
| SEQ ID NO: 40 | AHIVMVDAYKPTK | SpyTag |
| SEQ ID NO: 41 | KLGDIEFIKVNK | SnoopTag |
| SEQ ID NO: 42 | EVHTNQDPLD | Ty1 tag |
| SEQ ID NO: 43 | GGGGS | linker |
| SEQ ID NO: 44 | GGGGSGGGGS | linker |
| SEQ ID NO: 45 | GGGGSGGGGSGGGGS | linker |
| SEQ ID NO: 46 | GGGGSGGGGSGGGGSGGGGS | linker |
| SEQ ID NO: 47 | GGGGSGGGGSGGGGSGGGGSGGGGS | linker |
| SEQ ID NO: 48 | GGGGSGGGGSGGGGSGGGGSGGGGSGGGGS | linker |
| SEQ ID NO: 49 | FVGPPSPFLTSLHLS | linker |
| SEQ ID NO: 50 | GAASEAPGQGLAEPV | linker |
| SEQ ID NO: 51 | QGFTSVMAPFLPLLT | linker |
| SEQ ID NO: 52 | GEYTGGSLCATLMSM | linker |
| SEQ ID NO: 53 | QVQLAQYGGGAVQPGGSLRLSCVVSGFRFSLYGIHWVRQAPGKGLEWLSLIENHGRKIYYAESVKGRITVSRDNFKNVAYLEMYRLSTEDTAIYYCARNDGLGRYTDAGGTHRTAYLDYWGRGTLVTVSSEDLPRPSISAEPGTVIPLGSHVTFVCRGPVGVQTFRLERERNYLYSDTEDVSQTSPSESEARFRIDSVNAGNAGLFRCIYYKSRKWSEQSDYLELVVKASTKGPSVFPLAPSSKSTSGGTA | C2 heavy chain aa |

| TABLE OF SEQUENCES AND SEQ ID NUMBERS (SEQUENCE LISTING): | | |
|---|---|---|
| SEQ ID NO | Sequence | Remarks |
| | ALGCLVKDYFPEPVTVSWNSGALTSGVHTFPAVLQ SSGLYSLSSVVTVPSSSLGTQTYICNVNHKPSNTKVD KRVEPKSCDKTHTCPPCPAPELLGGPSVFLEPPKPKD TLMISRTPEVTCVVVDVSHEDPEVKFNWYVDGVEV HNAKTKPREEQYNSTYRVVSVLTVLHQDWLNGKE YKCKVSNKALPAPIEKTISKAKGQPREPQVYTLPPSRE EMTKNQVSLTCLVKGFYPSDIAVEWESNGQPENNY KTTPPVLDSDGSFELYSKLTVDKSRWQQGNVESCS VMHEALHNHYTQKSLSLSPGK | |
| SEQ ID NO: 54 | SYEVTQPPSVSVSPGQAARITCSGDELPRTDISWYQ QTSGQAPVLVIYEGTKRPSGIPERFSGSVSGAMATL MISEAQLEDEGDYYCFSIDTSGNHGGAFGTGTKLT VLGQPKAAPSVTLFPPSSEELQANKATLVCLISDFYP GAVTVAWKADSSPVKAGVETTTPSKQSNNKYAAS SYLSLTPEQWKSHRSYSCQVTHEGSTVEKTVAPTEC S | C2/C3 light chain aa |
| SEQ ID NO: 55 | QVQLAQYGGGAVQPGGSLRLSCVVSGFRFSLYGI HWVRQAPGKGLEWLSLIENHGRKIYYAESVKGRIT VSRDNFKNVAYLEMYRLSTEDTAIYYCARNDGLGR YTDAGGTHRTAYLDYWGRGTLVTVSSEDLPRPSIS AEPGTVIPLGSHVTFVCRGPVGVQTFRLERESRSTY NDTEDVSQASPSESEARFRIDSVSEGNAGPYRCIYY KPPKWSEQSDYLELLVKASTKGPSVFPLAPSSKSTSG GTAALGCLVKDYFPEPVTVSWNSGALTSGVHTFPA VLQSSGLYSLSSVVTVPSSSLGTQTYICNVNHKPSN TKVDKRVEPKSCDKTHTCPPCPAPELLGGPSVFLFP PKPKDTLMISRTPEVTCVVVDVSHEDPEVKFNWYV DGVEVHNAKTKPREEQYNSTYRVVSVLTVLHQD WLNGKEYKCKVSNKALPAPIEKTISKAKGQPREPQ VYTLPPSREEMTKNQVSLTCLVKGFYPSDIAVEWES NGQPENNYKIIPPVLDSDGSFFLYSKLTVDKSRW QQGNVFSCSVMHEALHNHYTQKSLSLSPGK | C3 heavy chain aa |
| SEQ ID NO: 56 | QLQLVQSGTEVKKPGASVKVSCKSSGYVFTSYYLV WVRQAPGQGLEWMATISPGDVNTSYEQRFQGR VTVTTDASTNTVDMELRSLRSEDTAVYYCARGPRS KPPYLYFALDVWGQGTAVTVSSEDLPRPSISAEPGT VIPLGSFIVTFVCRGPVGVQTFRLERESRSTYNDTED VSQASPSESEARFRIDSVSEGNAGPYRCIYYKPPKW SEQSDYLELLVKASTKGPSVFPLAPSSKSTSGGTAAL GCLVKDYFPEPVTVSWNSGALTSGVHTFPAVLQSS GLYSLSSVVTVPSSSLGTQTYICNVNHKPSNTKVDK RVEPKSCDKTHTCPPCPAPELLGGPSVFLEPPKPKD TLMISRTPEVTCVVVDVSHEDPEVKFNWYVDGVE VHNAKTKPREEQYNSTYRVVSVLTVLHQDWLNG KEYKCKVSNKALPAPIEKTISKAKGQPREPQVYTLPP SREEMTKNQVSLTCLVKGFYPSDIAVEWESNGQPE NNYKTTPPVLDSDGSFFLYSKLTVDKSRWQQGNV FSCSVMHEALHNHYTQKSLSLSPGK | C4 heavy chain aa |
| SEQ ID NO: 57 | EIVLTQSPGTLSLSPGETAILSCRASQSVSSSLLAWY QQKPGQAPRLLIYGASNRATGIRGRFSGSGSGTDF TLTISRLEPEDEVLYYCQHYGSRVTFGQGTKLEIKRT VAAPSVFIFPPSDEQLKSGTASVVCLLNNFYPREAK VQWKVDNALQSGNSQESVTEQDSKDSTYSLSSTL TLSKADYEKHKVYACEVTHQGLSSPVTKSENRGEC | C4/C5/C6 light chain aa |
| SEQ ID NO: 58 | QLQLVQSGTEVKKPGASVKVSCKSSGYVFTSYYLV WVRQAPGQGLEWMATISPGDVNTSYEQRFQGR VTVTTDASTNTVDMELRSLRSEDTAVYYCARGPRS KPPYLYFALDVWGQGTAVTVSSDSPDRPWNPPTF SPALLVVTEGDNATFTCSESNTSESFVLNWYRMSPS NQTDKLAAFPEDRSQPGQDCRERVTQLPNGRDF HMSVVRARRNDSGTYLCGAISLAPKAQIKESLRAEL RVTASTKGPSVFPLAPSSKSTSGGTAALGCLVKDYF PEPVTVSWNSGALTSGVHTFPAVLQSSGLYSLSSVV TVPSSSLGTQTYICNVNHKPSNTKVDKRVEPKSCD KTHTCPPCPAPELLGGPSVFLEPPKPKDTLMISRTPE VTCVVVDVSHEDPEVKFNWYVDGVEVHNAKTKP REEQYNSTYRVVSVLTVLHQDWLNGKEYKCKVSN | C5 heavy chain aa |

TABLE OF SEQUENCES AND SEQ ID NUMBERS (SEQUENCE LISTING):

| SEQ ID NO | Sequence | Remarks |
|---|---|---|
| | KALPAPIEKTISKAKGQPREPQVYTLPPSREEMTKNQ<br>VSLTCLVKGEYPSDIAVEWESNGQPENNYKTTPPV<br>LDSDGSFFLYSKLTVDKSRWQQGNVESCSVMHEA<br>LHNHYTQKSLSLSPGK | |
| SEQ ID NO: 59 | QLQLVQSGTEVKKPGASVKVSCKSSGYVFTSYYLV<br>WVRQAPGQGLEWMATISPGDVNTSYEQRFQGRV<br>TVTTDASTNTVDMELRSLRSEDTAVYYCARGPRSKP<br>PYLYFALDVWGQGTAVTVSSFVGPPSPFLTSLHLSD<br>SPDRPWNPPTESPALLVVTEGDNATETCSFSNTSESF<br>VLNWYRMSPSNQTDKLAAFPEDRSQPGQDCRFRV<br>TQLPNGRDFHMSVVRARRNDSGTYLCGAISLAPKA<br>QIKESLRAELRVTGAASEAPGQGLAEPVASTKGPSVF<br>PLAPSSKSTSGGTAALGCLVKDYFPEPVTVSWNSGA<br>LTSGVHTFPAVLQSSGLYSLSSVVTVPSSSLGTQTYIC<br>NVNHKPSNTKVDKRVEPKSCDKTHTCPPCPAPELL<br>GGPSVFLFPPKPKDTLMISRTPEVTCVVVDVSHEDPE<br>VKFNWYVDGVEVHNAKTKPREEQYNSTYRVVSVLT<br>VLHQDWLNGKEYKCKVSNKALPAPIEKTISKAKGQ<br>PREPQVYTLPPSREEMTKNQVSLTCLVKGFYPSDIAV<br>EWESNGQPENNYKIIPPVLDSDGSFFLYSKLTVDKS<br>RWQQGNVFSCSVMHEALHNHYTQKSLSLSPGK | C5b heavy chain aa |
| SEQ ID NO: 60 | QLQLVQSGTEVKKPGASVKVSCKSSGYVFTSYYLV<br>WVRQAPGQGLEWMATISPGDVNTSYEQRFQGRV<br>TVTTDASTNTVDMELRSLRSEDTAVYYCARGPRSKP<br>PYLYFALDVWGQGTAVTVSSFVGPPSPFLTSLHLSD<br>SPDRPWNPPTFSPALLVVTEGDNATFTCSFSNTSESF<br>VLNWYRMSPSNQTDKLAAFPEDRSQPGQDCRFRV<br>TQLPNGRDFHMSVVRARRNDSGTYLCGAISLAPKA<br>QIKESLRAELRVTGAASEAPGQGLAEPVASTKGPSVF<br>PLAPSSKSTSGGTAALGCLVKDYFPEPVTVSWNSGA<br>LTSGVHTFPAVLQSSGLYSLSSVVTVPSSSLGTQTYIC<br>NVNHKPSNTKVDKRVEPKSCDKTHTCPPCPAPELL<br>GGPSVFLFPPKPKDTLMISRTPEVTCVVVDVSHEDPE<br>VKFNWYVDGVEVHNAKTKPREEQYNSTYRVVSVLT<br>VLHQDWLNGKEYKCKVSNKALPAPIEKTISKAKGQ<br>PREPQVYTLPPSREEMTKNQVSLTCLVKGFYPSDIAV<br>EWESNGQPENNYKTTPPVLDSDGSFELYSKLTVDKS<br>RWQQGNVESCSVMHEALHNHYTQKSLSLSPGK | C6 heavy chain aa |
| SEQ ID NO: 61 | QLQLVQSGTEVKKPGASVKVSCKSSGYVFTSYYLV<br>WVRQAPGQGLEWMATISPGDVNTSYEQRFQGR<br>VTVTTDASTNTVDMELRSLRSEDTAVYYCARGPRS<br>KPPYLYFALDVWGQGTAVTVSSQGFTSVMAPFLPL<br>LTEQVSTPEIKVLNKTQENGTCTLILGCTVEKGDHV<br>AYSWSEKAGTHPLNPANSSHLLSLTLGPQHADNIY<br>ICTVSNPISNNSQTFSPWPGCRTDPSGEYTGGSLC<br>ATLMSMASTKGPSVFPLAPSSKSTSGGTAALGCLVK<br>DYFPEPVTVSWNSGALTSGVHTFPAVLQSSGLYSLS<br>SVVTVPSSSLGTQTYICNVNHKPSNTKVDKRVEPKS<br>CDKTHTCPPCPAPELLGGPSVFLFPPKPKDTLMISRT<br>PEVTCVVVDVSHEDPEVKFNWYVDGVEVHNAKT<br>KPREEQYNSTYRVVSVLTVLHQDWLNGKEYKCKV<br>SNKALPAPIEKTISKAKGQPREPQVYTLPPSREEMTK<br>NQVSLTCLVKGFYPSDIAVEWESNGQPENNYKTTP<br>PVLDSDGSFELYSKLTVDKSRWQQGNVESCSVMH<br>EALHNHYTQKSLSLSPGK | C6b heavy chain aa |
| SEQ ID NO: 62 | DVQLVESGGGVVRPGVSLRLSCVASGESEKNYDM<br>AWVRQVPGKGLEWVCGINWNGSLRGYADSVKG<br>RFLISRDHAKDSLYLQMSRLRAEDTALYYCARDPG<br>YNTGRDHPYDLWGQGTMVTVSSDSPDRPWNPP<br>TESPALLVVTEGDNATFTCSFSNTSESEVLNWYRMS<br>PSNQTDKLAAFPEDRSQPGQDCRFRVTQLPNGR<br>DFHMSVVRARRNDSGTYLCGAISLAPKAQIKESLR<br>AELRVTASTKGPSVFPLAPSSKSTSGGTAALGCLVK<br>DYFPEPVTVSWNSGALTSGVHTFPAVLQSSGLYSLS<br>SVVTVPSSSLGTQTYICNVNHKPSNTKVDKRVEPKS<br>CDKTHTCPPCPAPELLGGPSVFLFPPKPKDTLMISRT<br>PEVTCVVVDVSHEDPEVKFNWYVDGVEVHNAKT<br>KPREEQYNSTYRVVSVLTVLHQDWLNGKEYKCKV<br>SNKALPAPIEKTISKAKGQPREPQVYTLPPSREEMTK | C7 heavy chain aa |

TABLE OF SEQUENCES AND SEQ ID NUMBERS (SEQUENCE LISTING):

| SEQ ID NO | Sequence | Remarks |
|---|---|---|
| | NQVSLTCLVKGFYPSDIAVEWESNGQPENNYKTTP PVLDSDGSFFLYSKLTVDKSRWQQGNVFSCSVMH EALHNHYTQKSLSLSPGK | |
| SEQ ID NO: 63 | DIQMTQSPSTLSASVGDRVTITCRASQSISSWLAW YQQKPGKAPKWYKASSLGSGVPSRFSGSGSGTQF TLTISSLQPDDFATYYCQQYNNYPYTFGQGTKLEIK RTVAAPSVFIFPPSDEQLKSGTASVVCLLNNFYPREA KVQWKVDNALQSGNSQESVTEQDSKDSTYSLSST LTLSKADYEKHKVYACEVTHQGLSSPVTKSFNRGE C | C7/C8/C9 light chain aa |
| SEQ ID NO: 64 | DVQLVESGGGVVRPGVSLRLSCVASGESEKNYDMA WVRQVPGKGLEWVCGINWNGSLRGYADSVKGRF LISRDHAKDSLYLQMSRLRAEDTALYYCARDPGYNT GRDHPYDLWGQGTMVTVSSEQVSTPEIKVLNKTQ ENGTCTLILGCTVEKGDHVAYSWSEKAGTHPLNPA NSSHLLSLTLGPQHADNIYICTVSNPISNNSQTESPW PGCRTDPSASTKGPSVFPLAPSSKSTSGGTAALGCLV KDYFPEPVTVSWNSGALTSGVHTFPAVLQSSGLYSL SSVVIVPSSSLGTQTYICNVNHKPSNTKVDKRVEPK SCDKTHTCPPCPAPELLGGPSVFLFPPKPKDTLMISR TPEVTCVVVDVSHEDPEVKFNWYVDGVEVHNAKT KPREEQYNSTYRVVSVLTVLHQDWLNGKEYKCKVS NKALPAPIEKTISKAKGQPREPQVYTLPPSREEMTKN QVSLTCLVKGFYPSDIAVEWESNGQPENNYKTTPPV LDSDGSFELYSKLTVDKSRWQQGNVESCSVMHEAL HNHYTQKSLSLSPGK | C8 heavy chain aa |
| SEQ ID NO: 65 | DVQLVESGGGVVRPGVSLRLSCVASGESEKNYDM AWVRQVPGKGLEWVCGINWNGSLRGYADSVKG RFLISRDHAKDSLYLQMSRLRAEDTALYYCARDPG YNTGRDHPYDLWGQGTMVTVSSSAWSHPQFEK GGGSGGGSGGSAWSHPQFEKASTKGPSVFPLAPS SKSTSGGTAALGCLVKDYFPEPVTVSWNSGALTSG VHTFPAVLQSSGLYSLSSVVTVPSSSLGTQTYICNV NHKPSNTKVDKRVEPKSCDKTHTCPPCPAPELLGG PSVFLEPPKPKDTLMISRTPEVTCVVVDVSHEDPEVK FNWYVDGVEVHNAKTKPREEQYNSTYRVVSVLTV LHQDWLNGKEYKCKVSNKALPAPIEKTISKAKGQP REPQVYTLPPSREEMTKNQVSLTCLVKGFYPSDIAV EWESNGQPENNYKTTPPVLDSDGSFFLYSKLTVDK SRWQQGNVFSCSVMHEALHNHYTQKSLSLSPGK | C9 heavy chain aa |
| SEQ ID NO: 66 | QVQLVQSGAEVRKPGSSVKVSCKTSGGIIRKYALS WVRQAPGQGLEWMGGIIAIFGTTNYAQKEQGRV TINADESTSTVYLELSSLTSEDTAIYYCAGSATYYESR FDYWGQGTLVTVSSMAQVQLVESGGGLVQAGG SLTLSCAASGSTSRSYALGWFRQAPGKEREFVAHV GQTAEFAQGRFTISRDFAKNTVSLQMNDLKSDDT AIYYCVASNRGWSPSRVSYWGQGTQVTVSSASTK GPSVFPLAPSSKSTSGGTAALGCLVKDYFPEPVTVS WNSGALTSGVHTFPAVLQSSGLYSLSSVVTVPSSSL GTQTYICNVNHKPSNTKVDKRVEPKSCDKTHTCP PCPAPELLGGPSVFLFPPKPKDTLMISRTPEVTCVVV DVSHEDPEVKFNWYVDGVEVHNAKTKPREEQYN STYRVVSVLTVLHQDWLNGKEYKCKVSNKALPAPI EKTISKAKGQPREPQVYTLPPSREEMTKNQVSLTCL VKGFYPSDIAVEWESNGQPENNYKTTPPVLDSDGS FFLYSKLTVDKSRWQQGNVFSCSVMHEALHNHYT QKSLSLSPGK | C10 heavy chain aa |
| SEQ ID NO: 67 | EIVLTQSPGTLSLSPGARATLSCRASQSVSSSSLAWY QQKPGQAPRLLIYDASSRATGIPDRFSGSGSGTDF TLTISRLEPEDFAVYYCHQYGDSRKTFGQGTKVEIK RTVAAPSVFIFPPSDEQLKSGTASVVCLLNNFYPREA KVQWKVDNALQSGNSQESVTEQDSKDSTYSLSST LTLSKADYEKHKVYACEVTHQGLSSPVTKSFNRGE C | C10/C11/C12/C13 light chain aa |
| SEQ ID NO: 68 | QVQLVQSGAEVRKPGSSVKVSCKTSGGIIRKYALS WVRQAPGQGLEWMGGIIAIFGTTNYAQKFQGRV TINADESTSTVYLELSSLTSEDTANYYCAGSATYYESR FDYWGQGTLVTVSSQITLKESGPTLVKPTQTLTLTC TFSGFSLSTSRVGVGWIRQPPGKALEWLSLIYWDD | C11 heavy chain aa |

TABLE OF SEQUENCES AND SEQ ID NUMBERS (SEQUENCE LISTING):

| SEQ ID NO | Sequence | Remarks |
|---|---|---|
| | EKHYSPSLKNRVTISKDSSKNQVVLTLTDMDPVDT GTYYCAHRGVDTSGWGFDYWGQGALVTVSSGG GGSGGGGSGGGGSQSALTQPASVSGSPGQSITIS CSGAGSDVGGHNEVSWYQQYPGKAPKLMIYDV KNRPSGVSYRFSGSKSGYTASLTISGLQAEDEATYF CSSYSSSTLIIFGGGTRLTVLASTKGPSVFPLAPSSKS TSGGTAALGCLVKDYFPEPVTVSWNSGALTSGVH TFPAVLQSSGLYSLSSVVTVPSSSLGTQTYICNVNH KPSNTKVDKRVEPKSCDKTHTCPPCPAPELLGGPSV FLFPPKPKDTLMISRTPEVTCVVVDVSHEDPEVKFN WYVDGVEVHNAKTKPREEQYNSTYRVVSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK | |
| SEQ ID NO: 69 | QVQLVQSGAEVRKPGSSVKVSCKTSGGIIRKYALSW VRQAPGQGLEWMGGIIAIFGTTNYAQKFQGRVTI NADESTSTVYLELSSLTSEDTAIYYCAGSATYYESRFD YWGQGTLVTVSSQVQLQESGGGLVQPGGSLRLSC AASGFTLDYYYIGWFRQAPGKEREAVSCISGSSGST YYPDSVKGRFTISRDNAKNTVYLQMNSLKPEDTAV YYCATIRSSSWGGCVHYGMDYWGKGTQVTVSSAS TKGPSVFPLAPSSKSTSGGTAALGCLVKDYFPEPVTV SWNSGALTSGVHTFPAVLQSSGLYSLSSVVTVPSSSL GTQTYICNVNHKPSNTKVDKRVEPKSCDKTHTCPP CPAPELLGGPSVFLEPPKPKDTLMISRTPEVTCVVVD VSHEDPEVKFNWYVDGVEVHNAKTKPREEQYNST YRVVSVLTVLHQDWLNGKEYKCKVSNKALPAPIEKT ISKAKGQPREPQVYTLPPSREEMTKNQVSLTCLVKG FYPSDIAVEWESNGQPENNYKTTPPVLDSDGSFFLY SKLTVDKSRWQQGNVFSCSVMHEALHNHYTQKSL SLSPGK | C12 heavy chain aa |
| SEQ ID NO: 70 | QVQLVQSGAEVRKPGSSVKVSCKTSGGIIRKYALS WVRQAPGQGLEWMGGIIAIFGTTNYAQKFQGRV TINADESTSTVYLELSSLTSEDTAIYYCAGSATYYESR FDYWGQGTLVTVSSEVQLVESGGGLVKPGGSLRL SCAASGFTFSSYSMNWVRQAPGKGLEWVSSISASS SYSDYADSAKGRFTISRDNAKTSLFLQMNSLRAEDT AIYFCARARATGYSSITPYFDIWGQGTLVTVSSGG GGSGGGGSGGGGSQSVVTQPPSVSGAPGQRVTI SCTGSSSNIGAGYDVHWYQQLPGTAPKLLIYDNN NRPSGVPDRFSASKSGTSASLAITGLQAEDEADYYC QSYDRNLSGVEGTGTKVTVLASTKGPSVFPLAPSSK STSGGTAALGCLVKDYFPEPVTVSWNSGALTSGV HTFPAVLQSSGLYSLSSVVTVPSSSLGTQTYICNVN HKPSNTKVDKRVEPKSCDKTHTCPPCPAPELLGGP SVFLEPPKPKDTLMISRTPEVTCVVVDVSHEDPEVKF NWYVDGVEVHNAKTKPREEQYNSTYRVVSVLTVL HQDWLNGKEYKCKVSNKALPAPIEKTISKAKGQPR EPQVYTLPPSREEMTKNQVSLTCLVKGFYPSDIAVE WESNGQPENNYKTTPPVLDSDGSFFLYSKLTVDKS RWQQGNVFSCSVMHEALHNHYTQKSLSLSPGK | C13 heavy chain aa |
| SEQ ID NO: 71 | QVQLQESGPGLVKPSGUSLTCAVSGGSISSSNW WSWVRQPPGKGLEWIGEIYHSGSTNYNPSLKSRV TISVDKSKNQFSLKLSSVTAADTAVYYCARASPLKS QRDTEDLPRPSISAEPGTVIPLGSHVTFVCRGPVGV QTFRLERESRSTYNDTEDVSQASPSESEARFRIDSVS EGNAGPYRCIYYKPPKWSEQSDYLELLVKGEDVTW ALPQSQLDPRACPQGELPISTDIYYMDVWGKGTT VTVSS | MGD$^{UCA}$ VH aa |
| SEQ ID NO: 72 | AIRMTQSPSSFSASTGDRVTITCRASQGISSYLAWY QQKPGKAPKLLIYAASTLQSGVPSRFSGSGSGTDFT LTISCLQSEDFATYYCQQYYSYPPDFGQGTRLEIK | MGD$^{UCA}$ VL aa |
| SEQ ID NO: 73 | QVQLIQGGGGLVKPGGSLRLSCAASGFTFSDYYMS WIRQVPGKGLEWISVISATTGYTDYADSVKGRFTIS RDNAKNSVFLQMNSLRVDDMAVYYCAREVLGTA WFDYWGQGTLVTISS | TT107 VH aa |

-continued

TABLE OF SEQUENCES AND SEQ ID NUMBERS (SEQUENCE LISTING):

| SEQ ID NO | Sequence | Remarks |
|---|---|---|
| SEQ ID NO: 74 | EIVLTQSPGTLSLSPGERATLSCRASQSVTSNYLAWY QQKPGQAPRLLIYGVSRRATGIPDRFSGSGSGTDF ALTISRLEPEDFAVYYCQQYRSSPRTFGPGTKVEFK | TT107 VL aa |
| SEQ ID NO: 75 | EVQLVESGGGVVRPGESLRLSCAASGFIFNDEGMN WVRQPPGRGLEWVAGIKWRGGGVALVPSVTGRF TISGDNDKNSLYLQMTSLRDEDTAVYYCARDSGER GGRGHAFDLWGQGTMVTISAEDLPRPSISAEPGTV IPLGSHVITVCRGPVGVHTFRLERESRSTYNETEDVS QASPSESEARFRIDSVSEGNAGPYRCIYYKPPKWSEQ SDYLELLVK | MGJ1 VH |
| SEQ ID NO: 76 | EVQVVESGGRVARPGGSLRLSCAASGFHLDDYDM SWVRQPPGKGLEWVAGINWNGGRTGYADSVKG RLTISRDNAKKFLYLEMKSLRAEDTALYYCARDPGYS SGRRNALDIWGQGTMVTVSLEDLPRPSISAEPGTVI PLGSHVTFVCRGPVGVQTFRLERESRFTYNDTEDVS QASPSESEARFRIDSVSEGNAGPYRCIYYKPPKWSEQ SDYLELLVK | MGJ2 VH |
| SEQ ID NO: 77 | EVQLVQSGGGVVRPGGFLRLSCAASGFTFENYAVA WVRQVAGKGLEWLCVINWDAGTTNYADSVKGRF TISRDIVKNSLVLEMSSLRAEDTALYYCARDPVYGSD RGDVEDMWGQGTVVTVSSDLPRPSISAEPGTVIPL GSHVTFVCRGPVGVQTFRLERESRSTYNETEDVSQA SPSESEARFRIDSVSEGNAGPYRCIYYKPPKWSEQSD YLELLVK | MGJ3 VH |
| SEQ ID NO: 78 | DVQLVESGGGVVRPGVSLRLSCVASGESEKNYDMA WVRQVPGKGLEWVCGINWNGSLRGYADSVKGRF LISRDHAKDSLYLQMSRLRAEDTALYYCARDPGYNT GRDHPYDLWGQGTMVTVSSEDLPRPSISAEPGTVI PLGSHVTFVCRGPVGVQTFRLERESRSTYNETEDVS QVSPSESEARFRIDSVSEGNAGPYRCIYYKPPKWSEQ SDYLELLVK | MGJ5 VH |
| SEQ ID NO: 79 | EVQLVESGGRVVRPGESLRLSCEVSGVSINDYDMS WVRQPLGKGLEWVSGIDRKGVGTGYADSVKGRFT ISRDHAKNSLYLQMNSLTGDDTAFYYCVRDPGESS GRGHIFNIWGQGTMVTVSLEDLPRPSISAEPGTVIPL GSHVTFVCRGPVGVQTFRLERESRSTYNETEDVSQV SPSESEARFRIDSVSEGNAGPYRCIYYKPPKWSEQSD YLELLVK | MMJ1 VH |
| SEQ ID NO: 80 | EVQLVESGGGVVRPGESLRLSCEVSGVNINDYDMS WVRQFLGKGLEWVSGIDRKGVGTGYADSVKGRFT ISRDHAKNSLYLQMNSLRGEDTALYYCVRDPGDTS GRGHIFNVWGQGTMVTVSLEDLPRPSISAEPGTVIP LGSHVTFVCRGPVGVQTFRLERESRSTYNETEDVSQ VSPSESEARFRIDSVSEGNAGPYRCIYYKPPKWSEQS DYLELLVK | MMJ2 VH |
| SEQ ID NO: 81 | EVQLVESGGGVVRPGESLRLSCEVSGVNINDYDMS WVRQPLGKGLEWVSGIDRKGVGTGYADSVKGRFT ISRDNGKNSLYLQMNSLRGEDTALYYCVRDPGDRS GRGHIFNIWGQGTMVTVSLEDLPRPSISAEPGTVIPL GSHVTFVCRGPVGVQTFRLERESRSTYNETEDVSQV SPSESEARFRIDSVSEGNAGPYRCIYYKPPKWSEQSD YLELLVK | MMJ5 VH |
| SEQ ID NO: 82 | EVQLVESGGGVVRPGESLRLSCEVSGVSINDYDMS WVRQPLGKGLEWVSGIDRKGVGTGYADSVKGRFT ISRDHAKNSLYLQMNSLRGEDTALYYCVRDPGDSS GRGQIFNIWGQGTMVTVSLEDLPRPSISAEPGTVIPL GSHVTFVCRGPVGVQTFRLERESRSTYNETEDVSQV SPSESEARFRIDSVSEGNAGPYRCIYYKPPKWSEQSD YLELLVK | MMJ6 VH |
| SEQ ID NO: 83 | EVQLVESGGGVVRPGESLRLSCEVSGVSINDYDMS WVRQRLGKGLEWVSGIDRKGVGTGYADSVKGRFT ISRDHAKNSLYLQMNSLRGEDTALYYCVRDPGESS GRGHIFNIWGQGTMVTISLEDLPRPSISAEPGTVIPL | MMJ7 VH |

| TABLE OF SEQUENCES AND SEQ ID NUMBERS (SEQUENCE LISTING): | | |
|---|---|---|
| SEQ ID NO | Sequence | Remarks |
| | GSHVTFVCRGPVGVQTFRLERESRSTYNETEDVSQV SPSESEARFRIDSVSEGNAGPYRCIYYKPPKWSEQSD YLELLVK | |
| SEQ ID NO: 84 | EVQLVESGGGVVRPGESLRLSCEVSGVNINDYDMS WVRQFLGKGLEWVSGIDRKGVGTGYADSVKGRFT ISRDHAKNSLYLQMNSLRGEDTALYYCVRDPGDTS GRGHIFNVWGQGTMVTVSLEDLPRPSISAEPGTVIP LGSHVTFVCRGPVGVQTFRLERESRSTYNETEDVSQ VSPSESEARFRIDSVSEGNAGPYRCIYYKPPKWSEQS DYLELLVK | MMJ8 VH |
| SEQ ID NO: 85 | EVQLVESGGGVVRPGESLRLSCEVSGVNINDYDMS WVRQFLGKGLEWVSGIDRKGVGTGYADSVKGRFT ISRDHAKNSLYLQMNSLRGEDTALYYCVRDPGDTS GRGHIFNVWGQGTMVTVSLEDLPRPSISAEPGTVIP LGSHVTFVCRGPVGVQTFRLERESRSTYNETEDVSQ VSPSESEARFRIDSVSEGNAGPYRCIYYKPPKWSEQS DYLELLVK | MMJ10 VH |
| SEQ ID NO: 86 | EVQLVESGGGVVRPGESLRLSCEVSGVNINDYDMS WVRQFLGKGLEWVSGIDRKGVGTGYADSVKGRFT ISRDHAKNSLYLQMNSLRGEDTALYYCVRDPGDTS GRGHIFNVWGQGTMVTVSLEDLPRPSISAEPGTVIP LGSHVTEVCRGPVGVQTFRLERESRSTYNETEDVSQ VSPSESEARFRIDSVSEGNAGPYRCIYYKPPKWSEQS DYLELLGK | MMJ16 VH |
| SEQ ID NO: 87 | EVQLVESGGGVVRPGESLRLSCEVSGVNINDYDMS WVRQPLGKGLEWVSGIDRKGVGTGYADSVKGRFT ISRDNGKNSLYLQMNSLRGEDTALYYCVRDPGDRS GRGHIFNIWGQGTMVTVSLEDLPRPSISAEPGTVIPL GSHVTFVCRGPVGVQTFRLERESRSTYNETEDVSQV SPSESEARFRIDSVSEGNAGPYRCIYYKPPKWSEQSD YLELLVK | MMJ23 VH |
| SEQ ID NO: 88 | EVQLVESGGGVVRPGESLRLSCEVSGVSINDYDMS WVRQPLGKGLEWVSGIDRKGVGTGYADSVKGRFT ISRDHAKNSLYLQMNSLRGADTALYYCVRDPGDSS GRGHIFNIWGQGTMVTVSLEDLPRPSISAEPGTVIPL GSHVTFVCRGPVGVQTFRLERESRSTYNETEDVSQV SPSESEARFRIDSVSEGNAGPYRCIYYKPPKWSEQSD YLELLVK | MMJ25 VH |
| SEQ ID NO: 89 | QVQLAQYGGGAVQPGGSLRLSCVVSGFRFSLYGI HWVRQAPGKGLEWLSLIENHGRKIYYAESVKGRITV SRDNFKNVAYLEMYRLSTEDTAIYYCARNDGLGRY TDAGGTHRTAYLDYWGRGTLVTVSSEDLPRPSISAE PGTVIPLGSHVTFVCRGPVGVQTFRLERESRSTYND TEDVSQASPSESEARFRIDSVSEGNAGPYRCVYYKPP KWSEQSDYLDLLVK | MGM1 VH |
| SEQ ID NO: 90 | QVQLVESGGDVVQPGGSLRLSCAVSGEKENIYDIH WVRQAPGKGLEWVSFIRHDGNNQEYADSVKGRF TISRDNFKNIIDLQMHSLRTEDTALYYCATNQGSGG SDDTWETNRSAFFPHWGQGTLVTVSSDLPRPSISAE PGTVIPLGSHVTFVCRGPVGVQTFRLERESRSIYNDT EDVSQASPSESEARFRIDSVSEGNAGPYRCVYYKPPK WSEESDYLELLVK | MGM3 VH |
| SEQ ID NO: 91 | QVQLVESGGGVVQPGGSLRLSCEVSGFRESTYGIH WARQAPGKGLEWVAFIRYDGNNKSYADSVKGRFT ISRDNSKNTLYLQMNSLRIEDTAVYYCAKNQASGG YDDTWGTYRSAYLDYWGQGTLVTVSSEDLPRPSIS AEPGTVIPLGSHVTFVCRGPVGVQTFRLERESRSTYN DTEDVSQASPSESEARFRIDSVSEGNAGPYRCVYYKP PKWSEESDSLELLVK | MGM4 VH |
| SEQ ID NO: 92 | QVQLVESGGGVVQPGGSLRLSCKMSGEKESAFGIH WVRQAPGKGLEWVAFVRYDGGDKYYADSVKGRF TISRDNSKNTVHLQLNSLKPADTAVYYCAKNQPSG QSDDTWGTSLSAYLDYWGQGTQVSVSPEDLPRPSI SAEPGTVIPLGSHVTFVCRGPVGVQTFRLERESRSTY NDTEDVSQASPSESEARFRIDSVSEGNAGPYRCVYY KPPKWSEQSDYLELLVK | MGM5 VH |

-continued

| TABLE OF SEQUENCES AND SEQ ID NUMBERS (SEQUENCE LISTING): | | |
|---|---|---|
| SEQ ID NO | Sequence | Remarks |
| SEQ ID NO: 93 | EAQVVDHGNRGRARDLEDIKKRRARDLEYEDLPRP SISAEPGTVIPLGSRVTFVCRGPVGVQTFRLERESRSK YNETEDVSQASPSESEARFRIDSVSEGNAGPYRCIYY KPPKWSEHSDFLELLVK | MGB2 VH |
| SEQ ID NO: 94 | VAEVEEHINKRRARDLEYEDLPRPSISAEPGTVIPLGS HVTFVCRGPVGVQTFRLERESRSRYNETEDVSQTSP SESEARFRIDSVSEGNAGPYRCLYYKTPKWSEQSDFL ELLVK | MGB43 VH |
| SEQ ID NO: 95 | EAEVVEHVNKRRARALEYEDLPRPSISAEPGTVIPLGS HVTFVCRGPVGVQTFRLERESRSRYTETEDVSQTSPS ESEARFRIDSVSEGNAGPYRCLYYKPPKWSEQSDFLE LLVK | MGB47 VH |
| SEQ ID NO: 96 | DFQMTQSPSTLSASVGDRVTITCRASQNVNTWLA WYQQAAGKAPKLLIYEASTLQSGVPSRFRGGGSGT EFTLTITSLQPEDFATYYCHQYKSHPFTFGPGTKVDV R | MGJ1 VL |
| SEQ ID NO: 97 | DIQMTQSPSTLSASVGDRVTITCRASQTISSWLAWY QQKPGKAPKFLIYKASFLENGVPSRFSGSESGTEFTLT INSLQPDDFATYYCQQYKSYPFTFGPGTKVEIK | MGJ2 VL |
| SEQ ID NO: 98 | DIQMTQSPSTLSASVGDRVTFTCGASQSITDCLAW YQQKPGKDPKLLIYKASRLEAGVPARFSASGSGTEFT FTIRSMQPEDFATYYCQQCYSYPFTFGPGTKVDLK | MGJ3 VL |
| SEQ ID NO: 99 | DIQMTQSPSTLSASVGDRVTITCRASQSISSWLAWY QQKPGKAPKLLIYKASSLGSGVPSRFSGSGSGTQFTL TISSLQPDDFATYYCQQYNNYPYTFGQGTKLEIK | MGJ5 VL |
| SEQ ID NO: 100 | DIQMTQSPSTVSASIGDRVTITCRASQIIERSLAWYQ QKPGKSPKALIYKTSNLEDGVPSRFSGSGSGTDFTLT VSSLQPDDFANYYCQQYDTYPFTFGPGTTVTLR | MMJ1 VL |
| SEQ ID NO: 101 | DIQMTQSPSTLSASIGDRVTITCRASQVIDRSLAWF QQKPGKSPRPLIYKASTLEGGVPSRFSGSGSGTDFTL TVSSLQPDDFANYYCQQYDTYPFTFGPGTTVTLR | MMJ5 VL |
| SEQ ID NO: 102 | DIQMTQSPSTLSASIGDRVTITCRASQIIHRSLAWYQ QKPGKSPRALIYKASNLEGGVPSRFSGSGSGTDFTLT VSSLQPDDFAMYYCQQYDTYPFTFGPGTTVFLR | MMJ6 VL |
| SEQ ID NO: 103 | DIQMTQSPSTLSASIGDRVTITCRASQSIDRSLAWY QQKPGKSPKALIYKASNLEGGVPSRFSGSGSGTDFT LTVSSLQPDDFADYYCQQYDTYPFTFGPGTTVTLR | MMJ7 VL |
| SEQ ID NO: 104 | DIQMTQSPSTLSASIGDRVTITCRASQIIDRSLAWYQ QKPGKSPKALIYKASNLEGGVPSRFSGSGSGTDFTLT VSSLQPDDFANYYCQQYDTYPFTFGPGTTVTLR | MMJ8 VL |
| SEQ ID NO: 105 | DIQMTQSPSTLSASIGDRVTITCRASQIIDRSLAWYQ QKPGKSPKALIYKASNLEGGVPSRFSGSGSGTDFTLT VSSLQPDDFANYYCQQYDTYPFTFGPGTTVTLR | MMJ10 VL |
| SEQ ID NO: 106 | DIQMTQSPSTLSASIGDRVTITCRASQIIDRSLAWYQ QKPGKSPKALIYKASNLEGGVPSRFSGSGSGTDFTLT VSSLQPDDFANYYCQQYDTYPFTFGPGTTVTLR | MMJ16 VL |
| SEQ ID NO: 107 | DIQMTQSPSTLSASIGDRVTITCRASQVIDRSLAWF QQKPGKSPRPLIYKASTLEGGVPSRESGSGSGTDFTL TVSSLQPDDFANYYCQQYDTYPFTFGPGTTVTLR | MMJ23 VL |
| SEQ ID NO: 108 | DIQMTQSPSTLSASIGDRVTITCRASQNIDRSLAWY QQKPGKSPKALIYKASNLEDGVPSRFSGSGSGTDFT LTVSSLQPDDFALYYCQQYDTYPFTFGPGTTVTLR | MMJ25 VL |
| SEQ ID NO: 109 | SYEVTQPPSVSVSPGQAARITCSGDELPRTDISWYQ QTSGQAPVLVIYEGTKRPSGIPERFSGSVSGAMATL MISEAQLEDEGDYYCFSIDTSGNHGGAFGTGTKLT VL | MGM1 VL |

-continued

TABLE OF SEQUENCES AND SEQ ID NUMBERS (SEQUENCE LISTING):

| SEQ ID NO | Sequence | Remarks |
|---|---|---|
| SEQ ID NO: 110 | SYELIQPPSXSVSPGQTARITCSGEPLPRTSTSWYRQK<br>SGQAPVLIIYEVSKRPSGIPERXSGSNTGTKATLFIVG<br>AQVEDEGDYYCYSTNTSGGSRGAFGTGTSLTVL | MGM3 VL |
| SEQ ID NO: 111 | SYELTQPPSVSVSPGQTARITCSGDAVPNTYTYWYQ<br>QKSGQAPVLVIYEDSKRPSGIPERESGSSSGTMATFII<br>SGAQVEDEADYYCYSTDTSDDHRGAFGTGTKVTV<br>L | MGM4 VL |
| SEQ ID NO: 112 | SYELTQFPSVSVSPGQTARITCSGDALPRTFIYWYQ<br>QKSRQAPVVVIYEDVKRPSGIPERFSGSISGTQATLII<br>TGAQVEDEADYYCYSTDTNNTHRGAFGTGTKVTV<br>L | MGM5 VL |
| SEQ ID NO: 113 | EDLPRPSISAEPGTVIPLGSHVTFVCRGPVGVHTFRL<br>ERESRSTYNETEDVSQASPSESEARFRIDSVSEGNAGP<br>YRCIYYKPPKWSEQSDYLELLVK | MGJ1 LAIR1 |
| SEQ ID NO: 114 | EDLPRPSISAEPGTVIPLGSHVTFVCRGPVGVQTFRL<br>ERESRFTYNDTEDVSQASPSESEARFRIDSVSEGNAG<br>PYRCIYYKPPKWSEQSDYLELLVK | MGJ2 LAIR1 |
| SEQ ID NO: 115 | DLPRPSISAEPGTVIPLGSHVTFVCRGPVGVQTFRLE<br>RESRSTYNETEDVSQASPSESEARFRIDSVSEGNAGP<br>YRCIYYKPPKWSEQSDYLELLVK | MGJ3 LAIR1 |
| SEQ ID NO: 116 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MGJ5 LAIR1 |
| SEQ ID NO: 117 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ1 LAIR1 |
| SEQ ID NO: 118 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ2 LAIR1 |
| SEQ ID NO: 119 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ5 LAIR1 |
| SEQ ID NO: 120 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ6 LAIR1 |
| SEQ ID NO: 121 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ7 LAIR1 |
| SEQ ID NO: 122 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ8 LAIR1 |
| SEQ ID NO: 123 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ10 LAIR1 |
| SEQ ID NO: 124 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLGK | MMJ16 LAIR1 |
| SEQ ID NO: 125 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ23 LAIR1 |
| SEQ ID NO: 126 | EDLPRPSISAEPGTVIPLGSHVTFVCRGPVGVQTFRL<br>ERESRSTYNETEDVSQVSPSESEARFRIDSVSEGNAGP<br>YRCIYYKPPKWSEQSDYLELLVK | MMJ25 LAIR1 |
| SEQ ID NO: 127 | EDLPRPSISAEPGTVIPLGSHVTFVCRGPVGVQTFRL<br>ERESRSTYNDTEDVSQASPSESEARFRIDSVSEGNAG<br>PYRCVYYKPPKWSEQSDYLDLLVK | MGM1 LAIR1 |

TABLE OF SEQUENCES AND SEQ ID NUMBERS (SEQUENCE LISTING):

| SEQ ID NO | Sequence | Remarks |
|---|---|---|
| SEQ ID NO: 128 | DLPRPSISAEPGTVIPLGSHVTFVCRGPVGVQTFRLE<br>RESRSIYNDTEDVSQASPSESEARFRIDSVSEGNAGP<br>YRCVYYKPPKWSEESDYLELLVK | MGM3 LAIR1 |
| SEQ ID NO: 129 | EDLPRPSISAEPGTVIPLGSHVTFVCRGPVGVQTFRL<br>ERESRSTYNDTEDVSQASPSESEARFRIDSVSEGNAG<br>PYRCVYYKPPKWSEESDSLELLVK | MGM4 LAIR1 |
| SEQ ID NO: 130 | EDLPRPSISAEPGTVIPLGSHVTFVCRGPVGVQTFRL<br>ERESRSTYNDTEDVSQASPSESEARFRIDSVSEGNAG<br>PYRCVYYKPPKWSEQSDYLELLVK | MGM5 LAIR1 |
| SEQ ID NO: 131 | EDLPRPSISAEPGTVIPLGSRVTFVCRGPVGVQTFRLE<br>RESRSKYNETEDVSQASPSESEARFRIDSVSEGNAGP<br>YRCIYYKPPKWSEHSDFLELLVK | MGB2 LAIR1 |
| SEQ ID NO: 132 | EDLPRPSISAEPGTVIPLGSHVTFVCRGPVGVQTFRL<br>ERESRSRYNETEDVSQTSPSESEARFRIDSVSEGNAGP<br>YRCLYYKTPKWSEQSDFLELLVK | MGB43 LAIR1 |
| SEQ ID NO: 133 | EDLPRPSISAEPGTVIPLGSHVTFVCRGPVGVQTFRL<br>ERESRSRYTETEDVSQTSPSESEARFRIDSVSEGNAGP<br>YRCLYYKPPKWSEQSDFLELLVK | MGB47 LAIR1 |

The invention claimed is:

1. An antibody, or antigen binding fragment thereof, comprising:
   (a) a first polypeptide chain comprising, in N- to C-terminal direction:
      one or more variable domains,
      a first polypeptide chain functional domain, and
      one or more heavy chain constant domains; and
   (b) a second polypeptide chain comprising, in N- to C-terminal direction:
      one or more variable domains forming antigen binding sites with the one or more variable domains of the first polypeptide chain, and
      one or more light chain constant domains,
   wherein all amino acids required for or involved in functionality of said first polypeptide chain functional domain are contained in the first polypeptide chain functional domain and no fragments or amino acids of the second polypeptide chain are required for or involved in the functionality of the first polypeptide chain functional domain,
   wherein the first polypeptide chain functional domain comprises or consists of an Ig-like domain, an scFv, or a VHH, and
   wherein the first polypeptide functional domain is N-terminal to the most N-terminal heavy chain constant domain of the first polypeptide chain.

2. The antibody, or the antigen binding fragment thereof, according to claim 1, wherein the second polypeptide chain does not comprise a second polypeptide chain functional domain and wherein the C-terminus of the most C-terminal variable domain of the second polypeptide chain is directly coupled to the N-terminus of the most N-terminal light chain constant domain of the second polypeptide chain.

3. The antibody, or the antigen binding fragment thereof, according to claim 1, wherein the one or more variable domains of the first polypeptide chain is/are heavy chain variable domains (VH), and the one or more variable domains of the second polypeptide chain is/are light chain variable domains (VL).

4. The antibody, or the antigen binding fragment thereof, according to claim 1, wherein the one or more heavy chain constant domains comprise a CH1 domain.

5. The antibody, or the antigen binding fragment thereof, according to claim 1, wherein:
   (a) the first polypeptide chain comprises one single variable domain N-terminal of the first polypeptide chain functional domain and the second polypeptide chain comprises one single variable domain N-terminal of the one or more light chain constant domains, the one single variable domain of the second polypeptide chain forming an antigen binding site with the one single variable domain of the first polypeptide chain; or
   (b) the first polypeptide chain comprises two or more variable domains N-terminal of the first polypeptide chain functional domain and the second polypeptide chain comprises two or more variable domains N-terminal of the one or more light chain constant domains, the two or more variable domains of the second polypeptide chain forming antigen binding sites with the two or more variable domains of the first polypeptide chain.

6. The antibody, or the antigen binding fragment thereof, according to claim 1, wherein the first polypeptide chain and/or the second polypeptide chain comprises one or more linkers.

7. The antibody, or the antigen binding fragment thereof, according to claim 1, wherein:
   (a) the antibody, or the antigen binding fragment thereof, is bivalent for a target epitope; or
   (b) the antibody, or the antigen binding fragment thereof, is monovalent for a target epitope.

8. A composition comprising the antibody, or antigen-binding fragment thereof, according to claim 1, and a pharmaceutically acceptable carrier, excipient, or diluent.

9. An antibody, or antigen binding fragment thereof, comprising:
   (a) a first polypeptide chain comprising, in N- to C-terminal direction:
      one or more variable domains, and
      one or more heavy chain constant domains; and
   (b) a second polypeptide chain comprising, in N- to C-terminal direction:
      one or more variable domains forming antigen binding sites with the one or more variable domains of the first polypeptide chain,
      a second polypeptide chain functional domain, and
      one or more light chain constant domains,
   wherein all amino acids required for or involved in functionality of said second polypeptide chain functional domain are contained in the second polypeptide chain functional domain and no fragments or amino acids of the first polypeptide chain are required for or involved in the functionality of the second polypeptide chain functional domain, wherein the second polypeptide chain functional domain comprises or consists of an Ig-like domain, an scFv, or a VHH.

10. The antibody, or the antigen binding fragment thereof, according to claim 9, wherein the first polypeptide chain does not comprise a first polypeptide chain functional domain and wherein the C-terminus of the most C-terminal variable domain of the first polypeptide chain is directly coupled to the N-terminus of the most N-terminal heavy chain constant domain of the first polypeptide chain.

11. The antibody, or the antigen binding fragment thereof, according to claim 9, wherein the one or more variable domains of the first polypeptide chain is/are heavy chain variable domains (VH), and the one or more variable domains of the second polypeptide chain is/are light chain variable domains (VL).

12. The antibody, or the antigen binding fragment thereof, according to claim 9, wherein the one or more heavy chain constant domains comprise a CH1 domain.

13. The antibody, or the antigen binding fragment thereof, according to claim 9, wherein:
   (a) the first polypeptide chain comprises one single variable domain N-terminal of the one or more heavy chain constant domains and the second polypeptide chain comprises one single variable domain N-terminal of the second polypeptide chain functional domain, the one single variable domain of the second polypeptide chain forming an antigen binding site with the one single variable domain of the first polypeptide chain; or
   (b) the first polypeptide chain comprises two or more variable domains N-terminal of the one or more heavy chain constant domains and the second polypeptide chain comprises two or more variable domains N-terminal of the second polypeptide chain functional domain, the two or more variable domains of the second polypeptide chain forming antigen binding sites with the two or more variable domains of the first polypeptide chain.

14. The antibody, or the antigen binding fragment thereof, according to claim 9, wherein the first polypeptide chain and/or the second polypeptide chain comprises one or more linkers.

15. The antibody, or the antigen binding fragment thereof, according to claim 9, wherein:
   (a) the antibody, or the antigen binding fragment thereof, is bivalent for a target epitope; or
   (b) the antibody, or the antigen binding fragment thereof, is monovalent for a target epitope.

16. A composition comprising the antibody, or antigen-binding fragment thereof, according to claim 9, and a pharmaceutically acceptable carrier, excipient, or diluent.

17. An antibody, or antigen binding fragment thereof, comprising:
   (a) a first polypeptide chain comprising, in N- to C-terminal direction:
      one or more variable domains,
      a first polypeptide chain functional domain and
      one or more heavy chain constant domains; and
   (b) a second polypeptide chain comprising, in N- to C-terminal direction:
      one or more variable domains forming antigen binding sites with the one or more variable domains of the first polypeptide chain,
      a second polypeptide chain functional domain, and
      one or more light chain constant domains,
   wherein all amino acids required for or involved in functionality of said first polypeptide chain functional domain are contained in the first polypeptide chain functional domain and no fragments or amino acids of the second polypeptide chain are required for or involved in the functionality of the first polypeptide chain functional domain, and
   wherein all amino acids required for or involved in functionality of said second polypeptide chain functional domain are contained in the second polypeptide chain functional domain and no fragments or amino acids of the first polypeptide chain are required for or involved in the functionality of the second polypeptide chain functional domain, and
   wherein the first polypeptide chain functional domain and the second polypeptide chain functional domain each comprises or consists of an Ig-like domain, an scFv, or a VHH.

18. The antibody, or the antigen binding fragment thereof, according to claim 17, wherein the one or more variable domains of the first polypeptide chain is/are heavy chain variable domains (VH), and the one or more variable domains of the second polypeptide chain is/are light chain variable domains (VL).

19. The antibody, or the antigen binding fragment thereof, according to claim 17, wherein the one or more heavy chain constant domains comprise a CH1 domain.

20. The antibody, or the antigen binding fragment thereof, according to claim 17, wherein:
   (a) the first polypeptide chain comprises one single variable domain N-terminal of the first polypeptide chain functional domain and the second polypeptide chain comprises one single variable domain N-terminal of the second polypeptide chain functional domain, the one single variable domain of the second polypeptide chain forming an antigen binding site with the one single variable domain of the first polypeptide chain; or
   (b) the first polypeptide chain comprises two or more variable domains N-terminal of the first polypeptide chain functional domain and the second polypeptide chain comprises two or more variable domains N-terminal of the second polypeptide chain functional domain, the two or more variable domains of the second polypeptide chain forming antigen binding sites with the two or more variable domains of the first polypeptide chain.

21. The antibody, or the antigen binding fragment thereof, according to claim 17, wherein the first polypeptide chain and/or the second polypeptide chain comprises one or more linkers.

22. The antibody, or the antigen binding fragment thereof, according to claim 17, wherein:
   (a) the antibody, or the antigen binding fragment thereof, is bivalent for a target epitope; or
   (b) the antibody, or the antigen binding fragment thereof, is monovalent for a target epitope.

23. A composition comprising the antibody, or antigen-binding fragment thereof, according to claim 17, and a pharmaceutically acceptable carrier, excipient, or diluent.

24. The antibody, or the antigen binding fragment thereof, according to claim 17, wherein the first polypeptide chain functional domain is an scFv and the second polypeptide chain functional domain is an scFv.

25. The antibody, or the antigen binding fragment thereof, according to claim 1, wherein the Ig-like domain is selected from PD1, SLAM, CD2, CD3, CD4, CD8, CD19, CD22, CD33, CD80 or CD86.

26. The antibody, or the antigen binding fragment thereof, according to claim 9, wherein the Ig-like domain is selected from PD1, SLAM, CD2, CD3, CD4, CD8, CD19, CD22, CD33, CD80 or CD86.

27. The antibody, or the antigen binding fragment thereof, according to claim 17, wherein the Ig-like domain is selected from PD1, SLAM, CD2, CD3, CD4, CD8, CD19, CD22, CD33, CD80 or CD86.

28. The antibody, or the antigen binding fragment thereof, according to claim 1, wherein the antibody, or the antigen binding fragment thereof, is multispecific.

29. The antibody, or the antigen binding fragment thereof, according to claim 9, wherein the antibody, or the antigen binding fragment thereof, is multispecific.

30. The antibody, or the antigen binding fragment thereof, according to claim 17, wherein the antibody, or the antigen binding fragment thereof, is multispecific.

31. The antibody, or the antigen binding fragment thereof, according to claim 1, wherein the antibody, or the antigen binding fragment thereof, is bispecific.

32. The antibody, or the antigen binding fragment thereof, according to claim 9, wherein the antibody, or the antigen binding fragment thereof, is bispecific.

33. The antibody, or the antigen binding fragment thereof, according to claim 17, wherein the antibody, or the antigen binding fragment thereof, is bispecific.

34. The antibody, or the antigen binding fragment thereof, according to claim 1, wherein the antibody, or the antigen binding fragment thereof, is trispecific.

35. The antibody, or the antigen binding fragment thereof, according to claim 9, wherein the antibody, or the antigen binding fragment thereof, is trispecific.

36. The antibody, or the antigen binding fragment thereof, according to claim 17, wherein the antibody, or the antigen binding fragment thereof, is trispecific.

37. The antibody, or the antigen binding fragment thereof, according to claim 17, wherein the first polypeptide chain functional domain and the second polypeptide chain functional domain each bind to separate target antigens.

38. The antibody, or the antigen binding fragment thereof, according to claim 17, wherein the first polypeptide chain functional domain and the second polypeptide chain functional domain each bind to the same target antigen.

39. The antibody, or the antigen binding fragment thereof, according to claim 4, wherein the one or more heavy chain constant domains further comprise a CH2 domain and/or a CH3 domain.

40. The antibody, or the antigen binding fragment thereof, according to claim 12, wherein the one or more heavy chain constant domains further comprise a CH2 domain and/or a CH3 domain.

41. The antibody, or the antigen binding fragment thereof, according to claim 19, wherein the one or more heavy chain constant domains further comprise a CH2 domain and/or a CH3 domain.

42. The antibody, or the antigen binding fragment thereof, according to claim 39, further comprising a hinge region between the CH1 domain and CH2 domain.

43. The antibody, or the antigen binding fragment thereof, according to claim 40, further comprising a hinge region between the CH1 domain and CH2 domain.

44. The antibody, or the antigen binding fragment thereof, according to claim 41, further comprising a hinge region between the CH1 domain and CH2 domain.

45. An antibody, or antigen binding fragment thereof, comprising:
  (a) a first polypeptide chain comprising, in N- to C-terminal direction: a heavy chain variable domain (VH), an scFv, a CH1 domain, a CH2 domain, and a CH3 domain, and
  (b) a second polypeptide chain comprising, in N- to C-terminal direction: a light chain variable domain (VL) forming an antigen binding site with the VH of the first polypeptide chain, and a light chain constant domain (CL),
  wherein all amino acids required for or involved in functionality of said scFv are contained in the scFv and no fragments or amino acids of the second polypeptide chain are required for or involved in the functionality of the scFv.

46. An antibody, or antigen binding fragment thereof, comprising:
  (a) a first polypeptide chain comprising, in N-to C-terminal direction: a heavy chain variable domain (VH), a CH1 domain, a CH2 domain, and a CH3 domain, and
  (b) a second polypeptide chain comprising, in N-to C-terminal direction: a light chain variable domain (VL) forming an antigen binding site with the VH of the first polypeptide chain, an scFv, and a light chain constant domain (CL),
  wherein all amino acids required for or involved in functionality of said scFv are contained in the scFv and no fragments or amino acids of the first polypeptide chain are required for or involved in the functionality of the scFv.

47. An antibody, or antigen binding fragment thereof, comprising:
  (a) a first polypeptide chain comprising, in N- to C-terminal direction: a heavy chain variable domain (VH), a first scFv, a CH1 domain, a CH2 domain, and a CH3 domain, and
  (b) a second polypeptide chain comprising, in N- to C-terminal direction: a light chain variable domain (VL) forming an antigen binding site with the VH of the first polypeptide chain, a second scFv, and a light chain constant domain (CL),
  wherein all amino acids required for or involved in functionality of said first scFv are contained in the first scFv and no fragments or amino acids of the second polypeptide chain are required for or involved in the functionality of the first scFv, and
  wherein all amino acids required for or involved in functionality of said second scFv are contained in the second scFv and no fragments or amino acids of the first polypeptide chain are required for or involved in the functionality of the second scFv.

48. The antibody, or the antigen binding fragment thereof, according to claim 45, further comprising a hinge region between the CH1 domain and CH2 domain.

49. The antibody, or the antigen binding fragment thereof, according to claim 46, further comprising a hinge region between the CH1 domain and CH2 domain.

50. The antibody, or the antigen binding fragment thereof, according to claim 47, further comprising a hinge region between the CH1 domain and CH2 domain.

* * * * *

SEQUENCE LISTING

<160> NUMBER OF SEQ ID NOS: 133

<210> SEQ ID NO 1
<211> LENGTH: 124
<212> TYPE: PRT
<213> ORGANISM: Artificial Sequence
<220> FEATURE:
<223> OTHER INFORMATION: GCE536 VH aa

<400> SEQUENCE: 1

```
Gln Leu Gln Leu Val Gln Ser Gly Thr Glu Val Lys Pro Gly Ala
1               5                   10                  15

Ser Val Lys Val Ser Cys Lys Ser Gly Tyr Val Phe Thr Ser Tyr
                20                  25                  30

Tyr Leu Val Trp Val Arg Gln Ala Pro Gly Gln Gly Leu Glu Trp Met
            35                  40                  45

Ala Thr Ile Ser Pro Gly Asp Val Asn Thr Ser Tyr Glu Gln Arg Phe
        50                  55                  60

Gln Gly Arg Val Thr Val Thr Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser
        115                 120
```

<210> SEQ ID NO 2
<211> LENGTH: 107
<212> TYPE: PRT
<213> ORGANISM: Artificial Sequence
<220> FEATURE:
<223> OTHER INFORMATION: GCE536 VL aa

<400> SEQUENCE: 2

Glu Ile Val Leu Thr Gln Ser Pro Gly Thr Leu Ser Leu Ser Pro Gly
1               5                   10                  15

Glu Thr Ala Ile Leu Ser Cys Arg Ala Ser Gln Ser Val Ser Ser Ser
            20                  25                  30

Leu Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Arg Gly Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Val Leu Tyr Tyr Cys Gln His Tyr Gly Ser Arg Val
            85                  90                  95

Thr Phe Gly Gln Gly Thr Lys Leu Glu Ile Lys
            100                 105

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 4
<211> LENGTH: 107
<212> TYPE: PRT
<213> ORGANISM: Homo sapiens

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 130
<212> TYPE: PRT
<213> ORGANISM: Artificial Sequence
<220> FEATURE:
<223> OTHER INFORMATION: C1 VH aa

<400> SEQUENCE: 5

Gln Val Gln Leu Ala Gln Tyr Gly Gly Gly Ala Val Gln Pro Gly Gly
1               5                   10                  15

Ser Leu Arg Leu Ser Cys Val Val Ser Gly Phe Arg Phe Ser Leu Tyr
            20                  25                  30

Gly Ile His Trp Val Arg Gln Ala Pro Gly Lys Gly Leu Glu Trp Leu
        35                  40                  45

Ser Leu Ile Glu Asn His Gly Arg Lys Ile Tyr Tyr Ala Glu Ser Val
    50                  55                  60

Lys Gly Arg Ile Thr Val Ser Arg Asp Asn Phe Lys Asn Val Ala Tyr
65                  70                  75                  80

Leu Glu Met Tyr Arg Leu Ser Thr Glu Asp Thr Ala Ile Tyr Tyr Cys
                85                  90                  95

Ala Arg Asn Asp Gly Leu Gly Arg Tyr Thr Asp Ala Gly Gly Thr His
            100                 105                 110

Arg Thr Ala Tyr Leu Asp Tyr Trp Gly Arg Gly Thr Leu Val Thr Val
        115                 120                 125

Ser Ser
    130
```

<210> SEQ ID NO 6
<211> LENGTH: 109
<212> TYPE: PRT
<213> ORGANISM: Artificial Sequence
<220> FEATURE:
<223> OTHER INFORMATION: C1 VL aa

<400> SEQUENCE: 6

Ser Tyr Glu Val Thr Gln Pro Pro Ser Val Ser Val Ser Pro Gly Gln
1               5                   10                  15

Ala Ala Arg Ile Thr Cys Ser Gly Asp Glu Leu Pro Arg Thr Asp Ile
            20                  25                  30

Ser Trp Tyr Gln Gln Thr Ser Gly Gln Ala Pro Val Leu Val Ile Tyr
        35                  40                  45

Glu Gly Thr Lys Arg Pro Ser Gly Ile Pro Glu Arg Phe Ser Gly Ser
    50                  55                  60

Val Ser Gly Ala Met Ala Thr Leu Met Ile Ser Glu Ala Gln Leu Glu
65                  70                  75                  80

Asp Glu Gly Asp Tyr Tyr Cys Phe Ser Ile Asp Thr Ser Gly Asn His
                85                  90                  95

Gly Gly Ala Phe Gly Thr Gly Thr Lys Leu Thr Val Leu
            100                 105

<210> SEQ ID NO 7
<211> LENGTH: 106
<212> TYPE: PRT
<213> ORGANISM: Homo sapiens

<400> SEQUENCE: 7

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 8
<211> LENGTH: 123
<212> TYPE: PRT
<213> ORGANISM: Artificial Sequence
<220> FEATURE:
<223> OTHER INFORMATION: C1b VH aa

<400> SEQUENCE: 8

Asp Val Gln Leu Val Glu Ser Gly Gly Gly Val Val Arg Pro Gly Val
1               5                   10                  15

Ser Leu Arg Leu Ser Cys Val Ala Ser Gly Phe Ser Phe Lys Asn Tyr
            20                  25                  30

Asp Met Ala Trp Val Arg Gln Val Pro Gly Lys Gly Leu Glu Trp Val
        35                  40                  45

Cys Gly Ile Asn Trp Asn Gly Ser Leu Arg Gly Tyr Ala Asp Ser Val
            50                  55                  60

Lys Gly Arg Phe Leu Ile Ser Arg Asp His Ala Lys Asp Ser Leu Tyr
 65                  70                  75                  80

Leu Gln Met Ser Arg Leu Arg Ala Glu Asp Thr Ala Leu Tyr Tyr Cys
                85                  90                  95

Ala Arg Asp Pro Gly Tyr Asn Thr Gly Arg Asp His Pro Tyr Asp Leu
               100                 105                 110

Trp Gly Gln Gly Thr Met Val Thr Val Ser Ser
           115                 120

<210> SEQ ID NO 9
<211> LENGTH: 107
<212> TYPE: PRT
<213> ORGANISM: Artificial Sequence
<220> FEATURE:
<223> OTHER INFORMATION: C1b VL aa

<400> SEQUENCE: 9

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Gly Ser Gly Val Pro Ser Arg Phe Ser Gly
 50                  55                  60

Ser Gly Ser Gly Thr Gln Phe Thr Leu Thr Ile Ser Ser Leu Gln Pro
 65                  70                  75                  80

Asp Asp Phe Ala Thr Tyr Tyr Cys Gln Gln Tyr Asn Asn Tyr Pro Tyr
                85                  90                  95

Thr Phe Gly Gln Gly Thr Lys Leu Glu Ile Lys
               100                 105

<210> SEQ ID NO 10
<211> LENGTH: 120
<212> TYPE: PRT
<213> ORGANISM: Artificial Sequence
<220> FEATURE:
<223> OTHER INFORMATION: FI174 VH aa

<400> SEQUENCE: 10

Gln Val Gln Leu Val Gln Ser Gly Ala Glu Val Arg Lys Pro Gly Ser
 1               5                  10                  15

Ser Val Lys Val Ser Cys Lys Thr Ser Gly Gly Ile Ile Arg Lys Tyr
                20                  25                  30

Ala Leu Ser Trp Val Arg Gln Ala Pro Gly Gln Gly Leu Glu Trp Met
            35                  40                  45

Gly Gly Ile Ile Ala Ile Phe Gly Thr Thr Asn Tyr Ala Gln Lys Phe
 50                  55                  60

Gln Gly Arg Val Thr Ile Asn Ala Asp Glu Ser Thr Ser Thr Val Tyr
 65                  70                  75                  80

Leu Glu Leu Ser Ser Leu Thr Ser Glu Asp Thr Ala Ile Tyr Tyr Cys
                85                  90                  95

Ala Gly Ser Ala Thr Tyr Tyr Glu Ser Arg Phe Asp Tyr Trp Gly Gln
               100                 105                 110

Gly Thr Leu Val Thr Val Ser Ser
           115                 120

<210> SEQ ID NO 11
<211> LENGTH: 108
<212> TYPE: PRT
<213> ORGANISM: Artificial Sequence
<220> FEATURE:
<223> OTHER INFORMATION: FI174 VL aa

<400> SEQUENCE: 11

```
Glu Ile Val Leu Thr Gln Ser Pro Gly Thr Leu Ser Leu Ser Pro Gly
1               5                   10                  15

Ala Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Gly Asp Ser Arg
                85                  90                  95

Lys Thr Phe Gly Gln Gly Thr Lys Val Glu Ile Lys
            100                 105
```

<210> SEQ ID NO 12
<211> LENGTH: 98
<212> TYPE: PRT
<213> ORGANISM: Homo sapiens

<400> SEQUENCE: 12

```
Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

Gln Thr Phe Arg Leu Glu Arg Glu Ser Arg Ser Thr Tyr Asn Asp Thr
        35                  40                  45

Glu Asp Val Ser Gln Ala Ser Pro Ser Glu Ser Glu Ala Arg Phe Arg
    50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys
```

<210> SEQ ID NO 13
<211> LENGTH: 98
<212> TYPE: PRT
<213> ORGANISM: Artificial Sequence
<220> FEATURE:
<223> OTHER INFORMATION: mutated LAIR1 fragment aa

<400> SEQUENCE: 13

```
Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

Gln Thr Phe Arg Leu Glu Arg Glu Arg Asn Tyr Leu Tyr Ser Asp Thr
        35                  40                  45
```

```
Glu Asp Val Ser Gln Thr Ser Pro Ser Glu Ser Glu Ala Arg Phe Arg
    50                  55                  60

Ile Asp Ser Val Asn Ala Gly Asn Ala Gly Leu Phe Arg Cys Ile Tyr
 65                 70                  75                  80

Tyr Lys Ser Arg Lys Trp Ser Glu Gln Ser Asp Tyr Leu Glu Leu Val
                85                  90                  95

Val Lys

<210> SEQ ID NO 14
<211> LENGTH: 120
<212> TYPE: PRT
<213> ORGANISM: Artificial Sequence
<220> FEATURE:
<223> OTHER INFORMATION: PD-1 fragment aa

<400> SEQUENCE: 14

Asp Ser Pro Asp Arg Pro Trp Asn Pro Thr Phe Ser Pro Ala Leu
 1               5                  10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
         35                  40                  45

Asn Gln Thr Asp Lys Leu Ala Ala Phe Pro Glu Asp Arg Ser Gln Pro
 50                  55                  60

Gly Gln Asp Cys Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr
        115                 120

<210> SEQ ID NO 15
<211> LENGTH: 95
<212> TYPE: PRT
<213> ORGANISM: Artificial Sequence
<220> FEATURE:
<223> OTHER INFORMATION: SLAM fragment aa

<400> SEQUENCE: 15

Glu Gln Val Ser Thr Pro Glu Ile Lys Val Leu Asn Lys Thr Gln Glu
 1               5                  10                  15

Asn Gly Thr Cys Thr Leu Ile Leu Gly Cys Thr Val Glu Lys Gly Asp
            20                  25                  30

His Val Ala Tyr Ser Trp Ser Lys Ala Gly Thr His Pro Leu Asn
         35                  40                  45

Pro Ala Asn Ser Ser His Leu Leu Ser Leu Thr Leu Gly Pro Gln His
 50                  55                  60

Ala Asp Asn Ile Tyr Ile Cys Thr Val Ser Asn Pro Ile Ser Asn Asn
 65                  70                  75                  80

Ser Gln Thr Phe Ser Pro Trp Pro Gly Cys Arg Thr Asp Pro Ser
                85                  90                  95

<210> SEQ ID NO 16
<211> LENGTH: 117
<212> TYPE: PRT
<213> ORGANISM: Artificial Sequence
<220> FEATURE:
```

<223> OTHER INFORMATION: T3-VHH aa

<400> SEQUENCE: 16

```
Met Ala Gln Val Gln Leu Val Glu Ser Gly Gly Leu Val Gln Ala
1               5                   10                  15

Gly Gly Ser Leu Thr Leu Ser Cys Ala Ala Ser Gly Ser Thr Ser Arg
            20                  25                  30

Ser Tyr Ala Leu Gly Trp Phe Arg Gln Ala Pro Gly Lys Glu Arg Glu
        35                  40                  45

Phe Val Ala His Val Gly Gln Thr Ala Glu Phe Ala Gln Gly Arg Phe
    50                  55                  60

Thr Ile Ser Arg Asp Phe Ala Lys Asn Thr Val Ser Leu Gln Met Asn
65                  70                  75                  80

Asp Leu Lys Ser Asp Asp Thr Ala Ile Tyr Tyr Cys Val Ala Ser Asn
                85                  90                  95

Arg Gly Trp Ser Pro Ser Arg Val Ser Tyr Trp Gly Gln Gly Thr Gln
            100                 105                 110

Val Thr Val Ser Ser
            115
```

<210> SEQ ID NO 17
<211> LENGTH: 248
<212> TYPE: PRT
<213> ORGANISM: Artificial Sequence
<220> FEATURE:
<223> OTHER INFORMATION: TT39.7-scFv aa

<400> SEQUENCE: 17

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Arg Val Gly Val Gly Trp Ile Arg Gln Pro Pro Gly Lys Ala Leu Glu
        35                  40                  45

Trp Leu Ser Leu Ile Tyr Trp Asp Asp Glu Lys His Tyr Ser Pro Ser
    50                  55                  60

Leu Lys Asn Arg Val Thr Ile Ser Lys Asp Ser Ser Lys Asn Gln Val
65                  70                  75                  80

Val Leu Thr Leu Thr Asp Met Asp Pro Val Asp Thr Gly Thr Tyr Tyr
                85                  90                  95

Cys Ala His Arg Gly Val Asp Thr Ser Gly Trp Gly Phe Asp Tyr Trp
            100                 105                 110

Gly Gln Gly Ala Leu Val Thr Val Ser Ser Gly Gly Gly Gly Ser Gly
        115                 120                 125

Gly Gly Gly Ser Gly Gly Gly Gly Ser Gln Ser Ala Leu Thr Gln Pro
    130                 135                 140

Ala Ser Val Ser Gly Ser Pro Gly Gln Ser Ile Thr Ile Ser Cys Ser
145                 150                 155                 160

Gly Ala Gly Ser Asp Val Gly His Asn Phe Val Ser Trp Tyr Gln
                165                 170                 175

Gln Tyr Pro Gly Lys Ala Pro Lys Leu Met Ile Tyr Asp Val Lys Asn
            180                 185                 190

Arg Pro Ser Gly Val Ser Tyr Arg Phe Ser Gly Ser Lys Ser Gly Tyr
        195                 200                 205

Thr Ala Ser Leu Thr Ile Ser Gly Leu Gln Ala Glu Asp Glu Ala Thr
    210                 215                 220
```

```
Tyr Phe Cys Ser Ser Tyr Ser Ser Ser Thr Leu Ile Ile Phe Gly
225                 230                 235                 240

Gly Gly Thr Arg Leu Thr Val Leu
            245
```

<210> SEQ ID NO 18
<211> LENGTH: 125
<212> TYPE: PRT
<213> ORGANISM: Artificial Sequence
<220> FEATURE:
<223> OTHER INFORMATION: F4-VHH aa

<400> SEQUENCE: 18

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Tyr Ile Gly Trp Phe Arg Gln Ala Pro Gly Lys Glu Arg Glu Ala Val
        35                  40                  45

Ser Cys Ile Ser Gly Ser Ser Gly Ser Thr Tyr Tyr Pro Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Ile Arg Ser Ser Trp Gly Gly Cys Val His Tyr Gly Met
            100                 105                 110

Asp Tyr Trp Gly Lys Gly Thr Gln Val Thr Val Ser Ser
        115                 120                 125
```

<210> SEQ ID NO 19
<211> LENGTH: 249
<212> TYPE: PRT
<213> ORGANISM: Artificial Sequence
<220> FEATURE:
<223> OTHER INFORMATION: MPE8-scFv aa

<400> SEQUENCE: 19

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ala Ser Ser Tyr Ser Asp Tyr Ala Asp Ser Ala
50                  55                  60

Lys Gly Arg Phe Thr Ile Ser Arg Asp Asn Ala Lys Thr Ser Leu Phe
65                  70                  75                  80

Leu Gln Met Asn Ser Leu Arg Ala Glu Asp Thr Ala Ile Tyr Phe Cys
                85                  90                  95

Ala Arg Ala Arg Ala Thr Gly Tyr Ser Ser Ile Thr Pro Tyr Phe Asp
            100                 105                 110

Ile Trp Gly Gln Gly Thr Leu Val Thr Val Ser Ser Gly Gly Gly Gly
        115                 120                 125

Ser Gly Gly Gly Gly Ser Gly Gly Gly Ser Gln Ser Val Val Thr
    130                 135                 140

Gln Pro Pro Ser Val Ser Gly Ala Pro Gly Gln Arg Val Thr Ile Ser
```

```
                145                 150                 155                 160
Cys Thr Gly Ser Ser Ser Asn Ile Gly Ala Gly Tyr Asp Val His Trp
                    165                 170                 175

Tyr Gln Gln Leu Pro Gly Thr Ala Pro Lys Leu Leu Ile Tyr Asp Asn
                180                 185                 190

Asn Asn Arg Pro Ser Gly Val Pro Asp Arg Phe Ser Ala Ser Lys Ser
            195                 200                 205

Gly Thr Ser Ala Ser Leu Ala Ile Thr Gly Leu Gln Ala Glu Asp Glu
        210                 215                 220

Ala Asp Tyr Tyr Cys Gln Ser Tyr Asp Arg Asn Leu Ser Gly Val Phe
225                 230                 235                 240

Gly Thr Gly Thr Lys Val Thr Val Leu
                245

<210> SEQ ID NO 20
<211> LENGTH: 30
<212> TYPE: PRT
<213> ORGANISM: Artificial Sequence
<220> FEATURE:
<223> OTHER INFORMATION: twin StrepTag aa

<400> SEQUENCE: 20

Ser Ala Trp Ser His Pro Gln Phe Glu Lys Gly Gly Gly Ser Gly
1               5                   10                  15

Gly Ser Gly Gly Ser Ala Trp Ser His Pro Gln Phe Glu Lys
            20                  25                  30

<210> SEQ ID NO 21
<211> LENGTH: 15
<212> TYPE: PRT
<213> ORGANISM: Artificial Sequence
<220> FEATURE:
<223> OTHER INFORMATION: AviTag

<400> SEQUENCE: 21

Gly Leu Asn Asp Ile Phe Glu Ala Gln Lys Ile Glu Trp His Glu
1               5                   10                  15

<210> SEQ ID NO 22
<211> LENGTH: 26
<212> TYPE: PRT
<213> ORGANISM: Artificial Sequence
<220> FEATURE:
<223> OTHER INFORMATION: Calmodulin-tag

<400> SEQUENCE: 22

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 23
<211> LENGTH: 6
<212> TYPE: PRT
<213> ORGANISM: Artificial Sequence
<220> FEATURE:
<223> OTHER INFORMATION: polyglutamate tag

<400> SEQUENCE: 23

Glu Glu Glu Glu Glu Glu
1               5
```

```
<210> SEQ ID NO 24
<211> LENGTH: 13
<212> TYPE: PRT
<213> ORGANISM: Artificial Sequence
<220> FEATURE:
<223> OTHER INFORMATION: E-tag

<400> SEQUENCE: 24

Gly Ala Pro Val Pro Tyr Pro Asp Pro Leu Glu Pro Arg
1               5                   10

<210> SEQ ID NO 25
<211> LENGTH: 8
<212> TYPE: PRT
<213> ORGANISM: Artificial Sequence
<220> FEATURE:
<223> OTHER INFORMATION: FLAG-tag

<400> SEQUENCE: 25

Asp Tyr Lys Asp Asp Asp Asp Lys
1               5

<210> SEQ ID NO 26
<211> LENGTH: 9
<212> TYPE: PRT
<213> ORGANISM: Artificial Sequence
<220> FEATURE:
<223> OTHER INFORMATION: HA-tag

<400> SEQUENCE: 26

Tyr Pro Tyr Asp Val Pro Asp Tyr Ala
1               5

<210> SEQ ID NO 27
<211> LENGTH: 6
<212> TYPE: PRT
<213> ORGANISM: Artificial Sequence
<220> FEATURE:
<223> OTHER INFORMATION: His-tag

<400> SEQUENCE: 27

His His His His His His
1               5

<210> SEQ ID NO 28
<211> LENGTH: 10
<212> TYPE: PRT
<213> ORGANISM: Artificial Sequence
<220> FEATURE:
<223> OTHER INFORMATION: Myc-tag

<400> SEQUENCE: 28

Glu Gln Lys Leu Ile Ser Glu Glu Asp Leu
1               5                   10

<210> SEQ ID NO 29
<211> LENGTH: 18
<212> TYPE: PRT
<213> ORGANISM: Artificial Sequence
<220> FEATURE:
<223> OTHER INFORMATION: NE-tag

<400> SEQUENCE: 29

Thr Lys Glu Asn Pro Arg Ser Asn Gln Glu Glu Ser Tyr Asp Asp Asn
1               5                   10                  15

Glu Ser
```

```
<210> SEQ ID NO 30
<211> LENGTH: 15
<212> TYPE: PRT
<213> ORGANISM: Artificial Sequence
<220> FEATURE:
<223> OTHER INFORMATION: S-tag

<400> SEQUENCE: 30

Lys Glu Thr Ala Ala Ala Lys Phe Glu Arg Gln His Met Asp Ser
1               5                   10                  15

<210> SEQ ID NO 31
<211> LENGTH: 38
<212> TYPE: PRT
<213> ORGANISM: Artificial Sequence
<220> FEATURE:
<223> OTHER INFORMATION: SBP-tag

<400> SEQUENCE: 31

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 32
<211> LENGTH: 13
<212> TYPE: PRT
<213> ORGANISM: Artificial Sequence
<220> FEATURE:
<223> OTHER INFORMATION: Softag 1

<400> SEQUENCE: 32

Ser Leu Ala Glu Leu Leu Asn Ala Gly Leu Gly Gly Ser
1               5                   10

<210> SEQ ID NO 33
<211> LENGTH: 8
<212> TYPE: PRT
<213> ORGANISM: Artificial Sequence
<220> FEATURE:
<223> OTHER INFORMATION: Softag 3

<400> SEQUENCE: 33

Thr Gln Asp Pro Ser Arg Val Gly
1               5

<210> SEQ ID NO 34
<211> LENGTH: 8
<212> TYPE: PRT
<213> ORGANISM: Artificial Sequence
<220> FEATURE:
<223> OTHER INFORMATION: Strep-tag

<400> SEQUENCE: 34

Trp Ser His Pro Gln Phe Glu Lys
1               5

<210> SEQ ID NO 35
<211> LENGTH: 6
<212> TYPE: PRT
<213> ORGANISM: Artificial Sequence
<220> FEATURE:
<223> OTHER INFORMATION: TC tag
```

```
<400> SEQUENCE: 35

Cys Cys Pro Gly Cys Cys
1               5

<210> SEQ ID NO 36
<211> LENGTH: 14
<212> TYPE: PRT
<213> ORGANISM: Artificial Sequence
<220> FEATURE:
<223> OTHER INFORMATION: V5 tag

<400> SEQUENCE: 36

Gly Lys Pro Ile Pro Asn Pro Leu Leu Gly Leu Asp Ser Thr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: VSV-tag

<400> SEQUENCE: 37

Tyr Thr Asp Ile Glu Met Asn Arg Leu Gly Lys
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Xpress tag

<400> SEQUENCE: 38

Asp Leu Tyr Asp Asp Asp Asp Lys
1               5

<210> SEQ ID NO 39
<211> LENGTH: 16
<212> TYPE: PRT
<213> ORGANISM: Artificial Sequence
<220> FEATURE:
<223> OTHER INFORMATION: Isopeptag

<400> SEQUENCE: 39

Thr Asp Lys Asp Met Thr Ile Thr Phe Thr Asn Lys Lys Asp Ala Glu
1               5                   10                  15

<210> SEQ ID NO 40
<211> LENGTH: 13
<212> TYPE: PRT
<213> ORGANISM: Artificial Sequence
<220> FEATURE:
<223> OTHER INFORMATION: SpyTag

<400> SEQUENCE: 40

Ala His Ile Val Met Val Asp Ala Tyr Lys Pro Thr Lys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: SnoopTag

<400> SEQUENCE: 41
```

```
Lys Leu Gly Asp Ile Glu Phe Ile Lys Val Asn Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Ty1 tag

<400> SEQUENCE: 42

Glu Val His Thr Asn Gln Asp Pro Leu Asp
1               5                   10

<210> SEQ ID NO 43
<211> LENGTH: 5
<212> TYPE: PRT
<213> ORGANISM: Artificial Sequence
<220> FEATURE:
<223> OTHER INFORMATION: linker

<400> SEQUENCE: 43

Gly Gly Gly Gly Ser
1               5

<210> SEQ ID NO 44
<211> LENGTH: 10
<212> TYPE: PRT
<213> ORGANISM: Artificial Sequence
<220> FEATURE:
<223> OTHER INFORMATION: linker

<400> SEQUENCE: 44

Gly Gly Gly Gly Ser Gly Gly Gly Gly Ser
1               5                   10

<210> SEQ ID NO 45
<211> LENGTH: 15
<212> TYPE: PRT
<213> ORGANISM: Artificial Sequence
<220> FEATURE:
<223> OTHER INFORMATION: linker

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 20
<212> TYPE: PRT
<213> ORGANISM: Artificial Sequence
<220> FEATURE:
<223> OTHER INFORMATION: linker

<400> SEQUENCE: 46

Gly Gly Gly Gly Ser Gly Gly Gly Gly Ser Gly Gly Gly Gly Ser Gly
1               5                   10                  15

Gly Gly Gly Ser
            20

<210> SEQ ID NO 47
<211> LENGTH: 25
<212> TYPE: PRT
<213> ORGANISM: Artificial Sequence
<220> FEATURE:
<223> OTHER INFORMATION: linker
```

<400> SEQUENCE: 47

Gly Gly Gly Gly Ser Gly Gly Gly Gly Ser Gly Gly Gly Gly Ser Gly
1               5                   10                  15
Gly Gly Gly Ser Gly Gly Gly Gly Ser
            20                  25

<210> SEQ ID NO 48
<211> LENGTH: 30
<212> TYPE: PRT
<213> ORGANISM: Artificial Sequence
<220> FEATURE:
<223> OTHER INFORMATION: linker

<400> SEQUENCE: 48

Gly Gly Gly Gly Ser Gly Gly Gly Gly Ser Gly Gly Gly Gly Ser Gly
1               5                   10                  15
Gly Gly Gly Ser Gly Gly Gly Ser Gly Gly Gly Gly Ser
            20                  25                  30

<210> SEQ ID NO 49
<211> LENGTH: 15
<212> TYPE: PRT
<213> ORGANISM: Artificial Sequence
<220> FEATURE:
<223> OTHER INFORMATION: linker

<400> SEQUENCE: 49

Phe Val Gly Pro Pro Ser Pro Phe Leu Thr Ser Leu His Leu Ser
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: linker

<400> SEQUENCE: 50

Gly Ala Ala Ser Glu Ala Pro Gly Gln Gly Leu Ala Glu Pro Val
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: linker

<400> SEQUENCE: 51

Gln Gly Phe Thr Ser Val Met Ala Pro Phe Leu Pro Leu Leu Thr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: linker

<400> SEQUENCE: 52

Gly Glu Tyr Thr Gly Gly Ser Leu Cys Ala Thr Leu Met Ser Met
1               5                   10                  15

<210> SEQ ID NO 53

<211> LENGTH: 558
<212> TYPE: PRT
<213> ORGANISM: Artificial Sequence
<220> FEATURE:
<223> OTHER INFORMATION: C2 heavy chain aa

<400> SEQUENCE: 53

```
Gln Val Gln Leu Ala Gln Tyr Gly Gly Gly Ala Val Gln Pro Gly Gly
1               5                   10                  15

Ser Leu Arg Leu Ser Cys Val Val Ser Gly Phe Arg Phe Ser Leu Tyr
            20                  25                  30

Gly Ile His Trp Val Arg Gln Ala Pro Gly Lys Gly Leu Glu Trp Leu
        35                  40                  45

Ser Leu Ile Glu Asn His Gly Arg Lys Ile Tyr Tyr Ala Glu Ser Val
    50                  55                  60

Lys Gly Arg Ile Thr Val Ser Arg Asp Asn Phe Lys Asn Val Ala Tyr
65                  70                  75                  80

Leu Glu Met Tyr Arg Leu Ser Thr Glu Asp Thr Ala Ile Tyr Tyr Cys
                85                  90                  95

Ala Arg Asn Asp Gly Leu Gly Arg Tyr Thr Asp Ala Gly Gly Thr His
            100                 105                 110

Arg Thr Ala Tyr Leu Asp Tyr Trp Gly Arg Gly Thr Leu Val Thr Val
        115                 120                 125

Ser Ser Glu Asp Leu Pro Arg Pro Ser Ile Ser Ala Glu Pro Gly Thr
    130                 135                 140

Val Ile Pro Leu Gly Ser His Val Thr Phe Val Cys Arg Gly Pro Val
145                 150                 155                 160

Gly Val Gln Thr Phe Arg Leu Glu Arg Glu Arg Asn Tyr Leu Tyr Ser
                165                 170                 175

Asp Thr Glu Asp Val Ser Gln Thr Ser Pro Ser Glu Ser Glu Ala Arg
            180                 185                 190

Phe Arg Ile Asp Ser Val Asn Ala Gly Asn Ala Gly Leu Phe Arg Cys
        195                 200                 205

Ile Tyr Tyr Lys Ser Arg Lys Trp Ser Glu Gln Ser Asp Tyr Leu Glu
    210                 215                 220

Leu Val Val Lys Ala Ser Thr Lys Gly Pro Ser Val Phe Pro Leu Ala
225                 230                 235                 240

Pro Ser Ser Lys Ser Thr Ser Gly Gly Thr Ala Ala Leu Gly Cys Leu
                245                 250                 255

Val Lys Asp Tyr Phe Pro Glu Pro Val Thr Val Ser Trp Asn Ser Gly
            260                 265                 270

Ala Leu Thr Ser Gly Val His Thr Phe Pro Ala Val Leu Gln Ser Ser
        275                 280                 285

Gly Leu Tyr Ser Leu Ser Ser Val Val Thr Val Pro Ser Ser Ser Leu
    290                 295                 300

Gly Thr Gln Thr Tyr Ile Cys Asn Val Asn His Lys Pro Ser Asn Thr
305                 310                 315                 320

Lys Val Asp Lys Arg Val Glu Pro Lys Ser Cys Asp Lys Thr His Thr
                325                 330                 335

Cys Pro Pro Cys Pro Ala Pro Glu Leu Leu Gly Gly Pro Ser Val Phe
            340                 345                 350

Leu Phe Pro Pro Lys Pro Lys Asp Thr Leu Met Ile Ser Arg Thr Pro
        355                 360                 365

Glu Val Thr Cys Val Val Val Asp Val Ser His Glu Asp Pro Glu Val
    370                 375                 380
```

```
Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
            405                 410                 415

Leu Thr Val Leu His Gln Asp Trp Leu Asn Gly Lys Glu Tyr Lys Cys
        420                 425                 430

Lys Val Ser Asn Lys Ala Leu Pro Ala Pro Ile Glu Lys Thr Ile Ser
            435                 440                 445

Lys Ala Lys Gly Gln Pro Arg Glu Pro Gln Val Tyr Thr Leu Pro Pro
        450                 455                 460

Ser Arg Glu Glu Met Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
            485                 490                 495

Gln Pro Glu Asn Asn Tyr Lys Thr Thr Pro Pro Val Leu Asp Ser Asp
        500                 505                 510

Gly Ser Phe Phe Leu Tyr Ser Lys Leu Thr Val Asp Lys Ser Arg Trp
            515                 520                 525

Gln Gln Gly Asn Val Phe Ser Cys Ser Val Met His Glu Ala Leu His
        530                 535                 540

Asn His Tyr Thr Gln Lys Ser Leu Ser Leu Ser Pro Gly Lys
545                 550                 555

<210> SEQ ID NO 54
<211> LENGTH: 215
<212> TYPE: PRT
<213> ORGANISM: Artificial Sequence
<220> FEATURE:
<223> OTHER INFORMATION: C2/C3 light chain aa

<400> SEQUENCE: 54

Ser Tyr Glu Val Thr Gln Pro Pro Ser Val Ser Val Ser Pro Gly Gln
1               5                   10                  15

Ala Ala Arg Ile Thr Cys Ser Gly Asp Glu Leu Pro Arg Thr Asp Ile
            20                  25                  30

Ser Trp Tyr Gln Gln Thr Ser Gly Gln Ala Pro Val Leu Val Ile Tyr
        35                  40                  45

Glu Gly Thr Lys Arg Pro Ser Gly Ile Pro Glu Arg Phe Ser Gly Ser
    50                  55                  60

Val Ser Gly Ala Met Ala Thr Leu Met Ile Ser Glu Ala Gln Leu Glu
65                  70                  75                  80

Asp Glu Gly Asp Tyr Tyr Cys Phe Ser Ile Asp Thr Ser Gly Asn His
                85                  90                  95

Gly Gly Ala Phe Gly Thr Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190
```

```
Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 55
<211> LENGTH: 558
<212> TYPE: PRT
<213> ORGANISM: Artificial Sequence
<220> FEATURE:
<223> OTHER INFORMATION: C3 heavy chain aa

<400> SEQUENCE: 55

Gln Val Gln Leu Ala Gln Tyr Gly Gly Gly Ala Val Gln Pro Gly Gly
1               5                   10                  15

Ser Leu Arg Leu Ser Cys Val Val Ser Gly Phe Arg Phe Ser Leu Tyr
            20                  25                  30

Gly Ile His Trp Val Arg Gln Ala Pro Gly Lys Gly Leu Glu Trp Leu
        35                  40                  45

Ser Leu Ile Glu Asn His Gly Arg Lys Ile Tyr Tyr Ala Glu Ser Val
    50                  55                  60

Lys Gly Arg Ile Thr Val Ser Arg Asp Asn Phe Lys Asn Val Ala Tyr
65                  70                  75                  80

Leu Glu Met Tyr Arg Leu Ser Thr Glu Asp Thr Ala Ile Tyr Tyr Cys
                85                  90                  95

Ala Arg Asn Asp Gly Leu Gly Arg Tyr Thr Asp Ala Gly Gly Thr His
            100                 105                 110

Arg Thr Ala Tyr Leu Asp Tyr Trp Gly Arg Gly Thr Leu Val Thr Val
        115                 120                 125

Ser Ser Glu Asp Leu Pro Arg Pro Ser Ile Ser Ala Glu Pro Gly Thr
    130                 135                 140

Val Ile Pro Leu Gly Ser His Val Thr Phe Val Cys Arg Gly Pro Val
145                 150                 155                 160

Gly Val Gln Thr Phe Arg Leu Glu Arg Glu Ser Arg Ser Thr Tyr Asn
                165                 170                 175

Asp Thr Glu Asp Val Ser Gln Ala Ser Pro Ser Glu Ser Glu Ala Arg
            180                 185                 190

Phe Arg Ile Asp Ser Val Ser Glu Gly Asn Ala Gly Pro Tyr Arg Cys
        195                 200                 205

Ile Tyr Tyr Lys Pro Pro Lys Trp Ser Glu Gln Ser Asp Tyr Leu Glu
    210                 215                 220

Leu Leu Val Lys Ala Ser Thr Lys Gly Pro Ser Val Phe Pro Leu Ala
225                 230                 235                 240

Pro Ser Ser Lys Ser Thr Ser Gly Gly Thr Ala Ala Leu Gly Cys Leu
                245                 250                 255

Val Lys Asp Tyr Phe Pro Glu Pro Val Thr Val Ser Trp Asn Ser Gly
            260                 265                 270

Ala Leu Thr Ser Gly Val His Thr Phe Pro Ala Val Leu Gln Ser Ser
        275                 280                 285

Gly Leu Tyr Ser Leu Ser Val Val Thr Val Pro Ser Ser Ser Leu
    290                 295                 300

Gly Thr Gln Thr Tyr Ile Cys Asn Val Asn His Lys Pro Ser Asn Thr
305                 310                 315                 320

Lys Val Asp Lys Arg Val Glu Pro Lys Ser Cys Asp Lys Thr His Thr
                325                 330                 335
```

```
Cys Pro Pro Cys Pro Ala Pro Glu Leu Leu Gly Gly Pro Ser Val Phe
              340                 345                 350

Leu Phe Pro Pro Lys Pro Lys Asp Thr Leu Met Ile Ser Arg Thr Pro
            355                 360                 365

Glu Val Thr Cys Val Val Val Asp Val Ser His Glu Asp Pro Glu Val
        370                 375                 380

Lys Phe Asn Trp Tyr Val Asp Gly Val Glu Val His Asn Ala Lys Thr
385                 390                 395                 400

Lys Pro Arg Glu Glu Gln Tyr Asn Ser Thr Tyr Arg Val Val Ser Val
                405                 410                 415

Leu Thr Val Leu His Gln Asp Trp Leu Asn Gly Lys Glu Tyr Lys Cys
            420                 425                 430

Lys Val Ser Asn Lys Ala Leu Pro Ala Pro Ile Glu Lys Thr Ile Ser
        435                 440                 445

Lys Ala Lys Gly Gln Pro Arg Glu Pro Gln Val Tyr Thr Leu Pro Pro
    450                 455                 460

Ser Arg Glu Glu Met Thr Lys Asn Gln Val Ser Leu Thr Cys Leu Val
465                 470                 475                 480

Lys Gly Phe Tyr Pro Ser Asp Ile Ala Val Glu Trp Glu Ser Asn Gly
                485                 490                 495

Gln Pro Glu Asn Asn Tyr Lys Thr Thr Pro Pro Val Leu Asp Ser Asp
            500                 505                 510

Gly Ser Phe Phe Leu Tyr Ser Lys Leu Thr Val Asp Lys Ser Arg Trp
        515                 520                 525

Gln Gln Gly Asn Val Phe Ser Cys Ser Val Met His Glu Ala Leu His
    530                 535                 540

Asn His Tyr Thr Gln Lys Ser Leu Ser Leu Ser Pro Gly Lys
545                 550                 555

<210> SEQ ID NO 56
<211> LENGTH: 552
<212> TYPE: PRT
<213> ORGANISM: Artificial Sequence
<220> FEATURE:
<223> OTHER INFORMATION: C4 heavy chain aa

<400> SEQUENCE: 56

Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
            20                  25                  30

Tyr Leu Val Trp Val Arg Gln Ala Pro Gly Gln Gly Leu Glu Trp Met
        35                  40                  45

Ala Thr Ile Ser Pro Gly Asp Val Asn Thr Ser Tyr Glu Gln Arg Phe
    50                  55                  60

Gln Gly Arg Val Thr Val Thr Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95

Ala Arg Gly Pro Arg Ser Lys Pro Tyr Leu Tyr Phe Ala Leu Asp
            100                 105                 110

Val Trp Gly Gln Gly Thr Ala Val Thr Val Ser Ser Glu Asp Leu Pro
        115                 120                 125

Arg Pro Ser Ile Ser Ala Glu Pro Gly Thr Val Ile Pro Leu Gly Ser
    130                 135                 140
```

```
His Val Thr Phe Val Cys Arg Gly Pro Val Gly Val Gln Thr Phe Arg
145                 150                 155                 160

Leu Glu Arg Glu Ser Arg Ser Thr Tyr Asn Asp Thr Glu Asp Val Ser
            165                 170                 175

Gln Ala Ser Pro Ser Glu Ser Glu Ala Arg Phe Arg Ile Asp Ser Val
            180                 185                 190

Ser Glu Gly Asn Ala Gly Pro Tyr Arg Cys Ile Tyr Tyr Lys Pro Pro
            195                 200                 205

Lys Trp Ser Glu Gln Ser Asp Tyr Leu Glu Leu Leu Val Lys Ala Ser
            210                 215                 220

Thr Lys Gly Pro Ser Val Phe Pro Leu Ala Pro Ser Ser Lys Ser Thr
225                 230                 235                 240

Ser Gly Gly Thr Ala Ala Leu Gly Cys Leu Val Lys Asp Tyr Phe Pro
            245                 250                 255

Glu Pro Val Thr Val Ser Trp Asn Ser Gly Ala Leu Thr Ser Gly Val
            260                 265                 270

His Thr Phe Pro Ala Val Leu Gln Ser Ser Gly Leu Tyr Ser Leu Ser
            275                 280                 285

Ser Val Val Thr Val Pro Ser Ser Ser Leu Gly Thr Gln Thr Tyr Ile
            290                 295                 300

Cys Asn Val Asn His Lys Pro Ser Asn Thr Lys Val Asp Lys Arg Val
305                 310                 315                 320

Glu Pro Lys Ser Cys Asp Lys Thr His Thr Cys Pro Pro Cys Pro Ala
                325                 330                 335

Pro Glu Leu Leu Gly Gly Pro Ser Val Phe Leu Phe Pro Pro Lys Pro
                340                 345                 350

Lys Asp Thr Leu Met Ile Ser Arg Thr Pro Glu Val Thr Cys Val Val
                355                 360                 365

Val Asp Val Ser His Glu Asp Pro Glu Val Lys Phe Asn Trp Tyr Val
        370                 375                 380

Asp Gly Val Glu Val His Asn Ala Lys Thr Lys Pro Arg Glu Glu Gln
385                 390                 395                 400

Tyr Asn Ser Thr Tyr Arg Val Val Ser Val Leu Thr Val Leu His Gln
                405                 410                 415

Asp Trp Leu Asn Gly Lys Glu Tyr Lys Cys Lys Val Ser Asn Lys Ala
            420                 425                 430

Leu Pro Ala Pro Ile Glu Lys Thr Ile Ser Lys Ala Lys Gly Gln Pro
            435                 440                 445

Arg Glu Pro Gln Val Tyr Thr Leu Pro Pro Ser Arg Glu Glu Met Thr
            450                 455                 460

Lys Asn Gln Val Ser Leu Thr Cys Leu Val Lys Gly Phe Tyr Pro Ser
465                 470                 475                 480

Asp Ile Ala Val Glu Trp Glu Ser Asn Gly Gln Pro Glu Asn Asn Tyr
                485                 490                 495

Lys Thr Thr Pro Pro Val Leu Asp Ser Asp Gly Ser Phe Phe Leu Tyr
                500                 505                 510

Ser Lys Leu Thr Val Asp Lys Ser Arg Trp Gln Gln Gly Asn Val Phe
            515                 520                 525

Ser Cys Ser Val Met His Glu Ala Leu His Asn His Tyr Thr Gln Lys
            530                 535                 540

Ser Leu Ser Leu Ser Pro Gly Lys
545                 550
```

<210> SEQ ID NO 57
<211> LENGTH: 214
<212> TYPE: PRT
<213> ORGANISM: Artificial Sequence
<220> FEATURE:
<223> OTHER INFORMATION: C4/C5/C6 light chain aa

<400> SEQUENCE: 57

```
Glu Ile Val Leu Thr Gln Ser Pro Gly Thr Leu Ser Leu Ser Pro Gly
1               5                   10                  15

Glu Thr Ala Ile Leu Ser Cys Arg Ala Ser Gln Ser Val Ser Ser Ser
            20                  25                  30

Leu Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Arg Gly Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Val Leu Tyr Tyr Cys Gln His Tyr Gly Ser Arg Val
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 58
<211> LENGTH: 574
<212> TYPE: PRT
<213> ORGANISM: Artificial Sequence
<220> FEATURE:
<223> OTHER INFORMATION: C5 heavy chain aa

<400> SEQUENCE: 58

```
Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
            20                  25                  30

Tyr Leu Val Trp Val Arg Gln Ala Pro Gly Gln Gly Leu Glu Trp Met
        35                  40                  45

Ala Thr Ile Ser Pro Gly Asp Val Asn Thr Ser Tyr Glu Gln Arg Phe
    50                  55                  60

Gln Gly Arg Val Thr Val Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95
```

```
Ala Arg Gly Pro Arg Ser Lys Pro Tyr Leu Tyr Phe Ala Leu Asp
            100                 105                 110

Val Trp Gly Gln Gly Thr Ala Val Thr Val Ser Ser Asp Ser Pro Asp
            115                 120                 125

Arg Pro Trp Asn Pro Pro Thr Phe Ser Pro Ala Leu Leu Val Val Thr
130                 135                 140

Glu Gly Asp Asn Ala Thr Phe Thr Cys Ser Phe Ser Asn Thr Ser Glu
145                 150                 155                 160

Ser Phe Val Leu Asn Trp Tyr Arg Met Ser Pro Ser Asn Gln Thr Asp
                165                 170                 175

Lys Leu Ala Ala Phe Pro Glu Asp Arg Ser Gln Pro Gly Gln Asp Cys
            180                 185                 190

Arg Phe Arg Val Thr Gln Leu Pro Asn Gly Arg Asp Phe His Met Ser
        195                 200                 205

Val Val Arg Ala Arg Arg Asn Asp Ser Gly Thr Tyr Leu Cys Gly Ala
    210                 215                 220

Ile Ser Leu Ala Pro Lys Ala Gln Ile Lys Glu Ser Leu Arg Ala Glu
225                 230                 235                 240

Leu Arg Val Thr Ala Ser Thr Lys Gly Pro Ser Val Phe Pro Leu Ala
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Arg Val Glu Pro Lys Ser Cys Asp Lys Thr His Thr
            340                 345                 350

Cys Pro Pro Cys Pro Ala Pro Glu Leu Leu Gly Gly Pro Ser Val Phe
        355                 360                 365

Leu Phe Pro Pro Lys Pro Lys Asp Thr Leu Met Ile Ser Arg Thr Pro
    370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Arg Glu Glu Met Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
            500                 505                 510
```

```
Gln Pro Glu Asn Asn Tyr Lys Thr Thr Pro Val Leu Asp Ser Asp
            515                 520                 525

Gly Ser Phe Phe Leu Tyr Ser Lys Leu Thr Val Asp Lys Ser Arg Trp
530                 535                 540

Gln Gln Gly Asn Val Phe Ser Cys Ser Val Met His Glu Ala Leu His
545                 550                 555                 560

Asn His Tyr Thr Gln Lys Ser Leu Ser Leu Ser Pro Gly Lys
                565                 570

<210> SEQ ID NO 59
<211> LENGTH: 604
<212> TYPE: PRT
<213> ORGANISM: Artificial Sequence
<220> FEATURE:
<223> OTHER INFORMATION: C5b heavy chain aa

<400> SEQUENCE: 59

Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
                20                  25                  30

Tyr Leu Val Trp Val Arg Gln Ala Pro Gly Gln Gly Leu Glu Trp Met
            35                  40                  45

Ala Thr Ile Ser Pro Gly Asp Val Asn Thr Ser Tyr Glu Gln Arg Phe
    50                  55                  60

Gln Gly Arg Val Thr Val Thr Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser Phe Val Gly Pro
        115                 120                 125

Pro Ser Pro Phe Leu Thr Ser Leu His Leu Ser Asp Ser Pro Asp Arg
130                 135                 140

Pro Trp Asn Pro Pro Thr Phe Ser Pro Ala Leu Leu Val Val Thr Glu
145                 150                 155                 160

Gly Asp Asn Ala Thr Phe Thr Cys Ser Phe Ser Asn Thr Ser Glu Ser
                165                 170                 175

Phe Val Leu Asn Trp Tyr Arg Met Ser Pro Ser Asn Gln Thr Asp Lys
            180                 185                 190

Leu Ala Ala Phe Pro Glu Asp Arg Ser Gln Pro Gly Gln Asp Cys Arg
        195                 200                 205

Phe Arg Val Thr Gln Leu Pro Asn Gly Arg Asp Phe His Met Ser Val
    210                 215                 220

Val Arg Ala Arg Arg Asn Asp Ser Gly Thr Tyr Leu Cys Gly Ala Ile
225                 230                 235                 240

Ser Leu Ala Pro Lys Ala Gln Ile Lys Glu Ser Leu Arg Ala Glu Leu
                245                 250                 255

Arg Val Thr Gly Ala Ala Ser Glu Ala Pro Gly Gln Gly Leu Ala Glu
            260                 265                 270

Pro Val Ala Ser Thr Lys Gly Pro Ser Val Phe Pro Leu Ala Pro Ser
        275                 280                 285

Ser Lys Ser Thr Ser Gly Gly Thr Ala Ala Leu Gly Cys Leu Val Lys
    290                 295                 300
```

```
Asp Tyr Phe Pro Glu Pro Val Thr Val Ser Trp Asn Ser Gly Ala Leu
305                 310                 315                 320

Thr Ser Gly Val His Thr Phe Pro Ala Val Leu Gln Ser Ser Gly Leu
                325                 330                 335

Tyr Ser Leu Ser Ser Val Val Thr Val Pro Ser Ser Ser Leu Gly Thr
            340                 345                 350

Gln Thr Tyr Ile Cys Asn Val Asn His Lys Pro Ser Asn Thr Lys Val
        355                 360                 365

Asp Lys Arg Val Glu Pro Lys Ser Cys Asp Lys Thr His Thr Cys Pro
    370                 375                 380

Pro Cys Pro Ala Pro Glu Leu Leu Gly Gly Pro Ser Val Phe Leu Phe
385                 390                 395                 400

Pro Pro Lys Pro Lys Asp Thr Leu Met Ile Ser Arg Thr Pro Glu Val
                405                 410                 415

Thr Cys Val Val Val Asp Val Ser His Glu Asp Pro Glu Val Lys Phe
            420                 425                 430

Asn Trp Tyr Val Asp Gly Val Glu Val His Asn Ala Lys Thr Lys Pro
        435                 440                 445

Arg Glu Glu Gln Tyr Asn Ser Thr Tyr Arg Val Val Ser Val Leu Thr
    450                 455                 460

Val Leu His Gln Asp Trp Leu Asn Gly Lys Glu Tyr Lys Cys Lys Val
465                 470                 475                 480

Ser Asn Lys Ala Leu Pro Ala Pro Ile Glu Lys Thr Ile Ser Lys Ala
                485                 490                 495

Lys Gly Gln Pro Arg Glu Pro Gln Val Tyr Thr Leu Pro Pro Ser Arg
            500                 505                 510

Glu Glu Met Thr Lys Asn Gln Val Ser Leu Thr Cys Leu Val Lys Gly
        515                 520                 525

Phe Tyr Pro Ser Asp Ile Ala Val Glu Trp Glu Ser Asn Gly Gln Pro
    530                 535                 540

Glu Asn Asn Tyr Lys Thr Thr Pro Pro Val Leu Asp Ser Asp Gly Ser
545                 550                 555                 560

Phe Phe Leu Tyr Ser Lys Leu Thr Val Asp Lys Ser Arg Trp Gln Gln
                565                 570                 575

Gly Asn Val Phe Ser Cys Ser Val Met His Glu Ala Leu His Asn His
            580                 585                 590

Tyr Thr Gln Lys Ser Leu Ser Leu Ser Pro Gly Lys
        595                 600

<210> SEQ ID NO 60
<211> LENGTH: 604
<212> TYPE: PRT
<213> ORGANISM: Artificial Sequence
<220> FEATURE:
<223> OTHER INFORMATION: C6 heavy chain aa

<400> SEQUENCE: 60

Gln Leu Gln Leu Val Gln Ser Gly Thr Glu Val Lys Lys Pro Gly Ala
1               5                   10                  15

Ser Val Lys Val Ser Cys Lys Ser Ser Gly Tyr Val Phe Thr Ser Tyr
                20                  25                  30

Tyr Leu Val Trp Val Arg Gln Ala Pro Gly Gln Gly Leu Glu Trp Met
            35                  40                  45

Ala Thr Ile Ser Pro Gly Asp Val Asn Thr Ser Tyr Glu Gln Arg Phe
        50                  55                  60
```

```
Gln Gly Arg Val Thr Val Thr Thr Asp Ala Ser Thr Asn Thr Val Asp
 65                  70                  75                  80

Met Glu Leu Arg Ser Leu Arg Ser Glu Asp Thr Ala Val Tyr Tyr Cys
                 85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser Phe Val Gly Pro
        115                 120                 125

Pro Ser Pro Phe Leu Thr Ser Leu His Leu Ser Asp Ser Pro Asp Arg
    130                 135                 140

Pro Trp Asn Pro Pro Thr Phe Ser Pro Ala Leu Leu Val Val Thr Glu
145                 150                 155                 160

Gly Asp Asn Ala Thr Phe Thr Cys Ser Phe Ser Asn Thr Ser Glu Ser
                165                 170                 175

Phe Val Leu Asn Trp Tyr Arg Met Ser Pro Ser Asn Gln Thr Asp Lys
            180                 185                 190

Leu Ala Ala Phe Pro Glu Asp Arg Ser Gln Pro Gly Gln Asp Cys Arg
        195                 200                 205

Phe Arg Val Thr Gln Leu Pro Asn Gly Arg Asp Phe His Met Ser Val
    210                 215                 220

Val Arg Ala Arg Arg Asn Asp Ser Gly Thr Tyr Leu Cys Gly Ala Ile
225                 230                 235                 240

Ser Leu Ala Pro Lys Ala Gln Ile Lys Glu Ser Leu Arg Ala Glu Leu
                245                 250                 255

Arg Val Thr Gly Ala Ala Ser Glu Ala Pro Gly Gln Gly Leu Ala Glu
            260                 265                 270

Pro Val Ala Ser Thr Lys Gly Pro Ser Val Phe Pro Leu Ala Pro Ser
    275                 280                 285

Ser Lys Ser Thr Ser Gly Gly Thr Ala Ala Leu Gly Cys Leu Val Lys
290                 295                 300

Asp Tyr Phe Pro Glu Pro Val Thr Val Ser Trp Asn Ser Gly Ala Leu
305                 310                 315                 320

Thr Ser Gly Val His Thr Phe Pro Ala Val Leu Gln Ser Ser Gly Leu
                325                 330                 335

Tyr Ser Leu Ser Ser Val Val Thr Val Pro Ser Ser Ser Leu Gly Thr
            340                 345                 350

Gln Thr Tyr Ile Cys Asn Val Asn His Lys Pro Ser Asn Thr Lys Val
    355                 360                 365

Asp Lys Arg Val Glu Pro Lys Ser Cys Asp Lys Thr His Thr Cys Pro
370                 375                 380

Pro Cys Pro Ala Pro Glu Leu Leu Gly Gly Pro Ser Val Phe Leu Phe
385                 390                 395                 400

Pro Pro Lys Pro Lys Asp Thr Leu Met Ile Ser Arg Thr Pro Glu Val
                405                 410                 415

Thr Cys Val Val Val Asp Val Ser His Glu Asp Pro Glu Val Lys Phe
            420                 425                 430

Asn Trp Tyr Val Asp Gly Val Glu Val His Asn Ala Lys Thr Lys Pro
    435                 440                 445

Arg Glu Glu Gln Tyr Asn Ser Thr Tyr Arg Val Val Ser Val Leu Thr
    450                 455                 460

Val Leu His Gln Asp Trp Leu Asn Gly Lys Glu Tyr Lys Cys Lys Val
465                 470                 475                 480

Ser Asn Lys Ala Leu Pro Ala Pro Ile Glu Lys Thr Ile Ser Lys Ala
```

```
                      485                 490                 495
Lys Gly Gln Pro Arg Glu Pro Gln Val Tyr Thr Leu Pro Pro Ser Arg
                500                 505                 510

Glu Glu Met Thr Lys Asn Gln Val Ser Leu Thr Cys Leu Val Lys Gly
            515                 520                 525

Phe Tyr Pro Ser Asp Ile Ala Val Glu Trp Glu Ser Asn Gly Gln Pro
        530                 535                 540

Glu Asn Asn Tyr Lys Thr Thr Pro Pro Val Leu Asp Ser Asp Gly Ser
545                 550                 555                 560

Phe Phe Leu Tyr Ser Lys Leu Thr Val Asp Lys Ser Arg Trp Gln Gln
                565                 570                 575

Gly Asn Val Phe Ser Cys Ser Val Met His Glu Ala Leu His Asn His
            580                 585                 590

Tyr Thr Gln Lys Ser Leu Ser Leu Ser Pro Gly Lys
        595                 600

<210> SEQ ID NO 61
<211> LENGTH: 579
<212> TYPE: PRT
<213> ORGANISM: Artificial Sequence
<220> FEATURE:
<223> OTHER INFORMATION: C6b heavy chain aa

<400> SEQUENCE: 61

Gln Leu Gln Leu Val Gln Ser Gly Thr Glu Val Lys Lys Pro Gly Ala
1               5                   10                  15

Ser Val Lys Val Ser Cys Lys Ser Gly Tyr Val Phe Thr Ser Tyr
            20                  25                  30

Tyr Leu Val Trp Val Arg Gln Ala Pro Gly Gln Gly Leu Glu Trp Met
        35                  40                  45

Ala Thr Ile Ser Pro Gly Asp Val Asn Thr Ser Tyr Glu Gln Arg Phe
    50                  55                  60

Gln Gly Arg Val Thr Val Thr Thr Asp Ala Ser Thr Asn Thr Val Asp
65                  70                  75                  80

Met Glu Leu Arg Ser Leu Arg Ser Glu Asp Thr Ala Val Tyr Tyr Cys
                85                  90                  95

Ala Arg Gly Pro Arg Ser Lys Pro Pro Tyr Leu Tyr Phe Ala Leu Asp
            100                 105                 110

Val Trp Gly Gln Gly Thr Ala Val Thr Val Ser Ser Gln Gly Phe Thr
        115                 120                 125

Ser Val Met Ala Pro Phe Leu Pro Leu Leu Thr Glu Gln Val Ser Thr
    130                 135                 140

Pro Glu Ile Lys Val Leu Asn Lys Thr Gln Glu Asn Gly Thr Cys Thr
145                 150                 155                 160

Leu Ile Leu Gly Cys Thr Val Glu Lys Gly Asp His Val Ala Tyr Ser
                165                 170                 175

Trp Ser Glu Lys Ala Gly Thr His Pro Leu Asn Pro Ala Asn Ser Ser
            180                 185                 190

His Leu Leu Ser Leu Thr Leu Gly Pro Gln His Ala Asp Asn Ile Tyr
        195                 200                 205

Ile Cys Thr Val Ser Asn Pro Ile Ser Asn Asn Ser Gln Thr Phe Ser
    210                 215                 220

Pro Trp Pro Gly Cys Arg Thr Asp Pro Ser Gly Glu Tyr Thr Gly Gly
225                 230                 235                 240

Ser Leu Cys Ala Thr Leu Met Ser Met Ala Ser Thr Lys Gly Pro Ser
```

```
            245                 250                 255
Val Phe Pro Leu Ala Pro Ser Ser Lys Ser Thr Ser Gly Gly Thr Ala
            260                 265                 270

Ala Leu Gly Cys Leu Val Lys Asp Tyr Phe Pro Glu Pro Val Thr Val
        275                 280                 285

Ser Trp Asn Ser Gly Ala Leu Thr Ser Gly Val His Thr Phe Pro Ala
    290                 295                 300

Val Leu Gln Ser Ser Gly Leu Tyr Ser Leu Ser Ser Val Val Thr Val
305                 310                 315                 320

Pro Ser Ser Ser Leu Gly Thr Gln Thr Tyr Ile Cys Asn Val Asn His
                325                 330                 335

Lys Pro Ser Asn Thr Lys Val Asp Lys Arg Val Glu Pro Lys Ser Cys
            340                 345                 350

Asp Lys Thr His Thr Cys Pro Pro Cys Pro Ala Pro Glu Leu Leu Gly
        355                 360                 365

Gly Pro Ser Val Phe Leu Phe Pro Pro Lys Pro Lys Asp Thr Leu Met
    370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Asn Ser Thr Tyr
            420                 425                 430

Arg Val Val Ser Val Leu Thr Val Leu His Gln Asp Trp Leu Asn Gly
        435                 440                 445

Lys Glu Tyr Lys Cys Lys Val Ser Asn Lys Ala Leu Pro Ala Pro Ile
    450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Glu Glu Met Thr Lys Asn Gln Val Ser
                485                 490                 495

Leu Thr Cys Leu Val Lys Gly Phe Tyr Pro Ser Asp Ile Ala Val Glu
            500                 505                 510

Trp Glu Ser Asn Gly Gln Pro Glu Asn Asn Tyr Lys Thr Thr Pro Pro
        515                 520                 525

Val Leu Asp Ser Asp Gly Ser Phe Phe Leu Tyr Ser Lys Leu Thr Val
    530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
                565                 570                 575

Pro Gly Lys

<210> SEQ ID NO 62
<211> LENGTH: 573
<212> TYPE: PRT
<213> ORGANISM: Artificial Sequence
<220> FEATURE:
<223> OTHER INFORMATION: C7 heavy chain aa

<400> SEQUENCE: 62

Asp Val Gln Leu Val Glu Ser Gly Gly Gly Val Val Arg Pro Gly Val
1               5                   10                  15

Ser Leu Arg Leu Ser Cys Val Ala Ser Gly Phe Ser Phe Lys Asn Tyr
            20                  25                  30
```

Asp Met Ala Trp Val Arg Gln Val Pro Gly Lys Gly Leu Glu Trp Val
                35                  40                  45

Cys Gly Ile Asn Trp Asn Gly Ser Leu Arg Gly Tyr Ala Asp Ser Val
 50                  55                  60

Lys Gly Arg Phe Leu Ile Ser Arg Asp His Ala Lys Asp Ser Leu Tyr
 65                  70                  75                  80

Leu Gln Met Ser Arg Leu Arg Ala Glu Asp Thr Ala Leu Tyr Tyr Cys
                 85                  90                  95

Ala Arg Asp Pro Gly Tyr Asn Thr Gly Arg Asp His Pro Tyr Asp Leu
                100                 105                 110

Trp Gly Gln Gly Thr Met Val Thr Val Ser Ser Asp Ser Pro Asp Arg
                115                 120                 125

Pro Trp Asn Pro Pro Thr Phe Ser Pro Ala Leu Leu Val Val Thr Glu
        130                 135                 140

Gly Asp Asn Ala Thr Phe Thr Cys Ser Phe Ser Asn Thr Ser Glu Ser
145                 150                 155                 160

Phe Val Leu Asn Trp Tyr Arg Met Ser Pro Ser Asn Gln Thr Asp Lys
                165                 170                 175

Leu Ala Ala Phe Pro Glu Asp Arg Ser Gln Pro Gly Gln Asp Cys Arg
                180                 185                 190

Phe Arg Val Thr Gln Leu Pro Asn Gly Arg Asp Phe His Met Ser Val
            195                 200                 205

Val Arg Ala Arg Arg Asn Asp Ser Gly Thr Tyr Leu Cys Gly Ala Ile
        210                 215                 220

Ser Leu Ala Pro Lys Ala Gln Ile Lys Glu Ser Leu Arg Ala Glu Leu
225                 230                 235                 240

Arg Val Thr Ala Ser Thr Lys Gly Pro Ser Val Phe Pro Leu Ala Pro
                245                 250                 255

Ser Ser Lys Ser Thr Ser Gly Gly Thr Ala Ala Leu Gly Cys Leu Val
            260                 265                 270

Lys Asp Tyr Phe Pro Glu Pro Val Thr Val Ser Trp Asn Ser Gly Ala
            275                 280                 285

Leu Thr Ser Gly Val His Thr Phe Pro Ala Val Leu Gln Ser Ser Gly
            290                 295                 300

Leu Tyr Ser Leu Ser Ser Val Val Thr Val Pro Ser Ser Ser Leu Gly
305                 310                 315                 320

Thr Gln Thr Tyr Ile Cys Asn Val Asn His Lys Pro Ser Asn Thr Lys
                325                 330                 335

Val Asp Lys Arg Val Glu Pro Lys Ser Cys Asp Lys Thr His Thr Cys
            340                 345                 350

Pro Pro Cys Pro Ala Pro Glu Leu Leu Gly Gly Pro Ser Val Phe Leu
            355                 360                 365

Phe Pro Pro Lys Pro Lys Asp Thr Leu Met Ile Ser Arg Thr Pro Glu
        370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
        435                 440                 445

Val Ser Asn Lys Ala Leu Pro Ala Pro Ile Glu Lys Thr Ile Ser Lys
450                 455                 460

Ala Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
                500                 505                 510

Pro Glu Asn Asn Tyr Lys Thr Thr Pro Pro Val Leu Asp Ser Asp Gly
                515                 520                 525

Ser Phe Phe Leu Tyr Ser Lys Leu Thr Val Asp Lys Ser Arg Trp Gln
530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570

<210> SEQ ID NO 63
<211> LENGTH: 214
<212> TYPE: PRT
<213> ORGANISM: Artificial Sequence
<220> FEATURE:
<223> OTHER INFORMATION: C7/C8/C9 light chain aa

<400> SEQUENCE: 63

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Gly Ser Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Gln Tyr Asn Asn Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 64
<211> LENGTH: 548

```
<212> TYPE: PRT
<213> ORGANISM: Artificial Sequence
<220> FEATURE:
<223> OTHER INFORMATION: C8 heavy chain aa

<400> SEQUENCE: 64
```

| | | | | | | | | | | | | | | |
|---|---|---|---|---|---|---|---|---|---|---|---|---|---|---|
| Asp | Val | Gln | Leu | Val | Glu | Ser | Gly | Gly | Gly | Val | Val | Arg | Pro | Gly | Val |
| 1 | | | | 5 | | | | | 10 | | | | | 15 | |
| Ser | Leu | Arg | Leu | Ser | Cys | Val | Ala | Ser | Gly | Phe | Ser | Phe | Lys | Asn | Tyr |
| | | | 20 | | | | | 25 | | | | | 30 | | |
| Asp | Met | Ala | Trp | Val | Arg | Gln | Val | Pro | Gly | Lys | Gly | Leu | Glu | Trp | Val |
| | | 35 | | | | | 40 | | | | | 45 | | | |
| Cys | Gly | Ile | Asn | Trp | Asn | Gly | Ser | Leu | Arg | Gly | Tyr | Ala | Asp | Ser | Val |
| | 50 | | | | | 55 | | | | | 60 | | | | |
| Lys | Gly | Arg | Phe | Leu | Ile | Ser | Arg | Asp | His | Ala | Lys | Asp | Ser | Leu | Tyr |
| 65 | | | | | 70 | | | | | 75 | | | | | 80 |
| Leu | Gln | Met | Ser | Arg | Leu | Arg | Ala | Glu | Asp | Thr | Ala | Leu | Tyr | Tyr | Cys |
| | | | | 85 | | | | | 90 | | | | | 95 | |
| Ala | Arg | Asp | Pro | Gly | Tyr | Asn | Thr | Gly | Arg | Asp | His | Pro | Tyr | Asp | Leu |
| | | | 100 | | | | | 105 | | | | | 110 | | |
| Trp | Gly | Gln | Gly | Thr | Met | Val | Thr | Val | Ser | Ser | Glu | Gln | Val | Ser | Thr |
| | | 115 | | | | | 120 | | | | | 125 | | | |
| Pro | Glu | Ile | Lys | Val | Leu | Asn | Lys | Thr | Gln | Glu | Asn | Gly | Thr | Cys | Thr |
| | 130 | | | | | 135 | | | | | 140 | | | | |
| Leu | Ile | Leu | Gly | Cys | Thr | Val | Glu | Lys | Gly | Asp | His | Val | Ala | Tyr | Ser |
| 145 | | | | | 150 | | | | | 155 | | | | | 160 |
| Trp | Ser | Glu | Lys | Ala | Gly | Thr | His | Pro | Leu | Asn | Pro | Ala | Asn | Ser | Ser |
| | | | | 165 | | | | | 170 | | | | | 175 | |
| His | Leu | Leu | Ser | Leu | Thr | Leu | Gly | Pro | Gln | His | Ala | Asp | Asn | Ile | Tyr |
| | | | 180 | | | | | 185 | | | | | 190 | | |
| Ile | Cys | Thr | Val | Ser | Asn | Pro | Ile | Ser | Asn | Asn | Ser | Gln | Thr | Phe | Ser |
| | | 195 | | | | | 200 | | | | | 205 | | | |
| Pro | Trp | Pro | Gly | Cys | Arg | Thr | Asp | Pro | Ser | Ala | Ser | Thr | Lys | Gly | Pro |
| | 210 | | | | | 215 | | | | | 220 | | | | |
| Ser | Val | Phe | Pro | Leu | Ala | Pro | Ser | Ser | Lys | Ser | Thr | Ser | Gly | Gly | Thr |
| 225 | | | | | 230 | | | | | 235 | | | | | 240 |
| Ala | Ala | Leu | Gly | Cys | Leu | Val | Lys | Asp | Tyr | Phe | Pro | Glu | Pro | Val | Thr |
| | | | | 245 | | | | | 250 | | | | | 255 | |
| Val | Ser | Trp | Asn | Ser | Gly | Ala | Leu | Thr | Ser | Gly | Val | His | Thr | Phe | Pro |
| | | | 260 | | | | | 265 | | | | | 270 | | |
| Ala | Val | Leu | Gln | Ser | Ser | Gly | Leu | Tyr | Ser | Leu | Ser | Val | Val | Thr |
| | | 275 | | | | | 280 | | | | | 285 | | | |
| Val | Pro | Ser | Ser | Ser | Leu | Gly | Thr | Gln | Thr | Tyr | Ile | Cys | Asn | Val | Asn |
| | 290 | | | | | 295 | | | | | 300 | | | | |
| His | Lys | Pro | Ser | Asn | Thr | Lys | Val | Asp | Lys | Arg | Val | Glu | Pro | Lys | Ser |
| 305 | | | | | 310 | | | | | 315 | | | | | 320 |
| Cys | Asp | Lys | Thr | His | Thr | Cys | Pro | Pro | Cys | Pro | Ala | Pro | Glu | Leu | Leu |
| | | | | 325 | | | | | 330 | | | | | 335 | |
| Gly | Gly | Pro | Ser | Val | Phe | Leu | Phe | Pro | Pro | Lys | Pro | Lys | Asp | Thr | Leu |
| | | | 340 | | | | | 345 | | | | | 350 | | |
| Met | Ile | Ser | Arg | Thr | Pro | Glu | Val | Thr | Cys | Val | Val | Val | Asp | Val | Ser |
| | | 355 | | | | | 360 | | | | | 365 | | | |
| His | Glu | Asp | Pro | Glu | Val | Lys | Phe | Asn | Trp | Tyr | Val | Asp | Gly | Val | Glu |
| | 370 | | | | | 375 | | | | | 380 | | | | |

```
Val His Asn Ala Lys Thr Lys Pro Arg Glu Glu Gln Tyr Asn Ser Thr
385                 390                 395                 400

Tyr Arg Val Val Ser Val Leu Thr Val Leu His Gln Asp Trp Leu Asn
            405                 410                 415

Gly Lys Glu Tyr Lys Cys Lys Val Ser Asn Lys Ala Leu Pro Ala Pro
        420                 425                 430

Ile Glu Lys Thr Ile Ser Lys Ala Lys Gly Gln Pro Arg Glu Pro Gln
    435                 440                 445

Val Tyr Thr Leu Pro Pro Ser Arg Glu Glu Met Thr Lys Asn Gln Val
450                 455                 460

Ser Leu Thr Cys Leu Val Lys Gly Phe Tyr Pro Ser Asp Ile Ala Val
465                 470                 475                 480

Glu Trp Glu Ser Asn Gly Gln Pro Glu Asn Asn Tyr Lys Thr Thr Pro
            485                 490                 495

Pro Val Leu Asp Ser Asp Gly Ser Phe Phe Leu Tyr Ser Lys Leu Thr
        500                 505                 510

Val Asp Lys Ser Arg Trp Gln Gln Gly Asn Val Phe Ser Cys Ser Val
    515                 520                 525

Met His Glu Ala Leu His Asn His Tyr Thr Gln Lys Ser Leu Ser Leu
530                 535                 540

Ser Pro Gly Lys
545

<210> SEQ ID NO 65
<211> LENGTH: 483
<212> TYPE: PRT
<213> ORGANISM: Artificial Sequence
<220> FEATURE:
<223> OTHER INFORMATION: C9 heavy chain aa

<400> SEQUENCE: 65

Asp Val Gln Leu Val Glu Ser Gly Gly Gly Val Val Arg Pro Gly Val
1               5                   10                  15

Ser Leu Arg Leu Ser Cys Val Ala Ser Gly Phe Ser Phe Lys Asn Tyr
            20                  25                  30

Asp Met Ala Trp Val Arg Gln Val Pro Gly Lys Gly Leu Glu Trp Val
        35                  40                  45

Cys Gly Ile Asn Trp Asn Gly Ser Leu Arg Gly Tyr Ala Asp Ser Val
    50                  55                  60

Lys Gly Arg Phe Leu Ile Ser Arg Asp His Ala Lys Asp Ser Leu Tyr
65                  70                  75                  80

Leu Gln Met Ser Arg Leu Arg Ala Glu Asp Thr Ala Leu Tyr Tyr Cys
                85                  90                  95

Ala Arg Asp Pro Gly Tyr Asn Thr Gly Arg Asp His Pro Tyr Asp Leu
            100                 105                 110

Trp Gly Gln Gly Thr Met Val Thr Val Ser Ser Ala Trp Ser His
        115                 120                 125

Pro Gln Phe Glu Lys Gly Gly Ser Gly Gly Ser Gly Gly Ser
130                 135                 140

Ala Trp Ser His Pro Gln Phe Glu Lys Ala Ser Thr Lys Gly Pro Ser
145                 150                 155                 160

Val Phe Pro Leu Ala Pro Ser Ser Lys Ser Thr Ser Gly Gly Thr Ala
                165                 170                 175

Ala Leu Gly Cys Leu Val Lys Asp Tyr Phe Pro Glu Pro Val Thr Val
            180                 185                 190
```

```
Ser Trp Asn Ser Gly Ala Leu Thr Ser Gly Val His Thr Phe Pro Ala
            195                 200                 205

Val Leu Gln Ser Ser Gly Leu Tyr Ser Leu Ser Val Val Thr Val
210                 215                 220

Pro Ser Ser Ser Leu Gly Thr Gln Thr Tyr Ile Cys Asn Val Asn His
225                 230                 235                 240

Lys Pro Ser Asn Thr Lys Val Asp Lys Arg Val Glu Pro Lys Ser Cys
                245                 250                 255

Asp Lys Thr His Thr Cys Pro Pro Cys Pro Ala Pro Glu Leu Leu Gly
                260                 265                 270

Gly Pro Ser Val Phe Leu Phe Pro Pro Lys Pro Lys Asp Thr Leu Met
            275                 280                 285

Ile Ser Arg Thr Pro Glu Val Thr Cys Val Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
            355                 360                 365

Glu Lys Thr Ile Ser Lys Ala Lys Gly Gln Pro Arg Glu Pro Gln Val
            370                 375                 380

Tyr Thr Leu Pro Pro Ser Arg Glu Glu Met Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
                435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys

<210> SEQ ID NO 66
<211> LENGTH: 567
<212> TYPE: PRT
<213> ORGANISM: Artificial Sequence
<220> FEATURE:
<223> OTHER INFORMATION: C10 heavy chain aa

<400> SEQUENCE: 66

Gln Val Gln Leu Val Gln Ser Gly Ala Glu Val Arg Lys Pro Gly Ser
1               5                   10                  15

Ser Val Lys Val Ser Cys Lys Thr Ser Gly Gly Ile Ile Arg Lys Tyr
            20                  25                  30

Ala Leu Ser Trp Val Arg Gln Ala Pro Gly Gln Gly Leu Glu Trp Met
        35                  40                  45

Gly Gly Ile Ile Ala Ile Phe Gly Thr Thr Asn Tyr Ala Gln Lys Phe
    50                  55                  60

Gln Gly Arg Val Thr Ile Asn Ala Asp Glu Ser Thr Ser Thr Val Tyr
```

```
            65                  70                  75                  80
Leu Glu Leu Ser Ser Leu Thr Ser Glu Asp Thr Ala Ile Tyr Tyr Cys
                85                  90                  95
Ala Gly Ser Ala Thr Tyr Tyr Glu Ser Arg Phe Asp Tyr Trp Gly Gln
                100                 105                 110
Gly Thr Leu Val Thr Val Ser Ser Met Ala Gln Val Gln Leu Val Glu
            115                 120                 125
Ser Gly Gly Gly Leu Val Gln Ala Gly Gly Ser Leu Thr Leu Ser Cys
        130                 135                 140
Ala Ala Ser Gly Ser Thr Ser Arg Ser Tyr Ala Leu Gly Trp Phe Arg
145                 150                 155                 160
Gln Ala Pro Gly Lys Glu Arg Glu Phe Val Ala His Val Gly Gln Thr
                165                 170                 175
Ala Glu Phe Ala Gln Gly Arg Phe Thr Ile Ser Arg Asp Phe Ala Lys
                180                 185                 190
Asn Thr Val Ser Leu Gln Met Asn Asp Leu Lys Ser Asp Asp Thr Ala
            195                 200                 205
Ile Tyr Tyr Cys Val Ala Ser Asn Arg Gly Trp Ser Pro Ser Arg Val
        210                 215                 220
Ser Tyr Trp Gly Gln Gly Thr Gln Val Thr Val Ser Ser Ala Ser Thr
225                 230                 235                 240
Lys Gly Pro Ser Val Phe Pro Leu Ala Pro Ser Ser Lys Ser Thr Ser
                245                 250                 255
Gly Gly Thr Ala Ala Leu Gly Cys Leu Val Lys Asp Tyr Phe Pro Glu
                260                 265                 270
Pro Val Thr Val Ser Trp Asn Ser Gly Ala Leu Thr Ser Gly Val His
            275                 280                 285
Thr Phe Pro Ala Val Leu Gln Ser Ser Gly Leu Tyr Ser Leu Ser Ser
        290                 295                 300
Val Val Thr Val Pro Ser Ser Ser Leu Gly Thr Gln Thr Tyr Ile Cys
305                 310                 315                 320
Asn Val Asn His Lys Pro Ser Asn Thr Lys Val Asp Lys Arg Val Glu
                325                 330                 335
Pro Lys Ser Cys Asp Lys Thr His Thr Cys Pro Pro Cys Pro Ala Pro
                340                 345                 350
Glu Leu Leu Gly Gly Pro Ser Val Phe Leu Phe Pro Pro Lys Pro Lys
            355                 360                 365
Asp Thr Leu Met Ile Ser Arg Thr Pro Glu Val Thr Cys Val Val Val
        370                 375                 380
Asp Val Ser His Glu Asp Pro Glu Val Lys Phe Asn Trp Tyr Val Asp
385                 390                 395                 400
Gly Val Glu Val His Asn Ala Lys Thr Lys Pro Arg Glu Glu Gln Tyr
                405                 410                 415
Asn Ser Thr Tyr Arg Val Val Ser Val Leu Thr Val Leu His Gln Asp
            420                 425                 430
Trp Leu Asn Gly Lys Glu Tyr Lys Cys Lys Val Ser Asn Lys Ala Leu
        435                 440                 445
Pro Ala Pro Ile Glu Lys Thr Ile Ser Lys Ala Lys Gly Gln Pro Arg
        450                 455                 460
Glu Pro Gln Val Tyr Thr Leu Pro Pro Ser Arg Glu Glu Met Thr Lys
465                 470                 475                 480
Asn Gln Val Ser Leu Thr Cys Leu Val Lys Gly Phe Tyr Pro Ser Asp
                485                 490                 495
```

```
Ile Ala Val Glu Trp Glu Ser Asn Gly Gln Pro Glu Asn Asn Tyr Lys
            500                 505                 510

Thr Thr Pro Pro Val Leu Asp Ser Asp Gly Ser Phe Phe Leu Tyr Ser
            515                 520                 525

Lys Leu Thr Val Asp Lys Ser Arg Trp Gln Gln Gly Asn Val Phe Ser
530                 535                 540

Cys Ser Val Met His Glu Ala Leu His Asn His Tyr Thr Gln Lys Ser
545                 550                 555                 560

Leu Ser Leu Ser Pro Gly Lys
                565

<210> SEQ ID NO 67
<211> LENGTH: 215
<212> TYPE: PRT
<213> ORGANISM: Artificial Sequence
<220> FEATURE:
<223> OTHER INFORMATION: C10/C11/C12/C13 light chain aa

<400> SEQUENCE: 67

Glu Ile Val Leu Thr Gln Ser Pro Gly Thr Leu Ser Leu Ser Pro Gly
1               5                   10                  15

Ala Arg Ala Thr Leu Ser Cys Arg Ala Ser Gln Ser Val Ser Ser Ser
            20                  25                  30

Ser Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys His Gln Tyr Gly Asp Ser Arg
                85                  90                  95

Lys Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 68
<211> LENGTH: 698
<212> TYPE: PRT
<213> ORGANISM: Artificial Sequence
<220> FEATURE:
<223> OTHER INFORMATION: C11 heavy chain aa

<400> SEQUENCE: 68

Gln Val Gln Leu Val Gln Ser Gly Ala Glu Val Arg Lys Pro Gly Ser
```

-continued

```
1               5                   10                  15
Ser Val Lys Val Ser Cys Lys Thr Ser Gly Gly Ile Ile Arg Lys Tyr
                20                  25                  30
Ala Leu Ser Trp Val Arg Gln Ala Pro Gly Gln Gly Leu Glu Trp Met
                35                  40                  45
Gly Gly Ile Ile Ala Ile Phe Gly Thr Thr Asn Tyr Ala Gln Lys Phe
                50                  55                  60
Gln Gly Arg Val Thr Ile Asn Ala Asp Glu Ser Thr Ser Thr Val Tyr
65                  70                  75                  80
Leu Glu Leu Ser Ser Leu Thr Ser Glu Asp Thr Ala Ile Tyr Tyr Cys
                85                  90                  95
Ala Gly Ser Ala Thr Tyr Tyr Glu Ser Arg Phe Asp Tyr Trp Gly Gln
                100                 105                 110
Gly Thr Leu Val Thr Val Ser Ser Gln Ile Thr Leu Lys Glu Ser Gly
                115                 120                 125
Pro Thr Leu Val Lys Pro Thr Gln Thr Leu Thr Leu Thr Cys Thr Phe
                130                 135                 140
Ser Gly Phe Ser Leu Ser Thr Ser Arg Val Gly Val Gly Trp Ile Arg
145                 150                 155                 160
Gln Pro Pro Gly Lys Ala Leu Glu Trp Leu Ser Leu Ile Tyr Trp Asp
                165                 170                 175
Asp Glu Lys His Tyr Ser Pro Ser Leu Lys Asn Arg Val Thr Ile Ser
                180                 185                 190
Lys Asp Ser Ser Lys Asn Gln Val Val Leu Thr Leu Thr Asp Met Asp
                195                 200                 205
Pro Val Asp Thr Gly Thr Tyr Tyr Cys Ala His Arg Gly Val Asp Thr
                210                 215                 220
Ser Gly Trp Gly Phe Asp Tyr Trp Gly Gln Gly Ala Leu Val Thr Val
225                 230                 235                 240
Ser Ser Gly Gly Gly Gly Ser Gly Gly Gly Gly Ser Gly Gly Gly Gly
                245                 250                 255
Ser Gln Ser Ala Leu Thr Gln Pro Ala Ser Val Ser Gly Ser Pro Gly
                260                 265                 270
Gln Ser Ile Thr Ile Ser Cys Ser Gly Ala Gly Ser Asp Val Gly Gly
                275                 280                 285
His Asn Phe Val Ser Trp Tyr Gln Gln Tyr Pro Gly Lys Ala Pro Lys
                290                 295                 300
Leu Met Ile Tyr Asp Val Lys Asn Arg Pro Ser Gly Val Ser Tyr Arg
305                 310                 315                 320
Phe Ser Gly Ser Lys Ser Gly Tyr Thr Ala Ser Leu Thr Ile Ser Gly
                325                 330                 335
Leu Gln Ala Glu Asp Glu Ala Thr Tyr Phe Cys Ser Ser Tyr Ser Ser
                340                 345                 350
Ser Ser Thr Leu Ile Ile Phe Gly Gly Gly Thr Arg Leu Thr Val Leu
                355                 360                 365
Ala Ser Thr Lys Gly Pro Ser Val Phe Pro Leu Ala Pro Ser Ser Lys
                370                 375                 380
Ser Thr Ser Gly Gly Thr Ala Ala Leu Gly Cys Leu Val Lys Asp Tyr
385                 390                 395                 400
Phe Pro Glu Pro Val Thr Val Ser Trp Asn Ser Gly Ala Leu Thr Ser
                405                 410                 415
Gly Val His Thr Phe Pro Ala Val Leu Gln Ser Ser Gly Leu Tyr Ser
                420                 425                 430
```

Leu Ser Ser Val Thr Val Pro Ser Ser Leu Gly Thr Gln Thr
        435                 440                 445

Tyr Ile Cys Asn Val Asn His Lys Pro Ser Asn Thr Lys Val Asp Lys
    450                 455                 460

Arg Val Glu Pro Lys Ser Cys Asp Lys Thr His Thr Cys Pro Pro Cys
465                 470                 475                 480

Pro Ala Pro Glu Leu Leu Gly Gly Pro Ser Val Phe Leu Phe Pro Pro
                485                 490                 495

Lys Pro Lys Asp Thr Leu Met Ile Ser Arg Thr Pro Glu Val Thr Cys
                500                 505                 510

Val Val Val Asp Val Ser His Glu Asp Pro Glu Val Lys Phe Asn Trp
            515                 520                 525

Tyr Val Asp Gly Val Glu Val His Asn Ala Lys Thr Lys Pro Arg Glu
        530                 535                 540

Glu Gln Tyr Asn Ser Thr Tyr Arg Val Val Ser Val Leu Thr Val Leu
545                 550                 555                 560

His Gln Asp Trp Leu Asn Gly Lys Glu Tyr Lys Cys Lys Val Ser Asn
                565                 570                 575

Lys Ala Leu Pro Ala Pro Ile Glu Lys Thr Ile Ser Lys Ala Lys Gly
                580                 585                 590

Gln Pro Arg Glu Pro Gln Val Tyr Thr Leu Pro Pro Ser Arg Glu Glu
            595                 600                 605

Met Thr Lys Asn Gln Val Ser Leu Thr Cys Leu Val Lys Gly Phe Tyr
        610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Phe
                645                 650                 655

Leu Tyr Ser Lys Leu Thr Val Asp Lys Ser Arg Trp Gln Gln Gly Asn
                660                 665                 670

Val Phe Ser Cys Ser Val Met His Glu Ala Leu His Asn His Tyr Thr
            675                 680                 685

Gln Lys Ser Leu Ser Leu Ser Pro Gly Lys
        690                 695

<210> SEQ ID NO 69
<211> LENGTH: 575
<212> TYPE: PRT
<213> ORGANISM: Artificial Sequence
<220> FEATURE:
<223> OTHER INFORMATION: C12 heavy chain aa

<400> SEQUENCE: 69

Gln Val Gln Leu Val Gln Ser Gly Ala Glu Val Arg Lys Pro Gly Ser
1               5                   10                  15

Ser Val Lys Val Ser Cys Lys Thr Ser Gly Gly Ile Ile Arg Lys Tyr
            20                  25                  30

Ala Leu Ser Trp Val Arg Gln Ala Pro Gly Gln Gly Leu Glu Trp Met
        35                  40                  45

Gly Gly Ile Ile Ala Ile Phe Gly Thr Thr Asn Tyr Ala Gln Lys Phe
    50                  55                  60

Gln Gly Arg Val Thr Ile Asn Ala Asp Glu Ser Thr Ser Thr Val Tyr
65                  70                  75                  80

Leu Glu Leu Ser Ser Leu Thr Ser Glu Asp Thr Ala Ile Tyr Tyr Cys
                85                  90                  95

```
Ala Gly Ser Ala Thr Tyr Tyr Glu Ser Arg Phe Asp Tyr Trp Gly Gln
            100                 105                 110

Gly Thr Leu Val Thr Val Ser Gln Val Gln Leu Gln Glu Ser Gly
            115                 120                 125

Gly Gly Leu Val Gln Pro Gly Gly Ser Leu Arg Leu Ser Cys Ala Ala
            130                 135                 140

Ser Gly Phe Thr Leu Asp Tyr Tyr Ile Gly Trp Phe Arg Gln Ala
145                 150                 155                 160

Pro Gly Lys Glu Arg Glu Ala Val Ser Cys Ile Ser Gly Ser Ser Gly
                165                 170                 175

Ser Thr Tyr Tyr Pro Asp Ser Val Lys Gly Arg Phe Thr Ile Ser Arg
            180                 185                 190

Asp Asn Ala Lys Asn Thr Val Tyr Leu Gln Met Asn Ser Leu Lys Pro
            195                 200                 205

Glu Asp Thr Ala Val Tyr Tyr Cys Ala Thr Ile Arg Ser Ser Ser Trp
            210                 215                 220

Gly Gly Cys Val His Tyr Gly Met Asp Tyr Trp Gly Lys Gly Thr Gln
225                 230                 235                 240

Val Thr Val Ser Ser Ala Ser Thr Lys Gly Pro Ser Val Phe Pro Leu
            245                 250                 255

Ala Pro Ser Ser Lys Ser Thr Ser Gly Gly Thr Ala Ala Leu Gly Cys
            260                 265                 270

Leu Val Lys Asp Tyr Phe Pro Glu Pro Val Thr Val Ser Trp Asn Ser
            275                 280                 285

Gly Ala Leu Thr Ser Gly Val His Thr Phe Pro Ala Val Leu Gln Ser
            290                 295                 300

Ser Gly Leu Tyr Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
            325                 330                 335

Thr Lys Val Asp Lys Arg Val Glu Pro Lys Ser Cys Asp Lys Thr His
            340                 345                 350

Thr Cys Pro Pro Cys Pro Ala Pro Glu Leu Leu Gly Gly Pro Ser Val
            355                 360                 365

Phe Leu Phe Pro Pro Lys Pro Lys Asp Thr Leu Met Ile Ser Arg Thr
370                 375                 380

Pro Glu Val Thr Cys Val Val Asp Val Ser His Glu Asp Pro Glu
385                 390                 395                 400

Val Lys Phe Asn Trp Tyr Val Asp Gly Val Glu Val His Asn Ala Lys
            405                 410                 415

Thr Lys Pro Arg Glu Glu Gln Tyr Asn Ser Thr Tyr Arg Val Val Ser
            420                 425                 430

Val Leu Thr Val Leu His Gln Asp Trp Leu Asn Gly Lys Glu Tyr Lys
            435                 440                 445

Cys Lys Val Ser Asn Lys Ala Leu Pro Ala Pro Ile Glu Lys Thr Ile
            450                 455                 460

Ser Lys Ala Lys Gly Gln Pro Arg Glu Pro Gln Val Tyr Thr Leu Pro
465                 470                 475                 480

Pro Ser Arg Glu Glu Met Thr Lys Asn Gln Val Ser Leu Thr Cys Leu
                485                 490                 495

Val Lys Gly Phe Tyr Pro Ser Asp Ile Ala Val Glu Trp Glu Ser Asn
            500                 505                 510
```

```
Gly Gln Pro Glu Asn Asn Tyr Lys Thr Thr Pro Pro Val Leu Asp Ser
            515                 520                 525

Asp Gly Ser Phe Phe Leu Tyr Ser Lys Leu Thr Val Asp Lys Ser Arg
530                 535                 540

Trp Gln Gln Gly Asn Val Phe Ser Cys Ser Val Met His Glu Ala Leu
545                 550                 555                 560

His Asn His Tyr Thr Gln Lys Ser Leu Ser Leu Ser Pro Gly Lys
                565                 570                 575

<210> SEQ ID NO 70
<211> LENGTH: 699
<212> TYPE: PRT
<213> ORGANISM: Artificial Sequence
<220> FEATURE:
<223> OTHER INFORMATION: C13 heavy chain aa

<400> SEQUENCE: 70

Gln Val Gln Leu Val Gln Ser Gly Ala Glu Val Arg Lys Pro Gly Ser
1               5                   10                  15

Ser Val Lys Val Ser Cys Lys Thr Ser Gly Gly Ile Ile Arg Lys Tyr
                20                  25                  30

Ala Leu Ser Trp Val Arg Gln Ala Pro Gly Gln Gly Leu Glu Trp Met
            35                  40                  45

Gly Gly Ile Ile Ala Ile Phe Gly Thr Thr Asn Tyr Ala Gln Lys Phe
        50                  55                  60

Gln Gly Arg Val Thr Ile Asn Ala Asp Glu Ser Thr Ser Thr Val Tyr
65                  70                  75                  80

Leu Glu Leu Ser Ser Leu Thr Ser Glu Asp Thr Ala Ile Tyr Tyr Cys
                85                  90                  95

Ala Gly Ser Ala Thr Tyr Tyr Glu Ser Arg Phe Asp Tyr Trp Gly Gln
            100                 105                 110

Gly Thr Leu Val Thr Val Ser Ser Glu Val Gln Leu Val Glu Ser Gly
        115                 120                 125

Gly Gly Leu Val Lys Pro Gly Gly Ser Leu Arg Leu Ser Cys Ala Ala
    130                 135                 140

Ser Gly Phe Thr Phe Ser Ser Tyr Ser Met Asn Trp Val Arg Gln Ala
145                 150                 155                 160

Pro Gly Lys Gly Leu Glu Trp Val Ser Ser Ile Ser Ala Ser Ser Ser
                165                 170                 175

Tyr Ser Asp Tyr Ala Asp Ser Ala Lys Gly Arg Phe Thr Ile Ser Arg
            180                 185                 190

Asp Asn Ala Lys Thr Ser Leu Phe Leu Gln Met Asn Ser Leu Arg Ala
        195                 200                 205

Glu Asp Thr Ala Ile Tyr Phe Cys Ala Arg Ala Arg Ala Thr Gly Tyr
    210                 215                 220

Ser Ser Ile Thr Pro Tyr Phe Asp Ile Trp Gly Gln Gly Thr Leu Val
225                 230                 235                 240

Thr Val Ser Ser Gly Gly Gly Gly Ser Gly Gly Gly Gly Ser Gly Gly
                245                 250                 255

Gly Gly Ser Gln Ser Val Val Thr Gln Pro Pro Ser Val Ser Gly Ala
            260                 265                 270

Pro Gly Gln Arg Val Thr Ile Ser Cys Thr Gly Ser Ser Ser Asn Ile
        275                 280                 285

Gly Ala Gly Tyr Asp Val His Trp Tyr Gln Gln Leu Pro Gly Thr Ala
    290                 295                 300
```

```
Pro Lys Leu Leu Ile Tyr Asp Asn Asn Arg Pro Ser Gly Val Pro
305                 310                 315                 320

Asp Arg Phe Ser Ala Ser Lys Ser Gly Thr Ser Ala Ser Leu Ala Ile
            325                 330                 335

Thr Gly Leu Gln Ala Glu Asp Glu Ala Asp Tyr Tyr Cys Gln Ser Tyr
            340                 345                 350

Asp Arg Asn Leu Ser Gly Val Phe Gly Thr Gly Thr Lys Val Thr Val
            355                 360                 365

Leu Ala Ser Thr Lys Gly Pro Ser Val Phe Pro Leu Ala Pro Ser Ser
370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
            405                 410                 415

Ser Gly Val His Thr Phe Pro Ala Val Leu Gln Ser Ser Gly Leu Tyr
            420                 425                 430

Ser Leu Ser Ser Val Val Thr Val Pro Ser Ser Ser Leu Gly Thr Gln
            435                 440                 445

Thr Tyr Ile Cys Asn Val Asn His Lys Pro Ser Asn Thr Lys Val Asp
450                 455                 460

Lys Arg Val Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
            485                 490                 495

Pro Lys Pro Lys Asp Thr Leu Met Ile Ser Arg Thr Pro Glu Val Thr
            500                 505                 510

Cys Val Val Val Asp Val Ser His Glu Asp Pro Glu Val Lys Phe Asn
            515                 520                 525

Trp Tyr Val Asp Gly Val Glu Val His Asn Ala Lys Thr Lys Pro Arg
530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
            565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Tyr Thr Leu Pro Pro Ser Arg Glu
            595                 600                 605

Glu Met Thr Lys Asn Gln Val Ser Leu Thr Cys Leu Val Lys Gly Phe
610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
            645                 650                 655

Phe Leu Tyr Ser Lys Leu Thr Val Asp Lys Ser Arg Trp Gln Gln Gly
            660                 665                 670

Asn Val Phe Ser Cys Ser Val Met His Glu Ala Leu His Asn His Tyr
            675                 680                 685

Thr Gln Lys Ser Leu Ser Leu Ser Pro Gly Lys
            690                 695

<210> SEQ ID NO 71
<211> LENGTH: 251
<212> TYPE: PRT
```

<213> ORGANISM: Artificial Sequence
<220> FEATURE:
<223> OTHER INFORMATION: MGDUCA VH aa

<400> SEQUENCE: 71

```
Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ala Ser Pro Leu Lys Ser Gln Arg Asp Thr Glu Asp Leu Pro
            100                 105                 110

Arg Pro Ser Ile Ser Ala Glu Pro Gly Thr Val Ile Pro Leu Gly Ser
        115                 120                 125

His Val Thr Phe Val Cys Arg Gly Pro Val Gly Val Gln Thr Phe Arg
130                 135                 140

Leu Glu Arg Glu Ser Arg Ser Thr Tyr Asn Asp Thr Glu Asp Val Ser
145                 150                 155                 160

Gln Ala Ser Pro Ser Glu Ser Glu Ala Arg Phe Arg Ile Asp Ser Val
                165                 170                 175

Ser Glu Gly Asn Ala Gly Pro Tyr Arg Cys Ile Tyr Tyr Lys Pro Pro
            180                 185                 190

Lys Trp Ser Glu Gln Ser Asp Tyr Leu Glu Leu Val Lys Gly Glu
        195                 200                 205

Asp Val Thr Trp Ala Leu Pro Gln Ser Gln Leu Asp Pro Arg Ala Cys
            210                 215                 220

Pro Gln Gly Glu Leu Pro Ile Ser Thr Asp Ile Tyr Tyr Met Asp Val
225                 230                 235                 240

Trp Gly Lys Gly Thr Thr Val Thr Val Ser Ser
                245                 250
```

<210> SEQ ID NO 72
<211> LENGTH: 107
<212> TYPE: PRT
<213> ORGANISM: Artificial Sequence
<220> FEATURE:
<223> OTHER INFORMATION: MGDUCA VL aa

<400> SEQUENCE: 72

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Cys Leu Gln Ser
65                  70                  75                  80
```

Glu Asp Phe Ala Thr Tyr Tyr Cys Gln Gln Tyr Tyr Ser Tyr Pro Pro
                85                  90                  95

Asp Phe Gly Gln Gly Thr Arg Leu Glu Ile Lys
            100                 105

<210> SEQ ID NO 73
<211> LENGTH: 119
<212> TYPE: PRT
<213> ORGANISM: Artificial Sequence
<220> FEATURE:
<223> OTHER INFORMATION: TT107 VH aa

<400> SEQUENCE: 73

Gln Val Gln Leu Ile Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Val Pro Gly Lys Gly Leu Glu Trp Ile
        35                  40                  45

Ser Val Ile Ser Ala Thr Thr Gly Tyr Thr Asp Tyr Ala Asp Ser Val
    50                  55                  60

Lys Gly Arg Phe Thr Ile Ser Arg Asp Asn Ala Lys Asn Ser Val Phe
65                  70                  75                  80

Leu Gln Met Asn Ser Leu Arg Val Asp Asp Met Ala Val Tyr Tyr Cys
                85                  90                  95

Ala Arg Glu Val Leu Gly Thr Ala Trp Phe Asp Tyr Trp Gly Gln Gly
            100                 105                 110

Thr Leu Val Thr Ile Ser Ser
        115

<210> SEQ ID NO 74
<211> LENGTH: 108
<212> TYPE: PRT
<213> ORGANISM: Artificial Sequence
<220> FEATURE:
<223> OTHER INFORMATION: TT107 VL aa

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Asn
            20                  25                  30

Tyr Leu Ala Trp Tyr Gln Gln Lys Pro Gly Gln Ala Pro Arg Leu Leu
        35                  40                  45

Ile Tyr Gly Val Ser Arg Arg Ala Thr Gly Ile Pro Asp Arg Phe Ser
    50                  55                  60

Gly Ser Gly Ser Gly Thr Asp Phe Ala Leu Thr Ile Ser Arg Leu Glu
65                  70                  75                  80

Pro Glu Asp Phe Ala Val Tyr Tyr Cys Gln Gln Tyr Arg Ser Ser Pro
                85                  90                  95

Arg Thr Phe Gly Pro Gly Thr Lys Val Glu Phe Lys
            100                 105

<210> SEQ ID NO 75
<211> LENGTH: 221
<212> TYPE: PRT
<213> ORGANISM: Artificial Sequence
<220> FEATURE:
<223> OTHER INFORMATION: MGJ1 VH

<400> SEQUENCE: 75

| Glu | Val | Gln | Leu | Val | Glu | Ser | Gly | Gly | Val | Val | Arg | Pro | Gly | Glu |
|---|---|---|---|---|---|---|---|---|---|---|---|---|---|---|
| 1 | | | | 5 | | | | | 10 | | | | | 15 |

| Ser | Leu | Arg | Leu | Ser | Cys | Ala | Ala | Ser | Gly | Phe | Ile | Phe | Asn | Asp | Phe |
|---|---|---|---|---|---|---|---|---|---|---|---|---|---|---|---|
| | | | 20 | | | | | 25 | | | | | 30 | | |

Gly Met Asn Trp Val Arg Gln Pro Pro Gly Arg Gly Leu Glu Trp Val
         35                     40                     45

Ala Gly Ile Lys Trp Arg Gly Gly Val Ala Leu Val Pro Ser Val
 50                 55                 60

Thr Gly Arg Phe Thr Ile Ser Gly Asp Asn Asp Lys Asn Ser Leu Tyr
65                  70                  75                    80

Leu Gln Met Thr Ser Leu Arg Asp Glu Asp Thr Ala Val Tyr Tyr Cys
                  85                  90                  95

Ala Arg Asp Ser Gly Phe Arg Gly Arg Gly His Ala Phe Asp Leu
           100                105              110

Trp Gly Gln Gly Thr Met Val Thr Ile Ser Ala Glu Asp Leu Pro Arg
          115                120              125

Pro Ser Ile Ser Ala Glu Pro Gly Thr Val Ile Pro Leu Gly Ser His
   130                 135                140

Val Thr Phe Val Cys Arg Gly Pro Val Gly Val His Thr Phe Arg Leu
145                 150                155              160

Glu Arg Glu Ser Arg Ser Thr Tyr Asn Glu Thr Glu Asp Val Ser Gln
          165                170              175

Ala Ser Pro Ser Glu Ser Glu Ala Arg Phe Arg Ile Asp Ser Val Ser
        180                185              190

Glu Gly Asn Ala Gly Pro Tyr Arg Cys Ile Tyr Tyr Lys Pro Pro Lys
      195                200              205

Trp Ser Glu Gln Ser Asp Tyr Leu Glu Leu Leu Val Lys
   210                 215              220

<210> SEQ ID NO 76
<211> LENGTH: 221
<212> TYPE: PRT
<213> ORGANISM: Artificial Sequence
<220> FEATURE:
<223> OTHER INFORMATION: MGJ2 VH

<400> SEQUENCE: 76

Glu Val Gln Val Val Glu Ser Gly Gly Val Arg Pro Gly Gly
1               5                   10                  15

Ser Leu Arg Leu Ser Cys Ala Ala Ser Gly Phe His Leu Asp Asp Tyr
                20                  25                  30

Asp Met Ser Trp Val Arg Gln Pro Pro Gly Lys Gly Leu Glu Trp Val
                35                  40                  45

Ala Gly Ile Asn Trp Asn Gly Gly Arg Thr Gly Tyr Ala Asp Ser Val
    50                  55                  60

Lys Gly Arg Leu Thr Ile Ser Arg Asp Asn Ala Lys Lys Phe Leu Tyr
65                  70                  75                  80

Leu Glu Met Lys Ser Leu Arg Ala Glu Asp Thr Ala Leu Tyr Tyr Cys
                85                  90                  95

Ala Arg Asp Pro Gly Tyr Ser Gly Arg Arg Asn Ala Leu Asp Ile
                100                 105                 110

Trp Gly Gln Gly Thr Met Val Thr Val Ser Leu Glu Asp Leu Pro Arg
                115                 120                 125

Pro Ser Ile Ser Ala Glu Pro Gly Thr Val Ile Pro Leu Gly Ser His

```
                    130                 135                 140
Val Thr Phe Val Cys Arg Gly Pro Val Gly Val Gln Thr Phe Arg Leu
145                 150                 155                 160

Glu Arg Glu Ser Arg Phe Thr Tyr Asn Asp Thr Glu Asp Val Ser Gln
                165                 170                 175

Ala Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
        195                 200                 205

Trp Ser Glu Gln Ser Asp Tyr Leu Glu Leu Leu Val Lys
    210                 215                 220

<210> SEQ ID NO 77
<211> LENGTH: 220
<212> TYPE: PRT
<213> ORGANISM: Artificial Sequence
<220> FEATURE:
<223> OTHER INFORMATION: MGJ3 VH

<400> SEQUENCE: 77

Glu Val Gln Leu Val Gln Ser Gly Gly Gly Val Val Arg Pro Gly Gly
1               5                   10                  15

Phe Leu Arg Leu Ser Cys Ala Ala Ser Gly Phe Thr Phe Glu Asn Tyr
            20                  25                  30

Ala Val Ala Trp Val Arg Gln Val Ala Gly Lys Gly Leu Glu Trp Leu
        35                  40                  45

Cys Val Ile Asn Trp Asp Ala Gly Thr Thr Asn Tyr Ala Asp Ser Val
    50                  55                  60

Lys Gly Arg Phe Thr Ile Ser Arg Asp Ile Val Lys Asn Ser Leu Val
65                  70                  75                  80

Leu Glu Met Ser Ser Leu Arg Ala Glu Asp Thr Ala Leu Tyr Tyr Cys
                85                  90                  95

Ala Arg Asp Pro Val Tyr Gly Ser Asp Arg Gly Asp Val Phe Asp Met
            100                 105                 110

Trp Gly Gln Gly Thr Val Val Thr Val Ser Ser Asp Leu Pro Arg Pro
        115                 120                 125

Ser Ile Ser Ala Glu Pro Gly Thr Val Ile Pro Leu Gly Ser His Val
    130                 135                 140

Thr Phe Val Cys Arg Gly Pro Val Gly Val Gln Thr Phe Arg Leu Glu
145                 150                 155                 160

Arg Glu Ser Arg Ser Thr Tyr Asn Glu Thr Glu Asp Val Ser Gln Ala
                165                 170                 175

Ser Pro Ser Glu Ser Glu Ala Arg Phe Arg Ile Asp Ser Val Ser Glu
            180                 185                 190

Gly Asn Ala Gly Pro Tyr Arg Cys Ile Tyr Tyr Lys Pro Pro Lys Trp
        195                 200                 205

Ser Glu Gln Ser Asp Tyr Leu Glu Leu Leu Val Lys
    210                 215                 220

<210> SEQ ID NO 78
<211> LENGTH: 221
<212> TYPE: PRT
<213> ORGANISM: Artificial Sequence
<220> FEATURE:
<223> OTHER INFORMATION: MGJ5 VH

<400> SEQUENCE: 78
```

Asp Val Gln Leu Val Glu Ser Gly Gly Val Val Arg Pro Gly Val
1               5                   10                  15

Ser Leu Arg Leu Ser Cys Val Ala Ser Gly Phe Ser Phe Lys Asn Tyr
            20                  25                  30

Asp Met Ala Trp Val Arg Gln Val Pro Gly Lys Gly Leu Glu Trp Val
        35                  40                  45

Cys Gly Ile Asn Trp Asn Gly Ser Leu Arg Gly Tyr Ala Asp Ser Val
    50                  55                  60

Lys Gly Arg Phe Leu Ile Ser Arg Asp His Ala Lys Asp Ser Leu Tyr
65                  70                  75                  80

Leu Gln Met Ser Arg Leu Arg Ala Glu Asp Thr Ala Leu Tyr Tyr Cys
                85                  90                  95

Ala Arg Asp Pro Gly Tyr Asn Thr Gly Arg Asp His Pro Tyr Asp Leu
            100                 105                 110

Trp Gly Gln Gly Thr Met Val Thr Val Ser Ser Glu Asp Leu Pro Arg
            115                 120                 125

Pro Ser Ile Ser Ala Glu Pro Gly Thr Val Ile Pro Leu Gly Ser His
    130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
                165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
            195                 200                 205

Trp Ser Glu Gln Ser Asp Tyr Leu Glu Leu Leu Val Lys
    210                 215                 220

<210> SEQ ID NO 79
<211> LENGTH: 221
<212> TYPE: PRT
<213> ORGANISM: Artificial Sequence
<220> FEATURE:
<223> OTHER INFORMATION: MMJ1 VH

<400> SEQUENCE: 79

Glu Val Gln Leu Val Glu Ser Gly Gly Arg Val Val Arg Pro Gly Glu
1               5                   10                  15

Ser Leu Arg Leu Ser Cys Glu Val Ser Gly Val Ser Ile Asn Asp Tyr
            20                  25                  30

Asp Met Ser Trp Val Arg Gln Pro Leu Gly Lys Gly Leu Glu Trp Val
        35                  40                  45

Ser Gly Ile Asp Arg Lys Gly Val Gly Thr Gly Tyr Ala Asp Ser Val
    50                  55                  60

Lys Gly Arg Phe Thr Ile Ser Arg Asp His Ala Lys Asn Ser Leu Tyr
65                  70                  75                  80

Leu Gln Met Asn Ser Leu Thr Gly Asp Asp Thr Ala Phe Tyr Tyr Cys
                85                  90                  95

Val Arg Asp Pro Gly Glu Ser Ser Gly Arg Gly His Ile Phe Asn Ile
            100                 105                 110

Trp Gly Gln Gly Thr Met Val Thr Val Ser Leu Glu Asp Leu Pro Arg
            115                 120                 125

Pro Ser Ile Ser Ala Glu Pro Gly Thr Val Ile Pro Leu Gly Ser His
    130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
                165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
        195                 200                 205

Trp Ser Glu Gln Ser Asp Tyr Leu Glu Leu Leu Val Lys
    210                 215                 220

<210> SEQ ID NO 80
<211> LENGTH: 221
<212> TYPE: PRT
<213> ORGANISM: Artificial Sequence
<220> FEATURE:
<223> OTHER INFORMATION: MMJ2 VH

<400> SEQUENCE: 80

Glu Val Gln Leu Val Glu Ser Gly Gly Gly Val Val Arg Pro Gly Glu
1               5                   10                  15

Ser Leu Arg Leu Ser Cys Glu Val Ser Gly Val Asn Ile Asn Asp Tyr
            20                  25                  30

Asp Met Ser Trp Val Arg Gln Phe Leu Gly Lys Gly Leu Glu Trp Val
        35                  40                  45

Ser Gly Ile Asp Arg Lys Gly Val Gly Thr Gly Tyr Ala Asp Ser Val
    50                  55                  60

Lys Gly Arg Phe Thr Ile Ser Arg Asp His Ala Lys Asn Ser Leu Tyr
65                  70                  75                  80

Leu Gln Met Asn Ser Leu Arg Gly Glu Asp Thr Ala Leu Tyr Tyr Cys
                85                  90                  95

Val Arg Asp Pro Gly Asp Thr Ser Gly Arg Gly His Ile Phe Asn Val
            100                 105                 110

Trp Gly Gln Gly Thr Met Val Thr Val Ser Leu Glu Asp Leu Pro Arg
        115                 120                 125

Pro Ser Ile Ser Ala Glu Pro Gly Thr Val Ile Pro Leu Gly Ser His
    130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
                165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
        195                 200                 205

Trp Ser Glu Gln Ser Asp Tyr Leu Glu Leu Leu Val Lys
    210                 215                 220

<210> SEQ ID NO 81
<211> LENGTH: 221
<212> TYPE: PRT
<213> ORGANISM: Artificial Sequence
<220> FEATURE:
<223> OTHER INFORMATION: MMJ5 VH

<400> SEQUENCE: 81

Glu Val Gln Leu Val Glu Ser Gly Gly Gly Val Val Arg Pro Gly Glu
1               5                   10                  15

-continued

```
Ser Leu Arg Leu Ser Cys Glu Val Ser Gly Val Asn Ile Asn Asp Tyr
        20                  25                  30

Asp Met Ser Trp Val Arg Gln Pro Leu Gly Lys Gly Leu Glu Trp Val
        35                  40                  45

Ser Gly Ile Asp Arg Lys Gly Val Gly Thr Gly Tyr Ala Asp Ser Val
50                      55                  60

Lys Gly Arg Phe Thr Ile Ser Arg Asp Asn Gly Lys Asn Ser Leu Tyr
65                      70                  75                  80

Leu Gln Met Asn Ser Leu Arg Gly Glu Asp Thr Ala Leu Tyr Tyr Cys
                85                  90                  95

Val Arg Asp Pro Gly Asp Arg Ser Gly Arg Gly His Ile Phe Asn Ile
            100                 105                 110

Trp Gly Gln Gly Thr Met Val Thr Val Ser Leu Glu Asp Leu Pro Arg
            115                 120                 125

Pro Ser Ile Ser Ala Glu Pro Gly Thr Val Ile Pro Leu Gly Ser His
    130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
                165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
            195                 200                 205

Trp Ser Glu Gln Ser Asp Tyr Leu Glu Leu Leu Val Lys
    210                 215                 220
```

<210> SEQ ID NO 82
<211> LENGTH: 221
<212> TYPE: PRT
<213> ORGANISM: Artificial Sequence
<220> FEATURE:
<223> OTHER INFORMATION: MMJ6 VH

<400> SEQUENCE: 82

```
Glu Val Gln Leu Val Glu Ser Gly Gly Gly Val Val Arg Pro Gly Glu
1               5                   10                  15

Ser Leu Arg Leu Ser Cys Glu Val Ser Gly Val Ser Ile Asn Asp Tyr
        20                  25                  30

Asp Met Ser Trp Val Arg Gln Pro Leu Gly Lys Gly Leu Glu Trp Val
        35                  40                  45

Ser Gly Ile Asp Arg Lys Gly Val Gly Thr Gly Tyr Ala Asp Ser Val
50                      55                  60

Lys Gly Arg Phe Thr Ile Ser Arg Asp His Ala Lys Asn Ser Leu Tyr
65                      70                  75                  80

Leu Gln Met Asn Ser Leu Arg Gly Glu Asp Thr Ala Leu Tyr Tyr Cys
                85                  90                  95

Val Arg Asp Pro Gly Asp Ser Ser Gly Arg Gly Gln Ile Phe Asn Ile
            100                 105                 110

Trp Gly Gln Gly Thr Met Val Thr Val Ser Leu Glu Asp Leu Pro Arg
            115                 120                 125

Pro Ser Ile Ser Ala Glu Pro Gly Thr Val Ile Pro Leu Gly Ser His
    130                 135                 140

Val Thr Phe Val Cys Arg Gly Pro Val Gly Val Gln Thr Phe Arg Leu
145                 150                 155                 160
```

```
Glu Arg Glu Ser Arg Ser Thr Tyr Asn Glu Thr Glu Asp Val Ser Gln
            165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
            195                 200                 205

Trp Ser Glu Gln Ser Asp Tyr Leu Glu Leu Leu Val Lys
    210                 215                 220

<210> SEQ ID NO 83
<211> LENGTH: 221
<212> TYPE: PRT
<213> ORGANISM: Artificial Sequence
<220> FEATURE:
<223> OTHER INFORMATION: MMJ7 VH

<400> SEQUENCE: 83

Glu Val Gln Leu Val Glu Ser Gly Gly Gly Val Val Arg Pro Gly Glu
1               5                   10                  15

Ser Leu Arg Leu Ser Cys Glu Val Ser Gly Val Ser Ile Asn Asp Tyr
            20                  25                  30

Asp Met Ser Trp Val Arg Gln Arg Leu Gly Lys Gly Leu Glu Trp Val
        35                  40                  45

Ser Gly Ile Asp Arg Lys Gly Val Gly Thr Gly Tyr Ala Asp Ser Val
    50                  55                  60

Lys Gly Arg Phe Thr Ile Ser Arg Asp His Ala Lys Asn Ser Leu Tyr
65                  70                  75                  80

Leu Gln Met Asn Ser Leu Arg Gly Glu Asp Thr Ala Leu Tyr Tyr Cys
            85                  90                  95

Val Arg Asp Pro Gly Glu Ser Ser Gly Arg Gly His Ile Phe Asn Ile
            100                 105                 110

Trp Gly Gln Gly Thr Met Val Thr Ile Ser Leu Glu Asp Leu Pro Arg
            115                 120                 125

Pro Ser Ile Ser Ala Glu Pro Gly Thr Val Ile Pro Leu Gly Ser His
    130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
            165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
            195                 200                 205

Trp Ser Glu Gln Ser Asp Tyr Leu Glu Leu Leu Val Lys
    210                 215                 220

<210> SEQ ID NO 84
<211> LENGTH: 221
<212> TYPE: PRT
<213> ORGANISM: Artificial Sequence
<220> FEATURE:
<223> OTHER INFORMATION: MMJ8 VH

<400> SEQUENCE: 84

Glu Val Gln Leu Val Glu Ser Gly Gly Gly Val Val Arg Pro Gly Glu
1               5                   10                  15

Ser Leu Arg Leu Ser Cys Glu Val Ser Gly Val Asn Ile Asn Asp Tyr
```

```
            20                  25                  30
Asp Met Ser Trp Val Arg Gln Phe Leu Gly Lys Gly Leu Glu Trp Val
        35                  40                  45
Ser Gly Ile Asp Arg Lys Gly Val Gly Thr Gly Tyr Ala Asp Ser Val
    50                  55                  60
Lys Gly Arg Phe Thr Ile Ser Arg Asp His Ala Lys Asn Ser Leu Tyr
65                  70                  75                  80
Leu Gln Met Asn Ser Leu Arg Gly Glu Asp Thr Ala Leu Tyr Tyr Cys
                85                  90                  95
Val Arg Asp Pro Gly Asp Thr Ser Gly Arg Gly His Ile Phe Asn Val
            100                 105                 110
Trp Gly Gln Gly Thr Met Val Thr Val Ser Leu Glu Asp Leu Pro Arg
            115                 120                 125
Pro Ser Ile Ser Ala Glu Pro Gly Thr Val Ile Pro Leu Gly Ser His
            130                 135                 140
Val Thr Phe Val Cys Arg Gly Pro Val Gly Val Gln Thr Phe Arg Leu
145                 150                 155                 160
Glu Arg Glu Ser Arg Ser Thr Tyr Asn Glu Thr Glu Asp Val Ser Gln
                165                 170                 175
Val Ser Pro Ser Glu Ser Glu Ala Arg Phe Arg Ile Asp Ser Val Ser
            180                 185                 190
Glu Gly Asn Ala Gly Pro Tyr Arg Cys Ile Tyr Tyr Lys Pro Pro Lys
            195                 200                 205
Trp Ser Glu Gln Ser Asp Tyr Leu Glu Leu Leu Val Lys
        210                 215                 220

<210> SEQ ID NO 85
<211> LENGTH: 221
<212> TYPE: PRT
<213> ORGANISM: Artificial Sequence
<220> FEATURE:
<223> OTHER INFORMATION: MMJ10 VH

<400> SEQUENCE: 85

Glu Val Gln Leu Val Glu Ser Gly Gly Gly Val Val Arg Pro Gly Glu
1               5                   10                  15
Ser Leu Arg Leu Ser Cys Glu Val Ser Gly Val Asn Ile Asn Asp Tyr
            20                  25                  30
Asp Met Ser Trp Val Arg Gln Phe Leu Gly Lys Gly Leu Glu Trp Val
        35                  40                  45
Ser Gly Ile Asp Arg Lys Gly Val Gly Thr Gly Tyr Ala Asp Ser Val
    50                  55                  60
Lys Gly Arg Phe Thr Ile Ser Arg Asp His Ala Lys Asn Ser Leu Tyr
65                  70                  75                  80
Leu Gln Met Asn Ser Leu Arg Gly Glu Asp Thr Ala Leu Tyr Tyr Cys
                85                  90                  95
Val Arg Asp Pro Gly Asp Thr Ser Gly Arg Gly His Ile Phe Asn Val
            100                 105                 110
Trp Gly Gln Gly Thr Met Val Thr Val Ser Leu Glu Asp Leu Pro Arg
            115                 120                 125
Pro Ser Ile Ser Ala Glu Pro Gly Thr Val Ile Pro Leu Gly Ser His
            130                 135                 140
Val Thr Phe Val Cys Arg Gly Pro Val Gly Val Gln Thr Phe Arg Leu
145                 150                 155                 160
Glu Arg Glu Ser Arg Ser Thr Tyr Asn Glu Thr Glu Asp Val Ser Gln
```

```
                165                 170                 175
Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
        195                 200                 205

Trp Ser Glu Gln Ser Asp Tyr Leu Glu Leu Leu Val Lys
    210                 215                 220

<210> SEQ ID NO 86
<211> LENGTH: 221
<212> TYPE: PRT
<213> ORGANISM: Artificial Sequence
<220> FEATURE:
<223> OTHER INFORMATION: MMJ16 VH

<400> SEQUENCE: 86

Glu Val Gln Leu Val Glu Ser Gly Gly Gly Val Val Arg Pro Gly Glu
1               5                   10                  15

Ser Leu Arg Leu Ser Cys Glu Val Ser Gly Val Asn Ile Asn Asp Tyr
            20                  25                  30

Asp Met Ser Trp Val Arg Gln Phe Leu Gly Lys Gly Leu Glu Trp Val
        35                  40                  45

Ser Gly Ile Asp Arg Lys Gly Val Thr Gly Tyr Ala Asp Ser Val
    50                  55                  60

Lys Gly Arg Phe Thr Ile Ser Arg Asp His Ala Lys Asn Ser Leu Tyr
65                  70                  75                  80

Leu Gln Met Asn Ser Leu Arg Gly Glu Asp Thr Ala Leu Tyr Tyr Cys
                85                  90                  95

Val Arg Asp Pro Gly Asp Thr Ser Gly Arg Gly His Ile Phe Asn Val
            100                 105                 110

Trp Gly Gln Gly Thr Met Val Thr Val Ser Leu Glu Asp Leu Pro Arg
        115                 120                 125

Pro Ser Ile Ser Ala Glu Pro Gly Thr Val Ile Pro Leu Gly Ser His
    130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
                165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
        195                 200                 205

Trp Ser Glu Gln Ser Asp Tyr Leu Glu Leu Leu Gly Lys
    210                 215                 220

<210> SEQ ID NO 87
<211> LENGTH: 221
<212> TYPE: PRT
<213> ORGANISM: Artificial Sequence
<220> FEATURE:
<223> OTHER INFORMATION: MMJ23 VH

<400> SEQUENCE: 87

Glu Val Gln Leu Val Glu Ser Gly Gly Gly Val Val Arg Pro Gly Glu
1               5                   10                  15

Ser Leu Arg Leu Ser Cys Glu Val Ser Gly Val Asn Ile Asn Asp Tyr
            20                  25                  30
```

Asp Met Ser Trp Val Arg Gln Pro Leu Gly Lys Gly Leu Glu Trp Val
            35                  40                  45

Ser Gly Ile Asp Arg Lys Gly Val Gly Thr Gly Tyr Ala Asp Ser Val
 50                  55                  60

Lys Gly Arg Phe Thr Ile Ser Arg Asp Asn Gly Lys Asn Ser Leu Tyr
65                  70                  75                  80

Leu Gln Met Asn Ser Leu Arg Gly Glu Asp Thr Ala Leu Tyr Tyr Cys
                85                  90                  95

Val Arg Asp Pro Gly Asp Arg Ser Gly Arg Gly His Ile Phe Asn Ile
            100                 105                 110

Trp Gly Gln Gly Thr Met Val Thr Val Ser Leu Glu Asp Leu Pro Arg
            115                 120                 125

Pro Ser Ile Ser Ala Glu Pro Gly Thr Val Ile Pro Leu Gly Ser His
130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
                165                 170                 175

Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
            195                 200                 205

Trp Ser Glu Gln Ser Asp Tyr Leu Glu Leu Leu Val Lys
210                 215                 220

<210> SEQ ID NO 88
<211> LENGTH: 221
<212> TYPE: PRT
<213> ORGANISM: Artificial Sequence
<220> FEATURE:
<223> OTHER INFORMATION: MMJ25 VH

<400> SEQUENCE: 88

Glu Val Gln Leu Val Glu Ser Gly Gly Gly Val Val Arg Pro Gly Glu
1               5                   10                  15

Ser Leu Arg Leu Ser Cys Glu Val Ser Gly Val Ser Ile Asn Asp Tyr
            20                  25                  30

Asp Met Ser Trp Val Arg Gln Pro Leu Gly Lys Gly Leu Glu Trp Val
            35                  40                  45

Ser Gly Ile Asp Arg Lys Gly Val Gly Thr Gly Tyr Ala Asp Ser Val
 50                  55                  60

Lys Gly Arg Phe Thr Ile Ser Arg Asp His Ala Lys Asn Ser Leu Tyr
65                  70                  75                  80

Leu Gln Met Asn Ser Leu Arg Gly Ala Asp Thr Ala Leu Tyr Tyr Cys
                85                  90                  95

Val Arg Asp Pro Gly Asp Ser Ser Gly Arg Gly His Ile Phe Asn Ile
            100                 105                 110

Trp Gly Gln Gly Thr Met Val Thr Val Ser Leu Glu Asp Leu Pro Arg
            115                 120                 125

Pro Ser Ile Ser Ala Glu Pro Gly Thr Val Ile Pro Leu Gly Ser His
130                 135                 140

Val Thr Phe Val Cys Arg Gly Pro Val Gly Val Gln Thr Phe Arg Leu
145                 150                 155                 160

Glu Arg Glu Ser Arg Ser Thr Tyr Asn Glu Thr Glu Asp Val Ser Gln
                165                 170                 175

```
Val Ser Pro Ser Glu Ser Glu Ala Arg Phe Arg Ile Asp Ser Val Ser
            180                 185                 190

Glu Gly Asn Ala Gly Pro Tyr Arg Cys Ile Tyr Tyr Lys Pro Pro Lys
        195                 200                 205

Trp Ser Glu Gln Ser Asp Tyr Leu Glu Leu Leu Val Lys
    210                 215                 220

<210> SEQ ID NO 89
<211> LENGTH: 228
<212> TYPE: PRT
<213> ORGANISM: Artificial Sequence
<220> FEATURE:
<223> OTHER INFORMATION: MGM1 VH

<400> SEQUENCE: 89

Gln Val Gln Leu Ala Gln Tyr Gly Gly Gly Ala Val Gln Pro Gly Gly
1               5                   10                  15

Ser Leu Arg Leu Ser Cys Val Val Ser Gly Phe Arg Phe Ser Leu Tyr
            20                  25                  30

Gly Ile His Trp Val Arg Gln Ala Pro Gly Lys Gly Leu Glu Trp Leu
        35                  40                  45

Ser Leu Ile Glu Asn His Gly Arg Lys Ile Tyr Tyr Ala Glu Ser Val
    50                  55                  60

Lys Gly Arg Ile Thr Val Ser Arg Asp Asn Phe Lys Asn Val Ala Tyr
65                  70                  75                  80

Leu Glu Met Tyr Arg Leu Ser Thr Glu Asp Thr Ala Ile Tyr Tyr Cys
                85                  90                  95

Ala Arg Asn Asp Gly Leu Gly Arg Tyr Thr Asp Ala Gly Gly Thr His
            100                 105                 110

Arg Thr Ala Tyr Leu Asp Tyr Trp Gly Arg Gly Thr Leu Val Thr Val
        115                 120                 125

Ser Ser Glu Asp Leu Pro Arg Pro Ser Ile Ser Ala Glu Pro Gly Thr
    130                 135                 140

Val Ile Pro Leu Gly Ser His Val Thr Phe Val Cys Arg Gly Pro Val
145                 150                 155                 160

Gly Val Gln Thr Phe Arg Leu Glu Arg Glu Ser Arg Ser Thr Tyr Asn
                165                 170                 175

Asp Thr Glu Asp Val Ser Gln Ala Ser Pro Ser Glu Ser Glu Ala Arg
            180                 185                 190

Phe Arg Ile Asp Ser Val Ser Glu Gly Asn Ala Gly Pro Tyr Arg Cys
        195                 200                 205

Val Tyr Tyr Lys Pro Pro Lys Trp Ser Glu Gln Ser Asp Tyr Leu Asp
    210                 215                 220

Leu Leu Val Lys
225

<210> SEQ ID NO 90
<211> LENGTH: 227
<212> TYPE: PRT
<213> ORGANISM: Artificial Sequence
<220> FEATURE:
<223> OTHER INFORMATION: MGM3 VH

<400> SEQUENCE: 90

Gln Val Gln Leu Val Glu Ser Gly Gly Asp Val Val Gln Pro Gly Gly
1               5                   10                  15

Ser Leu Arg Leu Ser Cys Ala Val Ser Gly Phe Lys Phe Asn Ile Tyr
            20                  25                  30
```

```
Asp Ile His Trp Val Arg Gln Ala Pro Gly Lys Gly Leu Glu Trp Val
        35                  40                  45

Ser Phe Ile Arg His Asp Gly Asn Asn Gln Glu Tyr Ala Asp Ser Val
 50                  55                  60

Lys Gly Arg Phe Thr Ile Ser Arg Asp Asn Phe Lys Asn Ile Ile Asp
 65                  70                  75                  80

Leu Gln Met His Ser Leu Arg Thr Glu Asp Thr Ala Leu Tyr Tyr Cys
                 85                  90                  95

Ala Thr Asn Gln Gly Ser Gly Gly Ser Asp Asp Thr Trp Glu Thr Asn
            100                 105                 110

Arg Ser Ala Phe Phe Pro His Trp Gly Gln Gly Thr Leu Val Thr Val
            115                 120                 125

Ser Ser Asp Leu Pro Arg Pro Ser Ile Ser Ala Glu Pro Gly Thr Val
130                 135                 140

Ile Pro Leu Gly Ser His Val Thr Phe Val Cys Arg Gly Pro Val Gly
145                 150                 155                 160

Val Gln Thr Phe Arg Leu Glu Arg Glu Ser Arg Ser Ile Tyr Asn Asp
                165                 170                 175

Thr Glu Asp Val Ser Gln Ala Ser Pro Ser Glu Ser Glu Ala Arg Phe
            180                 185                 190

Arg Ile Asp Ser Val Ser Glu Gly Asn Ala Gly Pro Tyr Arg Cys Val
            195                 200                 205

Tyr Tyr Lys Pro Pro Lys Trp Ser Glu Glu Ser Asp Tyr Leu Glu Leu
210                 215                 220

Leu Val Lys
225

<210> SEQ ID NO 91
<211> LENGTH: 228
<212> TYPE: PRT
<213> ORGANISM: Artificial Sequence
<220> FEATURE:
<223> OTHER INFORMATION: MGM4 VH

<400> SEQUENCE: 91

Gln Val Gln Leu Val Glu Ser Gly Gly Gly Val Val Gln Pro Gly Gly
1               5                   10                  15

Ser Leu Arg Leu Ser Cys Glu Val Ser Gly Phe Arg Phe Ser Thr Tyr
            20                  25                  30

Gly Ile His Trp Ala Arg Gln Ala Pro Gly Lys Gly Leu Glu Trp Val
        35                  40                  45

Ala Phe Ile Arg Tyr Asp Gly Asn Asn Lys Ser Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ile Glu Asp Thr Ala Val Tyr Tyr Cys
                 85                  90                  95

Ala Lys Asn Gln Ala Ser Gly Gly Tyr Asp Asp Thr Trp Gly Thr Tyr
            100                 105                 110

Arg Ser Ala Tyr Leu Asp Tyr Trp Gly Gln Gly Thr Leu Val Thr Val
            115                 120                 125

Ser Ser Glu Asp Leu Pro Arg Pro Ser Ile Ser Ala Glu Pro Gly Thr
130                 135                 140

Val Ile Pro Leu Gly Ser His Val Thr Phe Val Cys Arg Gly Pro Val
145                 150                 155                 160
```

Gly Val Gln Thr Phe Arg Leu Glu Arg Glu Ser Arg Ser Thr Tyr Asn
                165                 170                 175

Asp Thr Glu Asp Val Ser Gln Ala Ser Pro Ser Glu Ser Glu Ala Arg
            180                 185                 190

Phe Arg Ile Asp Ser Val Ser Glu Gly Asn Ala Gly Pro Tyr Arg Cys
            195                 200                 205

Val Tyr Tyr Lys Pro Pro Lys Trp Ser Glu Glu Ser Asp Ser Leu Glu
            210                 215                 220

Leu Leu Val Lys
225

<210> SEQ ID NO 92
<211> LENGTH: 228
<212> TYPE: PRT
<213> ORGANISM: Artificial Sequence
<220> FEATURE:
<223> OTHER INFORMATION: MGM5 VH

<400> SEQUENCE: 92

Gln Val Gln Leu Val Glu Ser Gly Gly Val Val Gln Pro Gly Gly
1               5                   10                  15

Ser Leu Arg Leu Ser Cys Lys Met Ser Gly Phe Lys Phe Ser Ala Phe
            20                  25                  30

Gly Ile His Trp Val Arg Gln Ala Pro Gly Lys Gly Leu Glu Trp Val
            35                  40                  45

Ala Phe Val Arg Tyr Asp Gly Asp Lys Tyr Tyr Ala Asp Ser Val
        50                  55                  60

Lys Gly Arg Phe Thr Ile Ser Arg Asp Asn Ser Lys Asn Thr Val His
65                  70                  75                  80

Leu Gln Leu Asn Ser Leu Lys Pro Ala Asp Thr Ala Val Tyr Tyr Cys
                85                  90                  95

Ala Lys Asn Gln Pro Ser Gly Gln Ser Asp Asp Thr Trp Gly Thr Ser
            100                 105                 110

Leu Ser Ala Tyr Leu Asp Tyr Trp Gly Gln Gly Thr Gln Val Ser Val
            115                 120                 125

Ser Pro Glu Asp Leu Pro Arg Pro Ser Ile Ser Ala Glu Pro Gly Thr
            130                 135                 140

Val Ile Pro Leu Gly Ser His Val Thr Phe Val Cys Arg Gly Pro Val
145                 150                 155                 160

Gly Val Gln Thr Phe Arg Leu Glu Arg Glu Ser Arg Ser Thr Tyr Asn
                165                 170                 175

Asp Thr Glu Asp Val Ser Gln Ala Ser Pro Ser Glu Ser Glu Ala Arg
            180                 185                 190

Phe Arg Ile Asp Ser Val Ser Glu Gly Asn Ala Gly Pro Tyr Arg Cys
            195                 200                 205

Val Tyr Tyr Lys Pro Pro Lys Trp Ser Glu Gln Ser Asp Tyr Leu Glu
            210                 215                 220

Leu Leu Val Lys
225

<210> SEQ ID NO 93
<211> LENGTH: 127
<212> TYPE: PRT
<213> ORGANISM: Artificial Sequence
<220> FEATURE:
<223> OTHER INFORMATION: MGB2 VH -continued

```
<400> SEQUENCE: 93

Glu Ala Gln Val Val Asp His Gly Asn Arg Gly Arg Ala Arg Asp Leu
1               5                   10                  15

Glu Asp Ile Lys Lys Arg Arg Ala Arg Asp Leu Glu Tyr Glu Asp Leu
            20                  25                  30

Pro Arg Pro Ser Ile Ser Ala Glu Pro Gly Thr Val Ile Pro Leu Gly
        35                  40                  45

Ser Arg Val Thr Phe Val Cys Arg Gly Pro Val Gly Val Gln Thr Phe
    50                  55                  60

Arg Leu Glu Arg Glu Ser Arg Ser Lys Tyr Asn Glu Thr Glu Asp Val
65                  70                  75                  80

Ser Gln Ala Ser Pro Ser Glu Ser Glu Ala Arg Phe Arg Ile Asp Ser
                85                  90                  95

Val Ser Glu Gly Asn Ala Gly Pro Tyr Arg Cys Ile Tyr Tyr Lys Pro
            100                 105                 110

Pro Lys Trp Ser Glu His Ser Asp Phe Leu Glu Leu Leu Val Lys
        115                 120                 125

<210> SEQ ID NO 94
<211> LENGTH: 116
<212> TYPE: PRT
<213> ORGANISM: Artificial Sequence
<220> FEATURE:
<223> OTHER INFORMATION: MGB43 VH

<400> SEQUENCE: 94

Val Ala Glu Val Glu His Ile Asn Lys Arg Arg Ala Arg Asp Leu
1               5                   10                  15

Glu Tyr Glu Asp Leu Pro Arg Pro Ser Ile Ser Ala Glu Pro Gly Thr
            20                  25                  30

Val Ile Pro Leu Gly Ser His Val Thr Phe Val Cys Arg Gly Pro Val
        35                  40                  45

Gly Val Gln Thr Phe Arg Leu Glu Arg Glu Ser Arg Ser Arg Tyr Asn
    50                  55                  60

Glu Thr Glu Asp Val Ser Gln Thr Ser Pro Ser Glu Ser Glu Ala Arg
65                  70                  75                  80

Phe Arg Ile Asp Ser Val Ser Glu Gly Asn Ala Gly Pro Tyr Arg Cys
                85                  90                  95

Leu Tyr Tyr Lys Thr Pro Lys Trp Ser Glu Gln Ser Asp Phe Leu Glu
            100                 105                 110

Leu Leu Val Lys
        115

<210> SEQ ID NO 95
<211> LENGTH: 116
<212> TYPE: PRT
<213> ORGANISM: Artificial Sequence
<220> FEATURE:
<223> OTHER INFORMATION: MGB47 VH

<400> SEQUENCE: 95

Glu Ala Glu Val Val Glu His Val Asn Lys Arg Arg Ala Arg Ala Leu
1               5                   10                  15

Glu Tyr Glu Asp Leu Pro Arg Pro Ser Ile Ser Ala Glu Pro Gly Thr
            20                  25                  30

Val Ile Pro Leu Gly Ser His Val Thr Phe Val Cys Arg Gly Pro Val
        35                  40                  45
```

-continued

Gly Val Gln Thr Phe Arg Leu Glu Arg Glu Ser Ser Arg Tyr Thr
50                  55                  60

Glu Thr Glu Asp Val Ser Gln Thr Ser Pro Ser Glu Ser Glu Ala Arg
65                  70                  75                  80

Phe Arg Ile Asp Ser Val Ser Glu Gly Asn Ala Gly Pro Tyr Arg Cys
                85                  90                  95

Leu Tyr Tyr Lys Pro Pro Lys Trp Ser Glu Gln Ser Asp Phe Leu Glu
                100                 105                 110

Leu Leu Val Lys
        115

<210> SEQ ID NO 96
<211> LENGTH: 107
<212> TYPE: PRT
<213> ORGANISM: Artificial Sequence
<220> FEATURE:
<223> OTHER INFORMATION: MGJ1 VL

<400> SEQUENCE: 96

Asp Phe Gln Met Thr Gln Ser Pro Ser Thr Leu Ser Ala Ser Val Gly
1               5                   10                  15

Asp Arg Val Thr Ile Thr Cys Arg Ala Ser Gln Asn Val Asn Thr Trp
                20                  25                  30

Leu Ala Trp Tyr Gln Gln Ala Ala Gly Lys Ala Pro Lys Leu Leu Ile
            35                  40                  45

Tyr Glu Ala Ser Thr Leu Gln Ser Gly Val Pro Ser Arg Phe Arg Gly
    50                  55                  60

Gly Gly Ser Gly Thr Glu Phe Thr Leu Thr Ile Thr Ser Leu Gln Pro
65                  70                  75                  80

Glu Asp Phe Ala Thr Tyr Tyr Cys His Gln Tyr Lys Ser His Pro Phe
                85                  90                  95

Thr Phe Gly Pro Gly Thr Lys Val Asp Val Arg
                100                 105

<210> SEQ ID NO 97
<211> LENGTH: 107
<212> TYPE: PRT
<213> ORGANISM: Artificial Sequence
<220> FEATURE:
<223> OTHER INFORMATION: MGJ2 VL

<400> SEQUENCE: 97

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Ser Ser Trp
                20                  25                  30

Leu Ala Trp Tyr Gln Gln Lys Pro Gly Lys Ala Pro Lys Phe Leu Ile
            35                  40                  45

Tyr Lys Ala Ser Phe Leu Glu Asn Gly Val Pro Ser Arg Phe Ser Gly
    50                  55                  60

Ser Glu Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Lys Ser Tyr Pro Phe
                85                  90                  95

Thr Phe Gly Pro Gly Thr Lys Val Glu Ile Lys
                100                 105

<210> SEQ ID NO 98

```
<211> LENGTH: 107
<212> TYPE: PRT
<213> ORGANISM: Artificial Sequence
<220> FEATURE:
<223> OTHER INFORMATION: MGJ3 VL

<400> SEQUENCE: 98

Asp Ile Gln Met Thr Gln Ser Pro Ser Thr Leu Ser Ala Ser Val Gly
1               5                   10                  15

Asp Arg Val Thr Phe Thr Cys Gly Ala Ser Gln Ser Ile Thr Asp Cys
            20                  25                  30

Leu Ala Trp Tyr Gln Gln Lys Pro Gly Lys Asp Pro Lys Leu Leu Ile
        35                  40                  45

Tyr Lys Ala Ser Arg Leu Glu Ala Gly Val Pro Ala Arg Phe Ser Ala
    50                  55                  60

Ser Gly Ser Gly Thr Glu Phe Thr Phe Thr Ile Arg Ser Met Gln Pro
65                  70                  75                  80

Glu Asp Phe Ala Thr Tyr Tyr Cys Gln Gln Cys Tyr Ser Tyr Pro Phe
                85                  90                  95

Thr Phe Gly Pro Gly Thr Lys Val Asp Leu Lys
            100                 105

<210> SEQ ID NO 99
<211> LENGTH: 107
<212> TYPE: PRT
<213> ORGANISM: Artificial Sequence
<220> FEATURE:
<223> OTHER INFORMATION: MGJ5 VL

<400> SEQUENCE: 99

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gly Ser Gly Val Pro Ser Arg Phe Ser Gly
    50                  55                  60

Ser Gly Ser Gly Thr Gln Phe Thr Leu Thr Ile Ser Ser Leu Gln Pro
65                  70                  75                  80

Asp Asp Phe Ala Thr Tyr Tyr Cys Gln Gln Tyr Asn Asn Tyr Pro Tyr
                85                  90                  95

Thr Phe Gly Gln Gly Thr Lys Leu Glu Ile Lys
            100                 105

<210> SEQ ID NO 100
<211> LENGTH: 107
<212> TYPE: PRT
<213> ORGANISM: Artificial Sequence
<220> FEATURE:
<223> OTHER INFORMATION: MMJ1 VL

<400> SEQUENCE: 100

Asp Ile Gln Met Thr Gln Ser Pro Ser Thr Val Ser Ala Ser Ile Gly
1               5                   10                  15

Asp Arg Val Thr Ile Thr Cys Arg Ala Ser Gln Ile Ile Glu Arg Ser
            20                  25                  30

Leu Ala Trp Tyr Gln Gln Lys Pro Gly Lys Ser Pro Lys Ala Leu Ile
        35                  40                  45
```

```
Tyr Lys Thr Ser Asn Leu Glu Asp Gly Val Pro Ser Arg Phe Ser Gly
    50                  55                  60

Ser Gly Ser Gly Thr Asp Phe Thr Leu Thr Val Ser Ser Leu Gln Pro
 65                  70                  75                  80

Asp Asp Phe Ala Asn Tyr Tyr Cys Gln Gln Tyr Asp Thr Tyr Pro Phe
                 85                  90                  95

Thr Phe Gly Pro Gly Thr Thr Val Thr Leu Arg
            100                 105

<210> SEQ ID NO 101
<211> LENGTH: 107
<212> TYPE: PRT
<213> ORGANISM: Artificial Sequence
<220> FEATURE:
<223> OTHER INFORMATION: MMJ5 VL

<400> SEQUENCE: 101

Asp Ile Gln Met Thr Gln Ser Pro Ser Thr Leu Ser Ala Ser Ile Gly
  1               5                  10                  15

Asp Arg Val Thr Ile Thr Cys Arg Ala Ser Gln Val Ile Asp Arg Ser
                 20                  25                  30

Leu Ala Trp Phe Gln Gln Lys Pro Gly Lys Ser Pro Arg Pro Leu Ile
             35                  40                  45

Tyr Lys Ala Ser Thr Leu Glu Gly Gly Val Pro Ser Arg Phe Ser Gly
    50                  55                  60

Ser Gly Ser Gly Thr Asp Phe Thr Leu Thr Val Ser Ser Leu Gln Pro
 65                  70                  75                  80

Asp Asp Phe Ala Asn Tyr Tyr Cys Gln Gln Tyr Asp Thr Tyr Pro Phe
                 85                  90                  95

Thr Phe Gly Pro Gly Thr Thr Val Thr Leu Arg
            100                 105

<210> SEQ ID NO 102
<211> LENGTH: 107
<212> TYPE: PRT
<213> ORGANISM: Artificial Sequence
<220> FEATURE:
<223> OTHER INFORMATION: MMJ6 VL

<400> SEQUENCE: 102

Asp Ile Gln Met Thr Gln Ser Pro Ser Thr Leu Ser Ala Ser Ile Gly
  1               5                  10                  15

Asp Arg Val Thr Ile Thr Cys Arg Ala Ser Gln Ile Ile His Arg Ser
                 20                  25                  30

Leu Ala Trp Tyr Gln Gln Lys Pro Gly Lys Ser Pro Arg Ala Leu Ile
             35                  40                  45

Tyr Lys Ala Ser Asn Leu Glu Gly Gly Val Pro Ser Arg Phe Ser Gly
    50                  55                  60

Ser Gly Ser Gly Thr Asp Phe Thr Leu Thr Val Ser Ser Leu Gln Pro
 65                  70                  75                  80

Asp Asp Phe Ala Met Tyr Tyr Cys Gln Gln Tyr Asp Thr Tyr Pro Phe
                 85                  90                  95

Thr Phe Gly Pro Gly Thr Thr Val Thr Leu Arg
            100                 105

<210> SEQ ID NO 103
<211> LENGTH: 107
<212> TYPE: PRT
<213> ORGANISM: Artificial Sequence
```

<220> FEATURE:
<223> OTHER INFORMATION: MMJ7 VL

<400> SEQUENCE: 103

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Ser Ile Asp Arg Ser
            20                  25                  30

Leu Ala Trp Tyr Gln Gln Lys Pro Gly Lys Ser Pro Lys Ala Leu Ile
        35                  40                  45

Tyr Lys Ala Ser Asn Leu Glu Gly Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Asp Asp Phe Ala Asp Tyr Tyr Cys Gln Gln Tyr Asp Thr Tyr Pro Phe
                85                  90                  95

Thr Phe Gly Pro Gly Thr Thr Val Thr Leu Arg
            100                 105

<210> SEQ ID NO 104
<211> LENGTH: 107
<212> TYPE: PRT
<213> ORGANISM: Artificial Sequence
<220> FEATURE:
<223> OTHER INFORMATION: MMJ8 VL

<400> SEQUENCE: 104

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Ile Ile Asp Arg Ser
            20                  25                  30

Leu Ala Trp Tyr Gln Gln Lys Pro Gly Lys Ser Pro Lys Ala Leu Ile
        35                  40                  45

Tyr Lys Ala Ser Asn Leu Glu Gly Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Asp Asp Phe Ala Asn Tyr Tyr Cys Gln Gln Tyr Asp Thr Tyr Pro Phe
                85                  90                  95

Thr Phe Gly Pro Gly Thr Thr Val Thr Leu Arg
            100                 105

<210> SEQ ID NO 105
<211> LENGTH: 107
<212> TYPE: PRT
<213> ORGANISM: Artificial Sequence
<220> FEATURE:
<223> OTHER INFORMATION: MMJ10 VL

<400> SEQUENCE: 105

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Ile Ile Asp Arg Ser
            20                  25                  30

Leu Ala Trp Tyr Gln Gln Lys Pro Gly Lys Ser Pro Lys Ala Leu Ile
        35                  40                  45

Tyr Lys Ala Ser Asn Leu Glu Gly Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Asp Asp Phe Ala Asn Tyr Tyr Cys Gln Gln Tyr Asp Thr Tyr Pro Phe
                85                  90                  95

Thr Phe Gly Pro Gly Thr Thr Val Thr Leu Arg
            100                 105

<210> SEQ ID NO 106
<211> LENGTH: 107
<212> TYPE: PRT
<213> ORGANISM: Artificial Sequence
<220> FEATURE:
<223> OTHER INFORMATION: MMJ16 VL

<400> SEQUENCE: 106

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Ile Ile Asp Arg Ser
                20                  25                  30

Leu Ala Trp Tyr Gln Gln Lys Pro Gly Lys Ser Pro Lys Ala Leu Ile
            35                  40                  45

Tyr Lys Ala Ser Asn Leu Glu Gly Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Asp Asp Phe Ala Asn Tyr Tyr Cys Gln Gln Tyr Asp Thr Tyr Pro Phe
                85                  90                  95

Thr Phe Gly Pro Gly Thr Thr Val Thr Leu Arg
            100                 105

<210> SEQ ID NO 107
<211> LENGTH: 107
<212> TYPE: PRT
<213> ORGANISM: Artificial Sequence
<220> FEATURE:
<223> OTHER INFORMATION: MMJ23 VL

<400> SEQUENCE: 107

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Val Ile Asp Arg Ser
                20                  25                  30

Leu Ala Trp Phe Gln Gln Lys Pro Gly Lys Ser Pro Arg Pro Leu Ile
            35                  40                  45

Tyr Lys Ala Ser Thr Leu Glu Gly Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Asp Asp Phe Ala Asn Tyr Tyr Cys Gln Gln Tyr Asp Thr Tyr Pro Phe
                85                  90                  95

Thr Phe Gly Pro Gly Thr Thr Val Thr Leu Arg
            100                 105

<210> SEQ ID NO 108
<211> LENGTH: 107
<212> TYPE: PRT
<213> ORGANISM: Artificial Sequence
<220> FEATURE:
<223> OTHER INFORMATION: MMJ25 VL -continued

<400> SEQUENCE: 108

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Asn Ile Asp Arg Ser
            20                  25                  30

Leu Ala Trp Tyr Gln Gln Lys Pro Gly Lys Ser Pro Lys Ala Leu Ile
        35                  40                  45

Tyr Lys Ala Ser Asn Leu Glu Asp Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Asp Asp Phe Ala Leu Tyr Tyr Cys Gln Gln Tyr Asp Thr Tyr Pro Phe
                85                  90                  95

Thr Phe Gly Pro Gly Thr Thr Val Thr Leu Arg
            100                 105

<210> SEQ ID NO 109
<211> LENGTH: 109
<212> TYPE: PRT
<213> ORGANISM: Artificial Sequence
<220> FEATURE:
<223> OTHER INFORMATION: MGM1 VL

<400> SEQUENCE: 109

Ser Tyr Glu Val Thr Gln Pro Pro Ser Val Ser Val Ser Pro Gly Gln
1               5                   10                  15

Ala Ala Arg Ile Thr Cys Ser Gly Asp Glu Leu Pro Arg Thr Asp Ile
            20                  25                  30

Ser Trp Tyr Gln Gln Thr Ser Gly Gln Ala Pro Val Leu Val Ile Tyr
        35                  40                  45

Glu Gly Thr Lys Arg Pro Ser Gly Ile Pro Glu Arg Phe Ser Gly Ser
50                  55                  60

Val Ser Gly Ala Met Ala Thr Leu Met Ile Ser Glu Ala Gln Leu Glu
65                  70                  75                  80

Asp Glu Gly Asp Tyr Tyr Cys Phe Ser Ile Asp Thr Ser Gly Asn His
                85                  90                  95

Gly Gly Ala Phe Gly Thr Gly Thr Lys Leu Thr Val Leu
            100                 105

<210> SEQ ID NO 110
<211> LENGTH: 109
<212> TYPE: PRT
<213> ORGANISM: Artificial Sequence
<220> FEATURE:
<223> OTHER INFORMATION: MGM3 VL
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 110

Ser Tyr Glu Leu Ile Gln Pro Pro Ser Xaa Ser Val Ser Pro Gly Gln
1               5                   10                  15

Thr Ala Arg Ile Thr Cys Ser Gly Glu Pro Leu Pro Arg Thr Ser Thr
            20                  25                  30

Ser Trp Tyr Arg Gln Lys Ser Gly Gln Ala Pro Val Leu Ile Ile Tyr

```
                35                  40                  45
Glu Val Ser Lys Arg Pro Ser Gly Ile Pro Glu Arg Xaa Ser Gly Ser
 50                  55                  60

Asn Thr Gly Thr Lys Ala Thr Leu Phe Ile Val Gly Ala Gln Val Glu
 65                  70                  75                  80

Asp Glu Gly Asp Tyr Tyr Cys Tyr Ser Thr Asn Thr Ser Gly Gly Ser
                 85                  90                  95

Arg Gly Ala Phe Gly Thr Gly Thr Ser Leu Thr Val Leu
            100                 105
```

<210> SEQ ID NO 111
<211> LENGTH: 109
<212> TYPE: PRT
<213> ORGANISM: Artificial Sequence
<220> FEATURE:
<223> OTHER INFORMATION: MGM4 VL

<400> SEQUENCE: 111

```
Ser Tyr Glu Leu Thr Gln Pro Pro Ser Val Ser Val Ser Pro Gly Gln
 1               5                   10                  15

Thr Ala Arg Ile Thr Cys Ser Gly Asp Ala Val Pro Asn Thr Tyr Thr
             20                  25                  30

Tyr Trp Tyr Gln Gln Lys Ser Gly Gln Ala Pro Val Leu Val Ile Tyr
         35                  40                  45

Glu Asp Ser Lys Arg Pro Ser Gly Ile Pro Glu Arg Phe Ser Gly Ser
 50                  55                  60

Ser Ser Gly Thr Met Ala Thr Phe Ile Ile Ser Gly Ala Gln Val Glu
 65                  70                  75                  80

Asp Glu Ala Asp Tyr Tyr Cys Tyr Ser Thr Asp Thr Ser Asp Asp His
                 85                  90                  95

Arg Gly Ala Phe Gly Thr Gly Thr Lys Val Thr Val Leu
            100                 105
```

<210> SEQ ID NO 112
<211> LENGTH: 109
<212> TYPE: PRT
<213> ORGANISM: Artificial Sequence
<220> FEATURE:
<223> OTHER INFORMATION: MGM5 VL

<400> SEQUENCE: 112

```
Ser Tyr Glu Leu Thr Gln Pro Pro Ser Val Ser Val Ser Pro Gly Gln
 1               5                   10                  15

Thr Ala Arg Ile Thr Cys Ser Gly Asp Ala Leu Pro Arg Thr Phe Ile
             20                  25                  30

Tyr Trp Tyr Gln Gln Lys Ser Arg Gln Ala Pro Val Val Val Ile Tyr
         35                  40                  45

Glu Asp Val Lys Arg Pro Ser Gly Ile Pro Glu Arg Phe Ser Gly Ser
 50                  55                  60

Ile Ser Gly Thr Gln Ala Thr Leu Ile Ile Thr Gly Ala Gln Val Glu
 65                  70                  75                  80

Asp Glu Ala Asp Tyr Tyr Cys Tyr Ser Thr Asp Thr Asn Asn Thr His
                 85                  90                  95

Arg Gly Ala Phe Gly Thr Gly Thr Lys Val Thr Val Leu
            100                 105
```

<210> SEQ ID NO 113
<211> LENGTH: 98

-continued

```
<212> TYPE: PRT
<213> ORGANISM: Artificial Sequence
<220> FEATURE:
<223> OTHER INFORMATION: MGJ1 LAIR1

<400> SEQUENCE: 113

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

His Thr Phe Arg Leu Glu Arg Glu Ser Arg Ser Thr Tyr Asn Glu Thr
        35                  40                  45

Glu Asp Val Ser Gln Ala Ser Pro Ser Glu Ser Glu Ala Arg Phe Arg
    50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 114
<211> LENGTH: 98
<212> TYPE: PRT
<213> ORGANISM: Artificial Sequence
<220> FEATURE:
<223> OTHER INFORMATION: MGJ2 LAIR1

<400> SEQUENCE: 114

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

Gln Thr Phe Arg Leu Glu Arg Glu Ser Arg Phe Thr Tyr Asn Asp Thr
        35                  40                  45

Glu Asp Val Ser Gln Ala Ser Pro Ser Glu Ser Glu Ala Arg Phe Arg
    50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 115
<211> LENGTH: 97
<212> TYPE: PRT
<213> ORGANISM: Artificial Sequence
<220> FEATURE:
<223> OTHER INFORMATION: MGJ3 LAIR1

<400> SEQUENCE: 115

Asp Leu Pro Arg Pro Ser Ile Ser Ala Glu Pro Gly Thr Val Ile Pro
1               5                   10                  15

Leu Gly Ser His Val Thr Phe Val Cys Arg Gly Pro Val Gly Val Gln
            20                  25                  30

Thr Phe Arg Leu Glu Arg Glu Ser Arg Ser Thr Tyr Asn Glu Thr Glu
        35                  40                  45

Asp Val Ser Gln Ala Ser Pro Ser Glu Ser Glu Ala Arg Phe Arg Ile
    50                  55                  60
```

Asp Ser Val Ser Glu Gly Asn Ala Gly Pro Tyr Arg Cys Ile Tyr Tyr
65                  70                  75                  80

Lys Pro Pro Lys Trp Ser Glu Gln Ser Asp Tyr Leu Glu Leu Leu Val
                85                  90                  95

Lys

<210> SEQ ID NO 116
<211> LENGTH: 98
<212> TYPE: PRT
<213> ORGANISM: Artificial Sequence
<220> FEATURE:
<223> OTHER INFORMATION: MGJ5 LAIR1

<400> SEQUENCE: 116

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
            35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 117
<211> LENGTH: 98
<212> TYPE: PRT
<213> ORGANISM: Artificial Sequence
<220> FEATURE:
<223> OTHER INFORMATION: MMJ1 LAIR1

<400> SEQUENCE: 117

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
            35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 118
<211> LENGTH: 98
<212> TYPE: PRT
<213> ORGANISM: Artificial Sequence
<220> FEATURE:
<223> OTHER INFORMATION: MMJ2 LAIR1

<400> SEQUENCE: 118

Glu Asp Leu Pro Arg Pro Ser Ile Ser Ala Glu Pro Gly Thr Val Ile

```
1               5                   10                  15
Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
                35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 119
<211> LENGTH: 98
<212> TYPE: PRT
<213> ORGANISM: Artificial Sequence
<220> FEATURE:
<223> OTHER INFORMATION: MMJ5 LAIR1

<400> SEQUENCE: 119

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
                35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 120
<211> LENGTH: 98
<212> TYPE: PRT
<213> ORGANISM: Artificial Sequence
<220> FEATURE:
<223> OTHER INFORMATION: MMJ6 LAIR1

<400> SEQUENCE: 120

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
                35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys
```

<210> SEQ ID NO 121
<211> LENGTH: 98
<212> TYPE: PRT
<213> ORGANISM: Artificial Sequence
<220> FEATURE:
<223> OTHER INFORMATION: MMJ7 LAIR1

<400> SEQUENCE: 121

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
            35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 122
<211> LENGTH: 98
<212> TYPE: PRT
<213> ORGANISM: Artificial Sequence
<220> FEATURE:
<223> OTHER INFORMATION: MMJ8 LAIR1

<400> SEQUENCE: 122

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
            35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 123
<211> LENGTH: 98
<212> TYPE: PRT
<213> ORGANISM: Artificial Sequence
<220> FEATURE:
<223> OTHER INFORMATION: MMJ10 LAIR1

<400> SEQUENCE: 123

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
            35                  40                  45

```
Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
 65                  70                  75                  80

Tyr Lys Pro Pro Lys Trp Ser Glu Gln Ser Asp Tyr Leu Glu Leu Leu
                 85                  90                  95

Val Lys

<210> SEQ ID NO 124
<211> LENGTH: 98
<212> TYPE: PRT
<213> ORGANISM: Artificial Sequence
<220> FEATURE:
<223> OTHER INFORMATION: MMJ16 LAIR1

<400> SEQUENCE: 124

Glu Asp Leu Pro Arg Pro Ser Ile Ser Ala Glu Pro Gly Thr Val Ile
 1               5                  10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
            35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
 65                  70                  75                  80

Tyr Lys Pro Pro Lys Trp Ser Glu Gln Ser Asp Tyr Leu Glu Leu Leu
                 85                  90                  95

Gly Lys

<210> SEQ ID NO 125
<211> LENGTH: 98
<212> TYPE: PRT
<213> ORGANISM: Artificial Sequence
<220> FEATURE:
<223> OTHER INFORMATION: MMJ23 LAIR1

<400> SEQUENCE: 125

Glu Asp Leu Pro Arg Pro Ser Ile Ser Ala Glu Pro Gly Thr Val Ile
 1               5                  10                  15

Pro Leu Gly Ser His Val Thr Phe Val Cys Arg Gly Pro Val Gly Val
                20                  25                  30

Gln Thr Phe Arg Leu Glu Arg Glu Ser Arg Ser Thr Tyr Asn Glu Thr
            35                  40                  45

Glu Asp Val Ser Gln Val Ser Pro Ser Glu Ser Glu Ala Arg Phe Arg
        50                  55                  60

Ile Asp Ser Val Ser Glu Gly Asn Ala Gly Pro Tyr Arg Cys Ile Tyr
 65                  70                  75                  80

Tyr Lys Pro Pro Lys Trp Ser Glu Gln Ser Asp Tyr Leu Glu Leu Leu
                 85                  90                  95

Val Lys

<210> SEQ ID NO 126
<211> LENGTH: 98
<212> TYPE: PRT
<213> ORGANISM: Artificial Sequence
<220> FEATURE:
<223> OTHER INFORMATION: MMJ25 LAIR1
```

```
<400> SEQUENCE: 126

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

Gln Thr Phe Arg Leu Glu Arg Glu Ser Arg Ser Thr Tyr Asn Glu Thr
        35                  40                  45

Glu Asp Val Ser Gln Val Ser Pro Ser Glu Ser Glu Ala Arg Phe Arg
    50                  55                  60

Ile Asp Ser Val Ser Glu Gly Asn Ala Gly Pro Tyr Arg Cys Ile Tyr
65                  70                  75                  80

Tyr Lys Pro Pro Lys Trp Ser Glu Gln Ser Asp Tyr Leu Glu Leu Leu
                85                  90                  95

Val Lys

<210> SEQ ID NO 127
<211> LENGTH: 98
<212> TYPE: PRT
<213> ORGANISM: Artificial Sequence
<220> FEATURE:
<223> OTHER INFORMATION: MGM1 LAIR1

<400> SEQUENCE: 127

Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

Gln Thr Phe Arg Leu Glu Arg Glu Ser Arg Ser Thr Tyr Asn Asp Thr
        35                  40                  45

Glu Asp Val Ser Gln Ala Ser Pro Ser Glu Ser Glu Ala Arg Phe Arg
    50                  55                  60

Ile Asp Ser Val Ser Glu Gly Asn Ala Gly Pro Tyr Arg Cys Val Tyr
65                  70                  75                  80

Tyr Lys Pro Pro Lys Trp Ser Glu Gln Ser Asp Tyr Leu Asp Leu Leu
                85                  90                  95

Val Lys

<210> SEQ ID NO 128
<211> LENGTH: 97
<212> TYPE: PRT
<213> ORGANISM: Artificial Sequence
<220> FEATURE:
<223> OTHER INFORMATION: MGM3 LAIR1

<400> SEQUENCE: 128

Asp Leu Pro Arg Pro Ser Ile Ser Ala Glu Pro Gly Thr Val Ile Pro
1               5                   10                  15

Leu Gly Ser His Val Thr Phe Val Cys Arg Gly Pro Val Gly Val Gln
            20                  25                  30

Thr Phe Arg Leu Glu Arg Glu Ser Arg Ser Ile Tyr Asn Asp Thr Glu
        35                  40                  45

Asp Val Ser Gln Ala Ser Pro Ser Glu Ser Glu Ala Arg Phe Arg Ile
    50                  55                  60

Asp Ser Val Ser Glu Gly Asn Ala Gly Pro Tyr Arg Cys Val Tyr Tyr
65                  70                  75                  80

Lys Pro Pro Lys Trp Ser Glu Glu Ser Asp Tyr Leu Glu Leu Leu Val
                85                  90                  95
```

Lys

<210> SEQ ID NO 129
<211> LENGTH: 98
<212> TYPE: PRT
<213> ORGANISM: Artificial Sequence
<220> FEATURE:
<223> OTHER INFORMATION: MGM4 LAIR1

<400> SEQUENCE: 129

```
Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

Gln Thr Phe Arg Leu Glu Arg Glu Ser Arg Ser Thr Tyr Asn Asp Thr
        35                  40                  45

Glu Asp Val Ser Gln Ala Ser Pro Ser Glu Ser Glu Ala Arg Phe Arg
    50                  55                  60

Ile Asp Ser Val Ser Glu Gly Asn Ala Gly Pro Tyr Arg Cys Val Tyr
65                  70                  75                  80

Tyr Lys Pro Pro Lys Trp Ser Glu Glu Ser Asp Ser Leu Glu Leu Leu
                85                  90                  95

Val Lys
```

<210> SEQ ID NO 130
<211> LENGTH: 98
<212> TYPE: PRT
<213> ORGANISM: Artificial Sequence
<220> FEATURE:
<223> OTHER INFORMATION: MGM5 LAIR1

<400> SEQUENCE: 130

```
Glu Asp Leu Pro Arg Pro Ser Ile Ser Ala Glu Pro Gly Thr Val Ile
1               5                   10                  15

Pro Leu Gly Ser His Val Thr Phe Val Cys Arg Gly Pro Val Gly Val
            20                  25                  30

Gln Thr Phe Arg Leu Glu Arg Glu Ser Arg Ser Thr Tyr Asn Asp Thr
        35                  40                  45

Glu Asp Val Ser Gln Ala Ser Pro Ser Glu Ser Glu Ala Arg Phe Arg
    50                  55                  60

Ile Asp Ser Val Ser Glu Gly Asn Ala Gly Pro Tyr Arg Cys Val Tyr
65                  70                  75                  80

Tyr Lys Pro Pro Lys Trp Ser Glu Gln Ser Asp Tyr Leu Glu Leu Leu
                85                  90                  95

Val Lys
```

<210> SEQ ID NO 131
<211> LENGTH: 98
<212> TYPE: PRT
<213> ORGANISM: Artificial Sequence
<220> FEATURE:
<223> OTHER INFORMATION: MGB2 LAIR1

<400> SEQUENCE: 131

```
Glu Asp Leu Pro Arg Pro Ser Ile Ser Ala Glu Pro Gly Thr Val Ile
1               5                   10                  15

Pro Leu Gly Ser Arg Val Thr Phe Val Cys Arg Gly Pro Val Gly Val
            20                  25                  30
```

Gln Thr Phe Arg Leu Glu Arg Glu Ser Arg Ser Lys Tyr Asn Glu Thr
                35                  40                  45

Glu Asp Val Ser Gln Ala Ser Pro Ser Glu Ser Glu Ala Arg Phe Arg
         50                  55                  60

Ile Asp Ser Val Ser Glu Gly Asn Ala Gly Pro Tyr Arg Cys Ile Tyr
 65                  70                  75                  80

Tyr Lys Pro Pro Lys Trp Ser Glu His Ser Asp Phe Leu Glu Leu Leu
                 85                  90                  95

Val Lys

<210> SEQ ID NO 132
<211> LENGTH: 98
<212> TYPE: PRT
<213> ORGANISM: Artificial Sequence
<220> FEATURE:
<223> OTHER INFORMATION: MGB43 LAIR1

<400> SEQUENCE: 132

Glu Asp Leu Pro Arg Pro Ser Ile Ser Ala Glu Pro Gly Thr Val Ile
 1               5                  10                  15

Pro Leu Gly Ser His Val Thr Phe Val Cys Arg Gly Pro Val Gly Val
                 20                  25                  30

Gln Thr Phe Arg Leu Glu Arg Glu Ser Arg Ser Arg Tyr Asn Glu Thr
                35                  40                  45

Glu Asp Val Ser Gln Thr Ser Pro Ser Glu Ser Glu Ala Arg Phe Arg
         50                  55                  60

Ile Asp Ser Val Ser Glu Gly Asn Ala Gly Pro Tyr Arg Cys Leu Tyr
 65                  70                  75                  80

Tyr Lys Thr Pro Lys Trp Ser Glu Gln Ser Asp Phe Leu Glu Leu Leu
                 85                  90                  95

Val Lys

<210> SEQ ID NO 133
<211> LENGTH: 98
<212> TYPE: PRT
<213> ORGANISM: Artificial Sequence
<220> FEATURE:
<223> OTHER INFORMATION: MGB47 LAIR1

<400> SEQUENCE: 133

Glu Asp Leu Pro Arg Pro Ser Ile Ser Ala Glu Pro Gly Thr Val Ile
 1               5                  10                  15

Pro Leu Gly Ser His Val Thr Phe Val Cys Arg Gly Pro Val Gly Val
                 20                  25                  30

Gln Thr Phe Arg Leu Glu Arg Glu Ser Arg Ser Arg Tyr Thr Glu Thr
                35                  40                  45

Glu Asp Val Ser Gln Thr Ser Pro Ser Glu Ser Glu Ala Arg Phe Arg
         50                  55                  60

Ile Asp Ser Val Ser Glu Gly Asn Ala Gly Pro Tyr Arg Cys Leu Tyr
 65                  70                  75                  80

Tyr Lys Pro Pro Lys Trp Ser Glu Gln Ser Asp Phe Leu Glu Leu Leu
                 85                  90                  95

Val Lys